United States Patent
Sekoguchi et al.

(10) Patent No.: US 7,312,973 B2
(45) Date of Patent: *Dec. 25, 2007

(54) AIR CONDITIONING APPARATUS AND ION GENERATING DEVICE FOR USE THEREIN

(75) Inventors: Yoshinori Sekoguchi, Nara (JP); Mamoru Morikawa, Yamatokoriyama (JP)

(73) Assignee: Sharp Kabushiki Kaisha, Osaka (JP)

( * ) Notice: Subject to any disclaimer, the term of this patent is extended or adjusted under 35 U.S.C. 154(b) by 244 days.

This patent is subject to a terminal disclaimer.

(21) Appl. No.: 11/098,461

(22) Filed: Apr. 5, 2005

(65) Prior Publication Data

US 2005/0168907 A1    Aug. 4, 2005

Related U.S. Application Data

(62) Division of application No. 10/362,927, filed as application No. PCT/JP01/07326 on Aug. 27, 2001, now Pat. No. 7,040,101.

(30) Foreign Application Priority Data

| Aug. 28, 2000 | (JP) | ............................. 2000-258028 |
| Sep. 5, 2000 | (JP) | ............................. 2000-268789 |
| Sep. 20, 2000 | (JP) | ............................. 2000-284744 |
| Sep. 26, 2000 | (JP) | ............................. 2000-291436 |
| Oct. 2, 2000 | (JP) | ............................. 2000-302488 |
| Oct. 4, 2000 | (JP) | ............................. 2000-305358 |
| Oct. 4, 2000 | (JP) | ............................. 2000-305440 |
| Jan. 29, 2001 | (JP) | ............................. 2001-19701 |
| Feb. 13, 2001 | (JP) | ............................. 2001-35843 |
| Feb. 14, 2001 | (JP) | ............................. 2001-36407 |
| Feb. 16, 2001 | (JP) | ............................. 2001-40522 |
| Mar. 7, 2001 | (JP) | ............................. 2001-62924 |

(51) Int. Cl.
    *H02H 1/00* (2006.01)

(52) U.S. Cl. ..................................... 361/231
(58) Field of Classification Search ................ 361/230, 361/231
See application file for complete search history.

(56) References Cited

U.S. PATENT DOCUMENTS

| 2,264,495 A | 12/1941 | Torsten |
| 2,933,151 A | 4/1960 | Kurtz |
| 3,750,556 A | 8/1973 | Duke et al. |
| 3,936,698 A | 2/1976 | Meyer |

(Continued)

FOREIGN PATENT DOCUMENTS

EP    0654 640 A    5/1995

(Continued)

*Primary Examiner*—Michael Sherry
*Assistant Examiner*—Boris Benenson
(74) *Attorney, Agent, or Firm*—Birch, Stewart, Kolasch & Birch, LLP

(57) ABSTRACT

An air conditioning apparatus incorporates an ion generating device that generates positive and negative ions by applying an alternating-current voltage between electrodes. The generated positive and negative ions coexist in the air and, when they attach to the surfaces of airborne bacteria, they react chemically with each other and generate radical hydroxyl and hydrogen peroxide, which extract hydrogen atoms from the cells of the bacteria and thereby kill them. This sterilizing effect is combined with the temperature-conditioning, dehumidifying, humidifying, air-purifying, and other functions of the air conditioning apparatus to bring about a comfortable and healthful indoor environment.

6 Claims, 89 Drawing Sheets

U.S. PATENT DOCUMENTS

| | | | |
|---|---|---|---|
| 4,951,172 | A | 8/1990 | Steinman et al. |
| 5,055,115 | A | 10/1991 | Yikai et al. |
| 5,428,964 | A | 7/1995 | Lobdell |
| 5,433,772 | A | 7/1995 | Sikora |
| 5,527,459 | A | 6/1996 | Ikeda et al. |
| 5,728,288 | A | 3/1998 | Kubo |
| 6,432,367 | B1 | 8/2002 | Munk |
| 6,668,563 | B2 | 12/2003 | Mirosky et al. |
| 7,031,134 | B2 * | 4/2006 | Izumi et al. ............ 361/231 |
| 7,120,006 | B2 * | 10/2006 | Sekoguchi et al. ........ 361/230 |

FOREIGN PATENT DOCUMENTS

| | | | |
|---|---|---|---|
| GB | 2 304 576 A | | 3/1997 |
| JP | 55-54957 A | | 4/1980 |
| JP | 55-54958 A | | 4/1980 |
| JP | 4-90428 A | | 3/1992 |
| JP | 8-247529 A | | 9/1996 |
| JP | 8-255669 A | | 10/1996 |
| JP | 9-57032 A | | 3/1997 |
| JP | 10-22055 A | | 1/1998 |
| JP | 10-94739 A | | 4/1998 |
| JP | 10-225512 A | | 8/1998 |
| JP | 10-253104 A | | 9/1998 |
| JP | 10-314621 A | | 12/1998 |
| JP | 10-332166 A | | 12/1998 |
| JP | 11-8044 A | | 1/1999 |
| JP | 11-70158 A | | 3/1999 |
| JP | 11-72240 A | | 3/1999 |
| JP | 11-83073 A | | 3/1999 |
| JP | 11-159838 A | | 6/1999 |
| JP | 11-173611 A | | 7/1999 |
| JP | 11-191478 A | | 7/1999 |
| JP | EO2000058290 | * | 2/2000 |
| JP | 2000-102596 A | | 4/2000 |
| JP | 2000-268938 A | | 9/2000 |

* cited by examiner

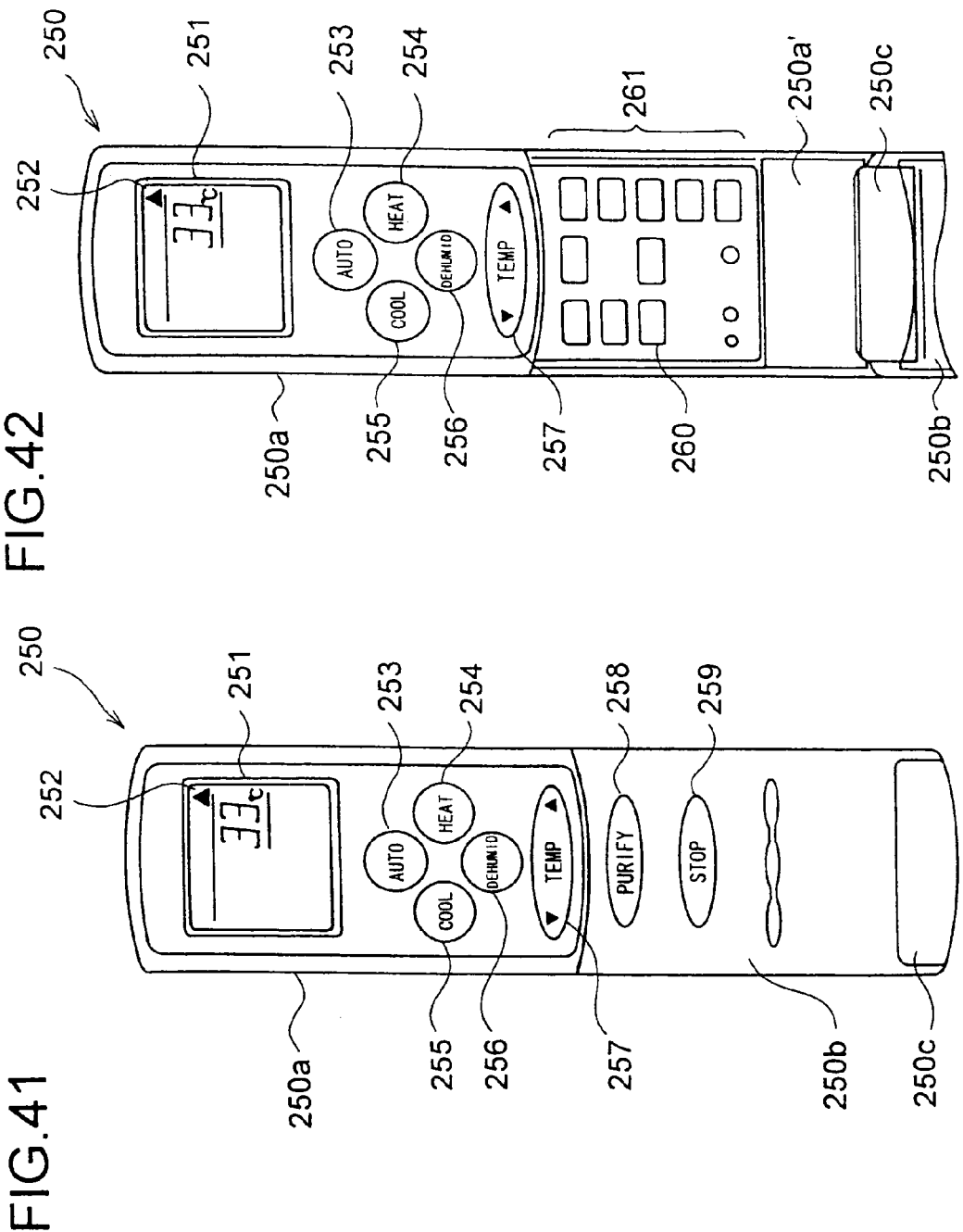

FIG.50

| AIR CONDITIONER OPERATION TIME (HOURS) | | | 0 | 1 | 2 | 3 | 4 | 5 |
|---|---|---|---|---|---|---|---|---|
| COMPARED ARRANGEMENT | COMMON BACTERIA | NUMBER (m$^{-3}$) | 230 | 85 | 45 | 30 | 20 | 15 |
| | | REDUCTION RATE (%) | 0 | 63 | 80 | 87 | 91 | 93 |
| | FUNGI | NUMBER (m$^{-3}$) | 500 | 150 | 85 | 50 | 40 | 30 |
| | | REDUCTION RATE (%) | 0 | 70 | 83 | 90 | 92 | 94 |
| 15TH EMBODIMENT | COMMON BACTERIA | NUMBER (m$^{-3}$) | 220 | 80 | 35 | 25 | 15 | 10 |
| | | REDUCTION RATE (%) | 0 | 64 | 84 | 89 | 93 | 95 |
| | FUNGI | NUMBER (m$^{-3}$) | 530 | 140 | 70 | 40 | 30 | 20 |
| | | REDUCTION RATE (%) | 0 | 74 | 87 | 92 | 94 | 96 |

FIG.52

| AIR PURIFIER OPERATION TIME (HOURS) | | 0 | 1 | 2 | 3 | 4 | 5 |
|---|---|---|---|---|---|---|---|
| COMPARED ARRANGEMENT | COMMON BACTERIA NUMBER (m$^{-3}$) | 240 | 90 | 55 | 40 | 30 | 25 |
| | REDUCTION RATE (%) | 0 | 60 | 77 | 83 | 88 | 90 |
| | FUNGI NUMBER (m$^{-3}$) | 520 | 165 | 105 | 65 | 45 | 40 |
| | REDUCTION RATE (%) | 0 | 68 | 80 | 88 | 91 | 92 |
| 16TH EMBODIMENT | COMMON BACTERIA NUMBER (m$^{-3}$) | 245 | 75 | 35 | 25 | 15 | 5 |
| | REDUCTION RATE (%) | 0 | 69 | 86 | 90 | 94 | 98 |
| | FUNGI NUMBER (m$^{-3}$) | 500 | 140 | 85 | 45 | 30 | 15 |
| | REDUCTION RATE (%) | 0 | 72 | 83 | 91 | 94 | 97 |

FIG.100

| CONDITIONS | POSITIVE IONS | NEGATIVE IONS |
|---|---|---|
| CONDITIONS 1 | 60% | 40% |
| CONDITIONS 2 | 55% | 45% |
| CONDITIONS 3 | 53% | 47% |
| CONDITIONS 4 | 50% | 50% |

FIG.101

| PERCENTAGE BY WEIGHT OF ANTISTATIC AGENT | POSITIVE IONS | NEGATIVE IONS |
|---|---|---|
| 0.0% | 60% | 40% |
| 0.7% | 54% | 46% |
| 1.4% | 50% | 50% |
| 2.0% | 50% | 50% |

AIR CONDITIONING APPARATUS AND ION GENERATING DEVICE FOR USE THEREIN

This application is a Divisional of application Ser. No. 10/362,927 filed on Aug. 11, 2003 now U.S. Pat. No. 7,040,101 and for which priority is claimed under 35 U.S.C. § 120. Application Ser. No. 10/362,927 is the national phase of PCT International Application No. PCT/JP01/07326 filed on Aug. 27, 2001 under 35 U.S.C. § 371. The entire contents of each of the above-identified applications are hereby incorporated by reference. This application also claims priority of application Ser. Nos. 2000-258028, 2000-268789, 2000-284744, 2000-291436, 2000-302488, 2000-305358, 2000-305440, 2001-19701, 2001-35843, 2001-36407, 2001-40522, 2001-62924 filed in Japan on Aug. 28, 2000, Sep. 5, 2000, Sep. 20, 2000, Sep. 26, 2000, Oct. 2, 2000, Oct. 4, 2000, Oct. 4, 2000, Jan. 29, 2001, Feb. 13, 2001, Feb. 14, 2001, Feb. 16, 2001, and Mar. 7, 2001 under 35 U.S.C. § 120 and/or § 119 are hereby reclaimed.

BACKGROUND OF THE INVENTION

1. Technical Field

The present invention relates to an air conditioning apparatus, and particularly to an air conditioning apparatus incorporating an ion generating device. An air conditioning apparatus refers to any apparatus that alters the various factors determining the properties of air, such as the temperature and humidity thereof and the substances contained therein, so as to make it comfortable and healthful to the human body. Practical examples of air conditioning apparatus include air conditioners, dehumidifiers, humidifiers, air purifiers, refrigerators, fan heaters, microwave ovens, laundry driers, vacuum cleaners, and sterilizers. These air conditioning apparatus are aimed at conditioning the air inside a finite space, such as a room in a house or a building, a sickroom or operating room in a hospital, the inside of a car, aircraft, or vessel, or the inside of a warehouse or refrigerator.

2. Description of the Related Art

It is needless to say that air plays an important role in the living environment of humans. Air is associated various parameters, such as the temperature and humidity thereof and the substances contained therein, and these parameters determine how comfortable and healthful it is to humans. Substances that may be contained in air are wide-ranging, examples including, in addition to dust, which is present everywhere, industrial pollutants such as mineral, metal, and other particles and exhaust gases, pollens and spores, microorganisms, odor-causing molecules, and carbon dioxide contained in exhaled breath.

In regions blessed with a favorable natural environment, it is largely possible to obtain comfortable air by natural ventilation alone. However, in regions with a poor outdoor environment, it is necessary to condition air artificially by some means to obtain comfortable air. Moreover, modern houses are increasingly built air-tight, which trend has been contributing to a greater demand for the conditioning of indoor air.

In conventional conditioning of air, the removal of airborne unpleasant or hazardous substances is achieved typically by filtering, absorbing, or decomposing them by means of a filter. However, filters are subject to poorer performance after an extended period of use, and thus inevitably require some form of maintenance such as replacement. In addition, it is difficult to ensure sufficiently high filtering performance to trap airborne bacteria effectively.

One important factor that determines the quality of air is the presence of ions in it. In particular, negative ions have been recognized to have a relaxing effect on humans. However, negative ions diminish as they bond to particular substances. For example, in the presence of cigarette smoke, negative ions may diminish down to about ½ to ⅕ of their normal concentration. To compensate for this loss, as a means for artificially augmenting negative ions in air, negative ion generators have been developed and put on the market.

Japanese Patent Application Published No. H7-23777 discloses an air conditioner in which a high alternating-current voltage is applied to a discharge needle unit provided in an air flow passage to generate negative ions so as to compensate for the negative ions that diminish as fine particles of pollutants increase in a room. Here, the use of a high alternating-current voltage prevents the product itself from being charged in an unbalanced fashion, i.e. either positively or negatively, and thus prevents the dust in the air inside the room from settling on the product. Moreover, the negative ions generated exert a relaxing effect.

In the air conditioner disclosed in the aforementioned application, however, the discharge needle unit is disposed near an air outlet located on the downstream side of a heat exchanger so that the ions generated are blown out into the room by a flow of air produced by a blower. Thus, in cooling operation, cool air directly hits the discharge needle unit. This may cause the discharge needle or another electrode to become frosted, leading to a short circuit. Moreover, the flow of air is disturbed as it hits the discharge needle unit. This may cause uneven blowing of air and a loss in the volume of air blown out, both undesirable effects in an air conditioner.

On the other hand, when an ion generating device generates ions, it simultaneously generates ozone as a byproduct. A high concentration of ozone is hazardous to the human body, such as by affecting the respiratory organs. This makes it necessary to devise some countermeasure against ozone.

SUMMARY OF THE INVENTION

According to one aspect of the present invention, an air conditioning apparatus is provided with an ion generating device that generates $H^+(H_2O)_m$ (where m is a natural number) as positive ions and $O_2^-(H_2O)_n$ (where n is a natural number) as negative ions. This makes it possible to kill airborne bacteria by the action of $H^+(H_2O)_m$ as positive ions and $O_2^-(H_2O)_n$ as negative ions, contributing to the conditioning of air.

According to another aspect of the present invention, an air conditioning apparatus generates $H^+(H_2O)_m$ (where m is a natural number) as positive ions and $O_2^-(H_2O)_n$ (where n is a natural number) as negative ions and blows out these ions into the air so as to kill airborne bacteria through an oxidation reaction by hydrogen peroxide $H_2O_2$ or radical hydroxyl .OH generated as a radical through a chemical reaction between the negative and positive ions. This makes it possible to condition the air to be free from airborne bacteria and healthful.

Here, the principle of how airborne bacteria are killed and removed by the action of positive and negative ions will be described briefly. When an alternating-current voltage is applied between two electrodes, arranged so as to face each other with a dielectric sandwiched in between, in such a way as to cause plasma discharge, the molecules of water contained as moisture in the air ionize to negative and positive ions, generating hydrogen ion hydrate $H^+(H_2O)_m$ as positive ions and oxygen ion hydrate $O_2^-(H_2O)_n$ as negative ions, where m and n each represent a natural number. When these ions attach to the surfaces of airborne bacteria, they generate radical hydroxyl (OH•) and $H_2O_2$ (hydrogen peroxide), which extract hydrogen atoms from the cells of the bacteria and thereby kill them. This chemical reaction is an oxidation reaction, and the aforementioned radical hydroxyl OH• exits not only a sterilizing effect, but also an effect of deodorizing the air by oxidizing various airborne odor-causing molecules.

According to another aspect of the present invention, an air conditioning apparatus is provided with a blower that circulates the air inside a room, a circulation passage through which the blower circulates the air, and an air flow passage provided separately from the circulation passage. Moreover, an ion generating device that generates positive and negative ions is provided in the air flow passage. In this arrangement, the ion generating device does not obstruct the circulation of the air inside the room, nor the air flowing through the circulation passage does affect the ion generating device adversely.

According to another aspect of the present invention, an air conditioning apparatus is provided with a blower that circulates the air inside a room, a circulation passage through which the blower circulates the air, and an air flow passage provided separately from the circulation passage. Moreover, an ion generating device that generates positive and negative ions and an ion blower that blows out the positive and negative ions are provided in the air flow passage. In this arrangement, the ion generating device does not obstruct the circulation of the air inside the room, nor the air flowing through the circulation passage does affect the ion generating device adversely. Furthermore, the ion blower blows out the ions effectively.

In the air conditioning apparatus described above, a common air inlet may be provided for the circulation passage and the air flow passage. This arrangement helps simplify the construction of the air conditioning apparatus.

Alternatively, in the air conditioning apparatus described above, separate air inlets may be provided for the circulation passage and the air flow passage. This arrangement permits the air inlets to be located as desired according to where the ion generating device is installed, and thus helps save space and thereby miniaturize the air conditioning apparatus.

Alternatively, in the air conditioning apparatus described above, a common air outlet may be provided for the circulation passage and the air flow passage. In this arrangement, the positive and negative ions generated by the ion generating device are spread all around the room by the flow of air blowing out of the circulation passage. This helps enhance the sterilizing effect.

Alternatively, in the air conditioning apparatus described above, separate air outlets may be provided for the circulation passage and the air flow passage. This arrangement makes it possible to blow out air containing ions irrespective of the operation status of the air conditioning apparatus, and thus to generate ions stably.

Thus, the air inlets and outlets of the circulation passage and the air flow passage can be selected from among these alternative combinations to suit given purposes; that is, the air flow passage can be formed in varying manners with respect to the circulation passage. This makes it possible, for example, to permit the ion generating device to operate independently or in concert with another mode of operation, or to enhance the functions of the air conditioning apparatus by exploiting the sterilizing effect of ions.

According to another aspect of the present invention, an air conditioning apparatus is provided with a blower that circulates the air inside a room, a circulation passage through which the blower circulates the air, a heat exchanger provided in the circulation passage for conditioning the temperature of the air flowing therethrough, and an air flow passage provided separately from the circulation passage. Moreover, an ion generating device that generates positive and negative ions is provided in the air flow passage. Here, the air outlet of the air flow passage communicates with the circulation passage, and the confluence between the air flow passage and the circulation passage is formed on the downstream side of the heat exchanger provided in the circulation passage. This arrangement permits the air having its temperature or humidity conditioned by the heat exchanger to be subjected to the conditioning effected by the positive and negative ions.

According to another aspect of the present invention, an air conditioning apparatus is provided with a blower that circulates the air inside a room, a circulation passage through which the blower circulates the air, and an air flow passage provided separately from the circulation passage. Moreover, an ion generating device unit including in a single unit an ion generating device that generates positive and negative ions and an ion blower that blows out the positive and negative ions is provided in the air flow passage. In this arrangement, it is possible to introduce air into the ion generating device unit effectively, to blow out air containing ions effectively, and thus to achieve a stable sterilizing effect. Moreover, the ion generating device unit can be mounted quite easily, because its mounting simply involves fitting it in position. Furthermore, the shape and specifications of the ion generating device unit can be determined to suit the product in which it is incorporated, and therefore it is easy to cope with design changes in the product.

In the air conditioning apparatus described above, a filter may be provided at the air inlet of the ion generating device unit. This arrangement prevents dust from settling on the ion generating device and thereby prevents degradation of performance after an extended period of use.

In air conditioning apparatus according to the present invention, a sight window may be provided through which to check an ion generating element provided as an ion generator in an ion generating device unit like the one described above. This arrangement permits the user to check for dust collected on the ion generating element and thereby makes its maintenance easier.

According to another aspect of the present invention, an air conditioning apparatus is provided with a blower that circulates the air inside a room, a circulation passage through which the blower circulates the air, and a heat exchanger provided in the circulation passage for conditioning the temperature of the air flowing therethrough. Moreover, an ion generating device that generates positive and negative ions is provided on the upstream side of the heat exchanger provided in the circulation passage. In this arrangement, the positive and negative ions generated by the ion generating device are blown out into the flow of air flowing through the circulation passage so that the generated ions are spread all around the room. Moreover, since the generated ions are passed through the heat exchanger and through the circulation passage, it is possible to kill airborne bacteria floating around these components. This helps prevent bacteria from attaching to those components and thereby keep them hygienic to ensure that clean air free from bacteria is blown out.

In air conditioning apparatus according to the present invention, in addition to an ion generating device, a dehumidifying/humidifying device that absorbs moisture from and then releases it back into the air may be provided. In this arrangement, it is possible to perform sterilization while conditioning the humidity of the air, and thus, by making the air properly dry and simultaneously generating ions, it is possible to enhance the sterilizing effect.

According to another aspect of the present invention, in an air conditioning apparatus provided with an ion generating device that generates positive and negative ions by applying an alternating-current voltage between electrodes, a controller is provided that controls the operation of the air conditioning apparatus and the driving of the ion generating device in an interlocked fashion. This arrangement offers a control system that controls the operation of the ion generating device and the air conditioning apparatus in an interlocked fashion, and thus with improved usability.

According to another aspect of the present invention, in an air conditioning apparatus provided with an ion generating device that generates positive and negative ions by applying an alternating-current voltage between electrodes, a controller is provided that controls the operation of the air conditioning apparatus and the driving of the ion generating device independently. This arrangement offers a control system that controls the operation of the ion generating device and the air conditioning apparatus independently, and thus with more precise controllability.

In the air conditioning apparatus described above, timer means for permitting the ion generating device to start being driven a predetermined time after the air conditioning apparatus starts operating may be provided. In this arrangement, the ions are carried by a stable volume of air that is blown out, and thus can be spread all around a given space efficiently.

Alternatively, in the air conditioning apparatus described above, means for controlling the amount of ions generated by the ion generating device according to the size of space in which the air condition apparatus is installed may be provided. In this arrangement, a proper amount of ions is generated according to the size of the room so that the radical having a sterilizing effect is spread all around the room.

Alternatively, in the air conditioning apparatus described above, the ion generating device may be provided inside a front panel provided to protect the front end of the air flow passage of the air conditioning apparatus, with stopping means additionally provided for stopping the driving of the ion generating device when the front panel is open. This arrangement helps secure sufficient safety on occasions of maintenance such as cleaning.

According to another aspect of the present invention, in an air conditioning apparatus provided with an ion generating device that generates positive and negative ions by applying an alternating-current voltage between electrodes and a controller that controls the operation of the air conditioning apparatus and the driving of the ion generating device independently, indicating means is provided for indicating the generation of the ions (1) with a particular form of indication when the ion generating device is operating together with the air conditioning apparatus and (2) with a different form of indication from that used in (1) when the ion generating device is operating alone.

In this arrangement, the indicating means makes it easier for the user to confirm that ions are actually being generated.

According to another aspect of the present invention, an air conditioning apparatus is provided with a first blower that blows out air having temperature, humidity, or cleanliness thereof conditioned into a room, an ion generating device that generates positive and negative ions by applying an alternating-current voltage between electrodes, and a second blower that blows out the ions generated by the ion generating device into the room with variable volume of air. In this arrangement, the first and second blowers blow out air having its temperature, humidity, or cleanliness conditioned, together with positive and negative ions, into the room. Here, by adjusting the volume of air blown out by the second blower, it is possible to vary the concentration of positive and negative ions blown out into the room.

In the air conditioning apparatus described above, the volume of air blown out by the second blower may be decreased as the volume of air blown out by the first blower decreases. In this arrangement, when the volume of air blown out by the first blower is decreased as when the user is about to go to bed, the volume of air blown out by the second blower is decreased so as to reduce noise.

In the air conditioning apparatus described above, a quiet operation mode may be provided that permits the volume of air blown out by the first and second blowers to be decreased through the operation by the user in this arrangement, when the quiet operation mode is selected through the operation by the user as when the user is about to go to bed, the volume of air blown out by the first and second blowers is decreased so as to reduce noise.

In the air conditioning apparatus described above, a photosensor may be provided that detects the brightness inside the room so that, when the photosensor detects that the brightness inside the room is lower than predetermined brightness, the volume of air blown out by the first and second blowers is decreased. In this arrangement, when the photosensor detects that it is dark inside the room, the user is recognized to be about to go to bed, and the volume of air blown out by the first and second blowers is decreased so as to reduce noise.

In the air conditioning apparatus described above, the amount of ions generated by the ion generating device may be increased or decreased as the volume of air blown out by the second blower increases or decreases. In this arrangement, even when the volume of air blown out by the second blower is decreased and thus the volume of air blown into the room is decreased, the amount of ions generated is adjusted accordingly to keep a proper concentration of ions.

In the air conditioning apparatus described above, the volume of air blown out by the second blower may be increased as the volume of air blown out by the first blower decreases. In this arrangement, for example, when the temperature inside the room becomes equal to a specified temperature, the volume of air blown out by the first blower is decreased. Simultaneously, the volume of air blown out by the second blower is increased to reduce an excessive increase in the concentration of ions.

According to another aspect of the present invention, in an air conditioning apparatus provided with a first blower that blows out air having its temperature or humidity conditioned into a room, an ion generating device that generates positive and negative ions by applying an alternating-current voltage between electrodes, and a second blower that blows out the ions generated by the ion generating device into the room, the ion generating device is stopped when the first blower is stopped. By stopping the ion generating device when the first blower is stopped, it is possible to stop the generation of ions and ozone and thereby prevent an increase in the concentration of ozone around the air outlet.

In the air conditioning apparatus described above, the second blower may be stopped when the first blower is stopped. Also in this arrangement, when the first blower is stopped, it is possible to prevent an increase in the concentration of ozone around the air outlet.

According to another aspect of the present invention, in an air conditioning apparatus provided with a first blower that blows out air having its temperature or humidity conditioned into a room, an ion generating device that generates positive and negative ions by applying an alternating-current voltage between electrodes, and a second blower that blows out the ions generated by the ion generating device into the room, the ion generating device is made to generate a smaller amount of ions when the first blower is stopped than when the first blower is operating. When the operation of the first blower is stopped, the ion generating device operates with a lower output power so as to limit the amounts of ions and ozone generated. This makes it possible to keep the amount of ozone blown out into the room proper.

Preferably, the air conditioning apparatus described above is so configured as to be capable of cooling and heating operation, and, when the cooling or heating operation is started, the first blower is stopped. In this arrangement, when the cooling operation is started, the temperature of the heat exchanger is high, and therefore the first blower is stopped to prevent hot air from being blown out. In this situation, the ion generating device is stopped or made to operate with a lower output power to prevent an increase in the concentration of ozone around the air outlet. On the other hand, when the heating operation is started, the temperature of the heat exchanger is low, and therefore the first blower is stopped to prevent cold air from being blown out.

Alternatively, the air conditioning apparatus described above may be so configured as to be capable of cooling and heating operation, and, when a specified temperature is reached in the heating operation, the first blower is stopped. In this arrangement, when the specified temperature is reached in the heating operation, the compressor and the first blower are stopped to prevent a further rise in the temperature inside the room. In this situation, the ion generating device is stopped or made to operate with a lower output power to prevent an increase in the concentration of ozone around the air outlet.

Alternatively, the air conditioning apparatus described above may be so configured as to be capable of cooling and heating operation, and, during defrosting in the heating operation, the first blower is stopped. In this arrangement, when the heat exchanger of the outdoor unit becomes frosted in the heating operation, the air conditioning apparatus performs defrosting by establishing a heat cycle in which the heat exchanger of the outdoor unit is placed on the high-temperature side and the heat exchanger of the indoor unit is placed on the low-temperature side.

Thus, the first blower is stopped to prevent cold air from being blown out. In this situation, the ion generating device is stopped or made to operate with a lower output power to prevent an increase in the concentration of ozone around the air outlet.

Alternatively, in the air conditioning apparatus described above, the first blower may be stopped when a compressor is stopped in dehumidifying operation. In this arrangement, when the temperature inside the room lowers until it reaches a specified temperature, the compressor and the first blower are stopped to prevent a further fall in the temperature inside the room and to prevent a rise in humidity resulting from the evaporation of drained water. In this situation, the ion generating device is stopped or made to operate with a lower ouput power to prevent an increase in the concentration of ozone around the air outlet.

According to another aspect of the present invention, an ion generating device unit is provided with an ion generating element that generates positive and negative ions when a voltage is applied thereto, a power supply that applies the voltage to the ion generating element, an ion blower that blows out the ions generated by the ion generating element, and a housing case in which the ion generating element, the power supply, and the ion blower are housed. Here, an element support portion that keeps the ion generating element in position is formed integrally with the housing case. In this arrangement, the ion generating device unit is built as a unit with the ion generating element, the ion blower, and the power supply housed in the housing case, and the ion generating element is kept in position by the element support portion without the need for screws.

In the ion generating device unit described above, preferably, the ion generating element has a cylindrical dielectric, an inner electrode formed along the inner surface of the dielectric, and an outer electrode formed along the outer surface of the dielectric, and the element support portion consists of ribs that hold the ion generating element at both ends. In this arrangement, the ion generating element that generates positive and negative ions when an alternating-current voltage is applied between the inner and outer electrodes arranged so as to sandwich the dielectric is formed in a cylindrical shape, and is, at both ends, kept in position by the element support portion consisting of ribs.

Moreover, in the ion generating device unit described above, the ribs may be formed along the flow of air produced by the ion blower. In this arrangement, the flow of air produced by the ion blower flows along the ribs. This helps trim the flow of air and prevent a loss in its pressure resulting from collision with the ribs.

Alternatively, in the ion generating device unit described above, a discharge outlet through which to blow out the ions may be formed in the housing case, with protecting means provided at the discharge outlet for preventing entry of a foreign object through the discharge outlet. In this arrangement, the protecting means prevents contact of a foreign object with the ion generating element charged at a high voltage, and thereby increases safety.

According to another aspect of the present invention, an ion generating device unit is provided with an ion generating element that generates positive and negative ions when a voltage is applied thereto, a power supply that applies the voltage to the ion generating element, an ion blower that blows out the ions generated by the ion generating element, and a housing case in which the ion generating element, the power supply, and the ion blower are housed. Here, inside the housing case, the ion generating element is arranged on one side of the ion blower and the power supply is arranged on the other side of the ion blower. The arrangement helps reduced that effect on the power supply of the noise generated by the ion generating element when it generates ions.

According to another aspect of the present invention, in an air conditioning apparatus that can condition the temperature, humidity, or cleanliness of the air, a control circuit that controls the operation of the air conditioning apparatus is arranged at one end of the air conditioning apparatus, and an ion generating device unit as described above is arranged at the other end of the air conditioning apparatus. This arrangement helps reduce the effect on the control circuit of the noise generated by the power supply charged at a high voltage.

Alternatively, in an air conditioning apparatus provided with a front panel that forms the front face of the air conditioning apparatus and that has an air inlet formed therein that leads to a circulation passage through which a blower provided inside the air conditioning apparatus passes a flow of air, and a heat exchanger provided in the circulation passage and having a function of conditioning the temperature of the air flowing therethrough, an ion generating device unit as described above is arranged between the front panel and the heat exchanger. This arrangement helps shorten the distance between the air inlet formed in the front face of the air conditioning apparatus and the ion generating device unit, and thus helps reduce loss of ions resulting from, for example, collision with the wall surface inside the distribution passages.

In the air conditioning apparatus described above, a heat insulator may be provided between the heat exchanger and the ion generating device unit. This arrangement helps prevent condensation around the ion generating device unit that occurs as the heat exchanger cools down.

Alternatively, in an air conditioning apparatus provided with a front panel that forms the front face of the air conditioning apparatus and that has an air inlet formed therein that leads to a circulation passage through which a blower provided inside the air conditioning apparatus passes a flow of air, and an ion generating device unit as described above, a filter is provided on the suction side of the ion blower in such a way as to be detachable through the front face of the air conditioning apparatus. This arrangement makes the cleaning of the filter easy, and thus helps keep dust off the ion generating element.

According to another aspect of the present invention, an air conditioning apparatus is provided with an ion generating device that generates positive and negative ions by applying an alternating-current voltage between electrodes and a filter portion that performs deodorization and/or dust collection. Here, the filter portion is arranged in the upstream-side portion of an air flow passage leading from an air inlet to an air outlet and the ion generating device is arranged in the downstream-side portion of the air flow passage. In this arrangement, the filter portion arranged on the upstream side of the ion generating device removes organic compounds, dust, and other foreign substances and thereby keeps the ion generating device almost free from dirt. This makes it possible to use the ion generating device for an extended period, to generate ions stably, and to achieve an excellent sterilizing effect by the application of a relatively low voltage.

According to another aspect of the present invention, an air conditioning apparatus is provided with a blower that circulates the air inside a room and an ion generating device that generates positive and negative ions by applying an alternating-current voltage between electrodes. Moreover, an ozone reducing device for reducing ozone is provided on the downstream side of the ion generating device. This arrangement makes it possible to reduce the concentration of ozone that is produced as a byproduct together with positive and negative ions as a result of the application of the alternating-current voltage and that affects the human body adversely.

In the air conditioning apparatus described above, an air flow passage may be bifurcated into branch passages at a branch portion thereof provided on the downstream side of the blower, with the ion generating device provided in one of the branch passages. In this arrangement, the volume of air flowing through the ion generating device is kept constant.

In the air conditioning apparatus described above, means for adjusting the flow rate of air may be provided at the branch portion. In this arrangement, it is possible to adjust the flow rate of air or how to distribute the flow of air, and thus it is possible to properly adjust the concentration of ions blown out of the ion generating device.

In the air conditioning apparatus described above, a light-emitting portion may be provided near the ion generating device so that the emission of light is controlled in an interlocked fashion with the operation of the ion generating device. In this arrangement, it is possible to confirm the operation status of the ion generating device by observing what is illuminated by the light emitted.

According to another aspect of the present invention, in an air conditioning apparatus provided with a blower that circulates the air inside a room, a filter that removes dust from the air sucked in, and an ion generating device that generates positive and negative ions by applying an alternating-current voltage between electrodes, part of the air that has passed through the filter is fed to the ion generating device so that air containing the ions generated by the ion generating device is mixed with the air that has passed through the filter so as to be circulated together therewith. In this arrangement, part of the air that has passed through the filer is fed to the ion generating device, and the resulting air containing ions is carried and scattered by the flow of the air that has passed through the filter so that the ions are spread quickly all around the room.

In the air conditioning apparatus described above, the air containing the ions generated by the ion generating device and the air that has passed through the filter may be mixed outside the body of the air condition apparatus. In this arrangement, it does not occur that the pressure of the air that has passed through the filter hinders the air containing ions from coming out of the ion generating device, as is the case in an arrangement in which those two flows of air are mixed inside the body of the air conditioning apparatus. Thus, it is possible to mix efficiently and smoothly the air containing ions with the main flow of air that has passed through the filter.

In the air conditioning apparatus described above, wind direction setting means may be provided at the outlet of the air that has passed through the ion generating device. In this arrangement, it is possible to mix effectively the air containing ions with the main flow of air that has passed through the filter.

According to another aspect of the present invention, in an air conditioning apparatus provided with a pair of electrodes arranged so as to face each other with a dielectric sandwiched in between that is cylindrical and has caps made of an elastic material fitted at both ends, an ion generating element is fixed inside the air conditioning apparatus by fitting one of the caps into the body of the air conditioning apparatus from the direction perpendicular to the axial direction of the dielectric and then putting the other of the caps into contact with the body of the air conditioning apparatus in such a way that a pressing force is applied to the dielectric from the axial direction thereof. This arrangement permits the ion generating element to be fitted easily and securely.

According to another aspect of the present invention, an ion generating device is provided with a dielectric, a pair of electrodes arranged so as to face each other with the dielectric sandwiched in between, high alternating-current voltage generating means for applying an alternating-current voltage between the pair of electrodes, first generating means for generating positive and negative ions, and second generating means for generating only negative ions. Moreover, switching means for switching between the first and second generating means is provided. In this arrangement, it is possible to switch between operation whereby only negative ions are generated to achieve a relaxing effect and operation whereby both positive and negative ions are generated to achieve a sterilizing effect.

In the ion generating device described above, the switching means for switching between the first and second generating means may be provided with a diode having its anode connected to one of the electrodes to which the voltage is not applied and having its cathode grounded and a switching device connected between both ends of the diode. In this arrangement, it is possible to achieve the aforementioned effects by switching the on/off state of the switching device. Moreover, it is possible to realize the switching means for switching between the first and second generating means with a simple configuration and thereby reduce costs.

The ion generating device described above may be so configured that positive and negative ions are generated when the switching device is turned on and only negative ions are generated when the switching device is turned off. In this arrangement, it is possible to switch between the first and second generating means through simple operation.

In the ion generating device described above, the switching device may be a relay. In this arrangement, the alternating-current generating means is insulated from the control circuit that controls the relay. This helps simplify the circuit design.

According to another aspect of the present invention, in an air conditioning apparatus that dehumidifies the air inside a room, an ion generating device that generates positive and negative ions by applying an alternating-current voltage between electrodes is provided, and dry air after being dehumidified is fed to the ion generating device so that the ions are blown out into the room by the dry air. In this arrangement, dry air after being dehumidified is fed to the ion generating device, and is blown out together with the ions into the room.

According to another aspect of the present invention, in an air conditioning apparatus that takes in the air inside a room and exchanges heat between the air and a heat exchanger performing a refrigerating cycle so as to condense the moisture contained in the air and blow out dry air through an air outlet into the room, an ion generating device that generates positive and negative ions by applying an alternating-current voltage between electrodes is provided on the air outlet side of the heat exchanger. In this arrangement, the air inside the room taken into the air conditioning apparatus is, in a refrigerating cycle, subjected to heat exchange with the heat exchanger so that the moisture contained in the air is condensed to produce dry air. This dry air is fed to the ion generating device so as to carry the positive and negative ions generated by the ion generating device and blow them out into the room. This makes it possible to blow out a stable amount of ions into the room even when the humidity inside the room is high.

In the air conditioning apparatus described above, part of the dry air may be fed to the ion generating device. In this arrangement, part of the dry air after being dehumidified is fed to the ion generating device, and the resulting dry air containing ions is mixed with the rest of the dry air so as to be blown out together therewith into the room.

In the air conditioning apparatus described above, the proportion of the air that is fed to the ion generating device may be varied according to the volume of the air that is blown out into the room. In this arrangement, it is possible to keep the volume of air fed to the ion generating device substantially constant irrespective of the volume of air blown out into the room.

In the air conditioning apparatus described above, preferably, the ion generating device generates the positive and negative ions by applying the alternating-current voltage between the electrodes so as to effect discharge, and the voltage applied to the ion generating device is varied according to humidity of the dry air. In this arrangement, for example, when the humidity of the dry air is high, the voltage applied is made higher to maintain the desired amount of ions generated.

In the air conditioning apparatus described above, the amount of ions generated by the ion generating device may be varied according to the volume of the air that is blown out into the room. In this arrangement, for example, when the volume of air that is blown out is large, to compensate for the smaller concentration of ions that are blown out into the room, the amount of ions generated is increased.

In the air conditioning apparatus described above, a swingable wind direction adjustment device for changing the flow direction of the air blown out into the room may be provided so that the amount of ions generated by the ion generating device is varied according to the swing angle of the wind direction adjustment device. In this arrangement, for example, when the swing angle of the wind direction adjustment device is large, to compensate for the higher degree of dispersion with which ions are blown out into the room, the amount of ions generated is increased.

In the air conditioning apparatus described above, the amount of ions generated by the ion generating device may be made larger when the wind direction adjustment device is swinging than when the wind direction adjustment device is not swinging. In this arrangement, when the wind direction adjustment device swings, to compensate for the higher degree of dispersion with which ions are blown out into the room, the amount of ions generated is increased.

In the air conditioning apparatus described above, preferably, a lamp that illuminates the ion generating device when the ion generating device is operating is provided to permit the ion generating device to be checked visually, and the lamp is extinguishable through the operation of the user even when the ion generating device is operating. In this arrangement, when the voltage is applied to the ion generating device, the lamp is lit so that the operation status of the ion generating device can be checked visually. The user can extinguish the lamp while keeping the ion generating device operating, for example, when the user goes to bed. This enhances usability, and helps reduce electric power consumption.

According to another aspect of the present invention, in an air conditioning apparatus provided with an ion generating device that generates positive and negative ions by applying an alternating-current voltage between electrodes, a passage constituting member constituting a passage through which the ions generated by the ion generating device are passed or a member arranged in the passage through which the ions generated by the ion generating device are passed is made antistatic. This arrangement makes it possible to maintain a proper balance between the amounts of positive and negative ions that are blown out of the air conditioning apparatus.

According to another aspect of the present invention, in an air conditioning apparatus provided with an ion generating device that generates positive and negative ions by applying an alternating-current voltage between electrodes so as to kill airborne bacteria by the action thereon of a radical generated when the negative and positive ions react chemically with each other on the surfaces of the bacteria, a passage constituting member constituting a passage through which the ions generated by the ion generating device are passed or a member arranged in the passage through which the ions generated by the ion generating device are passed is made antistatic. This arrangement makes it possible to maintain a proper balance between the amounts of positive and negative ions that are blown out of the air conditioning apparatus, and thus to kill airborne bacteria efficiently.

According to another aspect of the present invention, in an air conditioning apparatus provided with an ion generating device that generates positive and negative ions by applying an alternating-current voltage between electrodes, a passage constituting member constituting a passage through which the ions generated by the ion generating device are passed and a member arranged in the passage through which the ions generated by the ion generating device are passed are made antistatic. This arrangement makes it possible to maintain a proper balance between the amounts of positive and negative ions that are blown out of the air conditioning apparatus.

According to another aspect of the present invention, in an air conditioning apparatus provided with an ion generating device that generates positive and negative ions by applying an alternating-current voltage between electrodes so as to kill airborne bacteria by the action thereon of a radical generated when the negative and positive ions react chemically with each other on the surfaces of the bacteria, a passage constituting member constituting a passage through which the ions generated by the ion generating device are passed and a member arranged in the passage through which the ions generated by the ion generating device are passed are made antistatic. This arrangement makes it possible to maintain a proper balance between the amounts of positive and negative ions that are blown out of the air conditioning apparatus, and thus to kill airborne bacteria efficiently.

In the air conditioning apparatus described above, the passage constituting member constituting the passage through which the ions generated by the ion generating device are passed or the member arranged in the passage through which the ions generated by the ion generating device are passed may be made antistatic by forming the member out of a material having a surface resistivity of $4 \times 10^9$ $\Omega$ or lower. This arrangement ensures that a proper balance is maintained between the amounts of positive and negative ions that are blown out of the air conditioning apparatus.

Alternatively, in the air conditioning apparatus described above, the passage constituting member constituting the passage through which the ions generated by the ion generating device are passed or the member arranged in the passage through which the ions generated by the ion generating device are passed may be made antistatic by forming the member out of a metal, or a resin having the surface thereof plated with a metal, or a resin having an antistatic agent added thereto. This arrangement ensures that a proper balance is maintained between the amounts of positive and negative ions that are blown out of the air conditioning apparatus.

Preferably, the air conditioning apparatus described above is provided with a dehumidifying function, and air after being dehumidified is fed to the ion generating device. In this arrangement, by feeding air after being dehumidified to the ion generating device, it is possible to prevent lowering of the amount of ions generated and thereby obtain quite a proper amount of positive and negative ions. This makes it possible to kill airborne bacteria more efficiently.

BRIEF DESCRIPTION OF THE DRAWINGS

FIG. 41 is a front view of the remote control unit that comes along with the air conditioner of the fourteenth embodiment.

FIG. 42 is a front view of the remote control unit that comes along with the air conditioner of the fourteenth embodiment, showing the remote control unit in a different state.

FIG. 50 is a table showing the results of operation tests of the indoor unit of the air conditioner of the fifteenth embodiment.

FIG. 52 is a table showing the results of operation tests of the air purifier of the sixteenth embodiment.

FIG. 100 is a table showing the results of measurement of the proportion of ions generated by a twenty-first embodiment of the air conditioning apparatus of the invention.

FIG. 101 is a table showing the results of measurement of the proportion of ions generated by the air conditioning apparatus of the twenty-first embodiment with respect to the ratio by weight of the antistatic agent used.

DETAILED DESCRIPTION OF THE INVENTION

Figure 1:
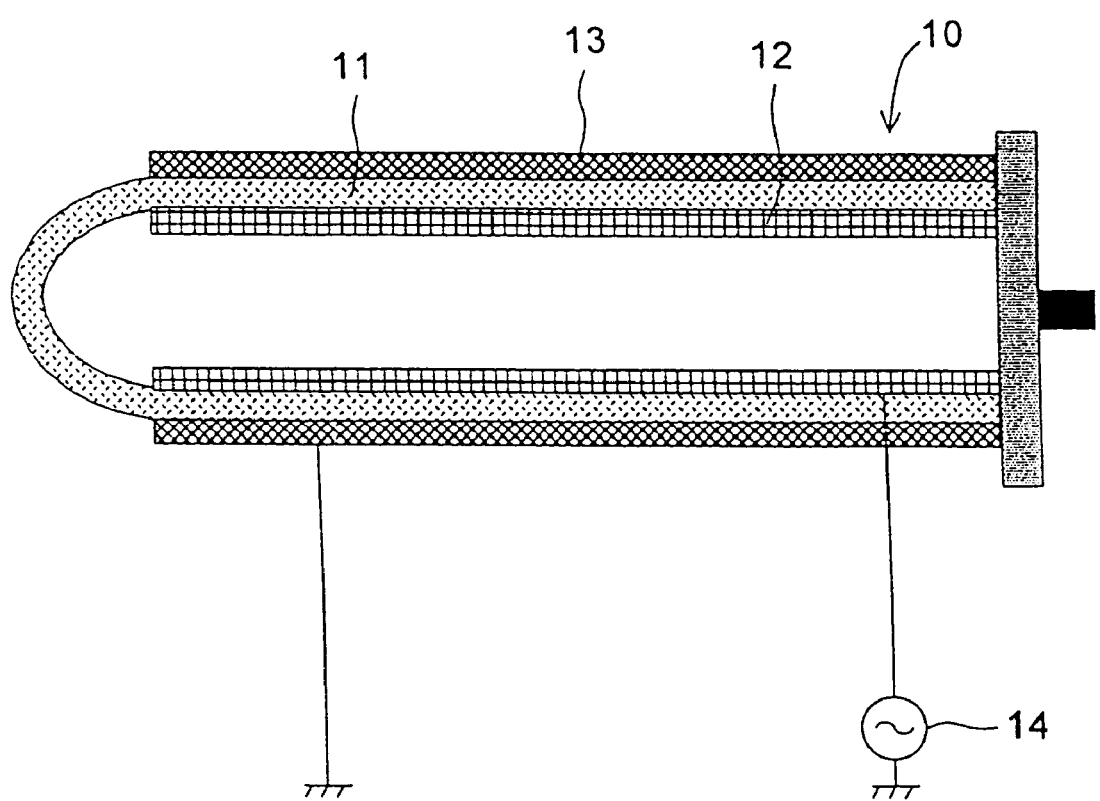
FIG. 1 is a sectional view showing the structure of a first embodiment of the ion generating device used in the invention.

Hereinafter, embodiments of the present invention will be described with reference to the accompanying drawings.

A high alternating-current voltage is applied between electrodes placed in the air so as to cause plasma discharge. This causes the molecules of water contained as moisture in the air to ionize to positive ions consisting of $H^+(H_2O)_n$ (hereinafter also referred to simply as "positive ions") and negative ions consisting of $O_2^-(H_2O)_m$ (hereinafter also referred to simply as "negative ions"), where n and m each represent a natural number. In the following descriptions, positive and negative ions are sometimes collectively referred to as "opposite ions." When negative and positive ions are made to coexist in a given space, $H^+(H_2O)_n$ and $O_2^-(H_2O)_m$ attach to the surfaces of airborne bacteria present in that space and surround them. Opposite ions then react chemically with each other as represented by formulae (1) to (3) below and generate [.OH] (radical hydroxyl) and $H_2O_2$ (hydrogen peroxide) as a radical. The radical thus generated extracts hydrogen atoms from the cells of the bacteria and thereby kills them. This effect is possible because airborne bacteria are so small that $H^+(H_2O)_n$ and $O_2^-(H_2O)_m$ can flock on the surfaces thereof. In other words, this effect is not brought about against objects, such as the human body, that are far larger than bacteria, and therefore the human health is not harmed in any way by the process described above.

$$H^+(H_2O)_n + O_2^-(H_2O)_m \rightarrow .OH + \tfrac{1}{2}O_2 + (n+m)\,H_2O \qquad (1)$$

$$H^+(H_2O)_n + H^+(H_2O)_{n'} + O_2^-(H_2O)_m + O_2^-(H_2O)_{m'} \rightarrow 2.OH + O_2 + (n+n'+m+m')H_2O \qquad (2)$$

$$H^+(H_2O)_n + H^+(H_2O)_{n'} + O_2^-(H_2O)_m + O_2^-(H_2O)_{m'} \rightarrow H_2O_2 + O_2 + (n+n'+m+m')H_2O \qquad (3)$$

Ion generating devices that generate positive and negative ions in the manner described above are realized as exemplified in the embodiments described below.

FIG. 1 shows an outline of the structure of the ion generating device 10 of the invention. An inner electrode 12 and an outer electrode 13, both cylindrical in shape, are arranged respectively inside and outside a glass tube 11 (1 mm thick) serving as an insulator and having the shape of a cylinder sealed at one end. Thus, the inner and outer electrodes 12 and 13 are arranged so as to face each other with the glass tube 11 sandwiched in between. Reference numeral 14 represents a high frequency circuit that applies an alternating-current voltage to the inner electrode 12 with the outer electrode 13 kept at the ground potential.

To permit the ion generating device 10 to generate positive and negative ions efficiently, it is preferable that the inner and outer electrodes 12 and 13 be formed out of a material having a large number of pores; for example, it is particularly preferable that the electrodes 12 and 13 be formed as meshes. In this embodiment, metal meshes of stainless steel (Japanese Industrial Standards SUS 304) were used.

In the ion generating device 10 structured as described above, using the high frequency circuit 14, an alternating-current voltage was applied to the inner electrode 12, with the outer electrode 13 kept at the ground potential. As a result, positive and negative ions were generated from the side surface of the glass tube 11 of the ion generating device 10. The alternating-current voltage used here had a frequency of 15 kHz and a voltage of 1.1 to 2.0 kV (as measured in root-mean-square values).

Figure 2A:
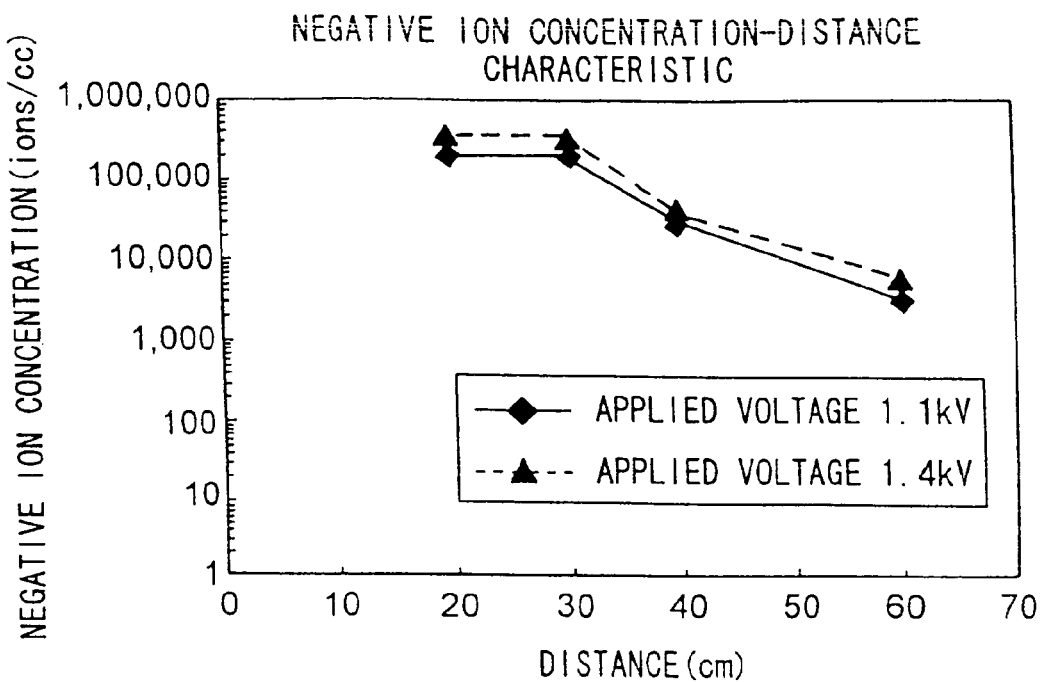
FIGS. 2(a) and 2(b) are graphs showing the characteristics of the concentration of ions generated by the ion generating device of the first embodiment with respect to the distance therefrom.
Figure 2B:
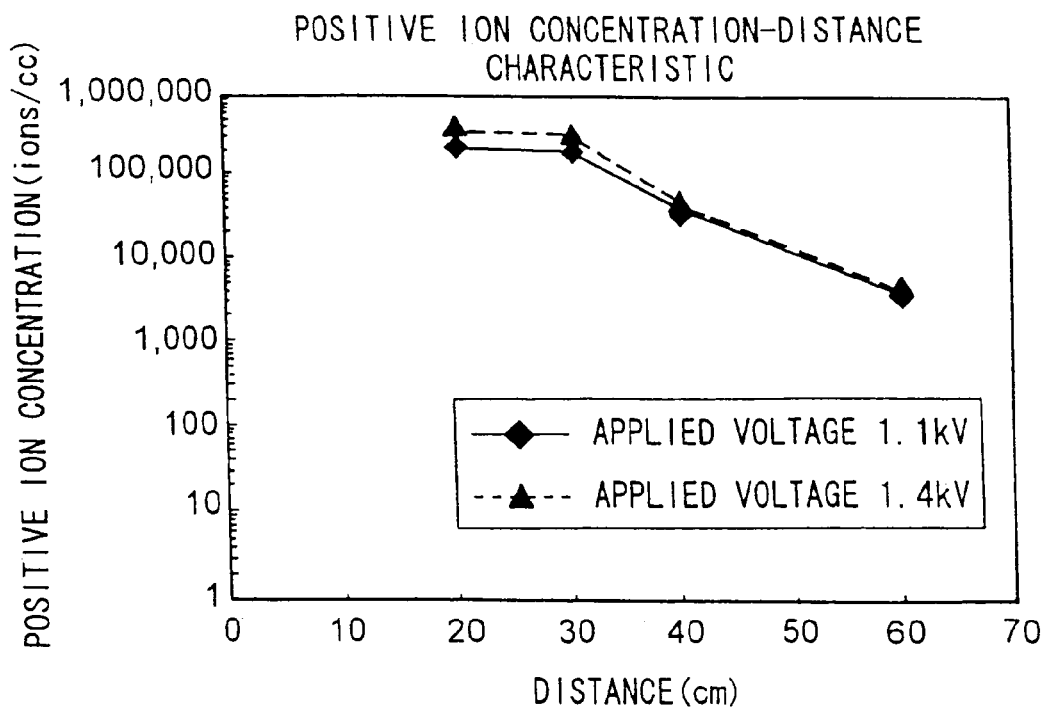

Under these conditions, the ions generated by the ion generating device 10 were measured using an ion counter (for example, model 83-1001B manufactured by Dan Kagaku Co., Ltd., Japan) to detect small ions with mobility of 1 cm$^2$/V. sec or higher. The results are shown in FIG. 2, which shows that about 200,000 to 400,000 ions/cc of positive and negative ions were measured at a distance of 20 cm from the side surface of the glass tube 11 of the ion generating device 10.

Figure 3:
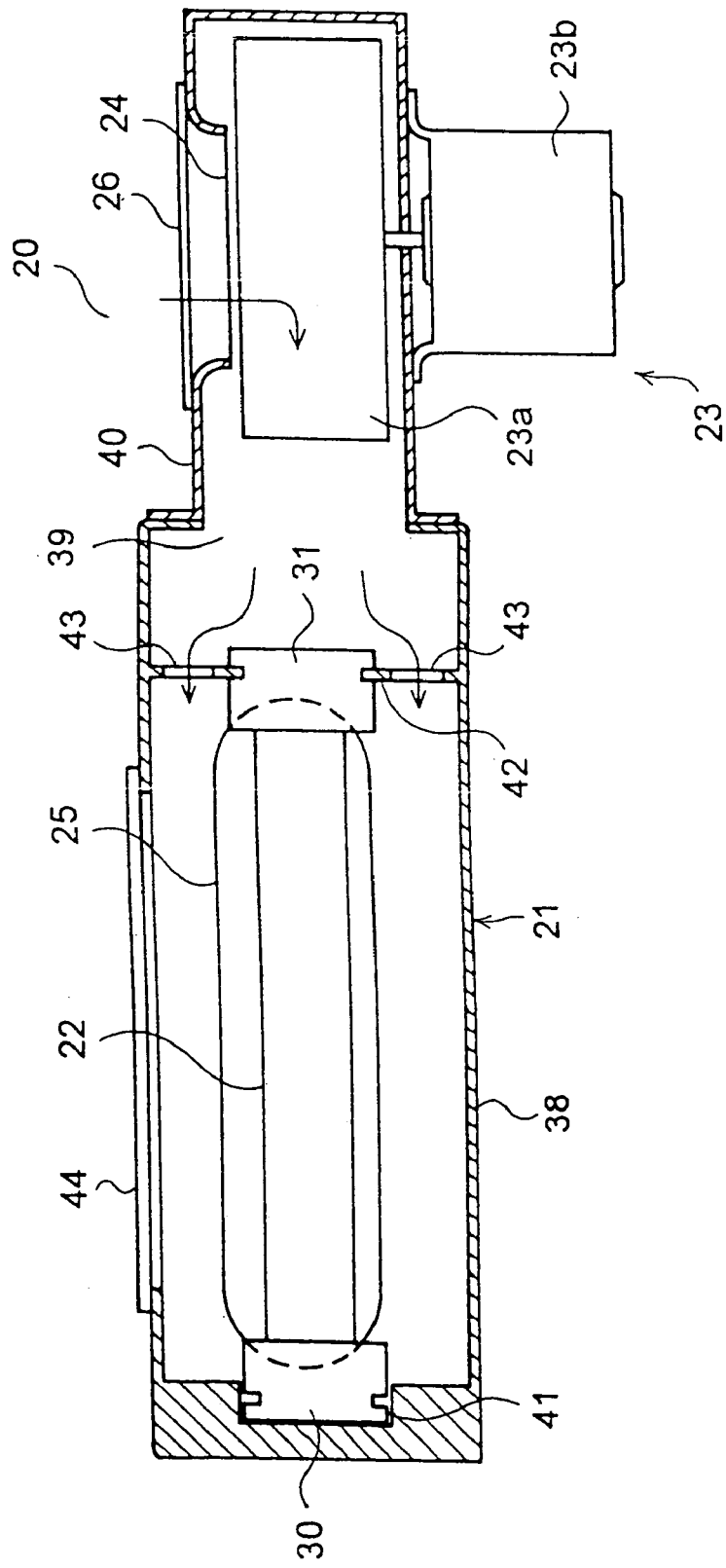
FIG. 3 is a sectional view showing the structure of a second embodiment of the ion generating device used in the invention, in which the ion generating device is built as a unit.

FIG. 3 shows an embodiment of the ion generating device of the invention that is built as a unit so as to be ready for incorporation in an air conditioning apparatus. The ion generating device unit 20 has an ion generating element 22 and a blower 23 held inside a unit case 21. The blower 23 is composed of a fan 23a and a motor 23b. The unit case 21 has an air inlet 24 formed so as to face the blower 23, and has an air outlet 25 formed so as to face the ion generating element 22. The air inlet 24 and the air outlet 25 are so formed that they are each perpendicular to the axis of the unit case 21 and that they are 90° apart from each other. The air inlet 24 is fitted with a filter 26. The filter 26 may be composed of a filter for filtering out dust and a deodorizing filter for absorbing odor-causing molecules combined together, or one of those filters used singly.

Figure 4:
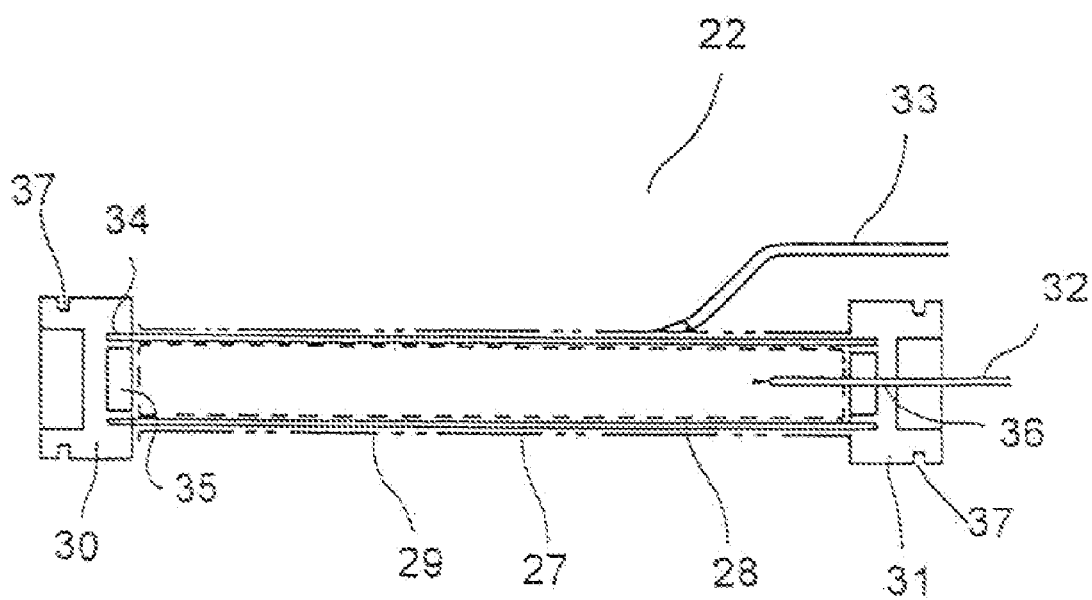
FIG. 4 is a sectional view showing the structure of the ion generating element, the principal component, of the ion generating device unit of the second embodiment.

As FIG. 4 shows, the ion generating element 22 includes a cylindrical dielectric 27, an inner electrode 28 fitted inside the dielectric 27, an outer electrode 29 fitted outside the dielectric 27 so as to face the inner electrode 28, and caps 30 and 31 made of an insulating material and fitted at each end of the dielectric 27.

The glass tube constituting the dielectric 27 has an external diameter of 10 mm and is open at both ends. The inner electrode 28 (high-voltage electrode) is formed out of a metal mesh having 40 meshes/inch and produced by plain-weaving wire of stainless steel (Japanese Industrial Standards SUS 316 or SUS 304). In predetermined positions on the inner and outer electrodes 28 and 29 are respectively welded leads 32 and 33 that are connected to a high-voltage circuit. The leads 32 and 33 each have a conductor of stainless steel covered with an insulating sheath of tetrafluoroethylene.

The caps 30 and 31 are molded out of chlorosulphonated ethylene or EP rubber. In the end surfaces of the caps 30 and 31 are respectively formed ring-shaped grooves 34 into which the end portions of the dielectric 27 are fitted. Moreover, in the end surfaces of the caps 30 and 31, recesses 35 are respectively formed so as to be surrounded by the grooves 34, and in the bottom surface of one of the recesses 35 is formed a hole 36 through which the lead 32 is laid. The hole 36 is covered with a thin film that is molded integrally with the caps 30 and 31, and this thin film is penetrated when the lead 32 is laid through the hole 36. In the peripheral surfaces of the caps 30 and 31 are respectively formed ring-shaped grooves 37 that permit the ion generating element 22 to be fitted to the unit case 21.

The ion generating element 22 is assembled in the following manner. First, the cylindrical inner electrode 28 having the lead 32 welded thereon is inserted into the dielectric 27. Then, the lead 32 is laid so as to penetrate the thin film portion of the recess 35 of the cap 31, and the cap 31 is fitted on one end of the dielectric 27. Next, the cylindrical outer electrode 29 having the lead 33 welded thereon is fitted outside the dielectric 27, and the cap 30 is fitted on the other end of the dielectric 27. Now, the ion generating element 22 is complete.

The unit case 21 is composed of an ion generating device casing 38, for housing the ion generating element 22, and a fan casing 40, for housing the fan of the blower 23, coupled integrally to a fitting opening 39 of the ion generating device casing 38, with screws or the like. Inside the ion generating device casing 38 are formed a recess 41 into which the cap 30 of the ion generating element 22 is fitted and a separation wall 42 that engages with and thereby supports the other cap 31. In the separation wall 42, ventilation openings 43 are formed.

The blower 23 is arranged in a predetermined orientation with respect to the axis of the ion generating element 22. The blower 23 takes in air through the air inlet 24, and passes the air through the fitting opening 39 and then through the ventilation openings 43 to the ion generating element 22. The air receives positive and negative ions around the ion generating element 22, and is then blown out of the unit case 21 through the air outlet 25.

The unit case 21 has a sight window 44 that permits the ion generating element 22 to be checked from the outside. The sight window 44 is covered with a cover made of a transparent synthetic resin.

When a high alternating-current voltage is applied between the inner and outer electrodes 28 and 29, plasma discharge occurs, generating positive ions consisting mainly of $H^+(H_2O)_n$ when the applied voltage is positive and negative ions consisting mainly of $O_2^-(H_2O)_m$ when the applied voltage is negative.

Figure 5:
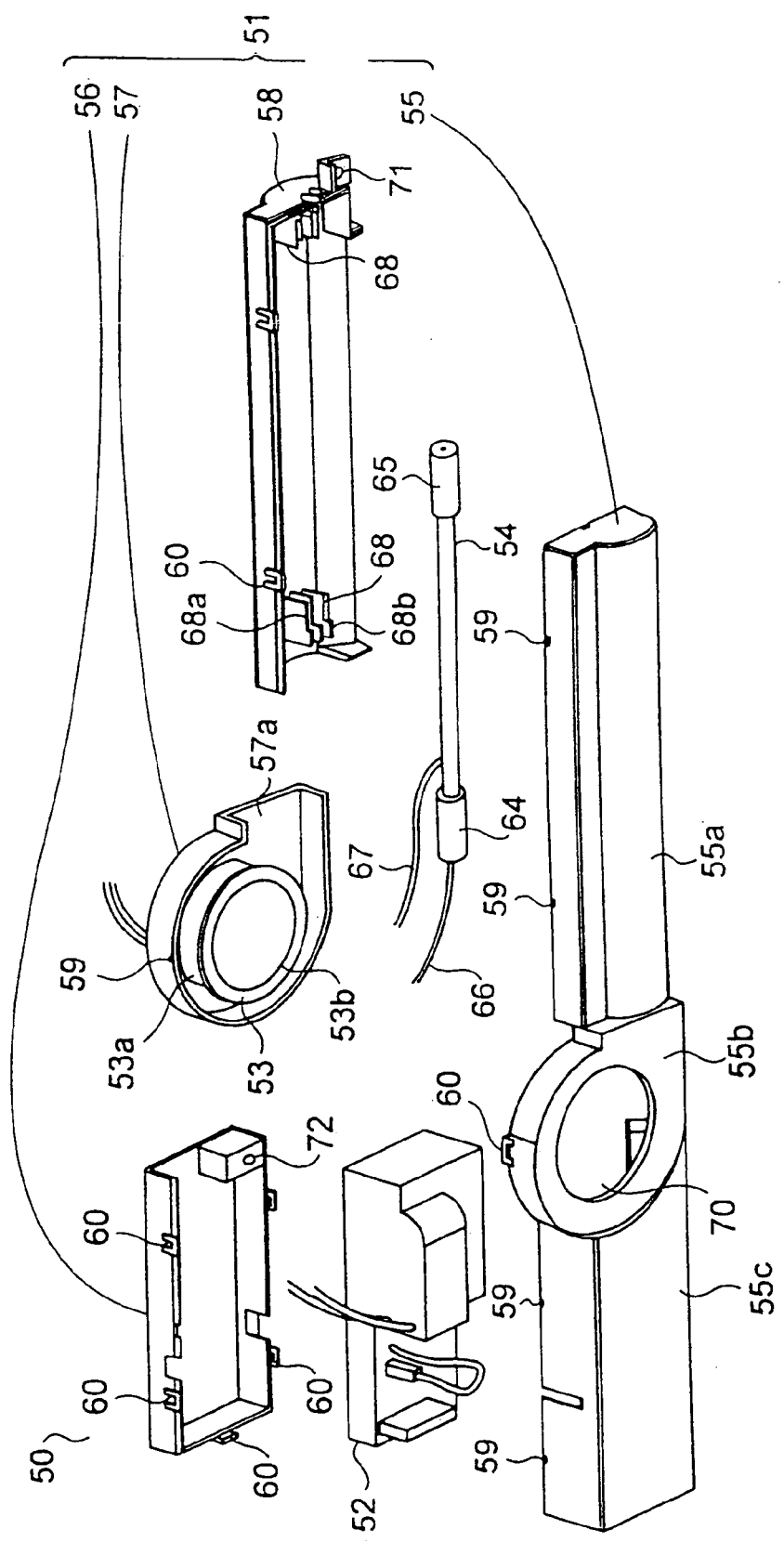
FIG. 5 is an exploded perspective view showing the structure of a third embedment of the ion generating device used in the invention, in which the ion generating device is built as a unit.

FIG. 5 is an exploded perspective view of an ion generating device unit 50. The ion generating device unit 50 is built as a unit, with a power supply 52, an ion blower 53, and an ion generating element 54 housed in a housing case 51. The housing case 51 is composed of a front cover 55 that covers the front side of the ion generating device unit 50, a power supply cover 56 that covers the rear side thereof, a fan case 57, and an electrode cover 58. These components are assembled together by engaging together projections 59 and claws 60 that are formed at their edges.

Figure 6:
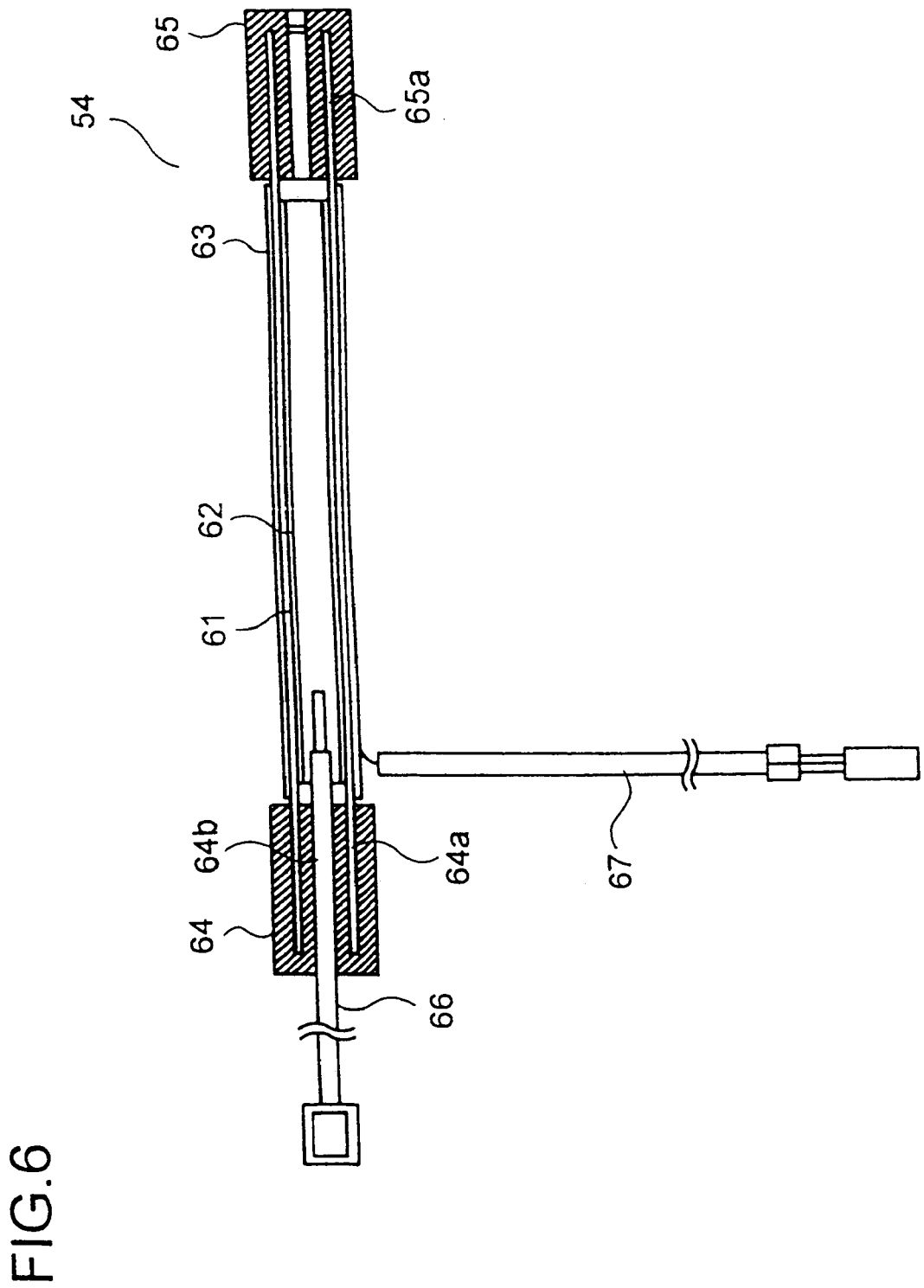
FIG. 6 is a sectional view of the ion generating element, the principal component, of the ion generating device unit of the third embodiment.

One end of the front cover 55 is formed into an electrode housing portion 55a, which together with the electrode cover 58 holds the ion generating element 54 that generates ions. As FIG. 6 shows, the ion generating element 54 has a cylindrical dielectric 61, an inner electrode 62 arranged along the inner surface of the dielectric 61, and an outer electrode 63 arranged along the outer surface of the dielectric 61. In this embodiment, as the dielectric 61, a glass tube having an external diameter of 10 mm is used. The inner electrode 62 is produced by rolling a sheet of stainless steel (Japanese Industrial Standards SUS 304), and the outer electrode 63 is produced by plain-weaving wire of stainless steel (Japanese Industrial Standards SUS 304 or SUS 316) into a metal mesh having 16 meshes/inch and then rolling this metal mesh. The outer electrode 63 is grounded.

On both ends of the dielectric 61 are fitted caps 64 and 65 made of an insulating material. The caps 64 and 65 have grooves 64a and 65a into which the end portions of the dielectric 61 are fitted. To the inner and outer electrodes 62 and 63 are respectively welded leads 66 and 67 that are connected to the power supply consisting of a high-voltage circuit. The lead 66 is laid through a through hole 64b formed substantially at the center of the cap 64.

As in the second embodiment, when a high alternating-current voltage is applied between the inner and outer electrodes 62 and 63, plasma discharge occurs, generating positive ions consisting mainly of $H^+(H_2O)_n$ when the applied voltage is positive and negative ions consisting mainly of $O_2^-(H_2O)_m$ when the applied voltage is negative.

Figure 8:
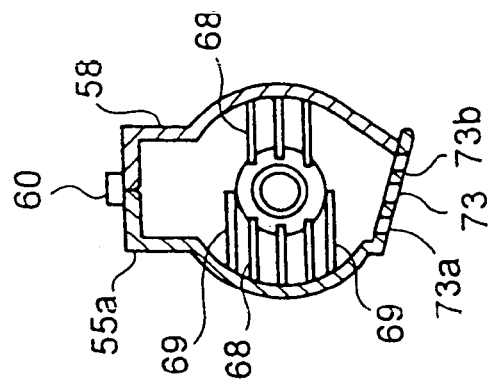
FIG. 8 is a sectional view showing a principal portion of the ion generating device unit of the third embodiment, taken along a different plane of section.
Figure 7:
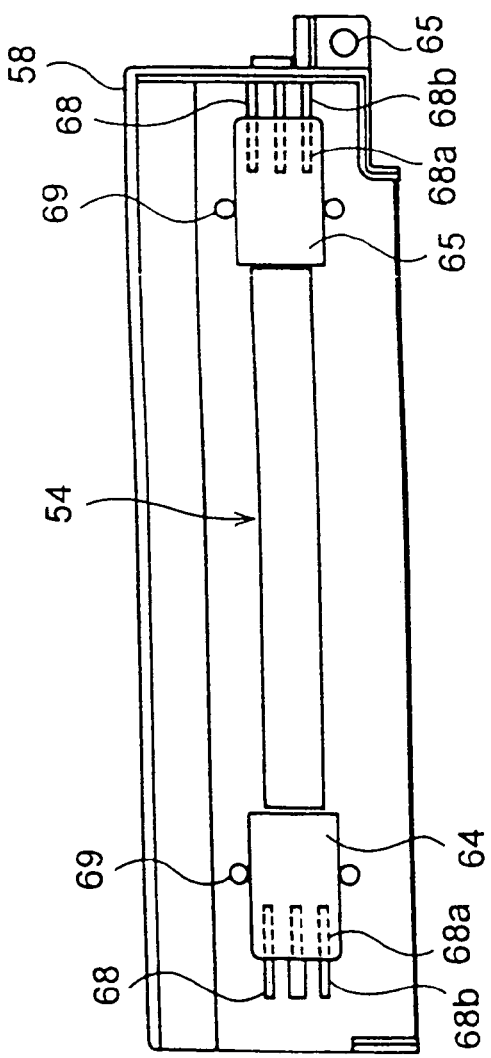
FIG. 7 is a sectional view showing a principal portion of the ion generating device unit of the third embodiment.

As FIGS. 7 and 8 show, on the inner surface of the electrode housing portion 55a of the front cover 55, and also on the inner surface of the electrode cover 58, three ribs 68 (an element support portion) are formed integrally therewith at each end. The ribs 68 are composed of R portions 68a and elevated portions 68b that are made higher than the R portions 68a (see FIG. 5). Of the three ribs 68, the R portions 68a make contact with the peripheral surface of the cap 64 or 65, and therefore the rib at the center is made lower than the ribs on both sides.

The elevated portions 68b keep the ion generating element 54 in position in the lateral direction of the figures. On the inner surface of the electrode housing portion 55a, bosses 69 are also formed integrally therewith. These bosses 69 keep the ion generating element 54 in position in the longitudinal direction of the figures. Moreover, the ribs 68 are arranged substantially parallel to the flow of air that is produced by the ion blower 53 (see FIG. 5) so as to flow substantially along the axis of the ion generating element 54. Thus, the ribs 68b serve to trim the flow of air and prevent the lowering of blowing efficiency without obstructing the flow of air so that ions are carried as far as possible.

The R portions 68a of the electrode housing portion 55a and of the electrode cover 58 hold the caps 64 and 65 between them, and thereby the ion generating element 54 is kept in position. This permits the ion generating element 54 to be kept in position easily without using screws. This helps simplify the assembly of the ion generating device unit 50 and thereby reduce the assembly steps.

Moreover, there is no need to form, in the ion generating element 54, screw holes or the like that are insulated from the inner and outer electrodes 62 and 63. This not only helps simplify the structure of the ion generating element 54 and thereby reduce costs, but also helps prevent poor isolation resulting from oxidation of screws or the like and thereby prevent short-circuiting or current leakage.

Moreover, the electrode housing portion 55a and the electrode cover 58 are so formed as to have a substantially arc-shaped cross section along the cross section of the ion generating element 54. This helps reduce generation of a vortex of air that flows around the ion generating element 54. It is thus possible to increase the blowing efficiency of the ion blower 54, and also to reduce the collision of ions with the wall surface and thereby reduce loss of ions.

In FIG. 5, in a substantially central portion of the front cover 55 is formed an air inlet portion 55b having an opening 70. The ion blower 53 is fitted to the fan case 57, and is covered by the fan case 57 and the air inlet portion 55b. The ion blower 53 is built as a so-called sirocco fan. Specifically, as a motor (not shown) provided at the bottom of an opening 53b formed at the center of the ion blower 53 is driven, an impeller 53a provided around the periphery of the ion blower 53 is rotated so that air is sucked in through the opening 53b and is blown out radially through the impeller 53a.

The inner walls of the fan case 57 and of the air inlet portion 55b are so formed that their cross section describe an involute curve, and thus the air blown out of the ion blower 53 is directed to a communicating opening 57a formed in the fan case 57. The opening 70 is formed so as to face the air inlet (not shown) of the air conditioning apparatus. Thus, the air taken in from outside the apparatus through the air inlet is introduced into the fan case 57 through the opening 70, and is then passed through the communicating opening 57a to the ion generating element 54 by the ion blower 53.

On the opposite side of the air inlet portion 55b of the front cover 55 to the electrode housing portion 55a, a power supply housing 55c is formed. In the power supply housing 55c, ribs (not shown) are formed at four corners so as to protrude inward, and the power supply 52 that applies a voltage to the ion generating element 54 is fitted on these ribs. A power supply cover 56 is fitted to the power supply housing 55c so as to cover and thereby hold the power supply 52. Preferably, the entire power supply 52 is shielded with a metal cover to reduce the adverse effects of the noise generated by the power supply 52.

The ion generating device unit 50 is assembled in the following manner. First, the fan case 57 with the ion blower 53 fitted thereto is fitted to the air inlet portion 55b of the front cover 55. Next, the power supply 52 is fitted in a predetermined position in the front cover 55, and the power supply cover 56 is fitted to the power supply housing 55c. Then, with the caps 64 and 65 of the ion generating element 54 placed on the ribs 68 formed in the electrode housing portion 55a of the front cover 55, the electrode cover 58 is fitted to the electrode housing portion 55a. In this way, the ion generating element 54, the ion blower 53, and the power supply 52 are arranged in a straight line.

Arranging the ion generating element 54 on one side of the ion blower 53 and the power supply 52 on the other side thereof makes it possible to widen the distance between the ion generating element 54 and the power supply 52. This helps reduce the adverse effects of the noise generated by the discharging of the ion generating element 54 on the circuit board (not shown) housed inside the power supply 52.

In the electrode cover 58 and the power supply cover 56 are respectively formed fitting holes 71 and 72 (see FIG. 5). These fitting holes 71 and 72 are used to fit the ion generating device unit 50 to the air conditioning apparatus.

As FIG. 8 shows, in the bottom surface of the electrode housing portion 55a, a discharge outlet 73 is formed. The discharge outlet 73 consists of a plurality of slits 73a formed by grid-like bars 73b.

Figure 9:
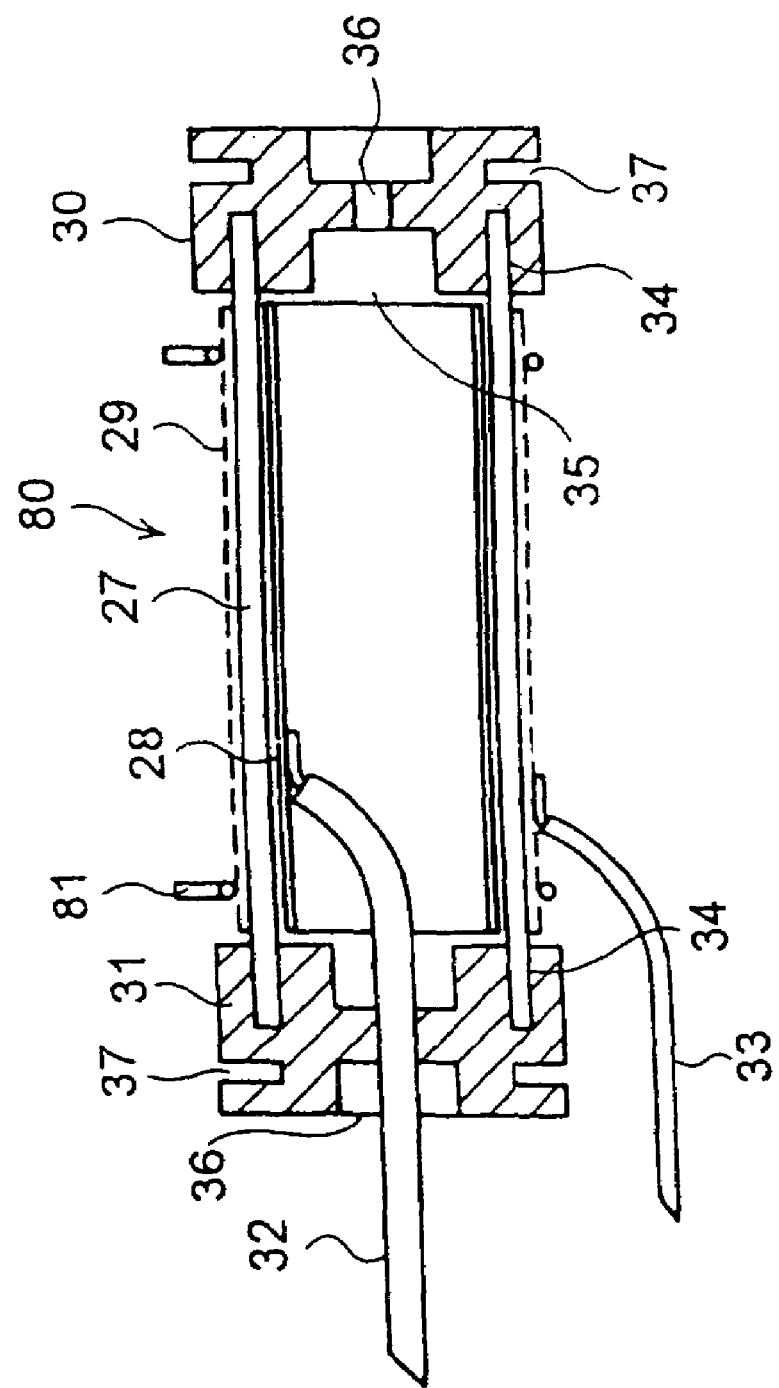
FIG. 9 is a sectional view showing the structure of the ion generating element, the principal component, of a fourth embodiment of the ion generating device used in the invention.

FIG. 9 shows a fourth embodiment of the ion generating device of the invention. The ion generating element 80 used in the ion generating device of the fourth embodiment has almost the same structure as the ion generating element 22 of the second embodiment. Therefore, in the following descriptions, such components as have already been described in connection with the ion generating element 22 are identified with the same reference numerals, and their explanations will not be repeated; that is, only features that are different from those already described or that have not yet been described will be explained.

Here, as the dielectric 27, a cylindrical glass tube having an external diameter of 20 mm and 1.6 mm thick is used. The length of this glass tube along its axis is, for example about 80 mm. The inner electrode 28 is produced by rolling a metal sheet of stainless steel (Japanese Industrial Standards SUS 304), and the outer electrode 29 is produced by plain-weaving wire of stainless steel (Japanese Industrial Standards SUS 304 or SUS 316) into a metal mesh having 16 meshes/inch and then rolling this metal mesh. It is to be noted that the mesh number given in "meshes/inch" denotes the number of holes found in a square area one inch along each side. Thus, the greater the mesh number, the finer the meshes. Moreover, to increase the capacitance involved and thereby increase the efficiency with which ions are generated, the inner and outer electrodes 28 and 29 are put in intimate contact with the glass tube. The outer electrode 29 is fixed to the dielectric 27 with bands 81 so that the inner and outer electrodes 28 and 29 are so arranged as to face each other with the dielectric sandwiched and a predetermined distance secured in between.

The lead 32 is held by being laid through the hole 36 formed substantially at the center of the cap 31. The point here is to achieve good insulation of the lead 32 to which a high voltage is applied. Moreover, to achieve a higher degree of insulation, the lead 32 is enclosed in a sheath made of a high insulation material.

Alternatively, it is also possible to use as the dielectric 27 a glass tube having an external diameter of 20 mm or less and 1.6 or less thick, use as the inner electrode 28 a metal mesh having 40 meshes/inch produced by plain-weaving wire of stainless steel (Japanese Industrial Standards SUS 316 or SUS 304), and use as the outer electrode 29 a metal mesh having 16 meshes/inch produced by plain-weaving wire of stainless steel (Japanese Industrial Standards SUS 316 or SUS 304).

When a high alternating-current voltage is applied between the inner and outer electrodes 28 and 29, plasma discharge occurs, generating positive ions consisting mainly of $H^+(H_2O)_n$ when the applied voltage is positive and negative ions consisting mainly of $O_2^-(H_2O)_m$ when the applied voltage is negative.

Here, for example, applying an alternating-current voltage of 1.8 kV (as measured at the peak of a half wave) having a frequency of 20 to 22 kHz results in generation of a suitable amount of positive and negative ions while keeping the amount of hazardous ozone generated together with opposite ions to a minimum.

It is to be understood, however, that the values specifically given above as the applied voltage and its frequency are merely an example, and that the optimum values vary according to the capacitance and other parameters that are determined by the shape, thickness, size, and other parameters of the dielectric and/or the electrodes of the ion generating device. Therefore, it is necessary to compare the amount of positive and negative ions generated with the amount of ozone generated under different conditions to obtain the optimum values that yield as large an amount of ions and as small an amount of ozone as possible.

It has been experimentally confirmed that certain concentrations of positive and negative ions are suitable to achieve the effect of killing airborne bacteria.

The relationship between the concentrations of opposite ions and the sterilizing effect is checked through experiments conducted in the following manner. In a room having a floor area corresponding to about three tatami mats, the ion generating device described specifically above is installed, and colon bacilli or fungi are sprayed. The opposite ions generated by the ion generating device are blown out of it by a blower with an air flow of 1 $m^3$/min. Using an air sampler, the air inside the room is collected, first, before the ion generating device and the blower start being operated (hereinafter referred to as "before operation") and, then, one hour after the ion generating device and the blower start being operated (hereinafter referred to as "after one-hour operation"). The air thus collected at different times is then each sprayed to a culture medium so that the bacteria attach to the culture medium. Thereafter, the bacteria are cultured, and the number of colonies formed by the fungi or colon bacilli thus cultured and grown is counted and compared between the air collected at one time and the other to calculate the sterilization rate. The amount of ions generated by the ion generating device is measured using an ion counter (for example, model 83-1001B manufactured by Dan Kagaku Co., Ltd., Japan) placed at a distance of 10 cm from the air outlet of the blower in the direction in which the blower blows out air containing ions.

Through experiments conducted as described above, it has been found that, when the concentrations of positive and negative ions are both about 30,000 ions/cc, the number of colonies after one-hour operation is 70% or more smaller than the number of colonies before operation, attesting that a satisfactory sterilizing effect is achieved.

It has also been found that, when the concentrations of positive and negative ions are both about 300,000 ions/cc, the number of colonies after one-hour operation is 93% or more smaller than the number of colonies before operation, attesting that a more powerful sterilizing effect is achieved.

The ion generating element 80 may be structured in any other manner than specifically described above: that is many modifications are possible in its structure, examples including: forming the dielectric 27 as a flat plate and arranging the first and second electrodes in intimate contact therewith so as to face each other; forming the first electrode, to which the voltage is applied, so as to have a pointed end (like a needle) and omitting the second electrode; forming the first electrode as a line and omitting the second electrode; etc. Even with a modified structure, as long as the ion generating element 80 generates both positive and negative ions, and is so operated as to yield concentrations of opposite ions of 10,000 ions/cc or more under the conditions for experiments conducted as described above, it is possible to achieve a satisfactory sterilizing effect. Moreover, with concentrations of opposite ions of 30,000 ions/cc or more, the higher the ion concentrations, the more powerful the sterilizing effect.

Next, embodiments of the air conditioning apparatus incorporating the ion generating device described above will be described.

Figure 10:
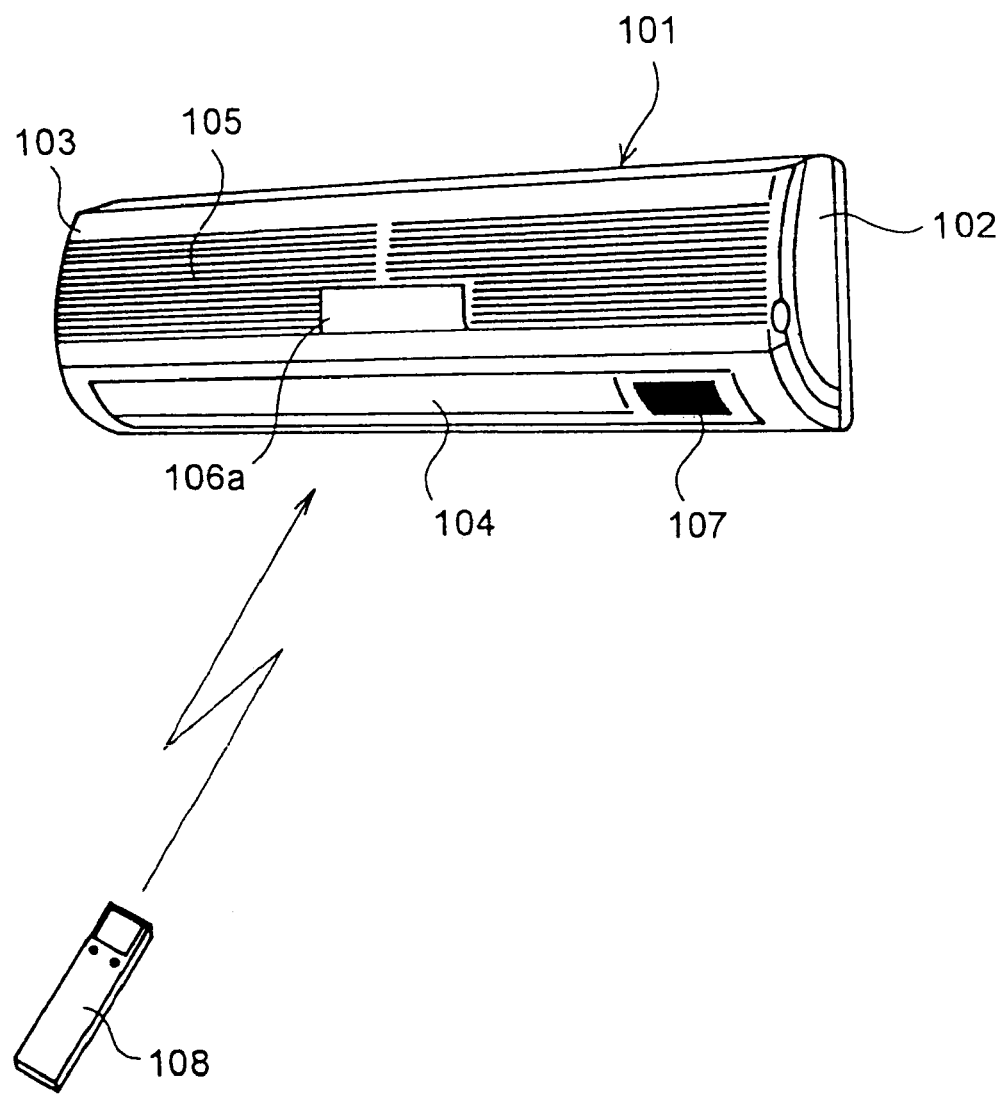
FIG. 10 is a perspective view of the indoor unit of an air conditioner as a first embodiment of the air conditioning apparatus of the invention.

FIGS. 10 to 16 show a first embodiment of the air conditioning apparatus of the invention. The air conditioning apparatus of this first embodiment is built as an air conditioner. FIG. 10 shows the indoor unit 101 of a separate-type air conditioner composed of an outdoor unit and an indoor unit. The indoor unit 101 incorporates a dehumidifying/humidifying device. The indoor unit 101 is provided with a body casing 102 having a heat exchanger, an indoor fan, and other components housed therein, a front panel 103 designed to be openable so that the inside of the body can be checked as when filters are checked for dirt, an air outlet 104 through which air having its temperature conditioned is blown out into the room, an air inlet 105 through which the air inside the room is taken in, a liquid crystal display device 106 on which the operation status is displayed, and a dehumidifying/humidifying outlet 107 through which dehumidified or humidified air from the dehumidifying/humidifying device is blown out. The indoor unit 101 is further provided with a remote control unit 108 that permits the operation of the air conditioner to be started and stopped and the operation mode thereof to be switched by remote control.

In the indoor unit 101, the body casing 102 has its front face covered with the front panel 103. In the front panel 103 is formed the air inlet 105, through which the air inside the room is taken in.

Figure 11:
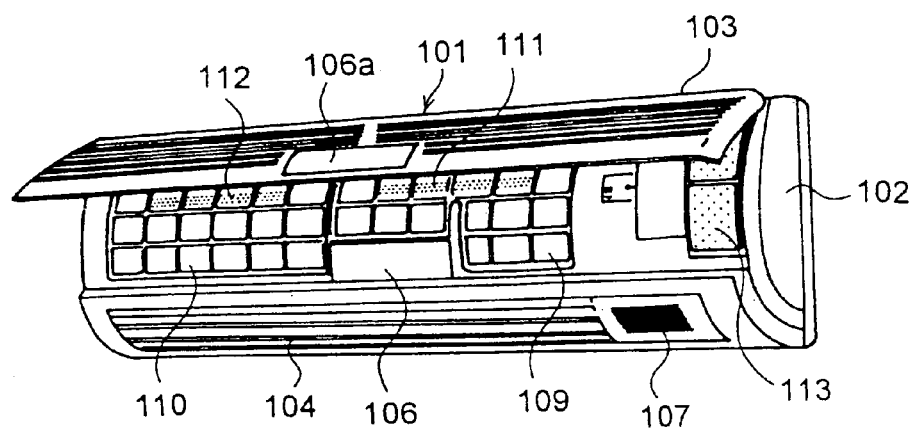
FIG. 11 is a perspective view of the indoor unit of the air conditioner of the first embodiment, with its front panel open.

Moreover, as FIG. 11 shows, the front panel 103 is openably supported on the body casing 102, and, in the body casing 102, a grid-like air inlet is formed so as to face the air inlet 105 formed in the front panel 103. In this air inlet, in the right-hand and left-hand portions thereof, filters 109 and 110 for filtering out the dust contained in the air taken in through the air inlet 105 are fitted respectively. The filters 109 and 110 are detachably fitted so that they can be detached and cleaned with the front panel 103 open. In substantially central portions of the filters 109 and 110, air purifying filters 111 and 112 are respectively fitted. In the right-hand end portion of the body casing 102 is formed a dehumidifying/humidifying inlet through which the air inside the room is taken in to be fed to the dehumidifying/humidifying device. In this dehumidifying/humidifying inlet, a dehumidifying/humidifying filter 113 is fitted.

Figure 12:
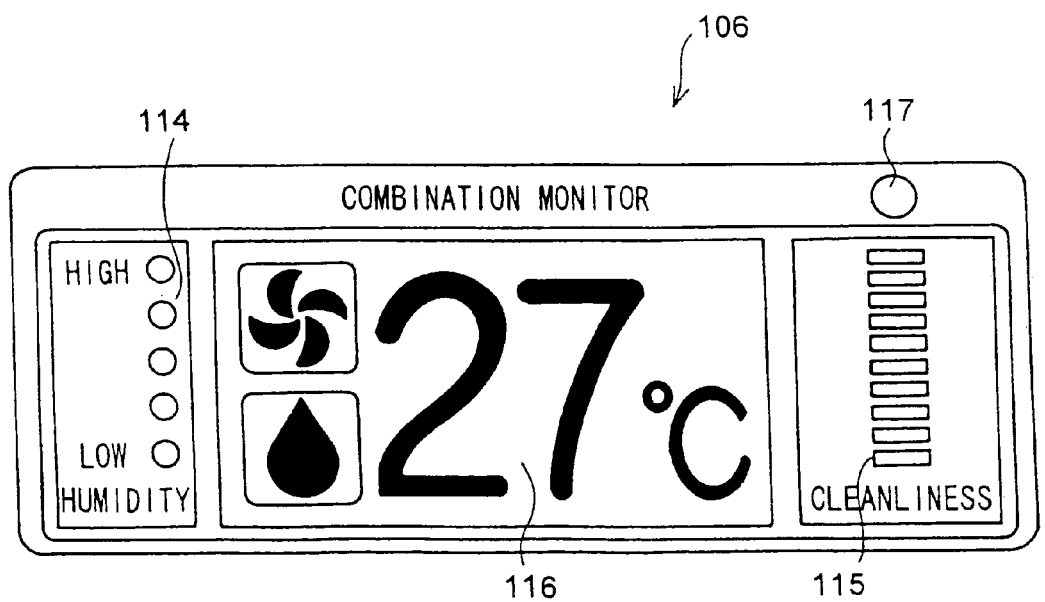
FIG. 12 is a front view of the liquid crystal display device portion of the indoor unit of the air conditioner of the first embodiment.

In a substantially central portion of the body casing 102, the liquid crystal display device 106 as shown in FIG. 12 is arranged. The filter 109 has a portion thereof cut out so as not to cover the liquid crystal display device 106. The liquid crystal display device 106 displays the operation status of the air conditioner, and can be viewed through a display window 106a provided in the front panel 103. The liquid crystal display device 106 is composed of a humidity lamp 114 that is lit according to the humidity inside the room, a purity lamp 115 that changes its color according to the degree of contamination of the air inside the room, a display portion 116 that displays the environmental conditions inside the room and the operation status according to the signals from the operation buttons of the remote control unit, and a light-sensing portion 117 that receives signals from the remote control unit.

Figure 13:
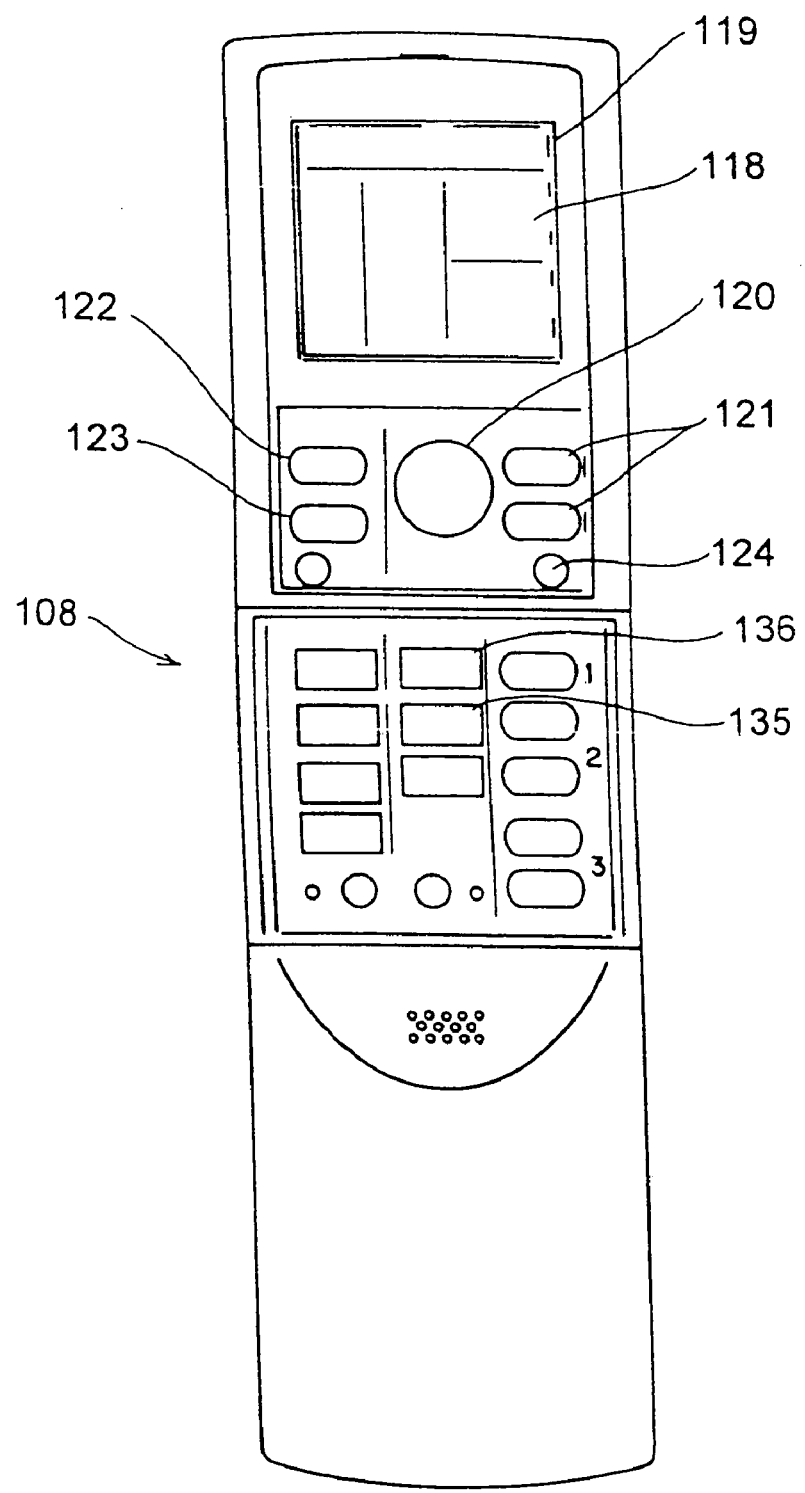
FIG. 13 is a front view of the remote control unit that comes along with the indoor unit of the air conditioner of the first embodiment.

As FIG. 13 shows, the remote control unit 108 is provided with a remote control unit display portion 118 that displays the operation status, a transmission display portion 119 that is lit when a signal is sent to the indoor unit 101, a start/stop switch 120 by which the operation of the air conditioner is turned on/off, a temperature switch 121 by which the temperature inside the room is set, a humidity switch 122 by which the dehumidifying operation of the dehumidifying/humidifying device is turned on/off, a ventilation switch 123 by which the ventilation operation of the dehumidifying/humidifying operation is turned on/off, a cluster switch 124 by which the ion generating device unit is turned on/off, and other components.

Figure 14:
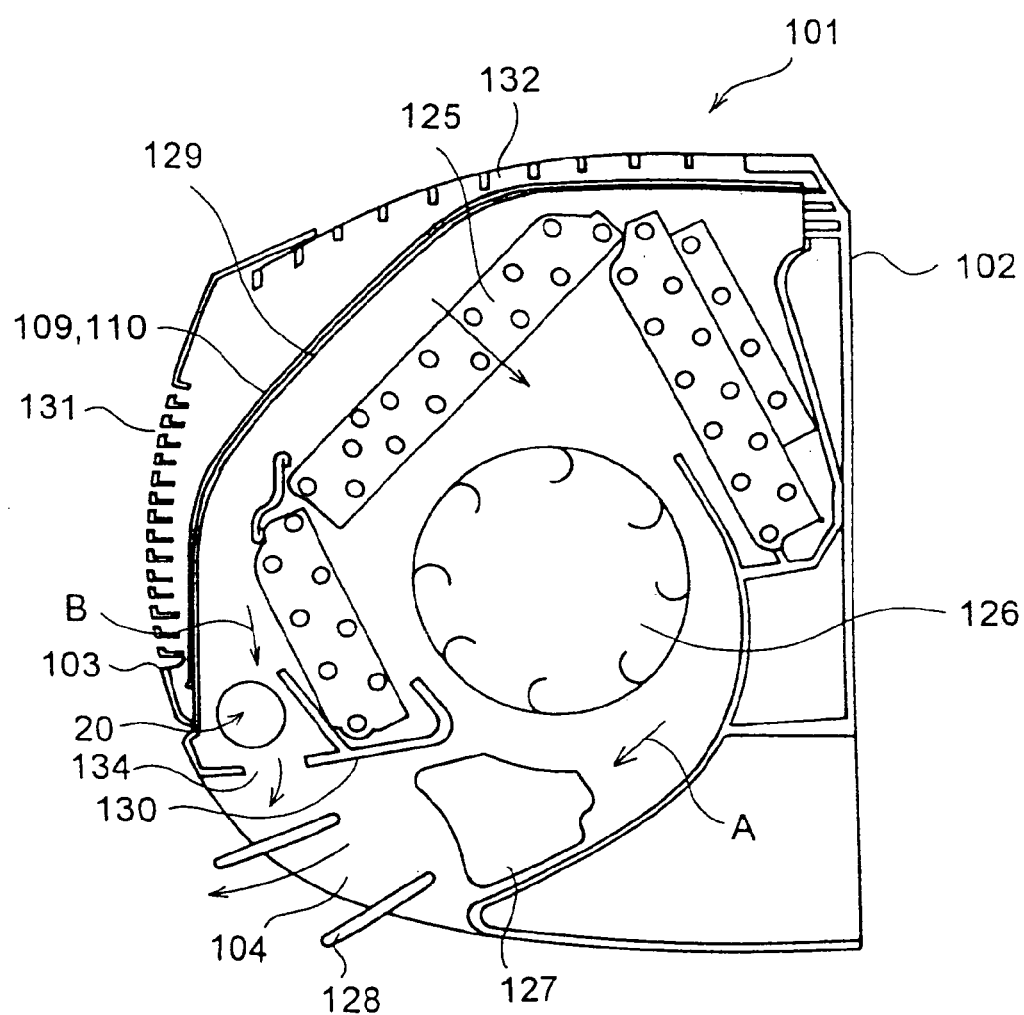
FIG. 14 is a sectional view of the indoor unit of the air conditioner of the first embodiment.

As FIG. 14 shows, inside the indoor unit 101 are arranged an indoor heat exchanger 125 that exchanges heat between a cooling medium circulating inside itself and the air inside the room fed externally thereto and an indoor fan 126 for blowing out the air that has undergone heat exchange in the heat exchanger 125. In the air outlet 104 formed in a lower portion of the front face of the body casing 102 are fitted a vertical louver 127 for changing the direction of the flow of air in the horizontal direction and a horizontal louver 128 for changing the direction of the flow of air in the vertical direction.

In the front face of the body casing 102, filter guides 129 are formed so that, with the front panel 103 open, the filters 109 and 110 can be fitted by being inserted along the filter guides 129. Below the indoor heat exchanger 125 is arranged a drain pan 130 that collects water drained when the air inside the room is cooled. The air inlet 105 is composed of a front inlet 131 formed so as to surround the display window 106a of the front panel 103 and an upper inlet 132 formed in the top surface of the body casing 102.

Thus, a circulation passage A is formed from the air inlet 105 to the filters 109 and 110, then through the indoor heat exchanger 125 to air outlet 104. Through this circulation passage A, the air inside the room taken in through the air inlet 105 is blown out back into the room, and is thereby circulated.

In the vicinity of the air outlet 104 of the body casing 102, the ion generating device unit 20 described under the section [A second embodiment of the ion generating device or the invention] is arranged. Through this ion generating device unit 20, an air flow passage B is formed separately from the circulation passage A. The air flow passage B is formed between the indoor heat exchanger 125 and the filters 109 and 110, and communicates with the circulation passage A through a confluence 134 in the vicinity of the air outlet 104 of the circulation passage A. Thus, the air that has entered through the air inlet 105 and passed through the filters 109 and 110 then, without passing through the indoor heat exchanger 125, directly passes through the ion generating device unit 20 and then flows into the circulation passage A through the confluence 134 located on the downstream side of the indoor heat exchanger 125 so as to be mixed with the air that has been passing through the circulation passage A and then blown out into the room. The reason that the ion generating device unit 20 is arranged in the air flow passage B that does not run through the indoor heat exchanger 125 is as follows. If the ion generating device unit 20 is arranged in the circulation passage A that runs through the indoor heat exchanger 125, it is cooled by cool air produced in cooling operation. As long as the ion generating device unit 20 is continuously receiving cool air, no problem arises. However, if the compressor stops, and air that is not cooled makes contact with the ion generating device unit 20, condensation forms thereon, lowering its ability to generate ions. To prevent this, the ion generating device unit 20 is arranged in the air flow passage B that does not run through the indoor heat exchanger 125. The ion generating device unit 20 is detachably fitted in a predetermined position within the air flow passage B with screws or the like.

Figure 15:
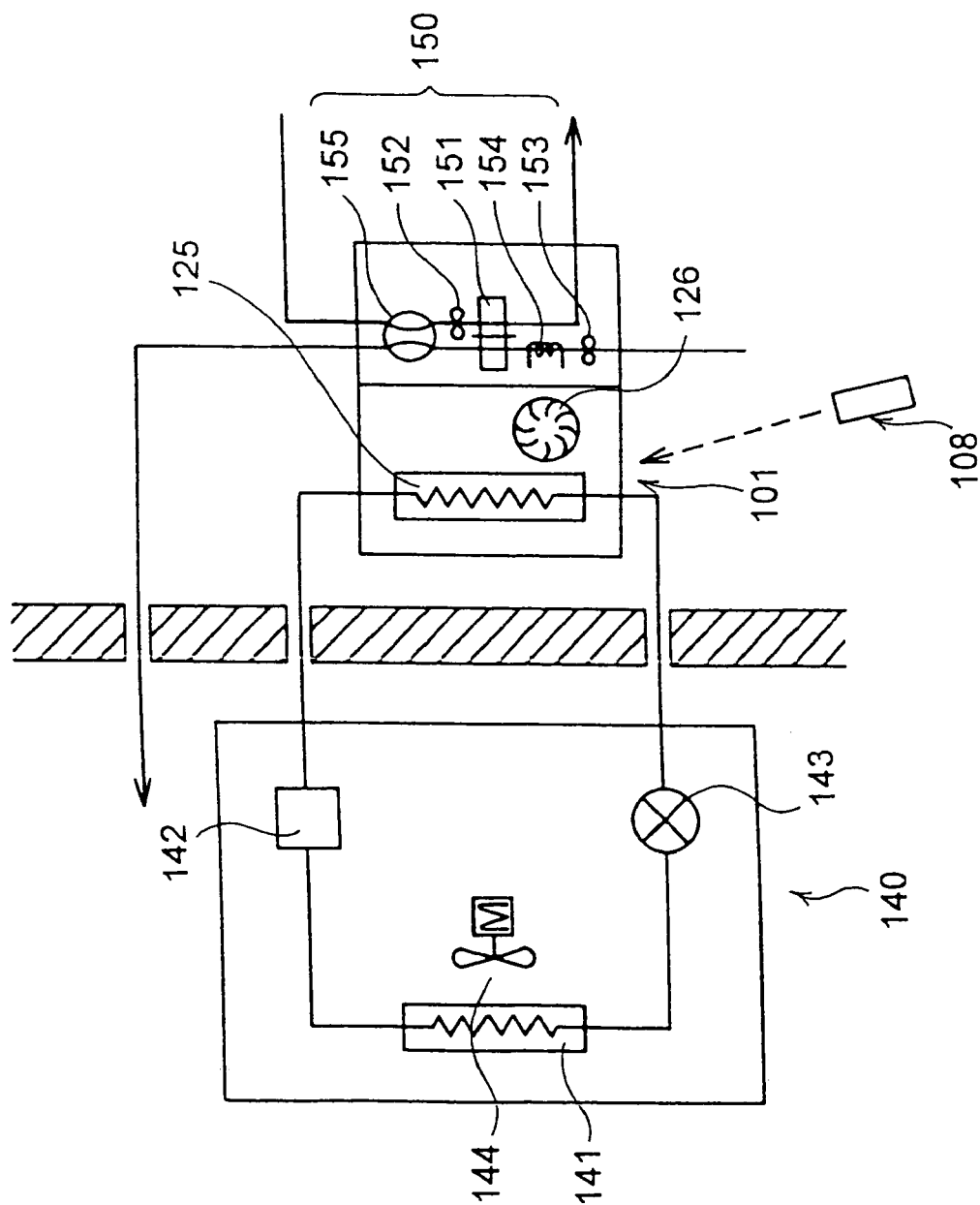
FIG. 15 is a diagram showing an outline of the overall configuration of the air conditioner of the first embodiment.

FIG. 15 shows the overall configuration of the separate-type air conditioner. Reference numeral 140 represents an outdoor unit, which is provided with an outdoor heat exchanger 141, a compressor 142, an expansion valve 143, and an outdoor fan 144. The indoor unit 101 incorporates a dehumidifying/humidifying device 150. The dehumidifying/humidifying device 150 is composed of a moisture-absorbing rotor 151 that absorbs and then releases moisture inside the room, a dehumidifying fan 152 that sucks in the air inside the room, a drier fan 153 that passes drying air to the moisture-absorbing rotor 151, a drier heater 154 that heats the drying air that is passed to the moisture-absorbing rotor 151, and a damper 155 that switches flow paths.

Next, the operation of the air conditioner described above will be described. The air conditioner is operated from the remote control unit 108. Every time the operation mode selection switch 136 on the control panel of the remote control unit 108 is pressed, the operation mode switches from "automatic" to "heating" to "cooling" to "automatic," and so forth, and the corresponding indications appear on the remote control unit display portion 118, permitting selection of a desired operation mode.

Figure 16:
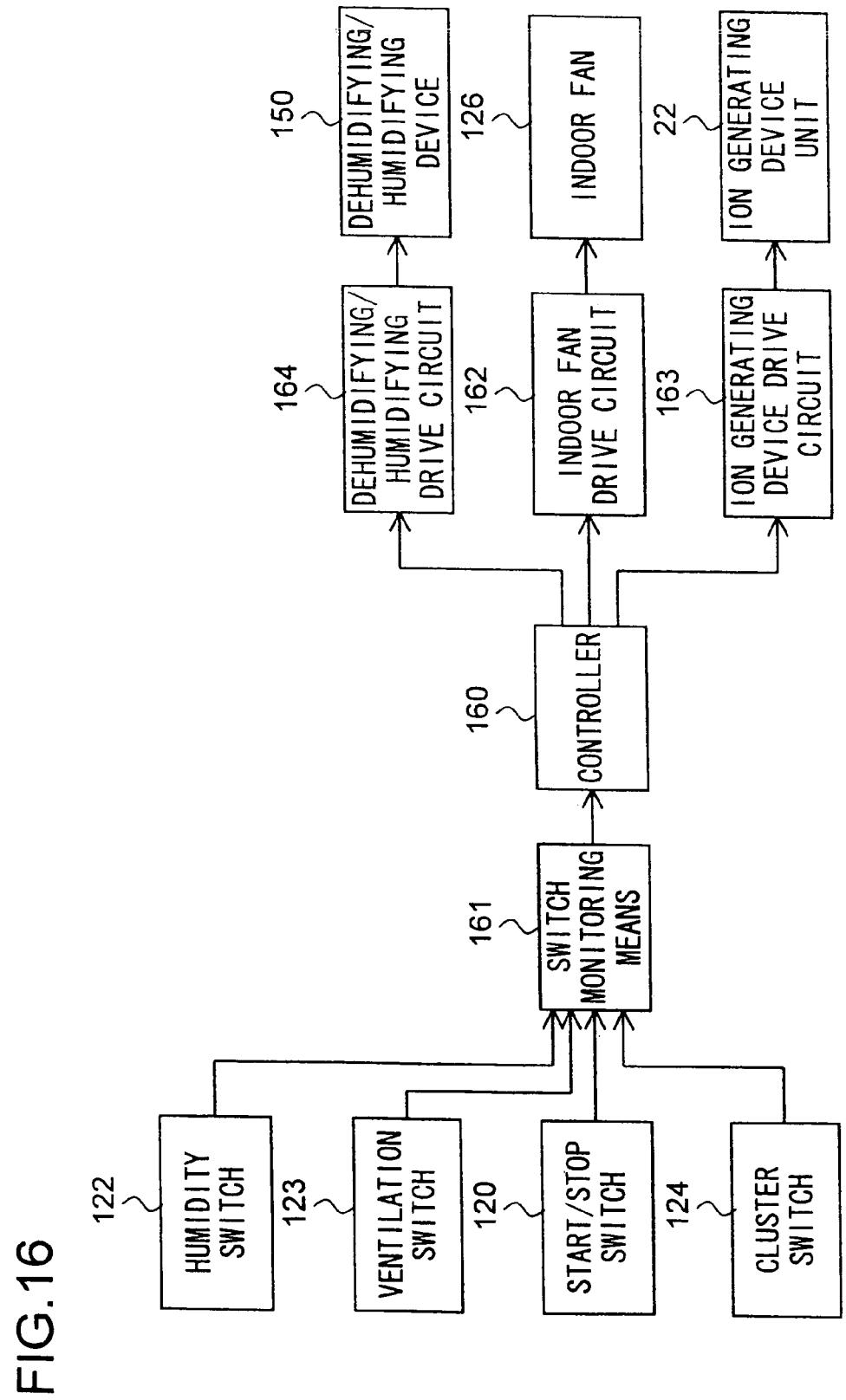
FIG. 16 is a control block diagram of the indoor unit of the air conditioner of the first embodiment.

The signals transmitted from the remote control unit 108 are received by the light-sensing portion 117 of the indoor unit 101. The indoor unit 101 incorporates a control system. As FIG. 16 shows, the control system is provided with a controller 160 including a CPU, a memory, and other components, a switch monitoring means 161, an indoor fan drive circuit 162, an ion generating device drive circuit 163, and a dehumidifying/humidifying device drive circuit 164. The control system activates the individual circuit blocks thereof according to the signals from the remote control unit 108.

When the start/stop switch 120 is pressed, the operation mode, target temperature, and indoor temperature are indicated one after another on the liquid crystal display device 106 of the indoor unit 101. During operation, the indoor temperature is kept indicated. To stop the operation, the start/stop switch 120 is pressed. This causes the indication on the liquid crystal display device 106 to go out and the operation to stop. To change the temperature, for example to raise the temperature by 1° C., the "Δ" switch of the temperature switch 121 is pressed once. This raises the target temperature by 1° C., and, in the heating or cooling operation mode, the target temperature is indicated on the remote control unit display portion 118 and on the liquid crystal display device 106. On the other hand, in the automatic or drying operation mode, the value by which the temperature is to be raised is indicated on the remote control unit display portion 118, and the target temperature is indicated on the liquid crystal display device 106. Here, the indication of the target temperature on the liquid crystal display device 106 switches back to the indication of the indoor temperature after about four seconds. To change the volume of air, every time an air volume switch 135 is pressed, the air volume is changed so that the indication on the remote control unit display portion 118 changes from "air volume auto" to "air volume Δ" to "air volume Δ Δ" to "air volume Δ Δ Δ" to "air volume auto," and so forth, and the indication on the liquid crystal display device 106 changes from "air volume auto" to "gentle wind" to "moderate wind" to "strong wind," to "air volume auto," and so forth.

In this way, the desired operation mode is selected. In the cooling operation mode, the cooling medium condensed and thereby brought into a high-temperature state by the compressor 142 is passed to the outdoor heat exchanger 141 of the outdoor unit 140. In the outdoor heat exchanger 141, the outdoor fan 144 passes outdoor air to the outdoor heat exchanger 141, which thus takes away heat from the cooling medium and thereby cools and liquefies it. The cooling medium is then passed through the expansion valve 143 to the indoor heat exchanger 125, where the cooling medium evaporates and thereby cools the indoor heat exchanger 125. The air inside the room sucked in by the indoor fan 126 into the body casing 102 is passed through the indoor heat exchanger 125, which takes heat away from the air. In this way, the air inside the room is cooled and circulated, and as a result the room is cooled.

In the heating operation mode, the cooling medium is circulated in the opposite direction to the direction in which it is circulated in the cooling operation mode. Specifically, the condensed cooling medium is passed to the indoor heat exchanger 125, and the air inside the room is passed through the indoor heat exchanger 125 and is thereby heated, so that the room is heated. The cooling medium is passed through the expansion valve 143 to the outdoor heat exchanger 141, where the cooling medium evaporates and thereby cools the outdoor heat exchanger 141. The heat of the cooling medium is exchanged with that of the outdoor air passed to the outdoor heat exchanger 141 by the outdoor fan 144, so that the cooling medium takes away heat from the outdoor air. After raising the temperature inside the room in this way, the cooling medium returns to the compressor 142.

The air inside the room is sucked in by the indoor fan 126 through the inlet 131 of the front panel 103 of the indoor unit 101 and through the inlet 132 of the body casing 102, and is then passed through the filters 9 and 10 to the indoor heat exchanger 125. The air inside the room is passed to the entire surface of the indoor heat exchanger 125 to achieve satisfactory heat exchange efficiency. The air that has passed through the indoor heat exchanger 125 is blown out through the air outlet 104.

When the air conditioner starts being operated, simultaneously a high alternating-current voltage is applied to the ion generating device unit 20 so that it starts generating positive and negative ions as described earlier.

Part of the air that has been sucked in through the inlet 131 and passed through the filters 109 and 110 enters the air flow passage B so as to be sucked into the ion generating device unit 20. As the air is sucked into the ion generating device unit 20, the dust and odor-causing molecules contained therein are removed by the filter 26. The air then receives the positive and negative ions generated by the ion generating element 22, and is then blown out through the air outlet 25. The air blown out of the ion generating device unit 20 is then passed through the air flow passage B to the confluence 134, where it is mixed with the air that has been passing through the circulation passage A and thus has undergone heat exchange. The mixed air is blown out through the air outlet 104 so as to be spread all around the room.

Through the chemical reaction described earlier, the positive and negative ions generated by the ion generating element 22 generate hydrogen peroxide $H_2O_2$ or radical hydroxyl .OH as a radical, of which the strong activity kills airborne bacteria. In three hours after the air conditioner incorporating the ion generating device unit 20 starts being operated, it was possible to remove 83% of the common bacteria and 88% of the fungi that had been present in the air.

The ion generating device unit 20 can be operated singly when the air conditioner is not operating. When the cluster switch 124 of the remote control unit 108 is turned to the "on" position, a high alternating-current voltage is applied to the ion generating device unit 20, and the indoor fan 126 of the indoor unit 101 is also energized. When the indoor fan 126 starts rotating, a flow of air is produced in the air flow passage B, and with this flow of air is mixed the positive and negative ions generated by the ion generating element 22. The air containing ions joins, through the confluence 134, the flow of air that has been passing through the circulation passage A (and thus has not undergone heat exchange) and is then blown out through the air outlet 104 into the room. This makes it possible to discharge ions and kill airborne bacteria irrespective of whether air-conditioning operation is being performed or not, increasing the added value of the air conditioner.

Furthermore, the indoor unit 101 can drive the dehumidifying/humidifying device 150 to dehumidify or humidify the air inside the room. Accordingly, the ion generating device unit 20 is so controlled that it is operated simultaneously when the dehumidifying/humidifying device 150 is driven. When the humidity switch 122 or the ventilation switch 123 of the remote control unit 108 is turned to the "on" position, a high alternating-current voltage is applied to the ion generating device unit 20, and the indoor fan 126 is also energized. As a result, air containing positive and negative ions is blown out through the air outlet 104, and simultaneously air having its humidity conditioned is blown out through the dehumidifying/humidifying outlet 107. This brings about a comfortable environment free from airborne bacteria.

Figure 17:
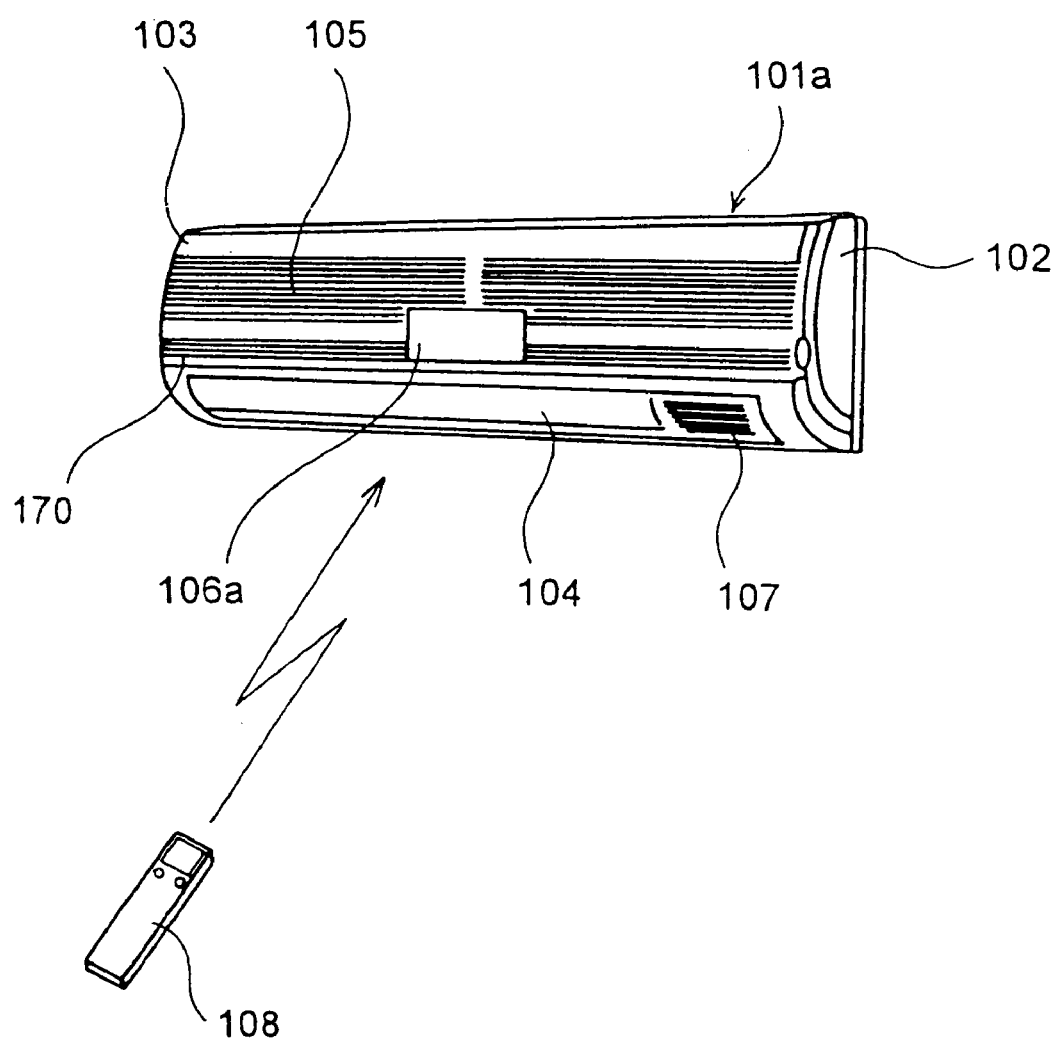
FIG. 17 is a perspective view of the indoor unit of an air conditioner as a second embodiment of the air conditioning apparatus of the invention.
Figure 18:
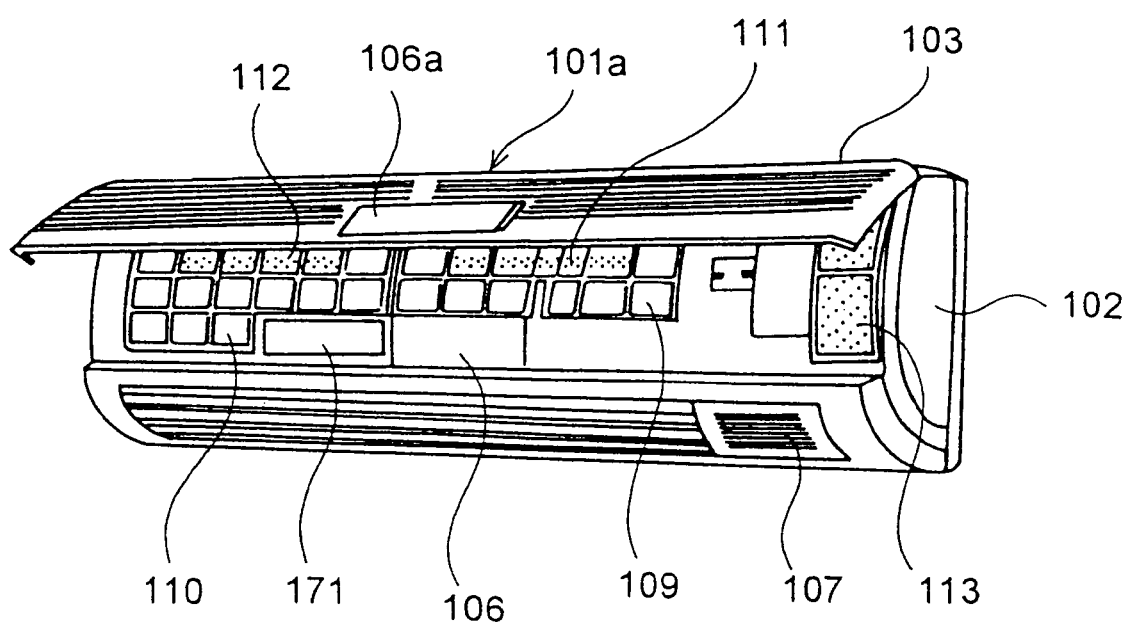
FIG. 18 is a perspective view of the indoor unit of the air conditioner of the second embodiment, with its front panel open.
Figure 19:
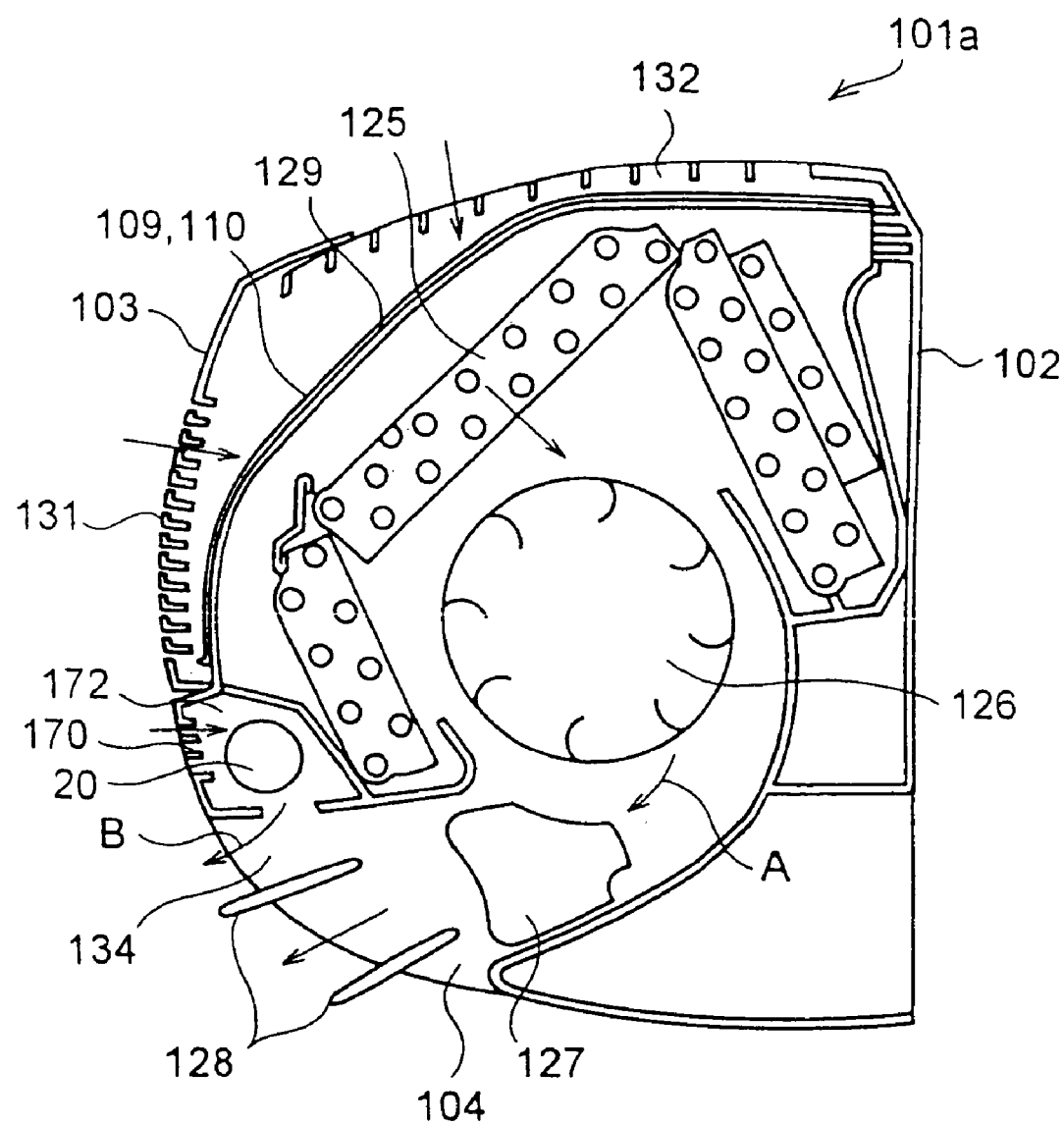
FIG. 19 is a sectional view of the indoor unit of the air conditioner of the second embodiment.

FIGS. 17 to 19 show a second embodiment of the air conditioning apparatus of the invention. The embodiments starting with this second embodiment and ending with the fifteenth embodiment all deal with separate-type air conditioners that have much in common in their construction. Therefore, in the following descriptions, such components as are common to the first embodiment are identified with the same reference numerals as those used for the first embodiment, and their explanations will not be repeated; that is, only features that are different from those already described will be explained.

In the indoor unit 101a of the air conditioner of the second embodiment, the air flow passage B for the ion generating device unit 20 is formed separately from the circulation passage A, and the two passages A and B share only the air outlet 104. In other respects, the construction here is the same as in the first embodiment.

Specifically, in the front panel 103 of the indoor unit 101a, an ion air inlet 170 is formed through which air is sucked in so as to be fed to the ion generating device unit 20. Correspondingly, an ion air inlet 171 is formed also in the body casing 102 so as to face the ion air inlet 170. Moreover, as FIG. 19 shows, below the filters 109 and 110 and the indoor heat exchanger 125 housed inside the body casing 102, a space 172 is secured that is separated from the upstream side of the circulation passage A. This space 172 communicates, through the confluence 134 located in the vicinity of the air outlet 104, with the downstream side of the circulation passage A. The ion generating device unit 20 is arranged in the space 172, and thus an air flow passage B is formed from the ion air inlet 170 through the confluence 134 to the air outlet 104.

When the ion generating device unit 20 is operated singly, its operation is started by turning to the "on" position a switch for turning on/off the operation of the ion generating device unit that is provide separately from the switch for turning on/off the operation of the air conditioner. The blower 23 of the ion generating device unit 20 sucks in the air inside the room through the ion air inlet 170. The air is then passed through the filter 26 so that the dust and odor-causing molecules contained therein are removed. The air then receives the ions generated by the ion generating element 22, and then passes through the confluence 134 so as to be blown out through the air outlet 104 into the room. By operating the ion generating device unit singly in this way, it is possible to reduce not only electric power consumption but also noise. The indoor fan 126 may be activated in concert with the operation of the ion generating device unit 20.

Figure 20:
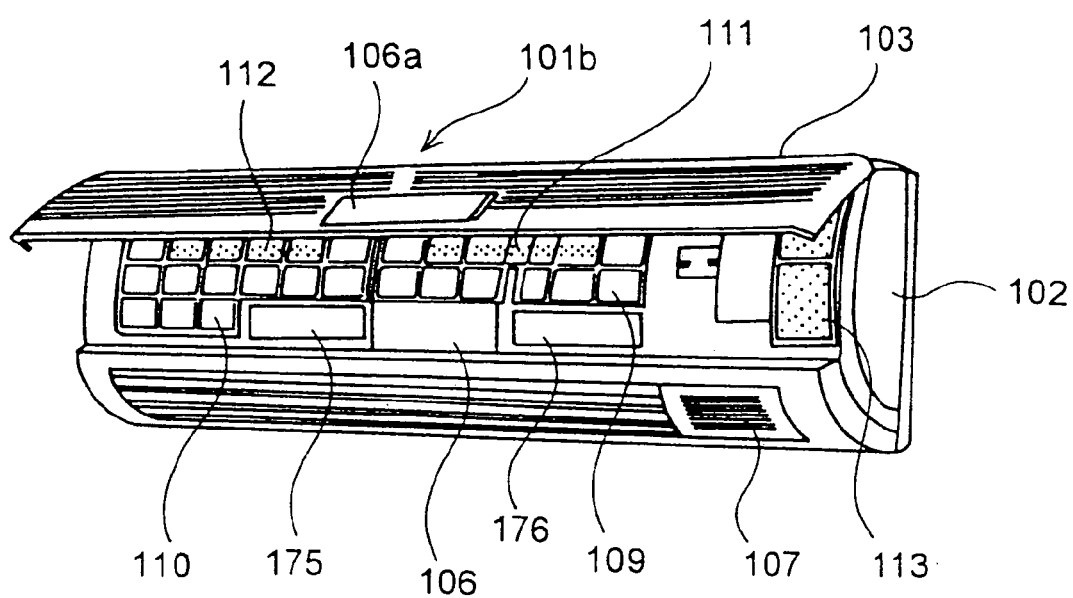
FIG. 20 is a perspective view of the indoor unit of an air conditioner as a third embodiment of the air conditioning apparatus of the invention.
Figure 21:
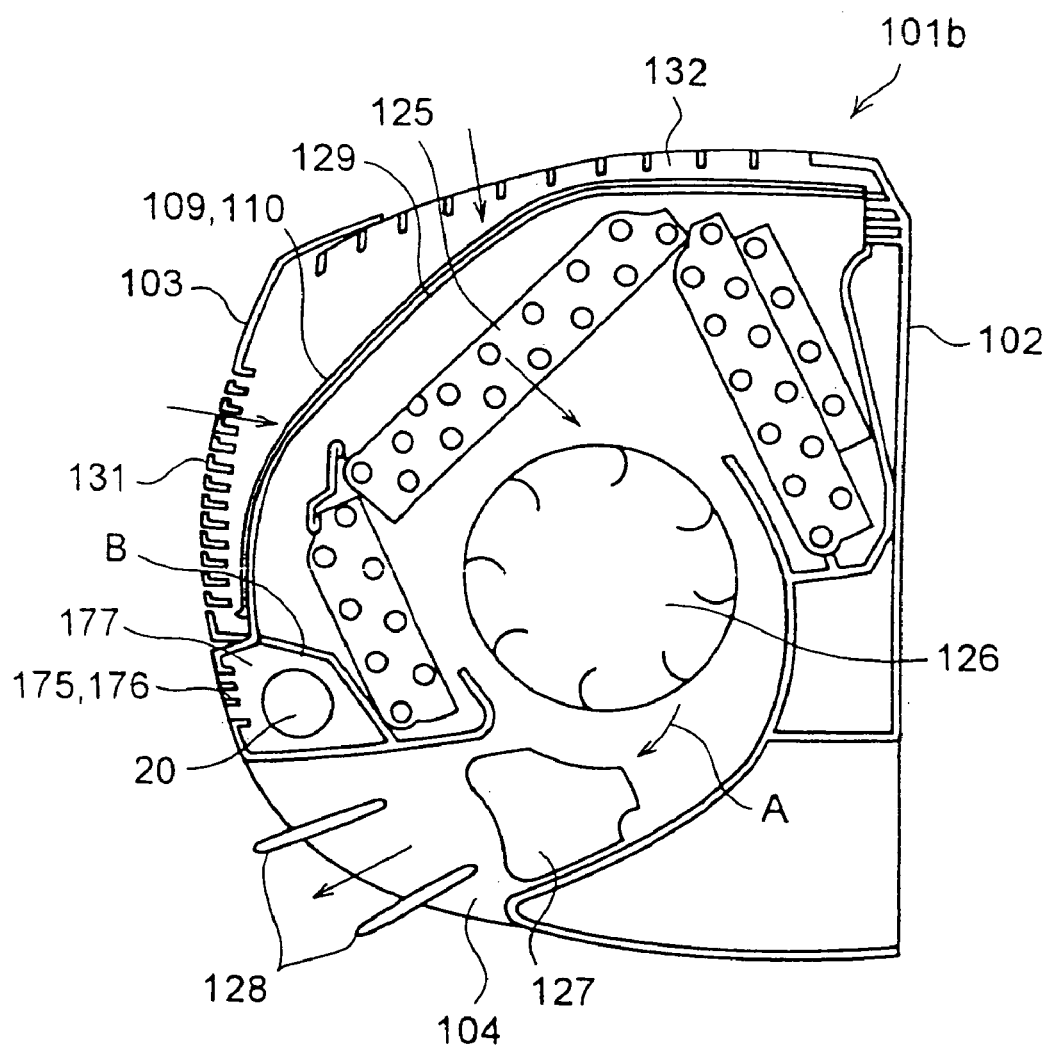
FIG. 21 is a sectional view of the indoor unit of the air conditioner of the third embodiment.

FIGS. 20 and 21 show a third embodiment of the air conditioning apparatus of the invention. In the indoor unit 101b of the air conditioner of the third embodiment, the air flow passage B in which the ion generating device unit 20 is arranged is completely separated from the circulation passage A. In other respects, the construction here is the same as in the first embodiment.

Specifically, as FIG. 20 shows, an air inlet 175 and an air outlet 176 for the ion generating device are formed respectively on both sides of the liquid crystal display device 106 of the body casing 102. Moreover, as FIG. 21 shows, below the filters 109 and 110 and the indoor heat exchanger 125 housed inside the body casing 102, a space 177 is secured that is completely separated from the circulation passage A, so that an air flow passage B is formed through which the air inlet 175 and an air outlet 176 communicate with each other.

Also in this construction, the air containing positive and negative ions is blown out through the air outlet 176 into the room by the action of the blower 23. Simultaneously, the air that has passed through the indoor heat exchanger 125 is also blown out through the air outlet 104 by the action of the indoor fan 126. In this way, even though the air flow passage B and the circulation passage A have separate air outlets, the air that has passed through one passage eventually joins the air that has passed through the other, and thus the air that is blown out of the indoor unit 101b contains positive and negative ions. Moreover, by operating the ion generating device unit singly, it is possible to reduce not only electric power consumption but also noise.

Figure 22:
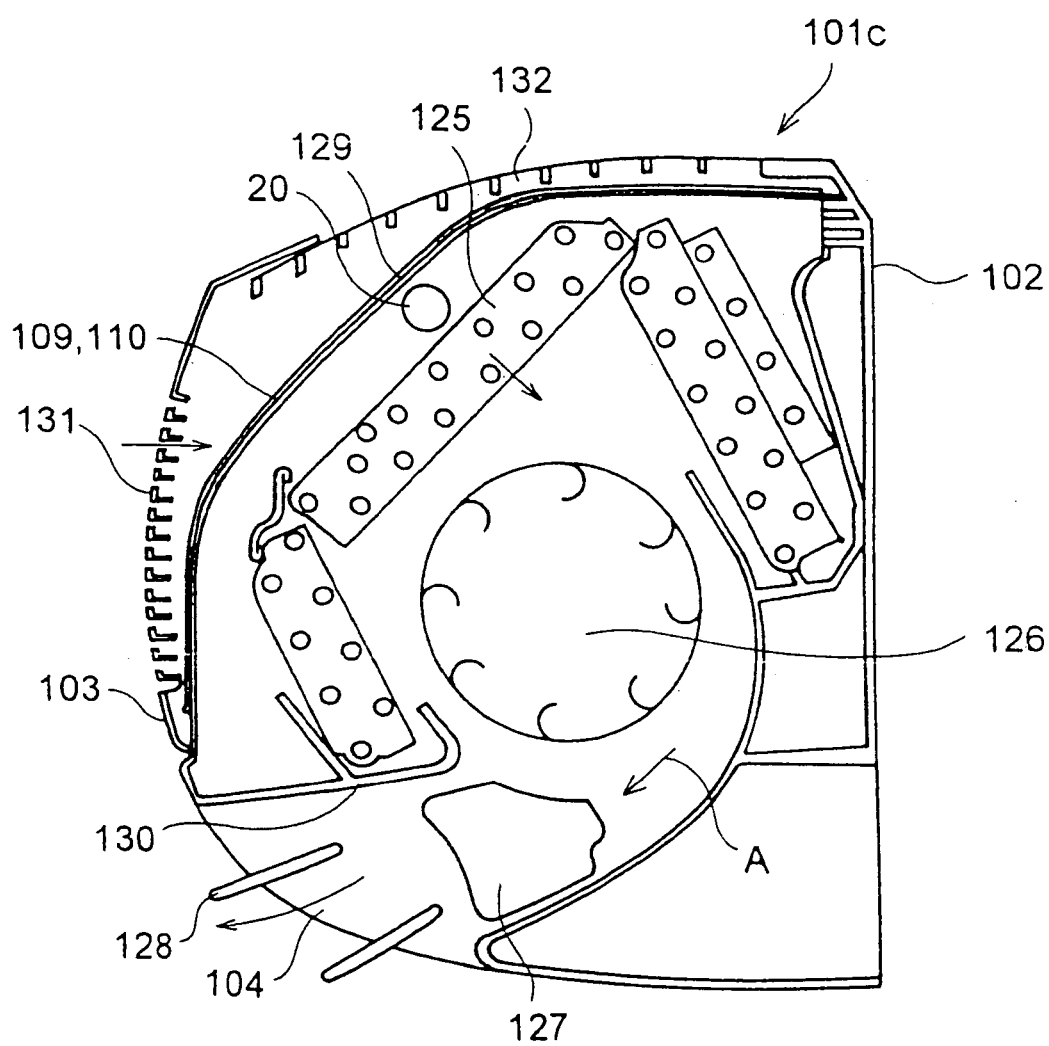
FIG. 22 is a sectional view of the indoor unit of an air conditioner as a fourth embodiment of the air conditioning apparatus of the invention.

FIG. 22 shows a fourth embodiment of the air conditioning apparatus of the invention. In the indoor unit 101c of the air conditioner of the fourth embodiment, the ion generating device unit 20 is arranged on the upstream side of the indoor heat exchanger 125. Specifically, the ion generating device unit 20 is arranged between the filters 109 and 110 and the indoor heat exchanger 125 within the circulation passage A. This makes the air flow passage B identical with the circulation passage A. In other respects, the construction here is the same as in the first embodiment.

The air inside the room sucked in through the inlets 131 and 132 is then passed through the filters 109 and 110 so that the dust and the like contained therein are removed, and is then sucked into the ion generating device unit 20. The air thus sucked in then receives the positive and negative ions generated by the ion generating element 22, and is then blown out of the ion generating device unit 20. Thereafter, the air, by being carried by the flow of air that has been passing through the circulation passage A, passes through the indoor heat exchanger 125 and is then blown out through the air outlet 104 into the room.

While the air containing positive and negative ions is passing through the indoor heat exchanger 125 and through the circulation passage A, it exerts a sterilizing effect on airborne bacteria and kills them. Thus, the air blown out through the air outlet 104 into the room is almost free from airborne bacteria and clean. Moreover, the air exerts a sterilizing effect also on airborne bacteria floating in the air inside the room, achieving a higher sterilizing effect.

Figure 23:
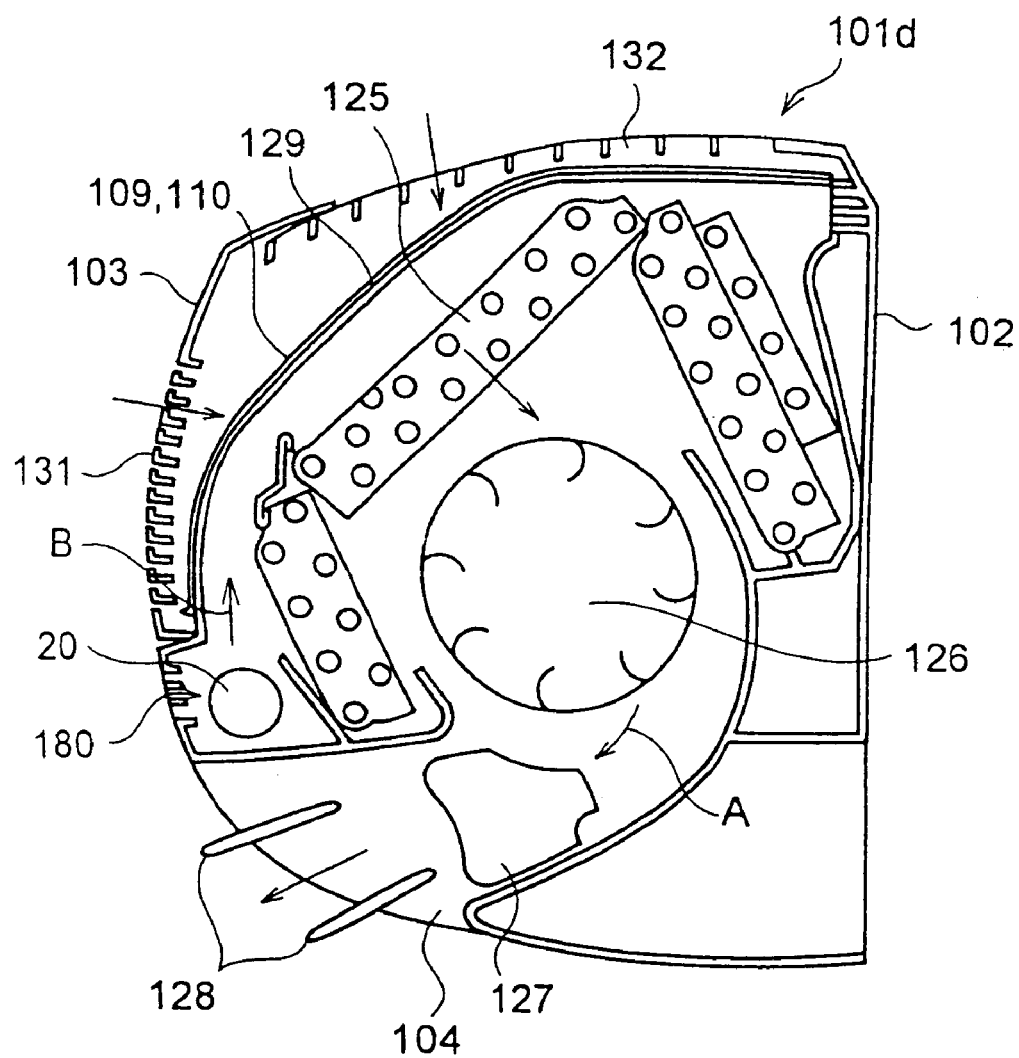
FIG. 23 is a sectional view of the indoor unit of an air conditioner as a fifth embodiment of the air conditioning apparatus of the invention.

FIG. 23 shows a fifth embodiment of the air conditioning apparatus of the invention. In the indoor unit 101d of the air conditioner of the fifth embodiment, an air inlet 180 for the ion generating device unit 20 is formed separately from the air inlet 105 of the circulation passage A, but the air outlet 104 of the circulation passage A is shared as an air outlet for the ion generating device unit 20. Moreover, the ion generating device unit 20 is arranged on the upstream side of the indoor heat exchanger 125. Specifically, the air flow passage B joins the circulation passage A between the filters 109 and 110 and the indoor heat exchanger 125. This makes it possible to sterilize the indoor heat exchanger 125 and the circulation passage A as in the fourth embodiment.

Needless to say, many more modifications are possible in the air conditioning apparatus of the first to fifth embodiments. In all these embodiments described above, the ion generating device unit is provided in the indoor unit of the air conditioners; however, it is also possible to provide the ion generating device unit in single-unit-type air conditioners that do not have separate indoor and outdoor units.

As will be clear from the descriptions above, by making the flow of air passing through the air flow passage for the ion generating device join the flow of air passing through the air circulation passage running through the heat exchanger, it is possible to spread air containing positive and negative ions all around the room and kill airborne bacteria floating in the room. Here, the ion generating device is not arranged on the downstream side of the heat exchanger, and therefore the air that has passed through the heat exchanger does not make contact with the ion generating device. This helps prevent problems resulting from condensation on the ion generating device or from disturbance of the flow of air.

Moreover, by arranging the ion generating device in front of the heat exchanger, i.e. on the upstream side thereof, it is possible to remove bacteria present near the heat exchanger, fan, and other components and thereby blow out clean air.

By building the ion generating device and the blower into a single unit, it is possible to make their mounting and thus their incorporation into air conditioning apparatus easy. By fitting a filter in the air inlet of the unit, it is possible to prevent dust from settling on the ion generating device and thereby maintain its performance for an extended period.

Moreover, unitization makes various designs of the air flow passage possible. As a result, it is possible to generate ions while performing ordinary operation, such as cooling or heating operation, and it is also possible to operate the ion generating device unit singly to achieve a sterilizing effect in quiet operation.

Figure 24:
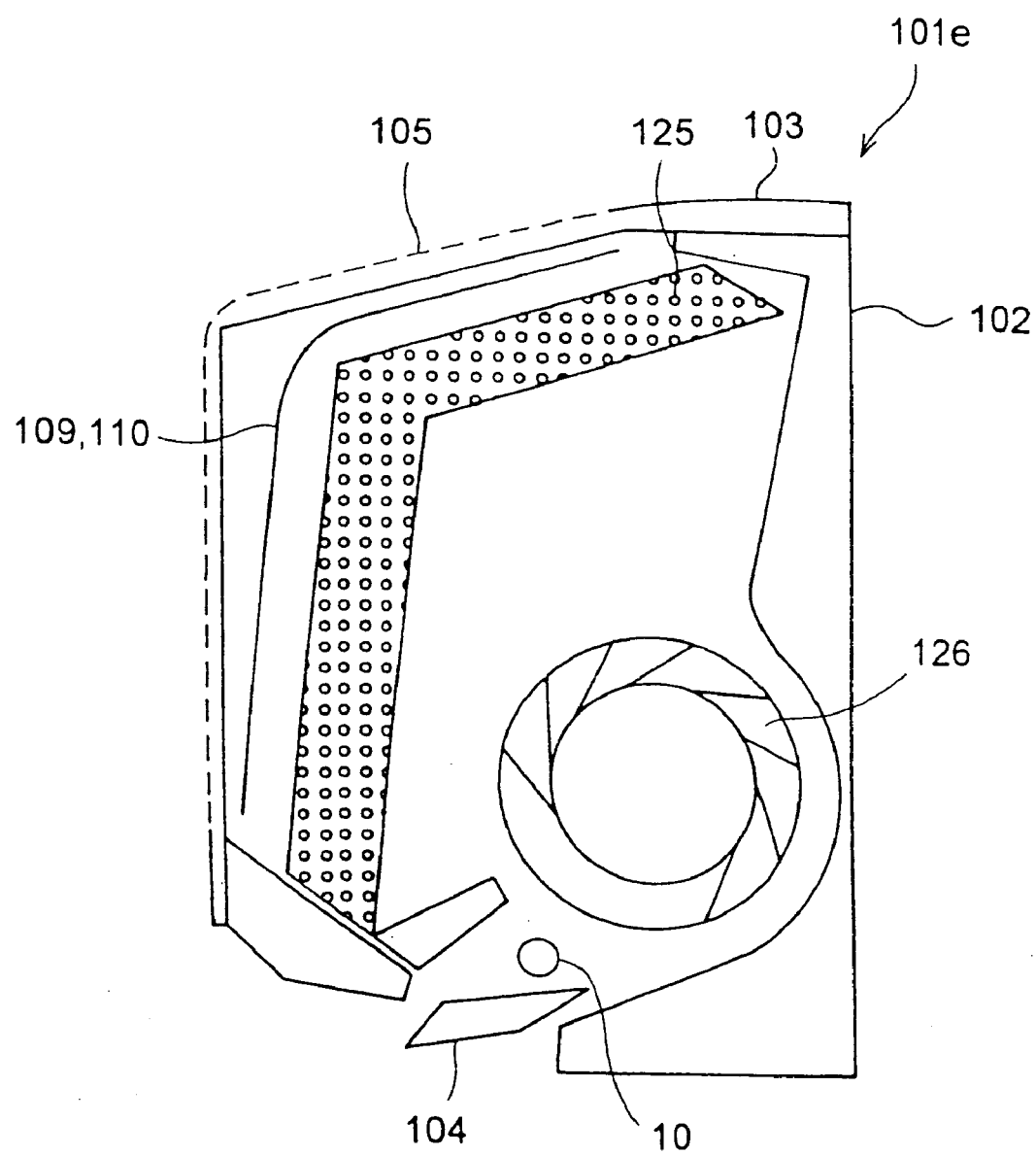
FIG. 24 is a sectional view of the indoor unit of an air conditioner as a sixth embodiment of the air conditioning apparatus of the invention.

FIG. 24 shows a sixth embodiment of the air conditioning apparatus of the invention. The indoor unit 101*e* of the air conditioner of the sixth embodiment is essentially of the same type as those used in the first to fifth embodiments, although illustrated with a different touch in the figure. In the indoor unit 101*e*, the ion generating device 10 described under the section [A first embodiment of the ion generating device of the invention] is arranged between the indoor fan 126 and the air outlet 104.

Figure 25:
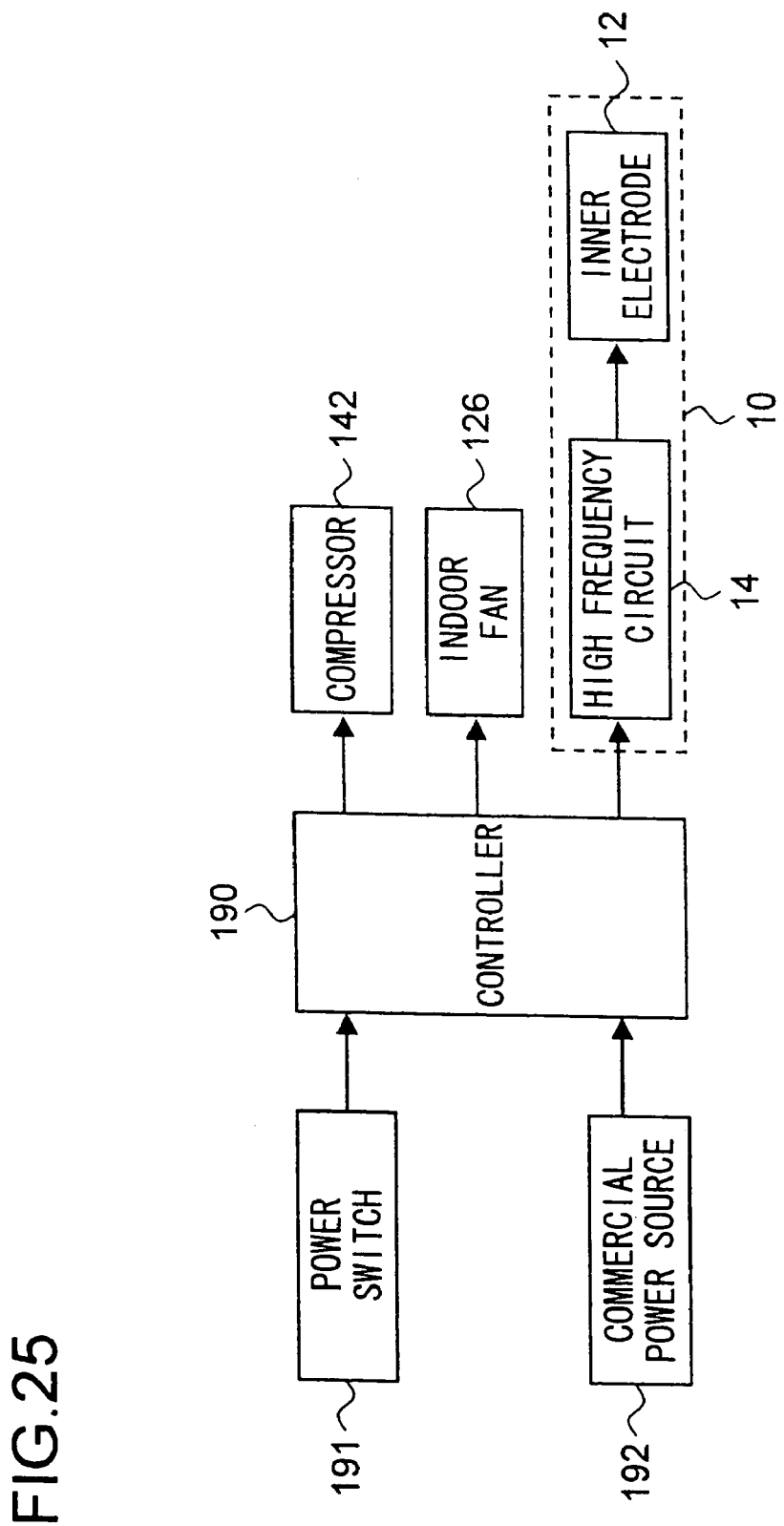
FIG. 25 is a block diagram of the control system of the air conditioner of the sixth embodiment.

FIG. 25 shows a block diagram of the control system of the air conditioner of the sixth embodiment. To the input side of a controller 190 are connected a power switch 191 with which the operation of the air conditioner is turned on/off and a commercial power source 192 from which electric power is supplied to the controller 190. On the other hand, to the output side of the controller 190 are connected a compressor 142 that constitutes a key element for a refrigerating cycle of the air conditioner, an indoor fan 126, and, through the high frequency circuit 14, the inner electrode 12 of the ion generating device 10.

Thus, in the air conditioner of the sixth embodiment, in concert with the operation of the air conditioner, i.e. the operation of the compressor 142 and the indoor fan 126, the controller 190 can activate the high frequency circuit 14 to apply an alternating-current voltage to the inner electrode 12 of the ion generating device 10.

Thus, for example, when the air conditioner is operated in the automatic operation mode, the ion generating device is always operated simultaneously. As a result, it is possible to achieve the desired air conditioning in the room together with an adequate sterilizing effect thanks to the radical generated through the reaction between positive and negative ions. In this way, it is possible to realize a comfortable living environment, and to enhance the operability of the air conditioner incorporating the ion generating device, making it easier to use.

Figure 26:
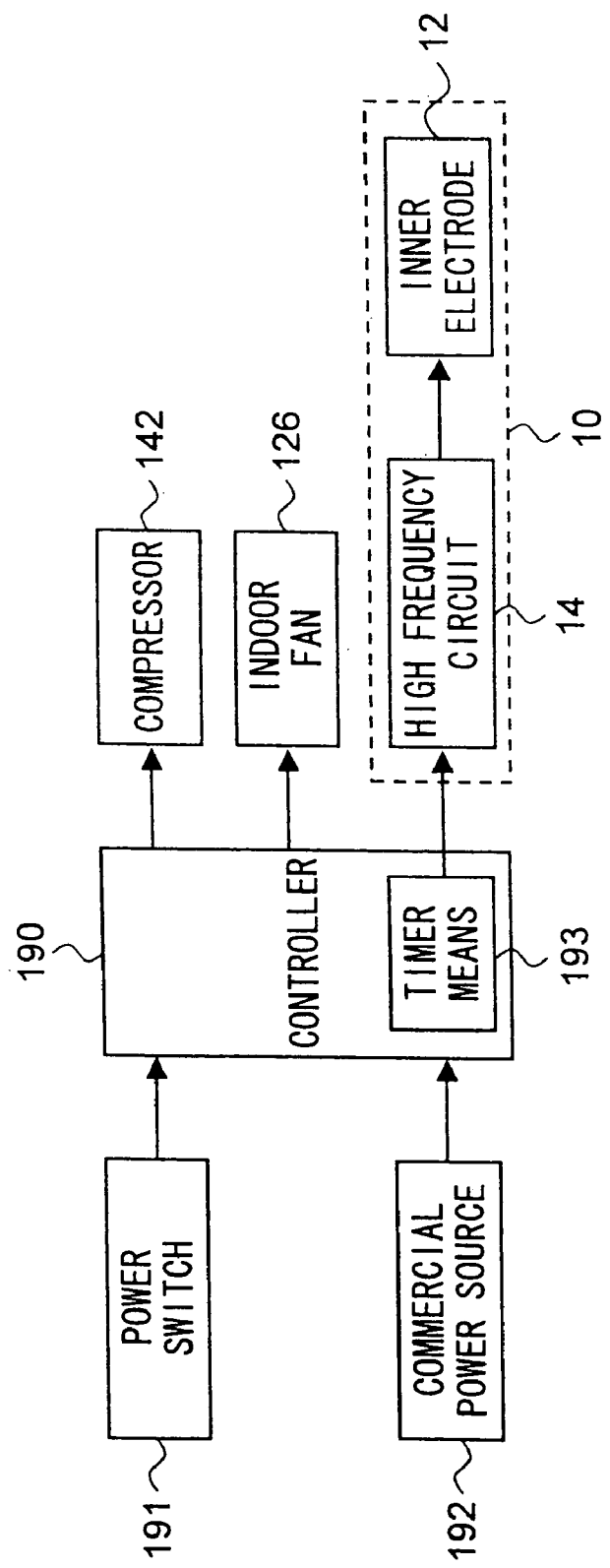
FIG. 26 is a block diagram of the control system of an air conditioner as a seventh embodiment of the air conditioning apparatus of the invention.

A seventh embodiment of the air conditioning apparatus of the invention will be described below with reference to FIGS. 24, 26, and 1. FIG. 26 shows a block diagram of the control system of the air conditioner of the seventh embodiment. To the input side of a controller 190 are connected a power switch 191 with which the operation of the air conditioner is turned on/off and a commercial power source 192 from which electric power is supplied to the controller 190. On the other hand, to the output side of the controller 190 are connected a compressor 142 that constitutes a key element for a refrigerating cycle of the air conditioner, an indoor fan 126, and, through the high frequency circuit 14, the inner electrode 12 of the ion generating device 10.

Moreover, the controller 190 incorporates a timer means 193 such as a delay circuit. Through this timer means, the high frequency circuit 14 is connected to the controller 190. Thus, for example, for a predetermined time after the compressor 142 and the indoor fan 126 of the air conditioner start being operated, the timer means 193 inhibits the high frequency circuit 14 from being energized, so that the ion generating device 10 starts being driven with a delay. After the lapse of the predetermined time, the timer means 193 enables the high frequency circuit 14 to start driving the ion generating device 10.

As a result, only the predetermined time after the compressor 142 and the indoor fan 126 of the air conditioner start being operated does the ion generating device 10 start generating ions. This makes it possible to spread positive and negative ions all around the room and achieve a sterilizing effect just starting from the time that ions start being generated. Thus, it is possible to achieve air conditioning together with an adequate sterilizing effect thanks to the radical generated through the reaction between positive an negative ions. In this way, it is possible to realize a comfortable living environment.

Figure 27:
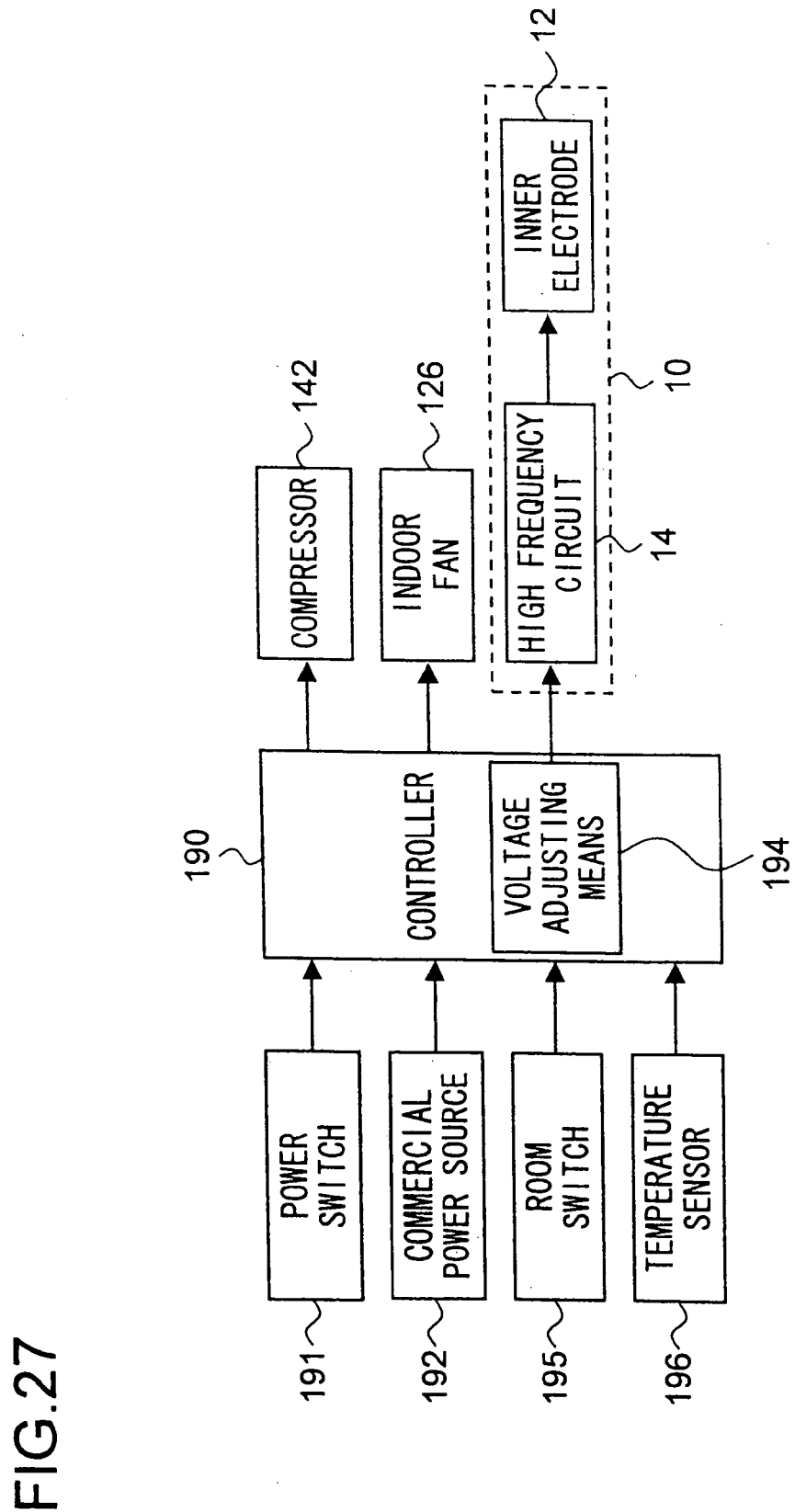
FIG. 27 is a block diagram of the control system of an air conditioner as an eighth embodiment of the air conditioning apparatus of the invention.

An eighth embodiment of the air conditioning apparatus of the invention will be described below with reference to FIGS. 24, 27, and 1. FIG. 27 shows a block diagram of the control system of the air conditioner of the eighth embodiment. To the input side of a controller 190 are connected a power switch 191 with which the operation of the air conditioner is turned on/off, a commercial power source 192 from which electric power is supplied to the controller 190, a room switch 195 by which the user can set the size of the room manually, and a temperature sensor 196 that detects the temperature inside the room. On the other hand, to the output side of the controller 190 are connected a compressor 142 that constitutes a key element for a refrigerating cycle of the air conditioner, an indoor fan 126, and, through the high frequency circuit 14, the inner electrode 12 of the ion generating device 10.

Moreover, the controller 190 incorporates a voltage adjusting means 194 that permits adjustment of the voltage that the high frequency circuit 14 applies to the inner electrode 12 of the ion generating device 10. Through this voltage adjusting means 194, the high frequency circuit 14 is connected to the controller 190.

First, a case in which the user enters the size of the room will be described. When the size of the room (as expressed, for example, in m$^2$) is entered from the remote control unit or by another means, the controller 190, on the basis of the signal entered, calculates the amount of ions adequate for the size of the room. When the power switch 191 is operated to turn on the air conditioner, the controller 190 energizes the compressor 142 and the indoor fan 126 to start operating them, and instructs the high frequency circuit 14 to apply an alternating-current voltage that yields roughly the amount of ions determined as described above.

In response, the high frequency circuit 14 applies the aforementioned alternating-current voltage to the inner electrode 12 of the ion generating device 10. As a result, the adequate amount of ions generated by the ion generating device 10 according to the size of the room is carried continuously all around the room by the air blown out. Thus, it is possible to achieve the desired air conditioning in the room together with an adequate sterilizing effect thanks to the radical generated by the reaction between positive and negative ions. In this way, it is possible to realize a comfortable living environment.

Next, a case in which the size of the room is automatically determined by the use of the temperature sensor 196 will be described. First, the target temperature for cooling or heating operation is entered, and the power switch 191 is turned on to start the operation of the air conditioner. Now, the temperature sensor 196 starts monitoring the variation in the temperature inside the room that is brought about by the cooling or heating operation.

On the basis of the signals (the variation in temperature) from the temperature sensor 196, the controller 190 calculates the rate at which the temperature inside the room is falling or rising, then compares the calculated rate with the aforementioned target temperature to determine the amount of ions adequate for the room, and then instructs the high frequency circuit 14 to apply an alternating-current voltage that yields roughly that amount of ions.

In response, the high frequency circuit 14 applies the aforementioned alternating-current voltage to the inner electrode 12 of the ion generating device 10. As a result, the adequate amount of positive and negative or is generated by the ion generating device 10 according to the size of the room is carried continuously all around the room by the indoor fan 126. Thus, it is possible to obtain a concentration of ions adequate for the room and thereby achieve a satisfactory sterilizing effect.

Figure 28:
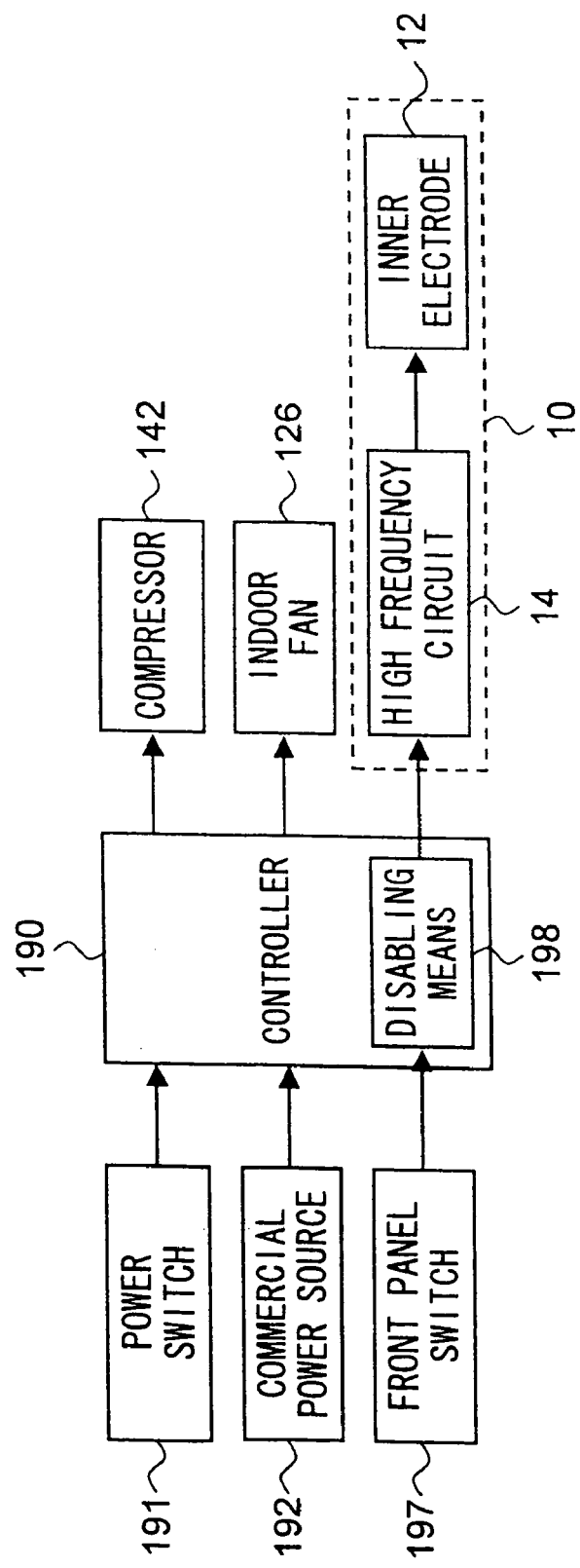
FIG. 28 is a block diagram of the control system of an air conditioner as a ninth embodiment of the air conditioning apparatus of the invention.

A ninth embodiment of the air conditioning apparatus of the invention will be described below with reference to FIGS. 24, 28, and 1. FIG. 28 is a block diagram of the control system of the air conditioner of the ninth embodiment. To the input side of a controller 190 are connected a power switch 191 with which the operation of the air conditioner is turned on/off, a commercial power source 192 from which electric power is supplied to the controller 190, and a front panel switch 197 that detects whether the front panel is open or closed as on or off. On the other hand, to the output side of the controller 190 are connected a compressor 142 that constitutes a key element for a refrigerating cycle of the air conditioner, an indoor fan 126, and, through the high frequency circuit 14, the inner electrode 12 of the ion generating device 10.

The controller 190 incorporates a disabling means 198 such as a disabling circuit that, in accordance with a signal from the front panel switch 197, turns on and off the driving of the ion generating device 10. Through this disabling means 198, the high frequency circuit 14 is connected to the controller 190.

Thus, for example, when the front panel is opened by mistake while the ion generating device 10 is being driven, the front panel switch 197 is turned off, and therefore the disabling means 198 stops energizing the high frequency circuit 14 so as to stop the application of the alternating-current voltage to the inner electrode 12. In this state, even if the user touches the glass tube 11 or the outer electrode 13 of the ion generating device 10, there is no risk of the user receiving an electric shock. This ensures sufficient safety of the user on occasions of maintenance as when the user cleans the inside of the air conditioner with the front panel open.

Figure 29:
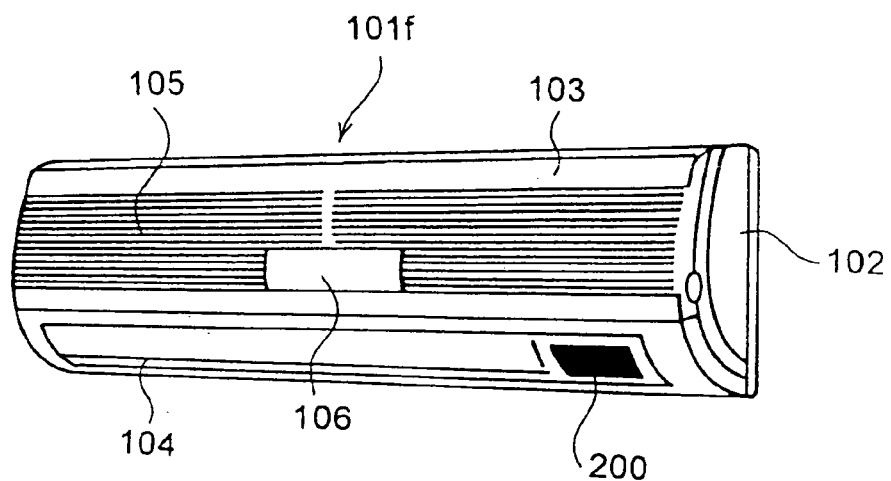
FIG. 29 is a perspective view of the indoor unit of an air conditioner as a tenth embodiment of the air conditioning apparatus of the invention.
Figure 30:
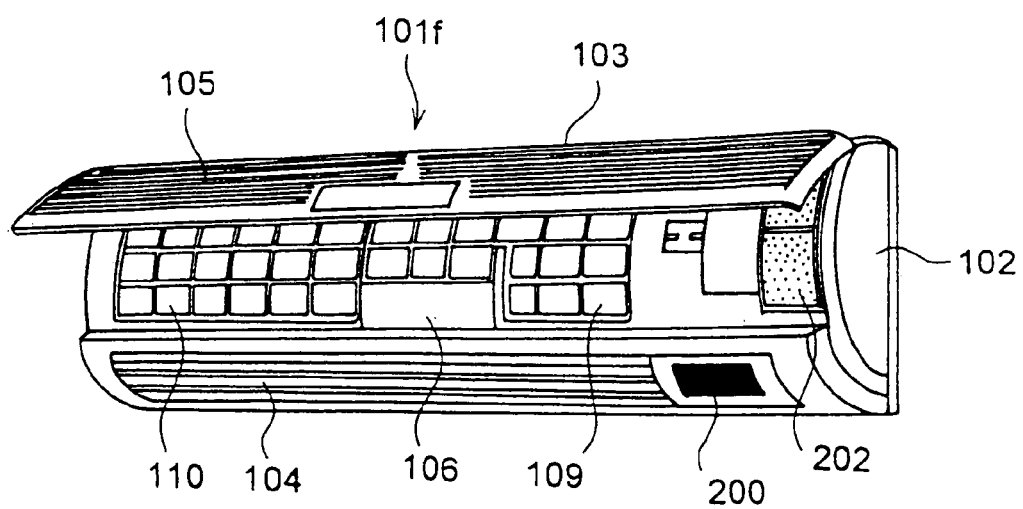
FIG. 30 is a perspective view of the indoor unit of the air conditioner of the tenth embodiment, with its front panel open.
Figure 31:
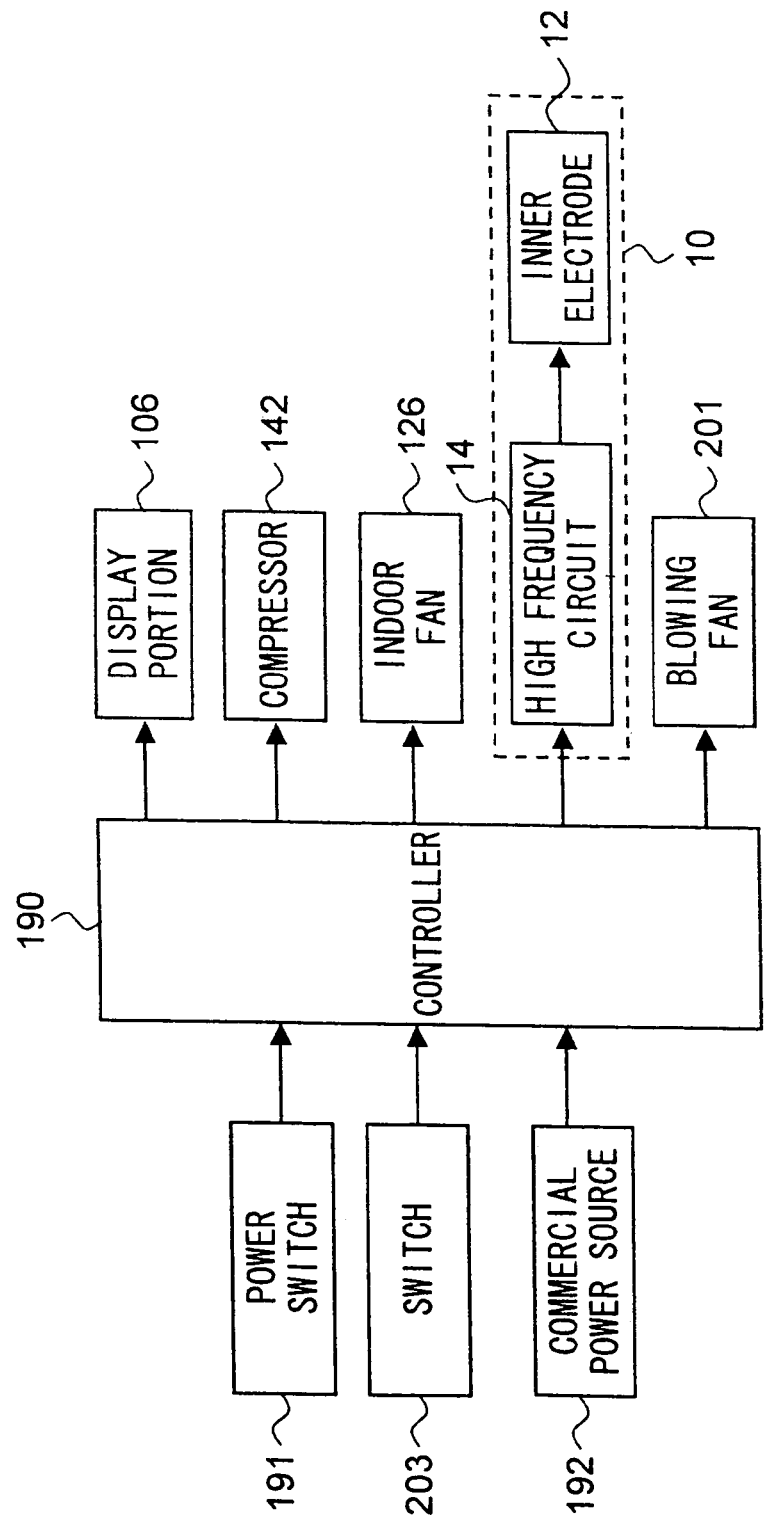
FIG. 31 is a block diagram of the control system of the air conditioner of the tenth embodiment.

A tenth embodiment of the air conditioning apparatus of the invention will be described below with reference to FIGS. 29 to 31. FIG. 29 shows the indoor unit 101f of this air conditioner with the front panel 103 closed, and FIG. 30 shows the indoor unit 101f with the front panel 103 opened. FIG. 31 is a block diagram of the control system of the air conditioner.

In the tenth embodiment, an ion outlet is provided separately from the air outlet 104 of the indoor unit 101f. In the figures, reference numeral 200 represents the ion outlet through which the ions generated by the ion generating device 10 is blown out, and behind this ion outlet 200 is arranged a blowing fan 201 (see FIG. 31) that blows out the ions generated by the ion generating device 10 that is provided separately from the air conditioning portion (composed of the compressor 142, the indoor fan 126, and other components).

The liquid crystal display device 106 displays the operation status of the ion generating device 10 and of the air condition portion. For example, when the ion generating device 10 is operating, the corresponding light-emitting means is lit. The indication here may be achieved in any other manner, for example by blinking the light-emitting means, or by displaying characters, or by giving a sound (playing a melody). Reference numeral 202 represents a dust removing filter provided in front of the ion generating device 10 to shut out the dust sucked in with the air.

Moreover, in the tenth embodiment, a switch 203 for starting and stopping the ion generating device 10 is provided so that it can be started and stopped independently of the air conditioning portion. Thus, even when the air conditioning portion including the compressor 142, the indoor fan 126, and other components is not operating, it is possible to drive the ion generating device 10 alone by applying an alternating-current voltage to the inner electrode 12 and activating the blowing fan 201 so as to blow out ions through the ion outlet 200 into the room and thereby achieve the desired sterilizing effect. The control methods used in the seventh to ninth embodiments described earlier can be applied also to this embodiment to achieve their respective effects.

As will be clear from the descriptions above, by interlocking the operation of the air conditioner and the driving of the ion generating device, it is possible to operate them simultaneously by simple operation. Moreover, by controlling the operation of the air conditioner and the driving of the ion generating device independently, it is possible to operate them flexibly in accordance with the conditions in the room.

In that case, by configuring the control system to incorporate a timer means that delays the starting of the driving of the ion generating device relative to the starting of the operation of the air conditioner, it is possible to permit the ion generating device to start generating ions a predetermined time after the compressor and the blower fan of the air conditioner start being operated so that opposite ions can be carried all around the room more efficiently by the wind. Thus, it is possible to achieve the desired air conditioning in the room together with an adequate sterilizing effect. In this way, it is possible to realize a comfortable living environment, and to enhance the operability of the air conditioner incorporating the ion generating device, making it easier to use.

Alternatively, by configuring the control system to incorporate a means that controls the amount of ions generated by the ion generating device according to the size of the room, it is possible to continuously blow out an adequate amount of opposite ions according to the size of the room and spread the ions all around the room. Thus, it is possible to obtain a concentration of ions adequate for the room and thereby achieve a satisfactory sterilizing effect.

Alternatively, by configuring the control system to incorporate a disabling means that turns on/off the driving of the ion generating device according to whether the front panel is open or closed, even if the front panels is opened by mistake while the ion generating device is being driven, the disabling means stops energizing the high-frequency circuit, and thus it is possible to stop the driving of the ion generating device immediately. In this state, even if the user touches the ion generating portion of the ion generating device, there is no risk of the user receiving an electric shock from the high voltage. This ensures sufficient safety of the user on occasions of maintenance as when the user cleans the inside of the air conditioner with the front panel open.

Figure 32:
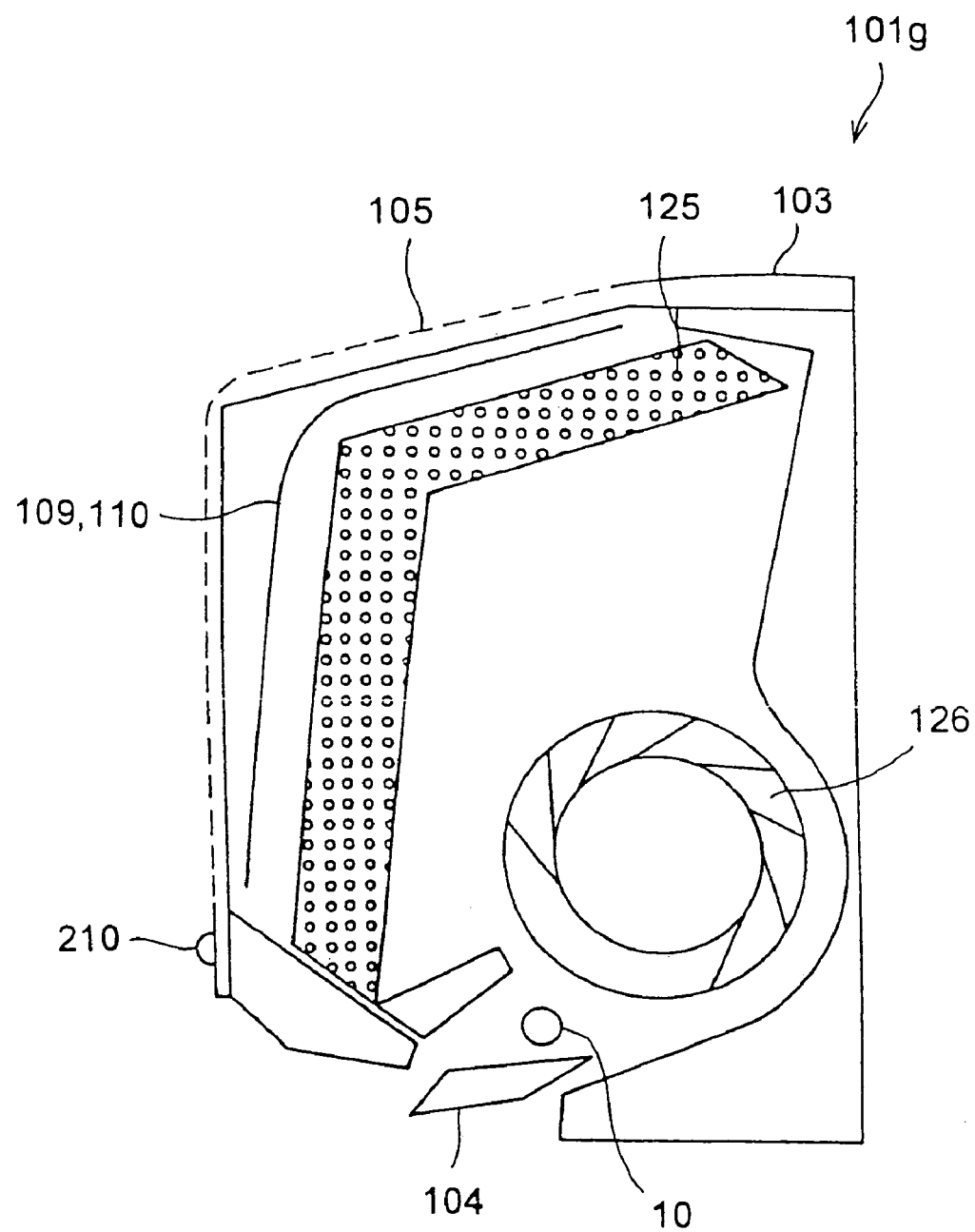
FIG. 32 is a sectional view of the indoor unit of an air conditioner as an eleventh embodiment of the air conditioning apparatus of the invention.

FIG. 32 shows an eleventh embodiment of the air conditioning apparatus of the invention. In the indoor unit 101g of the air conditioner of the eleventh embodiment, as in that of the sixth embodiment, the ion generating device 10 described under the section [A first embodiment of the ion generating device of the invention] is arranged between the indoor fan 126 and the air outlet 104. Moreover, on the front panel 103, a light-emitting diode 210 is provided as an indicating means.

Figure 33:
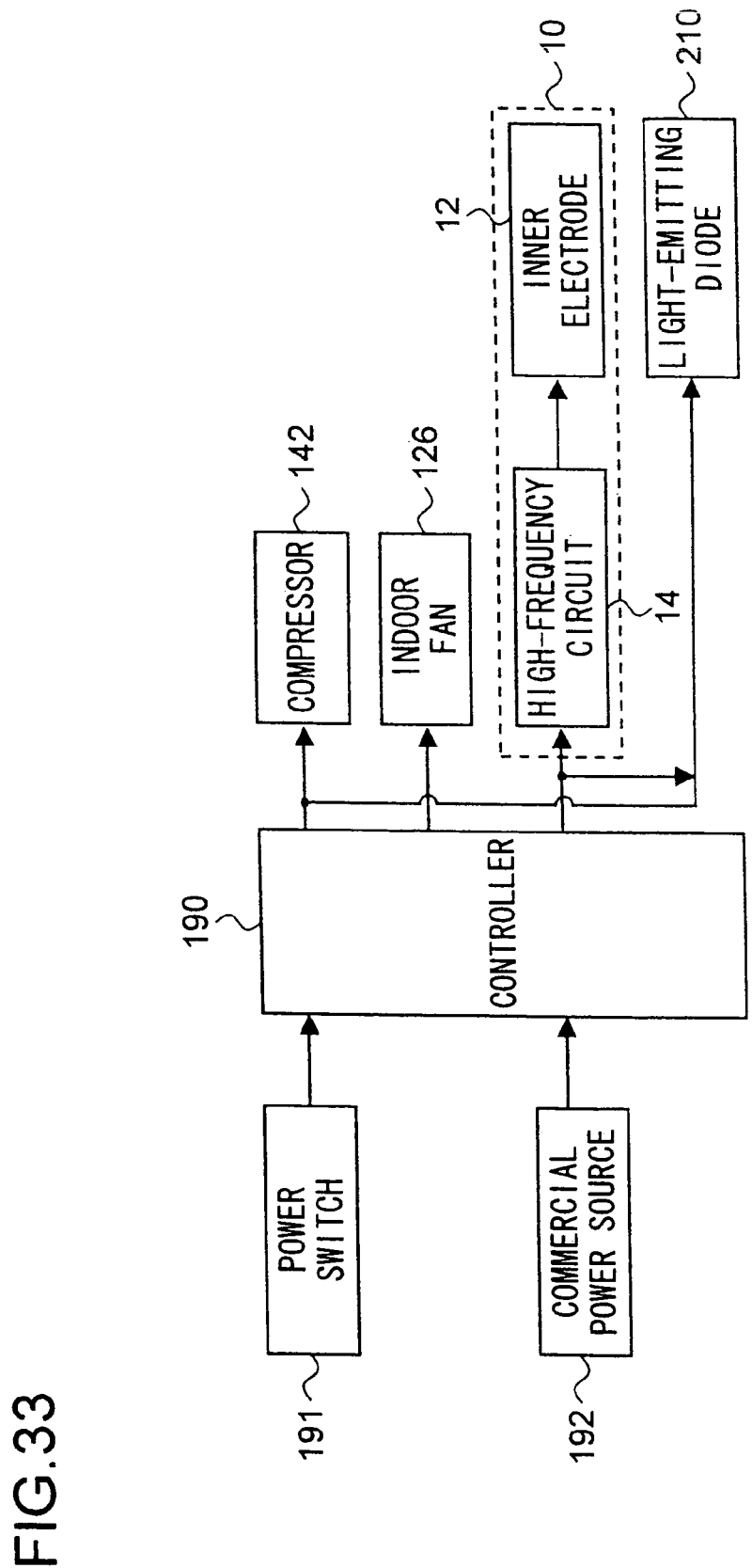
FIG. 33 is a block diagram of the control system of the air conditioner of the eleventh embodiment.

FIG. 33 is a block diagram of the control system of this air conditioner. To the input side of a controller 190 are connected a power switch 191 with which the operation of the air conditioner or the driving of the ion generating device 1 is turned on/off and a commercial power source 192 from which electric power is supplied to the controller 190. On the other hand, to the output side of the controller 190 are connected a compressor 142 that constitutes a key element for a refrigerating cycle of the air conditioner, an indoor fan 126, and, through the high frequency circuit 14, the inner electrode 12 of the ion generating device 10. Here, the outputs from the controller 190 to the compressor 142 and to the high frequency circuit 14 branch off to the light-emitting diode 210.

The controller 190 is so configured as to control the operation of the air conditioning portion (composed of the compressor 142, the indoor fan 126, and other components) and the driving of the ion generating device 10 independently on the basis of signals from the power switch 191. For example, when the temperature inside the room detected by the temperature sensor is such that cooling or heating is necessary, the controller 190 operates the air conditioner together with the ion generating device 10, and otherwise it operates the ion generating device 10 alone.

Next, an example of how this air conditioner is used will be described below with reference to FIG. 33. When the power switch 191 is turned to the "on" position, electric power is supplied from the commercial power source 192 to the controller 190.

(1) When the Controller 190 Operates both the Ion Generating Device 10 and the Air Conditioner The controller 190 activates the compressor 142 and the indoor fan 126 to start operating the air conditioner. Simultaneously, the controller 190 instructs the high frequency circuit 14 to apply an alternating-current voltage to the inner electrode 12 of the ion generating device 10.

In this case, from the signal paths leading to the compressor 142 and to the high frequency circuit 14, two signals are simultaneously fed to the light-emitting diode 210. This causes the light-emitting diode 210 to emit light continuously; that is, it is lit. Thus, it is possible to achieve the desired air conditioning together with a sterilizing effect thanks to the positive and negative ions generated by the ion generating device 10, and the light-emitting diode 210 lit permits the user to visually confirm this operation status.

(2) When the Controller 190 Operates the Ion Generating Device 10 Alone

The controller 190 activates the indoor fan 126, and simultaneously instructs the high frequency circuit 14 to apply an alternating-current voltage to the inner electrode 12 of the 10.

In this case, only the signal from the signal path leading to the high frequency circuit 14 is fed to the light-emitting diode 210. This causes the light-emitting diode 210 to emit light intermittently; that is, it blinks. Thus, it is possible, without performing air conditioning, to achieve a sterilizing effect thanks to the positive and negative ions generated by the ion generating device 10, and the blinking light-emitting diode 210 permits the user to visually confirm this operation status.

(3) When the Controller 190 Operates the Air Conditioner Alone

The controller 190 activates the compressor 142 and the indoor fan 126 to start operating the air conditioner.

In this case, only the signal from the signal path leading to the compressor 142 is fed to the light-emitting diode 210, but the light-emitting diode 210 is kept extinguished. Thus, it is possible to achieve the described air conditioning, and the light-emitting diode 210 extinguished permits the user to visually confirm this operation status.

In the case (1) or (2) described above, if no discharge occurs between the inner and outer electrodes 12 and 13 because of a fault or malfunction in the ion generating device 10, the high frequency circuit 14 stops energizing its destination components including the light-emitting diode 210. Thus, the light-emitting diode 210 is not lit, nor does it blink. In this way, while the air conditioner is operating, the user can visually confirm whether the ion generating device 10 is generating colorless, odorless ions.

In this embodiment, a light-emitting diode is used as an example of the indicating means by which the user is notified of the generation of ions. However, it is also possible to use instead another light-emitting means such as an electric bulb or lamp, or use an auditory indicating means that indicates the generation of ions by giving a sound or playing a melody. The light-emitting means used as the indicating means may be controlled in any other manner than being lit continuously or blinked.

As will be clear from the descriptions above, providing an indicating means for indicating the driving of the generating device makes it possible to realize a user friendly air conditioner that permits the user to confirm easily the generation of colorless, odorless ions. Moreover, not only whether the ion generating device is operating, but also whether the air conditioner is operating or not is indicated by a different mode of indication, and this permits the user to confirm also the operation status of the air conditioner. In this case, using a light-emitting diode as the indicating means enables the user to visually confirm the generation of ions.

Figure 34:
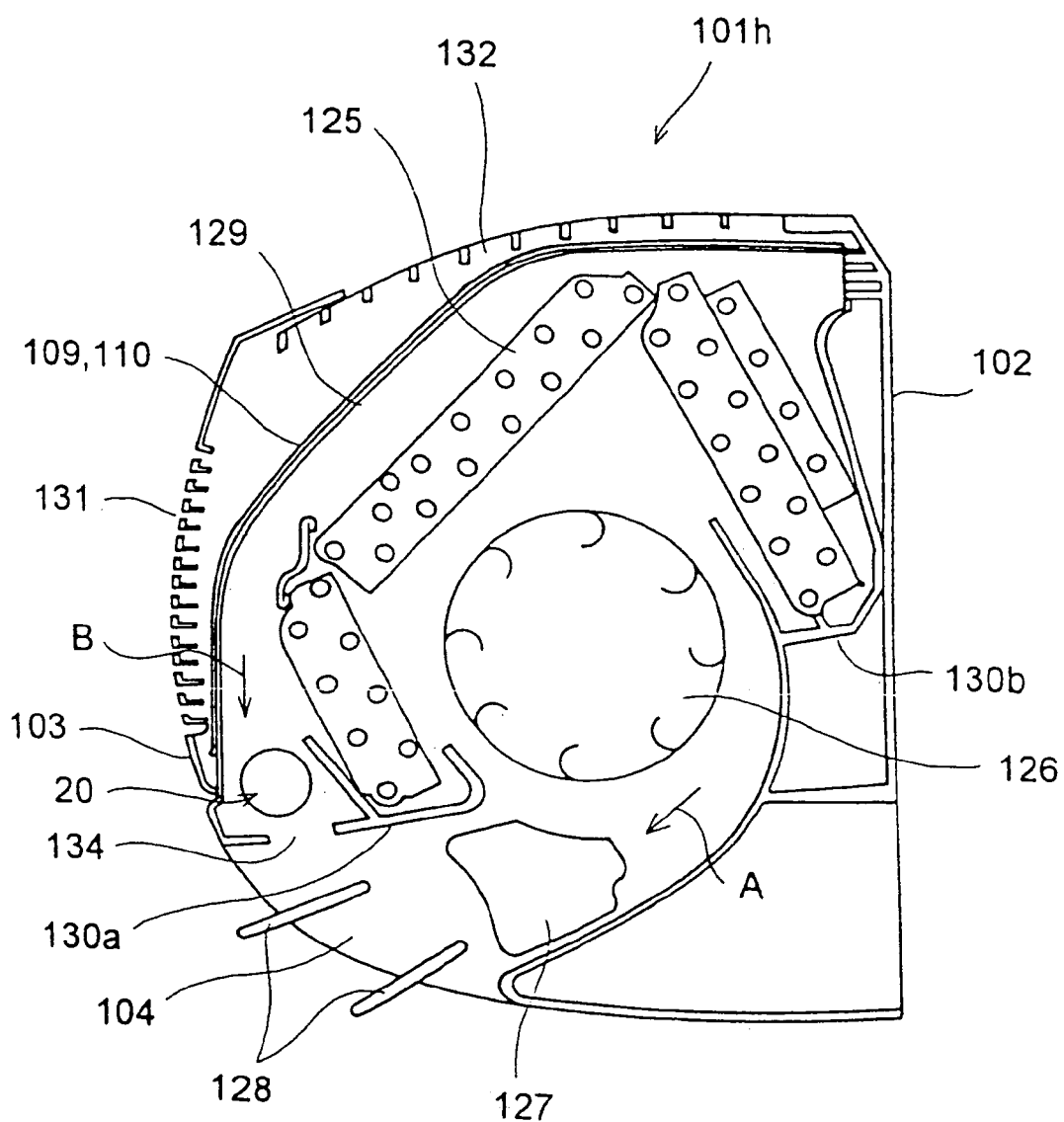
FIG. 34 is a sectional view of the indoor unit of an air conditioner as a twelfth embodiment of the air conditioning apparatus of the invention.

FIG. 34 shows a twelfth embodiment of the air conditioning apparatus of the invention. The indoor unit 101h of the air conditioner of the twelfth embodiment is the same in appearance as that of the first embodiment. Inside the indoor unit 101h, the indoor heat exchanger 125 is arranged so as to face the filter guides 129 and surround the indoor fan 126 from three directions. Here, the indoor fan 126 serves as a "first blower." Below the indoor fan 126, the circulation passage A through which the air is passed is formed, and the air outlet 104 is so formed as to open toward the room. In the air outlet 104 is provided a horizontal louver 128 for changing the direction of the flow of air in the vertical direction, and, inside the horizontal louver 128 is provided a vertical louver 127 for changing the direction of the flow of air in the horizontal direction.

When the indoor fan 126 is driven, the air inside the room sucked in through the front inlet 131 and the upper inlet 132 is subjected to heat exchange by the indoor heat exchanger 125. Then, as indicated by arrow A, the air having its temperature conditioned passes through the circulation passage 181 and is then blown out through the air outlet 104.

Figure 35:
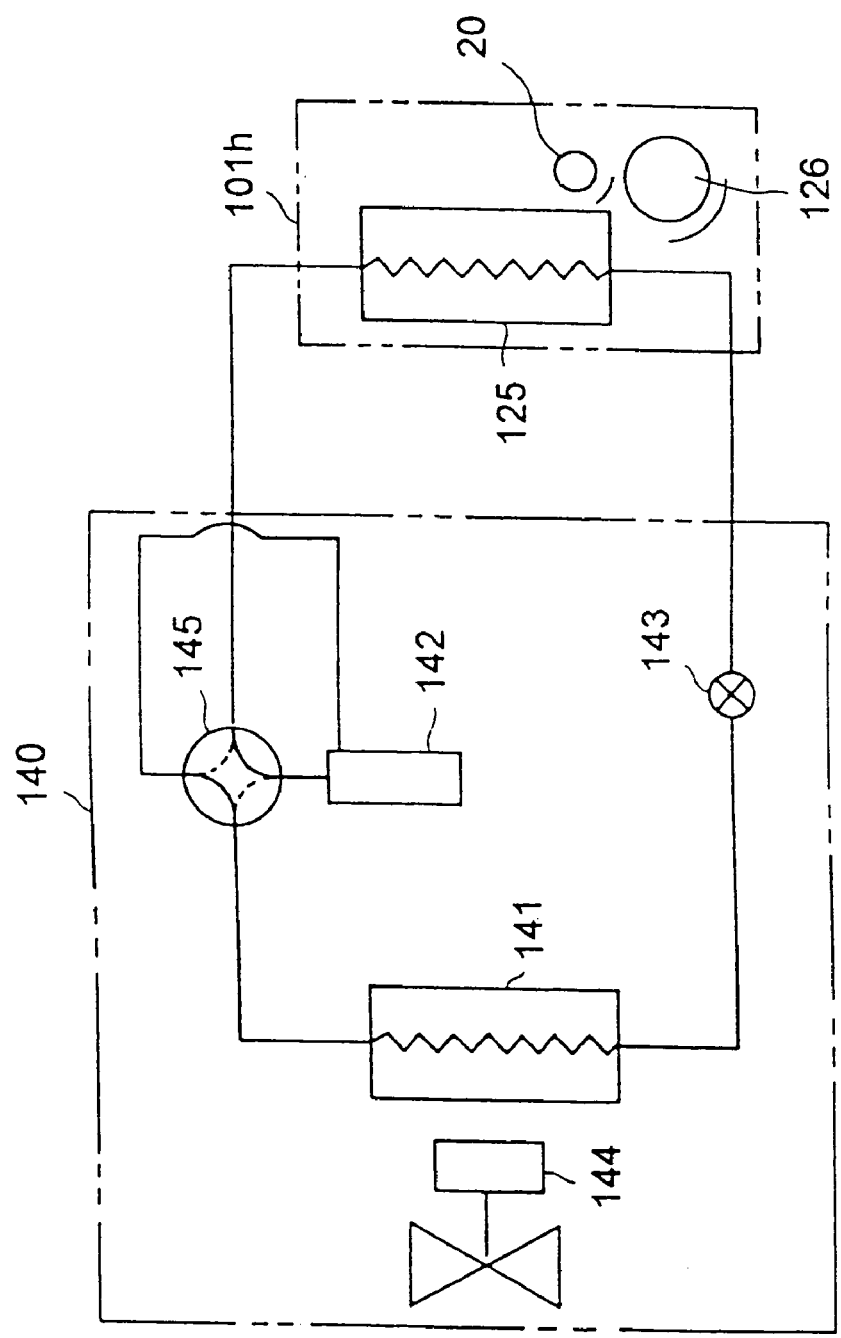
FIG. 35 is a circuit diagram showing the heat cycle of the air conditioner of the twelfth embodiment.

FIG. 35 is a circuit diagram showing the heat cycle of the air conditioner of the twelfth embodiment. The indoor heat exchanger 125 arranged inside the indoor unit 101h is connected through a four-way valve 145 to the compressor 142. One end of the outdoor heat exchanger 141 is connected through the four-way valve 145 to the compressor 142, and the other end of the outdoor heat exchanger 141 is connected through the expansion valve 143 to the indoor heat exchanger 125. Reference numeral 144 represents the outdoor blower that releases heat to or takes in heat from outside the room.

The hot cooling medium compressed by the compressor 142 releases heat in the indoor heat exchanger 125 and condenses. The cooling medium thus condensed and liquefied is decompressed by the expansion valve 143, and, as it vaporizes as a result, it takes away heat of vaporization in the outdoor heat exchanger 141, and then returns to the compressor 142. In this way, heating is achieved inside the room.

When the four-way valve 145 is switched, the hot cooling medium compressed by the compressor 142 releases heat in the outdoor heat exchanger 141 and condenses. The cooling medium thus condensed and liquefied is then decompressed by the expansion valve 143, and, as it vaporizes as a result, it takes away heat of vaporization in the indoor heat exchanger 125, and then returns to the compressor 142. In this way, cooling is achieved inside the room.

In FIG. 34, below the indoor heat exchanger 125 are arranged drain pans 130a and 103b that collect water drained when heat exchange takes place. The drain pans 130a and 130b are fitted to the body casing 102, and the front drain pan 130a forms a space between the indoor heat exchanger 125 and the filter guides 129. The ion generating device unit 20 is arranged in this space. The ion generating device unit 20 has the construction as shown in FIGS. 3 and 4. Here, the blower 23 serves as a "second blower."

In FIG. 34, part of the air sucked in through the front inlet 131 and the upper inlet 132 when the indoor fan 126 is driven is passed through the air flow passage B by the blower 23 and is sucked in by the ion generating device unit 20. Then, the air is, together with ions, blown out through the air outlet 25 of ion generating device unit 20, and then joins, through the confluence 134 provided in the drain pan 130a, the conditioned air. Thus, the ions and the conditioned air are blown out through the air outlet 104 into the room.

Figure 36:
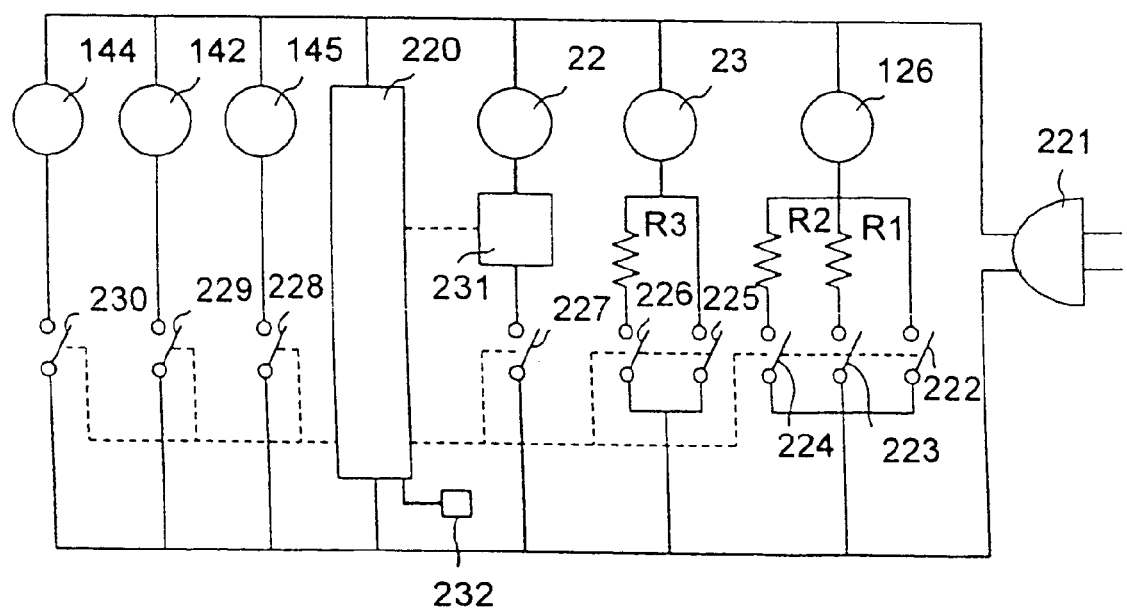
FIG. 36 is a circuit diagram showing the electrical circuit of the air conditioner of the twelfth embodiment.

FIG. 36 is a circuit diagram of the electric circuit of the air conditioner of the twelfth embodiment. To a power plug 221 that is connected to the commercial power source, a control circuit 220, the indoor fan 126 serving as the fist blower, the blower 23 serving as the second blower, the four-way valve 145, the compressor 142, the outdoor fan 144, and the ion generating element 22 are connected in parallel. A power supply 231 permits the voltage applied to the ion generating element 22 to be varied. Moreover, to the electric components mentioned above, relay switches 222 to 230 are connected individually.

When the remote control unit 108 is operated, instructions are transmitted to the control circuit 220, which then switches the relay switches 222 to 230 to control the operation of the individual electric components appropriately. Moreover, a photosensor 232 for detecting the brightness inside the room is provided so that an instruction is transmitted to the control circuit 220 when the brightness inside the room reaches predetermined brightness.

The relay switches 222, 223, and 224 are so configured that only one of them is closed at a time. When the relay switch 222 is closed, the indoor fan 126 serving as the first blower is driven with its maximum output power to produce "strong" wind. To the relay switch 223, a resistor R1 is connected. When the relay switch 223 is closed, the indoor fan 126 is driven with an output power lower than its maximum output power to produce "moderate" wind. To the relay switch 224, a resistor R2 having a higher resistance than the resistor R1 is connected. When the relay switch 224 is closed, the indoor fan 126 is driven with a still lower output power to produce "gentle" wind.

The relay switches 225 and 226 are so configured that only one of them is closed at a time. When the relay switch 225 is closed, the blower 23 serving as the second blower is driven with its maximum output power to produce "strong" wind. To the relay switch 226, a resistor R3 is connected. When the relay switch 226 is closed, the blower 23 is driven with an output power lower than its maximum output power to produce "gentle" wind.

Figure 37:
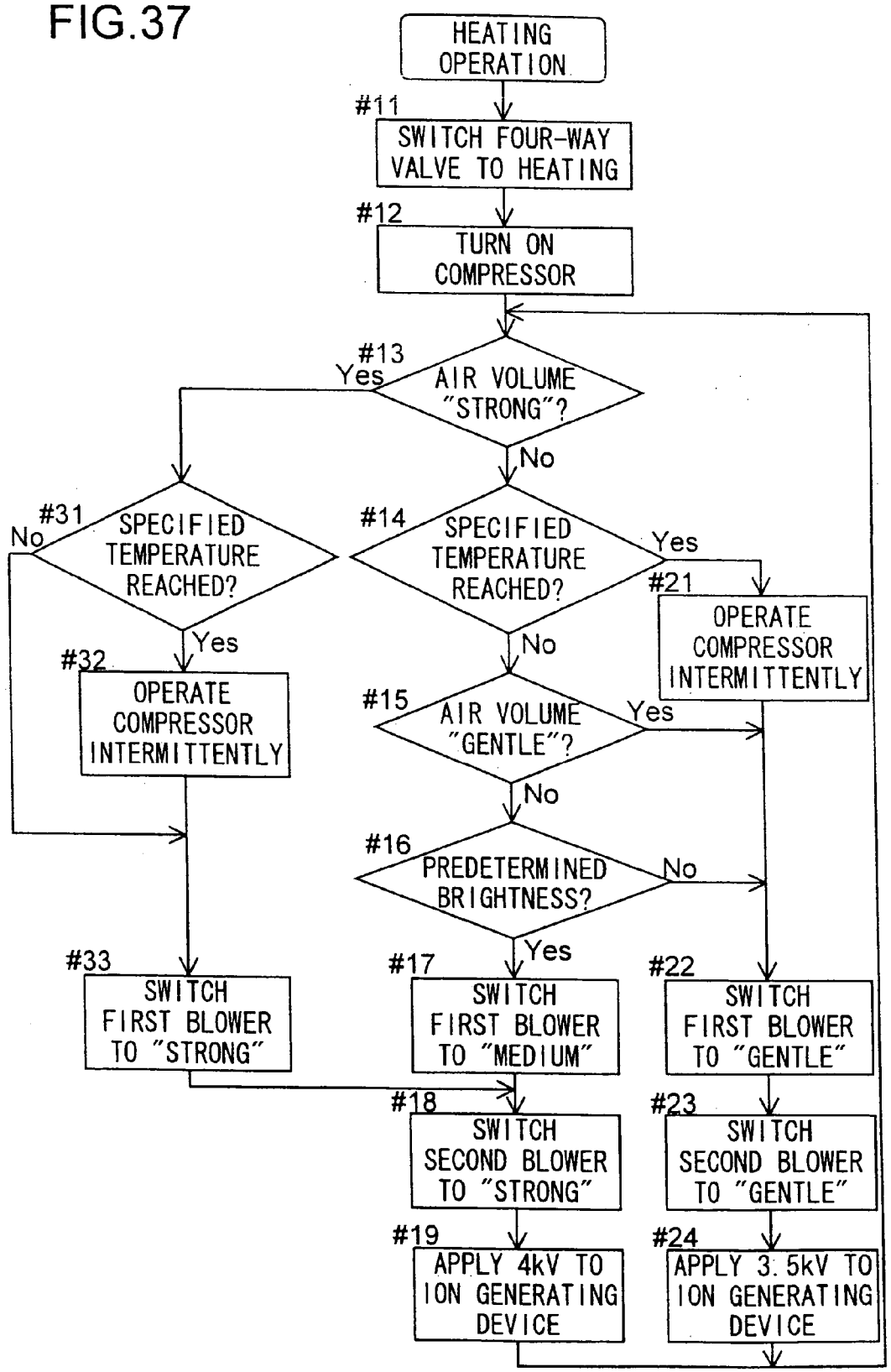
FIG. 37 is a flow chart showing the operation of the air conditioner of the twelfth embodiment.

The remote control unit 108 (see FIG. 13) permits switching between cooling and heating, setting of the temperature inside the room, switching of the air volume, and other operations. For example, when "heating" is selected, heating operation is performed following the flow of operations shown in a flow chart in FIG. 37. First, in step #11, the relay switch 228 is so switched that the four-way valve 145 is switched to the "heating" position. Then, in step #12, the relay switches 229 and 230 are closed to start driving the compressor 142 and the outdoor fan 144.

In step #13, whether "strong" wind is selected from the remote control unit 108 or not is checked, and, if not, then, in step #14, whether the temperature inside the room is equal to the specified temperature or not is checked. If the temperature inside the room has not reached the specified temperature, then, in step #15, whether "gentle" wind is selected from the remote control unit 108 or not is checked, and then, in step #16, whether the brightness inside the room is equal to predetermined brightness or not is checked. If "gentle" wind is not selected from the remote control unit 108, and the brightness inside the room is equal to the predetermined brightness, then the flow proceeds to step #17.

In step #17, the relay switch 223 is closed, and the indoor fan 126 blows, with "moderate" wind, the air that has exchanged heat with the indoor heat exchanger 125 out into the room. In this way, heating operation is performed. Simultaneously, in step #18, the relay switch 225 is closed so that the blower 23 is so driven as to produce "strong" wind. Then, in step #19, the relay switch 227 is closed so that a voltage is applied to the ion generating element 22 to generate positive and negative ions.

As a result, positive and negative ions are blown out into the room with "strong" wind, and thereby airborne bacteria inside the room are killed. Moreover, the air inside the room containing positive and negative ions flows into the indoor unit 101h through the front inlet 131 and the upper inlet 132. Thus, airborne bacteria inside the indoor unit 101h are killed.

Back in step #13, if, in step #14, the temperature inside the room is found to have reached the specified temperature, then, in step #21, the compressor 142 and the outdoor fan 144 are driven intermittently by opening and closing the relay switches 229 and 230. Then, in steps #22 and #23, the relay switches 224 and 226 are closed so that the indoor fan 126 serving as the first blower and the blower 23 serving as the second blower are so driven as to produce "gentle" wind. This helps reduce the noise produced by the indoor fan 126 and the blower 23.

Simultaneously, in step #24, the power supply 231 is so controlled as to decrease the voltage applied to the ion generating element 22. This reduces the amount of ion generated by the ion generating element 22. In this way, it is possible to prevent an increase in the concentration of ions inside the room and maintain an adequate concentration of ions.

The amount of ions generated may be controlled by varying the timing with which the relay switch 227 is turned on and off. For example, by keeping the relay switch 227 on for 5 seconds and then off for 5 seconds repeatedly so that the ion generating element 22 is driven intermittently, it is possible to reduce the amount of ions generated. Moreover, one or more additional resistors having different resistances from the resistor R3 may be provided so that the air volume of the blower 23 can be switched in three or more steps; alternatively, a variable resistor may by used as the resistor R3 so that the air volume can be varied continuously.

Here, it is possible to vary the amount of ions generated in multiple steps by varying the off periods of the relay switch 227, for example by keeping it on for 5 seconds and then off for 5 seconds repeatedly in one case, on for 5 seconds and then off for 10 seconds in another case, and so forth. Alternatively, it is also possible to vary the on periods of the relay switch 227, for example by keeping it on for 5 seconds and then off for 5 seconds repeatedly in one case, on for 2 seconds and then off for 5 seconds in another case, and so forth. It is possible even to vary both the on and off periods.

When the "strong" wind is selected from the remote control unit 108, it is recognized in step #13, and the flow proceeds to step #31. In step #31, whether the temperature inside the room has reached the target temperature or not is checked. If not, the flow proceeds to step #33, and, if so, the flow proceeds to step #32, where the relay switches 229 and 230 are opened and closed in such a way that the compressor 142 and the outdoor fan 144 are operated intermittently.

In step #33, the relay switch 222 is closed and the indoor fan 126 is set to produce "strong" wind. Simultaneously, in step #18, the relay switch 225 is closed, and the blower 23 is set to produce "strong" wind. Then, in step #19, the power supply 231 sets the voltage applied to the ion generating device at a predetermined voltage, so that ions are blown out into the room. As a result, quick heating is performed, and thus the user can obtain the desired temperature quickly.

Even if the temperature inside the room has already reached the target temperature, the indoor fan 126 serving as the first blower and the blower 23 serving as the second blower are operated to produce "strong" wind. In this case, the voltage applied to the ion generating device is higher and thus the ion generating element 22 generates a larger amount of ions than when the indoor fan 126 and the blower 23 are set to produce "gentle" wind. This prevents the concentration of ions from lowering as the air volume is increased, and thus makes it possible to maintain an adequate concentration of ions and achieve a satisfactory sterilizing effect.

When the "gentle" wind is selected from the remote control unit 108, it is recognized in step #15, and, even if the temperature inside the room has not reached the target temperature, the flow proceeds to step #22. Then, the relay switches 224 and 226 are closed so that the indoor fan 126 and the blower 23 are set to produce "gentle" wind (steps #22 and #23). As a result, the air conditioner starts operating in a "quiet operation mode" in which it operates with reduced noise so as not to hinder the user from falling asleep when the user has just gone to bed. In this case, in step #24, the amount of ions generated is reduced to maintain an adequate concentration of ions.

If, in step #16, the brightness inside the room is found to be lower than predetermined brightness by the photosensor 232, the corresponding signal is transmitted to the control circuit 220. The control circuit 220 judges that the user is about to go to bed, and the flow proceeds to step #22. Then, the relay switches 224 and 226 are closed so that the indoor fan 126 and the blower 23 are set to produce "gentle" wind (steps #22 and #23). This permits the air conditioner to start operating with reduced noise without operation by the user so as not to hinder the user from falling asleep when the user has just gone to bed.

In a case where the air conditioner cannot vary the amount of ions generated, when the relay switch 224 is closed so that the indoor fan 126 is set to produce "gentle" wind, the concentration of ions that are blown out into the room rises. Therefore, when the indoor fan 126 is set to produce "gentle" wind, it is preferable that the relay switch 225 be closed so that the blower 23 is set to produce "strong" wind. This makes it possible to maintain an adequate concentration of ions even with an air conditioner that cannot vary the amount of ions generated.

This embodiment deals with an air conditioner that blows out air having its temperature conditioned through cooling or heating into the room. However, the configuration of this embodiment can be applied to air conditioners of other types to achieve the same effects; for example, it can be applied to an air conditioner that blows out air having its humidity conditioned, such as a dehumidifier that dehumidifies the air inside the room or a humidifier that humidifies the air inside the room, or an air conditioner that collects dust and the like in the air and thereby cleans the air so as to blow out air having its cleanliness conditioned as desired into the room.

As will be clear from the descriptions above, by permitting the air volume of the first blower that blows out conditioned air into the room and the air volume of the second blower that blows out ions into the room to be varied, it is possible to decrease the air volume of the second blower when the air volume of the first blower is low and thereby prevent noise.

Moreover, when the user selects a quiet operation mode, the air volumes of the first and second blowers can be decreased. This makes it possible to prevent noise in certain situations as when the user is about to go to bed.

Moreover, the provision of the photosensor that detects the brightness inside the room makes it possible to decrease the air volumes of the first and second blowers when the brightness inside the room becomes lower than predetermined brightness and thus the user is recognized as about to go to bed. This eliminates the need for the user to perform a special operation when going to bed and thereby enhances the operability of the air conditioner.

Moreover, by varying the amount of ions generated according to the air volume of the second blower, it is possible to prevent the lowering of the concentration of ions blown out into the room and thereby prevent the lowering of the sterilizing effect. Moreover, it is also possible to prevent the concentration of ions from becoming higher than is necessary and thereby maintain an adequate concentration of ions.

Moreover, by increasing the air volume of the second blower as the air volume of the first blower decreases, it is possible to prevent the concentration of ions from increasing in situations where the amount of ions generated cannot be decreased and thereby maintain an adequate concentration of ions.

Figure 38:
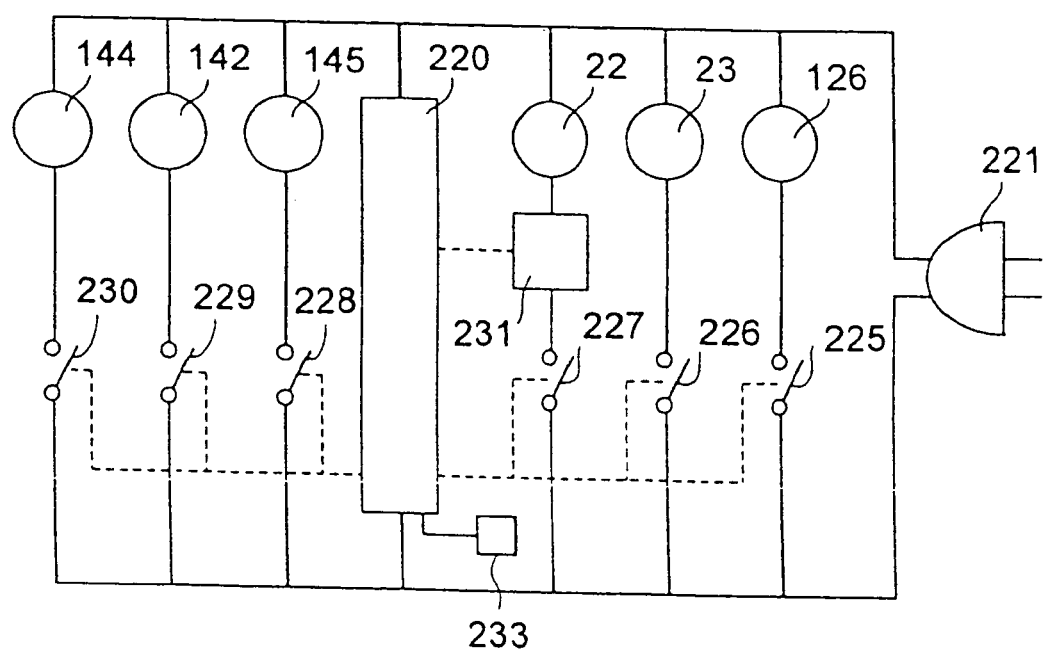
FIG. 38 is a circuit diagram showing the electrical circuit of an air conditioner as a thirteenth embodiment of the air conditioning apparatus of the invention.
Figure 39:
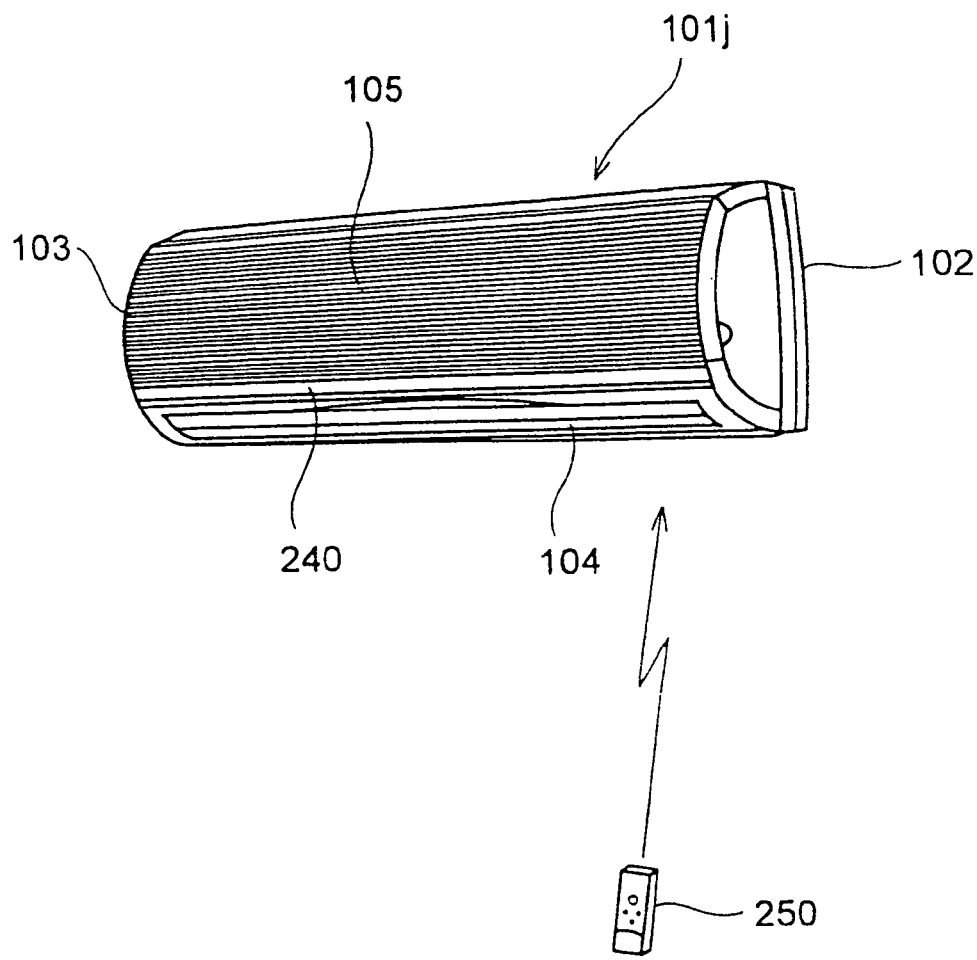
FIG. 39 is a perspective view of the indoor unit of an air conditioner as a fourteenth embodiment of the air conditioning apparatus of the invention.

FIG. 38 shows a thirteenth embodiment of the air conditioning apparatus of the invention. In the air conditioner of the thirteenth embodiment, the construction of the indoor unit and the circuit of the heat cycle are the same as in the twelfth embodiment. The electric circuit shown in FIG. 38 also is almost the same as that shown in FIG. 36, the only differences being the configuration of the relay switches connected to the indoor fan 126 and the blower 23. Specifically, to the indoor fan 126, the relay switch 225 is connected without a serial resistor, and, to the blower 23, the relay switch 226 is connected without a serial resistor. Moreover, here, instead of the photosensor 232, a temperature sensor 233 is used. The temperature sensor 233 is for detecting the temperature of the indoor heat exchanger 125.

The remote control unit 108 permits switching among heating, cooling, and dehumidifying operation, setting of the temperature inside the room, switching of the air volume, and other operations. For example, when "heating" is selected, the relay switch 228 is opened so that the four-way valve 145 is switched to the "heating" position. Then, the relay switches 229 and 230 are closed to start driving the compressor 142 and the outdoor fan 144 and thereby start heating operation.

When heating operation is started, the temperature of the indoor heat exchanger 125 is low, and therefore, if the indoor fan 126 is driven, cool air is blown out into the room. To avoid this, the relay switch 225 is opened to inhibit the driving of the indoor fan 126.

When the temperature sensor 233 detects that the temperature of the indoor heat exchanger 125 has reached a predetermined temperature, the relay switch 225 is closed so that air that has been subject to heat exchange with the indoor heat exchanger 125 by the indoor fan 126 is blown out into the room. Thus, heated air is blown out into the room.

Simultaneously, the relay switch 227 is closed so that the ion generating element 22 generates positive and negative ions, and the relay switch 226 is closed so that the positive and negative ions are blown out into the room. Thus, airborne bacteria inside the room are killed. Moreover, as in the twelfth embodiment, the air inside the room containing positive and negative ions flows into the indoor unit through the front air inlet and the upper air inlet, and thus air borne bacteria inside the indoor unit are killed.

A small amount of ions may be generated and blown out into the room before the indoor heat exchanger 125 reaches the predetermined temperature. Specifically, the relay switch 227 is closed so that the control circuit 220 instructs the power supply 231 to lower the voltage applied to the ion generating element 22. Then, the relay switch 226 is closed to operate the blower 23 so that a small amount of ions is blown out into the room.

This causes a small amount of cold air to be blown out through the air outlet 104, but permits sterilization of airborne bacteria inside the room to be started simultaneously when heating operation is started, and thus helps enhance the sterilizing effect. Moreover, since only a small amount of ions is generated, it is possible to prevent an increase in the concentration of ozone that is generated together with the ions and thereby realize an air conditioner safe for the human body.

The amount of ions generated by the ion generating element 22 may be controlled by varying the timing with which the relay switch 227 is turned on and off. For example, by keeping the relay switch 227 on for 5 seconds and then off for 5 seconds repeatedly so that the ion generating element 22 is driven intermittently, it is possible to decrease the amount of ions generated.

When the temperature inside the room reaches the specified temperature, the relay switches 229 and 230 are opened to step the compressor 142 and the outdoor fan 144. Simultaneously, the relay switches 225 and 226 are opened to stop the indoor fan 126 serving as the first blower and the blower 23 serving as the second blower. Moreover, the relay switch 227 is opened so that the ion generating element 22 stops generating ions. This prevents an increase in the concentration of ozone around the air outlet 104.

Here, a small amount of ions may be generated by the ion generating element 22 and blown out into the room. Specifically, in the same manner as described above, the relay switch 227 is closed so that the control circuit 220 instructs the power supply 231 to lower the voltage applied to the ion generating element 22. Then, the relay switch 226 is closed to operate the blower 23 so that a small amount of ions is blown out into the room.

This not only helps prevent an increase in the concentration of ozone, but also permits sterilization of airborne bacteria inside the room to be performed even when heating operations is halted, and thus helps enhance the sterilizing effect. Thereafter, when the temperature inside the room becomes lower than the specified temperature, the compressor 142, the outdoor fan 144, the indoor fan 126, the blower 23, and the ion generating element 22 start being driven to perform heating operation.

Also when cooling operation is started, the indoor fan 126 is stopped in the same manner as described above. Here, the blower 23 and the ion generating element 22 are stopped to prevent an increase in the concentration of ozone around the air outlet 104. By operating the blower 23 with a reduced amount of ions generated by the ion generating element 22, it is possible to prevent an increase in the concentration of ozone and simultaneously kill airborne bacteria inside the room.

When a detector (not shown) detects formation of frost in the outdoor heat exchanger 141 during heating operation, the relay switch 228 is closed so that the four-way valve 145 is switched to the "cooling" position. In this way, defrosting operation is performed to raise the temperature of the outdoor heat exchanger 141 and thereby defrost it.

Here, the indoor heat exchanger 125 is placed on the low-temperature side, and therefore the relay switches 225 and 226 are opened to stop the blowing operation of the indoor fan 126 and the blower 23 so that cool air is not blown out into the room. Simultaneously, the relay switch 227 is opened so that the ion generating element 22 stops generating ions. This prevents an increase in the concentration of ozone around the air outlet 104.

Here, a small amount of ions may be generated by the ion generating element 22 with the blower 23 operated so that the small amount of ions is blown out into the room in the same manner as described above. This not only helps prevent an increase in the concentration of ozone, but also permits sterilization of airborne bacteria inside the room to be performed even during defrosting operation, and thus helps enhance the sterilizing effect.

When dehumidifying operation is specified from the remote control unit 108, the relay switch 228 is closed so that the four-way valve 145 is switched to the "cooling" position. Then the relay switches 229 and 230 are closed to start driving the compressor 142 and the outdoor fan 144 and thereby start dehumidifying operation. Dehumidifying operation is accompanied by the cooling of the indoor heat exchanger 125, and therefore, when the temperature inside the room reaches the specified temperature, the relay switches 229 and 230 are opened to stop the compressor 142 and the outdoor fan 144.

Then, the relay switch 225 is opened to stop the indoor fan 126 so as to prevent the air blown out through the air outlet 104 from being humidified as a result of the water condensed in the indoor heat exchanger 125 being evaporated again by the flow of air produced by the indoor fan 126. Simultaneously, the relay switches 226 and 227 are opened to stop the blower 23 and the ion generating element 22. This prevents an increase in the concentration of ozone around the air outlet 104.

Here, a small amount of ions may be generated by the ion generating element 22 and blown out into the room. Specifically, in the same manner as described above, the relay switch 227 is closed so that the control circuit 220 instructs the power supply 231 to lower the voltage applied to the ion generating element 220. Then, the relay switch 226 is closed to operate the blower 23 so that the small amount of ions is blown out into the room. This not only helps prevent an increase in the concentration of ozone, but also permits sterilization of airborne bacteria inside the room to be performed even when the compressor 142 is halted, and thus helps enhance the sterilizing effect.

This embodiment deals with an air conditioner that performs cooling, heating, and dehumidifying operation. However, the configuration of this embodiment can be applied to air conditioners of other types to achieve the same effects; for example, it can be applied to a dehumidifier that dehumidifies the air inside the room, a humidifier that humidifies the air inside the room, or an air purifier that collects dust and the like in the air and blows out clean air.

As will be clear from the descriptions above, by stopping the operation of the ion generating device when the first blower is stopped as when cooling or heating operation is started, when the specified temperature has been reached in heating or dehumidifying operation, or during defrosting operation, it is possible to prevent an increase in the concentrations of ions and of ozone around the air outlet and thereby realize an air conditioner safe for the human body.

Moreover, by limiting to a small amount the amount of ions generated by the ion generating device and blown out into the room when the first blower is stopped as when cooling or heating operation is started, when the specified temperature has been reached in heating or dehumidifying operation, or during defrosting operation, it is possible to prevent an increase in the concentrations of ions and of ozone around the air outlet and still achieve sterilization of airborne bacteria inside the air by the action of positive and negative ions.

FIGS. 39 to 48 show a fourteenth embodiment of the air conditioning apparatus of the invention. In the indoor unit 101*j* of the air conditioner of the fourteenth embodiment, between the air outlet 104 and the air inlet 105, a strip-shaped display panel 240 is provided that indicates the operation status of the air conditioner as specified from the remote control unit 108*a*. The display panel 240 may be placed in any other position as long as it can be viewed by the user.

Figure 40:
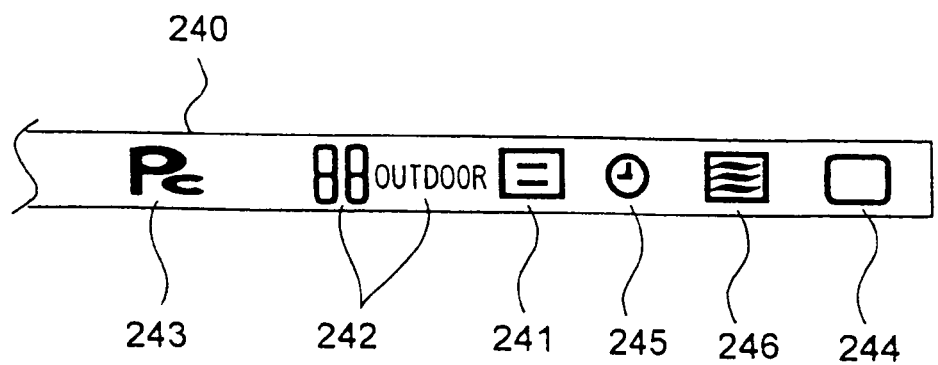
FIG. 40 is a diagram showing the display panel of the indoor unit of the air conditioner of the fourteenth embodiment.

FIG. 40 shows the details of the display panel 240. On the display panel 240 are provided an operation lamp 241 that is lit when the air conditioner is being operated, a temperature indicator 242 that indicates the indoor or outdoor temperature, an air purification lamp 243 that indicates that air-purifying operation is being performed by the ion generating device unit 50 described later, a light-sensing portion 244 that receives optical signals from the remote control unit 250, a timer lamp 245 that indicates that a timer-driven operation is reserved, and an odor elimination lamp 246 that indicates odor-eliminating operation is being performed.

The remote control unit 250 is configured as shown in FIGS. 41 and 42. The remote control unit 250 has a body portion 250*a* of which a lower portion, as viewed in the figures, is covered by a lid portion 250*b* pivoted on a hinge portion 250*c*. Thus, when the lid portion 250*b* is opened, the lower portion 250*a*' of the body portion is exposed a shown in FIG. 42.

In an upper portion, as viewed in the figures, of the body portion 250*a*, a remote control unit display portion 251 is provided that indicates the operation status. In the remote control unit display portion 251, a transmission indicator 252 is provided that is lit as signals are transmitted to the indoor unit 101*j*. Below the remote control unit display portion 251, as viewed in the figures, are arranged an "auto" button 253 that is operated to bring the air conditioner into automatic operation, a "heating" button 254 that is operated to bring it into heating operation, a "cooling" button 255 that is operated to bring it into cooling operation, a "dehumidifying" button 256 that is operated to bring it into dehumidifying operation, and a temperature button 257 that is operated to specify the temperature inside the room.

On the lid portion 250*b* are provided an "air purification" button 258 that is operated to turn on/off the operation of the ion generating device unit 50 described later, and a "stop" button 259 that is operated to stop the operation of the air conditioner. Exposed when the lid portion 250*b* is opened are an "odor elimination" button 260 that is operated to reduce the odors of the air blown out through the air outlet 104, a timer setting button 261, and other controls.

Figure 43:
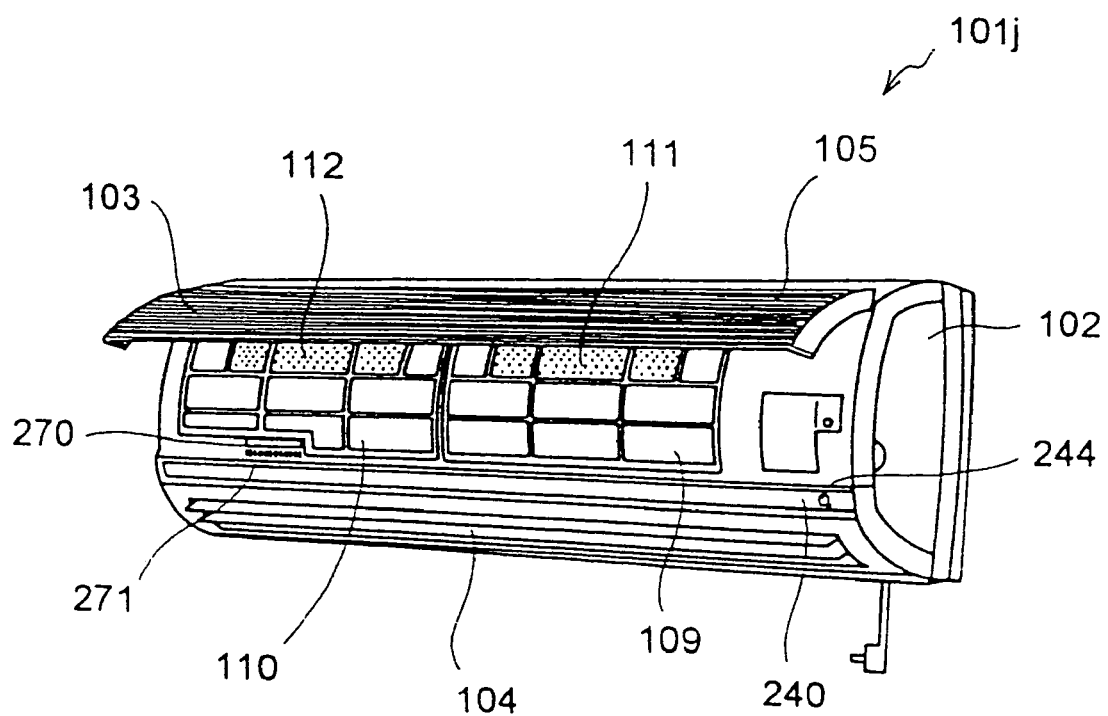
FIG. 43 is a perspective view of the indoor unit of the air conditioner of the fourteenth embodiment, with its front panel open.

As FIG. 43 shows, the filter 110 has a portion thereof cut out so that a subfilter slot 270 and an air intake opening 271 are exposed. Through the subfilter slot 270, a subfilter 272, described later (see FIG. 44), is attached and detached.

Figure 44:
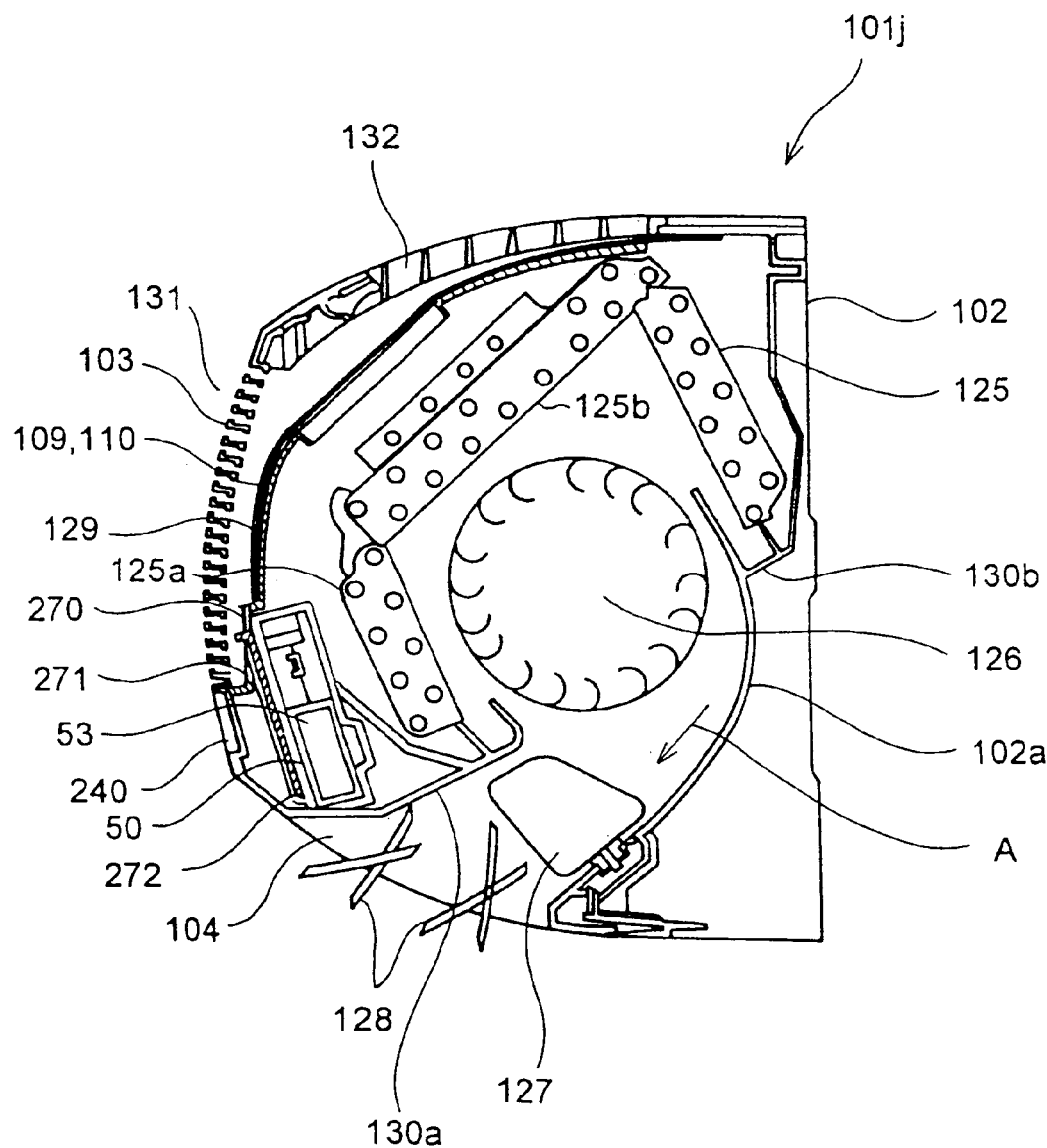
FIG. 44 is a sectional view of the indoor unit of the air conditioner of the fourteenth embodiment.

FIG. 44 is a sectional view, as seen from the side, of the indoor unit 101*j*, taken along a plane that cuts the air intake opening 271. Inside the indoor unit 101*j*, a C-shaped indoor heat exchanger 125 is provided, with a lower front portion 125*a* and an upper front portion 125*b* thereof facing the filter guides 129. In the top surface of the body casing 102, an upper inlet 132 is formed so that the air sucked in through the upper inlet 132 and a front inlet 131 are subjected to heat exchange by the indoor heat exchanger 125.

Figure 45:
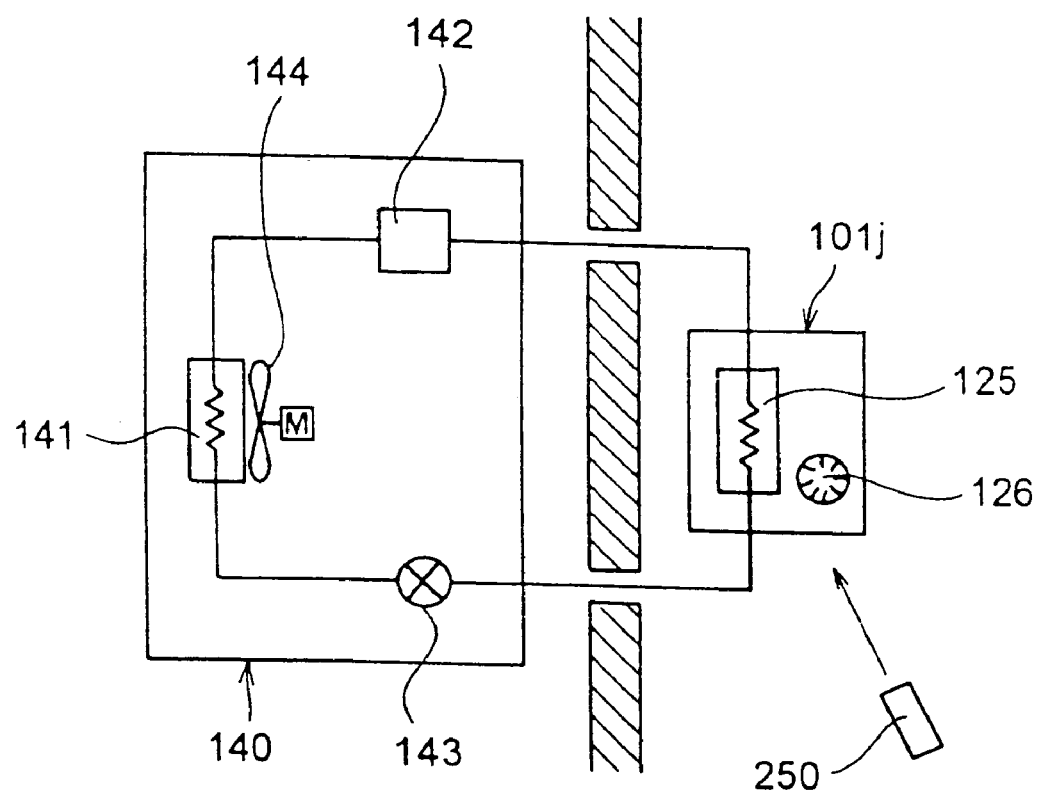
FIG. 45 is a circuit diagram showing the heat cycle of the air conditioner of the fourteenth embodiment.

FIG. 45 is a circuit diagram showing the heat cycle of the air conditioner of this embodiment. The indoor heat exchanger 125 provided inside the indoor unit 101j is connected to the compressor 142 provided in the outdoor unit 140. One end of the outdoor heat exchanger 141 is connected to the compressor 142, and the other end of the outdoor heat exchanger 141 is connected through the expansion valve 143 to the indoor heat exchanger 125. Reference numeral 144 represents the outdoor blower that releases heat to or takes in heat from outside the room.

The hot cooling medium compressed by the compressor 142 releases heat in the indoor heat exchanger 125 and condenses. The cooling medium thus condensed and liquefied is decompressed by the expansion valve 143, and, as it vaporizes as a result, it takes away heat of vaporization in the outdoor heat exchanger 141, and then returns to the compressor 142. In this way, heating is achieved inside the room. When a switching valve (not shown) is switched, the hot cooling medium compressed by the compressor 142 releases heat in the outdoor heat exchanger 141 and condenses. The cooling medium thus condensed and liquefied is then decompressed by the expansion valve 143, and, as it vaporizes as a result, it takes away heat of vaporization in the indoor heat exchanger 125, and then returns to the compressor 142. In this way, cooling is achieved inside the room.

The indoor fan 126, which serves as a main blower, is arranged so as to be surrounded by the C-shaped indoor heat exchanger 125 from three directions. When the indoor fan 126 is driven, the air inside the room is sucked in through the upper inlet 132 and the front inlet 131. Then, the conditioned air, i.e. the air that has been subjected to heat exchange by the indoor heat exchanger 125 so as to have its temperature conditioned is passed through the circulation passage A so as to be blown out through the air outlet 104 into the room. In the air outlet 104 is provided a horizontal louver 128 for changing the direction of the flow of air in the vertical direction, and, inside the horizontal louver 128 is provided a vertical louver 129 for changing the direction of the flow of air in the horizontal direction.

Below the indoor fan 126, as viewed in the figure, are arranged drain pans 130a and 130b for collecting the water drained when heat exchange takes place. These drain pans 130a and 130b are arranged respectively in a front portion and a rear portion inside the body casing 102. The drain pans 130a and 130b are fitted to the body casing 102, and a guide portion 102a provided integrally with the drain pan 130b forms, together with the drain pan 130a, a circulation passage A. The front drain pan 130a forms a space between the indoor heat exchanger 125 and the filter guides 129. In this space, the ion generating device unit 50 described under the section [A third embodiment of the ion generating device of the invention] is arranged. The ion generating device unit 50 is fitted to the drain pan 130a with screws.

In front of the ion blower 53 of the ion generating device unit 50 is provided a subfilter 272. The subfilter 272 is so arranged as to face the air intake opening 271 with one end protruding from the subfilter slot 270. As described earlier, the subfilter 272 can be attached and detached by being pulled substantially upward, as viewed in the figure, through the subfilter slot 270. When the ion blower 53 is driven, air is taken in through the air intake opening 271 provided in the body casing 102 and then through the subfilter 272 into the ion generating device unit 50.

Thus, the subfilter 272 prevents dust from flowing into the ion generating device unit 50 and thereby permits it to generate ions stably. Moreover, providing the subfilter 272 separately from the filters 109 and 110 through which the air to be subjected to heat exchange is passed makes maintenance easier.

As shown in FIG. 5, the ion generating device unit 50 has the ion generating element 54, the ion blower 53, and the power supply 52 arranged in a straight line. This permits the ion generating device unit 50 to be placed in the narrow space between the indoor heat exchanger 125 and the front panel 103 with the axis of the ion generating element 54 parallel to the lower front portion 125a of the indoor heat exchanger 125. Thus, it is possible to use the space inside the indoor unit 101j effectively and save space, and thereby make the indoor unit 101j compact.

Figure 46:
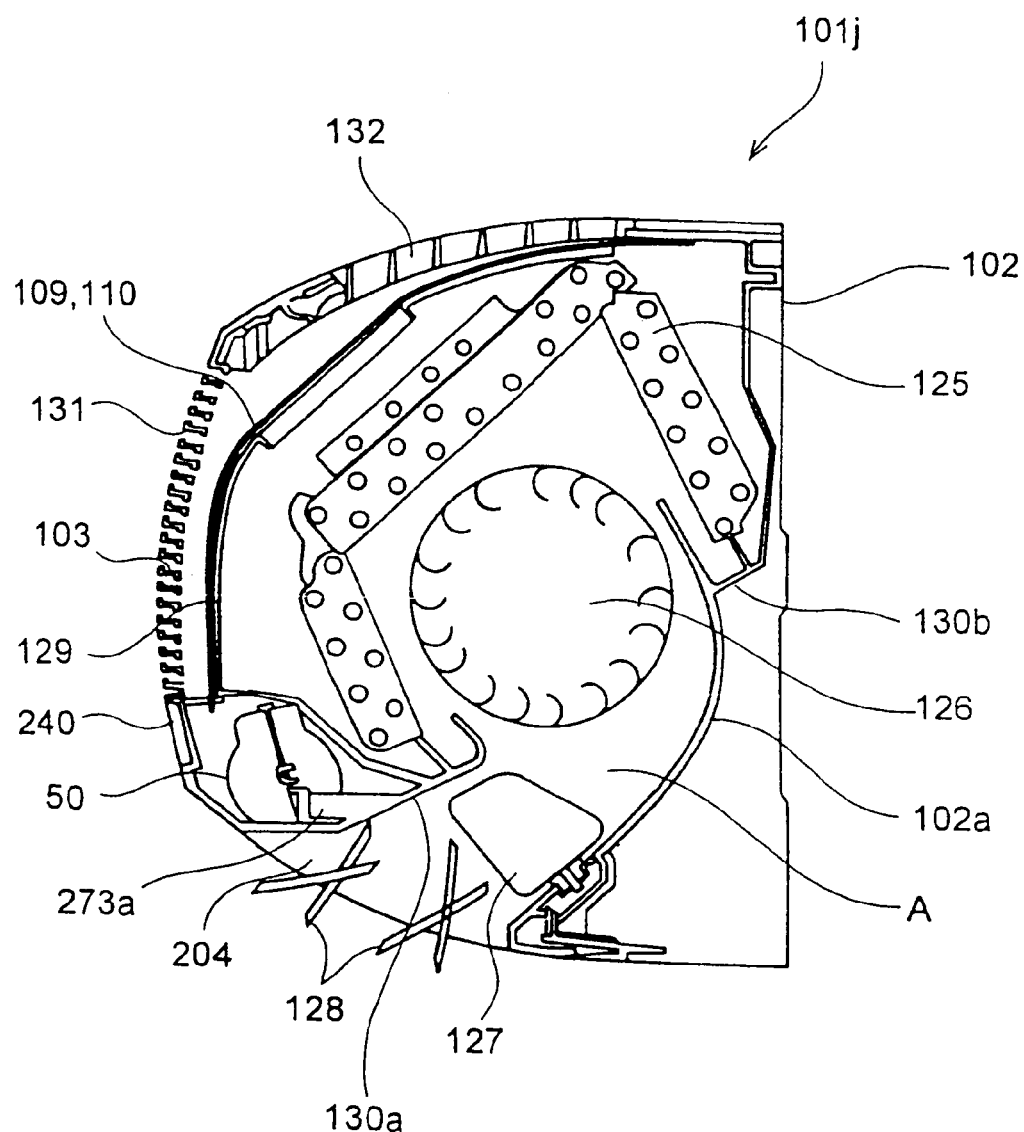
FIG. 46 is a sectional view of the indoor unit of the air conditioner of the fourteenth embodiment, taken along a plane that cuts one end of the ion generating device.
Figure 47:
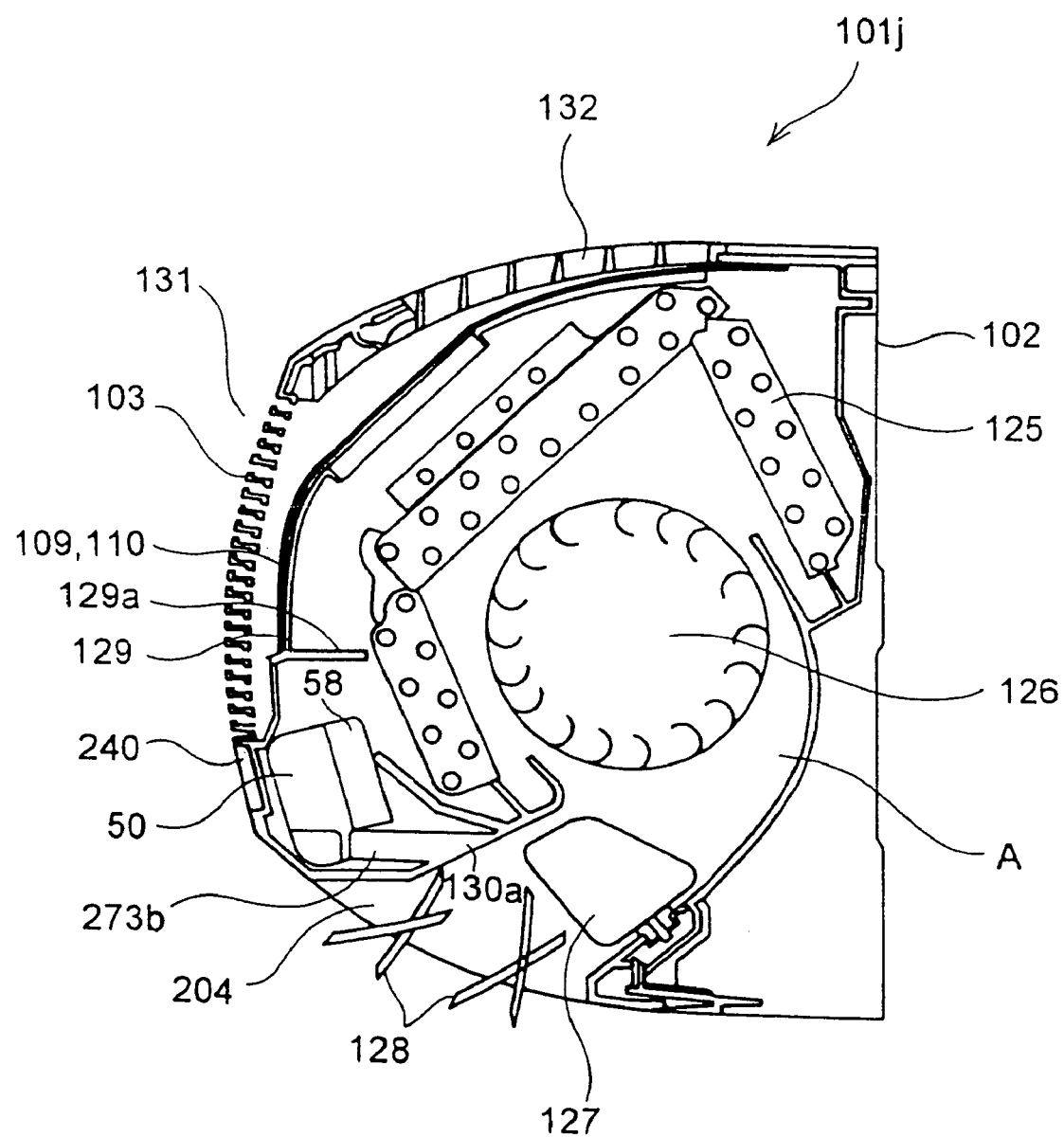
FIG. 47 is a sectional view of the indoor unit of the air conditioner of the fourteenth embodiment, taken along a plane that cuts the other end of the ion generating device.

FIGS. 46 and 47 are sectional views of the indoor unit 101j taken at each end of the ion generating device unit 50. The ion generating device unit 50 is kept in position in the direction of its length by ribs 273a and 273b provided integrally with the drain pan 130a, and is fitted to the drain pan 130a with screws put through fitting holes 71 and 72 (see FIG. 5) formed respectively in the electrode cover 58 and the power supply cover 56. The ion generating device unit 50 has the ion generating element 54, the power supply 52, and the ion blower 53 housed integrally therein to form a single unit, and this makes the assembly of the indoor unit 101j easy and thus helps reduce assembly steps.

In FIG. 43, the air intake opening 271 is formed in the vicinity of one side wall of the indoor unit 101j, and the light-sensing portion 244 is provided in the vicinity of the other side wall of the indoor unit 101j. Thus, the ion generating device unit 50, which faces the air intake opening 271, is provided in the vicinity of one side wall, and the power supply 52 is arranged in a portion inside the ion generating device unit 50 near this side wall. On the other hand, the control circuit (not shown) that drives the indoor fan 126, i.e. the main blower, the compressor 142, and other components is provided behind the light-sensing portion 244, and is thus arranged in the vicinity of the other side wall. In this way, the control circuit is arranged away from the power supply 52, which is charged with a high voltage, to reduce the effects of the noise generated by the power supply 52 on the control circuit.

In FIG. 47, on the filter guides 129, a shielding plate 129a is formed so as to cover the power supply cover 56 from above, as viewed in the figure. The shielding plate 129a prevents the risk of the user's hand or finger being put through the open filter guides 129 and making contact with the power supply 52 generating a high voltage when the filters 109 and 110 are removed.

Figure 48:
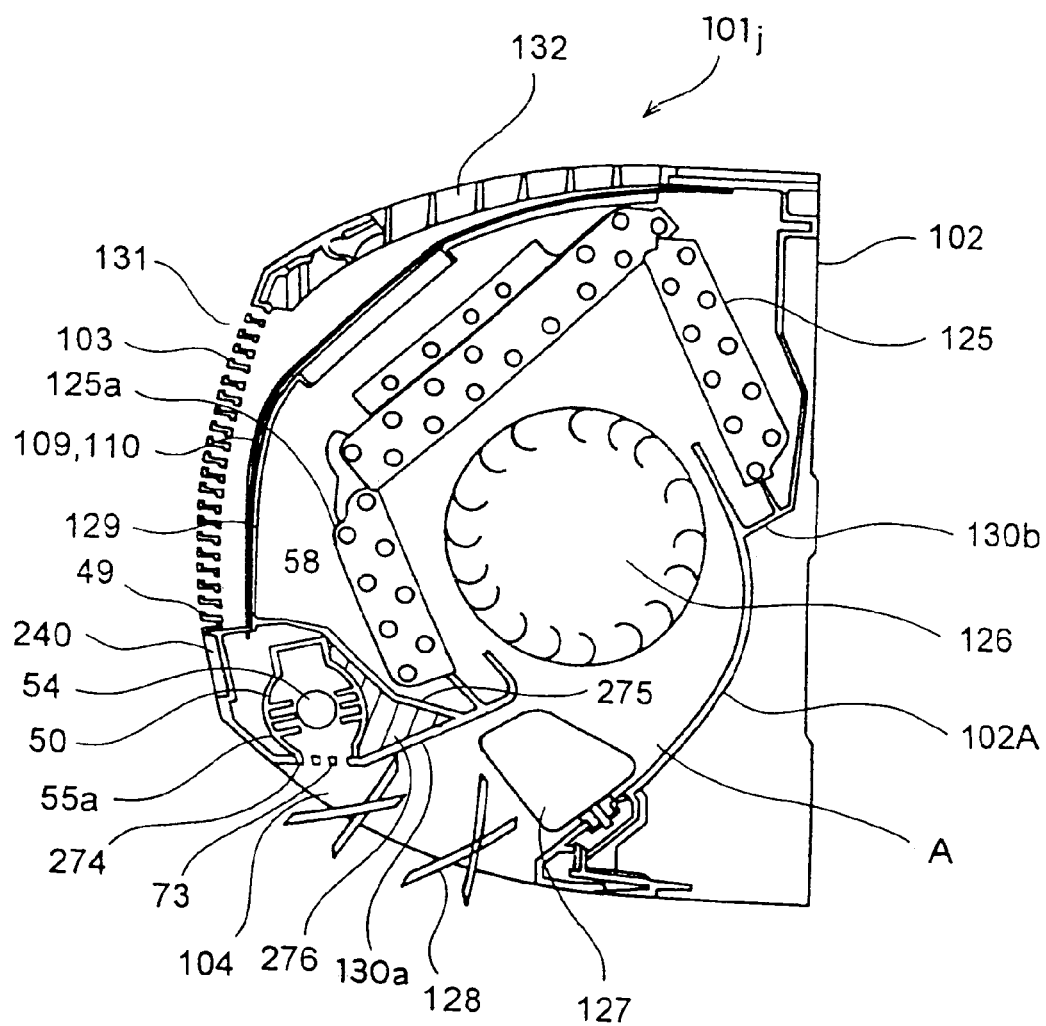
FIG. 48 is a sectional view of the indoor unit of the air conditioner of the fourteenth embodiment, taken along a plane that cuts the ion generating element.

As FIG. 48 shows, the electrode housing portion 55a of the front cover 55 of the ion generating device unit 50 is fitted into an opening 274 formed in the drain pan 130a. In the bottom surface of the electrode housing portion 55a, a discharge outlet 73 (see FIG. 8) is formed. The ions generated by the ion generating element 54 are discharged through the discharge outlet 73 by ion blower 53 driven, and then flow through the drain pan 130a into the circulation passage A. The ions are then mixed with the conditioned air and blown out through the air outlet 104 into the room by the indoor fan 126, i.e. the main blower.

Thus, by providing the ion blower 53, it is possible to prevent backflow of the air that is blown out by the indoor fan 126, i.e. the main blower. Specifically, when the horizontal louver 128 is in a predetermined orientation, it may occur that the air from the indoor fan 126 is reflected from the horizontal louver 128 so as to flow into the ion generating device unit 50, preventing the ions from being blown out into the room. Even in this situation, the ion blower 53 ensures that the ions generated by the ion generating element 54 are mixed with the conditioned air flowing through the circulation passage A so as to be blown out through the air outlet 104 into the room. This makes stable discharge of ions possible.

Moreover, the ion blower 53 does not blow out the ions directly into the room, but simply passes the ions into the circulation passage A so that they are blown out into the room by the indoor fan 126. Thus, as compared with a case where the ion blower 53 blows out the ions directly into the room, it can blow out the ions into the room with a lower output power. This helps reduce the electric power consumption by the ion generating device unit 50.

Furthermore, the discharge outlet 73 is formed directly in the opening 274 of the drain pan 130a forming the circulation passage A. This permits the ions generated by the ion generating device unit 50 to be mixed directly with the air flowing through the circulation passage A. This helps reduce loss of ions before mixing and thereby enhance the sterilizing effect achieved inside the room.

In addition, by arranging the ion generating device unit 50 between the front cover 103 and the indoor heat exchanger 125, it is possible to shorten the distance between the air outlet 104 provided in the front face of the indoor unit 101j and the ion generating element 54. This helps reduce loss of ions after mixing with the conditioned air and thereby further enhance the sterilizing effect. Since the ion generating device unit 50 is fitted to the drain pan 130a, it is easy to arrange the ion generating device unit 50 in the vicinity of the air outlet 104.

Moreover, the opening 274 of the drain pan 130a is formed in the vicinity of the horizontal louver 128, and thus the ions, after being mixed with the conditioned air flowing through the circulation passage A, are discharged into the room so as to flow in a direction determined by the horizontal louver 128. Thus, the horizontal louver 128 permits the air containing ions to be circulated all around the room, enhancing the sterilizing effect achieved inside the room.

As FIG. 8 shows, the discharge outlet 73 consists of a plurality of slits 73a formed by grid-like bars 73b (a protecting means). In this embodiment, three slits 73a are arranged in each of two rows, and each slit 73a is formed in the shape of a rectangle measuring 33 mm×50 mm. This prevents entry of foreign objects, such as a stick or the user's hand or finger, into the ion generating device unit 50 charged with a high voltage that can now be reached more easily through the air outlet 104 as a result of the air outlet 104 and the ion generating device unit 50 being placed closer together, and thus helps increase safety.

As FIG. 48 shows, with the drain pan 130a is integrally formed a separation plate 275 that separates the air directed to the indoor heat exchanger 125 and the air directed to the ion generating device unit 50. The space between the separation plate 275 and the electrode cover 58 of the ion generating device unit 50 is filled with a heat insulating material 276 such as polystyrene foam.

This prevents condensation in the ion generating device unit 50 and on the separation plate 275 caused by the indoor heat exchanger 125, which is placed on the low-temperature side during cooling or dehumidifying operation. In this way, it is possible to prevent the amount of ions generated from lowering as the humidity around the ion generating device unit 50 rises. Moreover, it is also possible to increase the insulation resistance between the drained water and the ion generating element 54 and thereby avoid hazards such as a short circuit.

Moreover, the separation plate 275 is formed with a downward inclination from front to back. Thus, even if the water drained in a front portion 125a of the indoor heat exchanger 125 splashes, it flows down the separation plate 275 and is collected in the drain pan 130a. This helps prevent hazards such as a short circuit resulting from the ion generating device unit 50 becoming wet with drained water.

Next, the operation of the air conditioner of the fourteenth embodiment will be described. When the "auto" button 253 on the remote control unit 250 is pressed, the operation lamp 241 on the display panel 240 of the indoor unit 101j is lit, and the indoor temperature is indicated on the temperature indicator 242. On the remote control unit display portion 251 of the remote control unit 250, indications appear indicating the current operation mode, i.e. automatic operation here, the volume of air, the direction of wind, and other information. Then, heating or cooling operation is performed according to the indoor temperature.

When the "cooling" button 255 on the remote control unit 250 is pressed, cooling operation is performed; when the "heating" button 254 is pressed, heating operation is performed. During cooling or heating operation, every time the right-hand side of the temperature button 257 is pressed, the specified temperature is incremented by 1° C. and, every time the left-hand side thereof is pressed, the specified temperature is decremented by 1° C. The specified temperature is indicated on the remote control unit display portion 251.

When cooling operation is performed, the switching valve (not shown) is so switched as to drive the compressor 142 with the indoor heat exchanger 125 placed on the low-temperature side. The indoor fan 126, i.e. the main blower, is driven so that the air inside the room is taken in through the air inlet 105 into the body casing 102, and the conditioned air having been subjected to heat exchange with the indoor heat exchanger 125 is passed through the circulation passage A below the drain pan 130a.

Furthermore, when the "air purification" button 258 on the remote control unit 250 is pressed, the air purification lamp 243 on the display panel 240 is lit, and the ion generating device unit 50 starts being driven. Thus, the air inside the room is taken in through the air intake opening 271 into the ion generating device unit 50 by the ion blower 53. The positive and negative ions generated by the ion generating element 54 are carried by the air flowing from the communicating opening 57a and are thereby directed through the discharge outlet 73 to the air outlet 104.

Thus, cool, conditioned air containing ions is discharged into the room so as to be spread all around. In this way, the temperature inside the room is adjusted to the specified temperature, and the airborne bacteria such as microorganisms present inside the room are killed. When the temperature inside the room reaches the specified temperature, the compressor 142 is stopped; when the temperature inside the room rises above the specified temperature, the compressor 142 starts being driven again. In this way, the specified temperature is maintained.

The amount of positive and negative ions generated varies according to the voltage applied to the ion generating element 54. In this embodiment, the voltage applied to the ion generating element 54 is set at 1.8 kV, and this permits about 80% of the airborne bacteria present inside the room to be removed in one hour after the ion generating device unit 50 starts being driven.

When heating operation is performed, the switching valve (not shown) is so switched as to drive the compressor 142 with the indoor heat exchanger 125 placed on the high-temperature side. As a result, in the same manner as described above, positive and negative ions are, together with heated, conditioned air, discharged through the air outlet 104 into the room so as to be spread all around.

When the "dehumidifying" button 256 on the remote control unit 250 is pressed, the switching valve is so switched as to drive the compressor 142 with the indoor heat exchanger 125 on the low-temperature side, and dehumidifying operation is performed. Through heat exchange with the indoor heat exchanger 125, the moisture contained in the air inside the room is condensed, and is collected in the drain pans 130a and 130b. When the temperature inside the room falls down to a predetermined temperature, the compressor 142 is stopped. At this point, the indoor fan 126, i.e. the main blower, is also stopped so as to prevent the release of moisture back into the air resulting from the evaporation of the drained water.

When the "odor elimination" button 260 on the remote control unit 250 is pressed, at the start of cooling or dehumidifying operation, the indoor fan 126 starts being driven with a predetermined delay. When the surface temperature of the indoor heat exchanger 125 is high, the dust that has settled on the surface of the indoor heat exchanger 125 produces stronger odors. By starting the driving of the indoor fan 126 with a delay, the conditioned air starts being discharged into the room after the surface temperature of the indoor heat exchanger 125 has fallen and thus with less odors. This makes it possible to deodorize the air inside the room.

When no operation is being performed, pressing the "air purification" button 258 on the remote control unit 250 causes the ion generating device unit 50, the horizontal louver 128, and the vertical louver 127 to be energized so that the ion blower 53 blows out ions into the room. This makes it possible to kill airborne bacteria inside the room and thereby purify the air inside the room even in situations such as when the temperature inside the room is such that no air conditioning is needed.

As will be clear from the descriptions above, in the ion generating device unit used in the air conditioner of this embodiment, an element support portion for keeping the ion generating element in position is provided integrally with a housing case. This makes the assembly of the ion generating device unit easy, and thus helps reduce assembly steps. Moreover, the ion generating device unit has the ion generating element, the power supply, and the ion blower housed integrally therein to form a single unit. This helps reduce the assembly steps of the apparatus that incorporates the ion generating device unit. Furthermore, there is no need to form, in the ion generating element, screw holes or the like that are insulated from the electrodes. This not only helps simplify the structure of the ion generating element and thereby reduce costs, but also helps prevent poor isolation resulting from oxidation of screws or the like and thereby prevent short-circuiting or current leakage.

Moreover, in the ion generating device unit used in the air conditioner of this embodiment, the ion generating element is formed in a cylindrical shape, and is supported at both ends by ribs formed in the housing case. This makes it easy to form the element support portion integrally with the housing case, and to support the ion generating element in position.

Moreover, in the ion generating device unit used in the air conditioner of this embodiment, the ribs are formed along the flow of air produced by the ion blower. Thus, the ribs serve to trim the flow of air and prevent the lowering of blowing efficiency without obstructing the flow of air so that ions are carried as far as possible.

Moreover, in the ion generating device unit used in the air conditioner of this embodiment, a protecting means is provided to prevent entry of foreign objects through the discharge outlet of the ion generating device unit. Thus, it is possible to prevent entry of foreign objects, such as a stick or the user's hand or finger, into the ion generating device charged with a high voltage and thereby increase safety.

Moreover, in the air conditioner of this embodiment, the incorporation of the aforementioned ion generating device unit makes it possible to kill airborne bacteria inside the room and thereby purify the air inside the room, and the unitization of the ion generating device reduces assembly steps. Moreover, there is no need to form, in the ion generating element, screw holes or the like that are insulated from the electrodes. This not only helps simplify the structure of the ion generating element and thereby reduce costs, but also helps prevent poor isolation resulting from oxidation of screws or the like and thereby prevent short-circuiting or current leakage.

Moreover, in the air conditioner of this embodiment, the ion blower, the ion generating element, and the power supply are arranged in a straight line. As a result, for example, the ion generating device unit can be arranged in the space between the heat exchanger and the front panel. This makes it possible to use the space inside the air conditioner efficiently and save space, and thereby make the air conditioner compact.

Moreover, in the air conditioner of this embodiment, the ion generating element is arranged on one side of the ion blower, and the power supply is arranged on the opposite side. This makes it possible to place the ion generating element and the power supply away from each other. Thus, it is possible to reduce the adverse effects of the noise generated by the discharging of the ion generating element on the circuit board provided inside the power supply.

Moreover, in the air conditioner of this embodiment, the control circuit that controls the operation of the air conditioner is arranged at one end of the air conditioner, and the ion generating device unit is arranged at the opposite end. This makes it possible to arrange the control circuit away from the power supply, which is charged with a high voltage, and thereby reduce the effects of the noise generated by the power supply on the control circuit.

Moreover, in the air conditioner of this embodiment, within the ion generating device unit, the power supply is arranged away from the control circuit. This makes it possible to further reduce the effects of noise.

Moreover, in the air conditioner of this embodiment, the ion blower passes ions to the air outlet, and the main blower blows them out into the room. This makes it possible to reduce the output power of the ion blower and thereby reduce the electric power consumption by the ion generating device unit.

Moreover, in the air conditioner of this embodiment, the ion generating device unit is arranged between the front cover and the heat exchanger so as to shorten the distance between the air outlet formed in the front face of the indoor unit and the ion generating device. This helps reduce loss of ions resulting from, for example, collision with the wall surface inside the distribution passages and thereby increase the ions that are blown out into the room. Thus, it is possible to enhance the sterilizing effect.

Moreover, in the air conditioner of this embodiment, a heat insulating material is arranged between the heat exchanger and the ion generating device unit. This prevents condensation around the ion generating device unit caused by the heat exchanger placed on the low-temperature side and thereby prevent the amount of ions generated from lowering as the humidity around the ion generating device unit rises.

Moreover, in the air conditioner of this embodiment, the filter provided on the suction side of the ion blower can be attached and detached through the front face of the air conditioner. This makes the cleaning of the filter easy, and thus helps keep the air blown out into the room clean.

Figure 49:
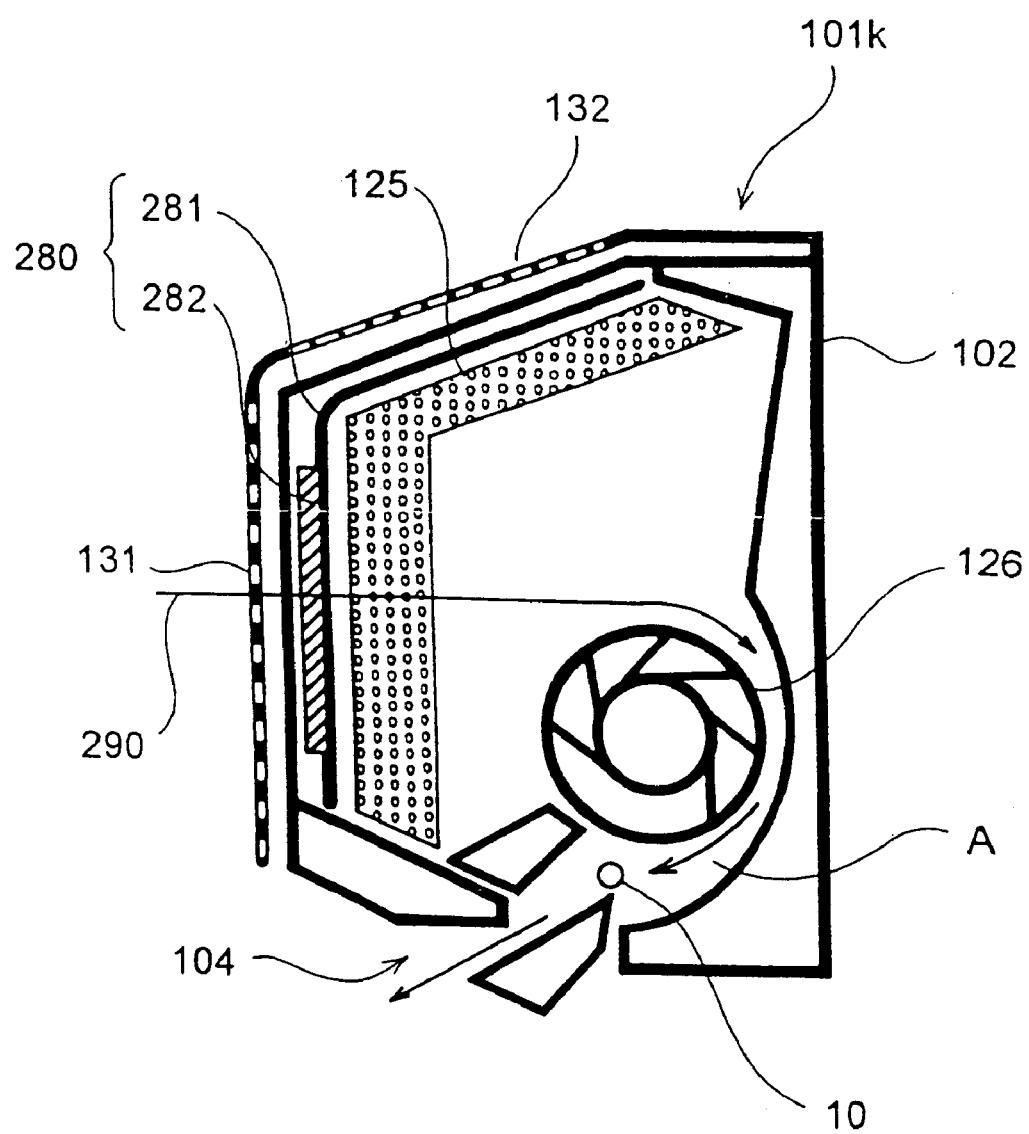
FIG. 49 is a sectional view of the indoor unit of an air conditioner as a fifteenth embodiment of the air conditioning apparatus of the invention.

FIG. 49 shows a fifteenth embodiment of the air conditioning apparatus of the invention. This embodiment is also realized as an air conditioner. This air conditioner is provided with an ion generating device that generates positive and negative ions when an alternating-current voltage is applied between the electrodes thereof and a filter portion that performs deodorization and/or dust collection, with the filter portion arranged on the upstream side of an air flow passage leading from an air inlet to an air outlet and the ion generating device arranged on the downstream side of the air flow passage.

In this construction, the filter portion arranged on the upstream side of the ion generating device removes organic compounds, dust, and the like, and thereby keeps the ion generating device almost free from dirt. This makes it possible to use the ion generating device for an extended period, to generate ions stably, and to achieve an excellent sterilizing effect by the application of a relatively low voltage as will be described later.

When ions are generated, ozone is also generated as a byproduct. The sterilizing effect of ozone can be used to synergistically augment the sterilizing effect of positive and negative ions. In that case, it is advisable to keep the concentration of ozone in the air about equal to the concentration at which it occurs naturally; specifically, it is preferable to keep the concentration of ozone equal to or lower than the level 0.1 ppm stipulated as a safety standard by Japan Society for Occupational Health.

The amount of ozone generated by the ion generating device can be controlled by controlling the root-mean-square value of the alternating-current voltage applied between the electrodes and the volume of air that passes through the air flow passage. By providing the air conditioner with an ozone sensor so that the concentration of ozone can be monitored and feeding the results of detection back to the ion generating device, it is possible to keep the concentration of ozone at a previously set level.

By keeping the root-mean-square value of the alternating-current voltage applied to the ion generating device within the range of 1.1 to 2.0 kV, it is possible to omit the safety device that is required when a higher voltage is applied between the electrodes of the ion generating device. This makes it possible to reduce costs and still obtain a sufficient amount of the radical, $H_2O_2$ or radical .OH, that exerts the sterilizing effect.

As the filter portion for deodorization and/or dust collection, it is possible to use a deodorizing filter or dust-collecting filter singly, or a combination of both. As the deodorizing filter is used a filter that can remove foul-smelling, hazardous gasses, such as ozone, and volatile organic compounds (VOCs), such as formaldehyde and toluene. More specifically, it is possible to use a filter of a type having an absorption function by containing an absorber such as activated carbon, or of a type having a decomposition function by being impregnated with a photocatalyst that decomposes substances when irradiated with light such as ultraviolet light.

In particular, when a deodorizing filter is used as the filter portion, and the deodorizing filter and the ion generating device are arranged respectively on the upstream and downstream sides of the air flow passage, it is possible to effectively use the ozone produced as a byproduct by the ion generating device while controlling its concentration in the air within the safe range.

The reason is as follows. Ozone has a longer life than positive and negative ions. Therefore, when the ion generating device is so operated as to discharge a fixed concentration of ions into the air, even if the operation conditions of the ion generating device is adjusted in an attempt to control the amount of ozone generated, there is a risk of the concentration of ozone in the air increasing above the set level. This can be avoided by adopting the construction described above in which, whereas the ion generating device discharges ions and ozone, the ions and ozone taken in together with the air through the air inlet are passed through the deodorizing filter and thus a certain amount of ozone is recaptured, with the result that the concentration of ozone in the air is kept within the permissible range. In this way, it is possible to effectively use the ozone generated by the ion generating device while controlling the concentration of ozone in the air within the safe range. The positive and negative ions that have passed through the deodorizing filter are, together with the ions generated anew by the ion generating device, discharged back into the air.

As the dust-collecting filter, it is possible to use one type of filter singly, or two or more types of filter in combination.

As described above, the deodorizing filter may be of any type as long as it can remove ozone. However, when the filter is of an absorption type that uses activated carbon, the activated carbon itself is likely to be degraded by the absorbed ozone, leading to poor filtering performance. To avoid this, as the deodorizing filter, an activated carbon filter impregnated with an ozone decomposition catalyst may be adopted. This helps prevent degradation of active carbon by ozone, and thus makes it possible to use the deodorizing filter for an extended period. Examples of the ozone decomposition catalyst include manganese dioxide and activated alumina, a particularly preferred example being manganese dioxide.

Moreover, using a granular absorbent such as granular activated carbon as the gas absorbent in the deodorizing filter offers the advantage that the gaps formed among granules of the absorbent function as a kind of dust-collecting filter, making it possible to remove dust.

Moreover, arranging the ion generating device in the vicinity of the inside of the air outlet of the air flow passage formed inside the air conditioner makes it possible to spread opposite ions efficiently all around the room.

In a case, as in this embodiment, where the air conditioning apparatus is an air conditioner, the air conditioner is provided with a heat exchanger. Dust settling on the heat exchanger lowers its heat exchange efficiency, and the heat exchanger is subject to corrosion by a corrosive substance such as ozone. For these reasons, it is preferable to configure the filter portion to perform both deodorization and dust collection; more specifically, it is preferable to use, as the filter portion, a prefilter for dust collection and a deodorizing filter for removing ozone in combination.

The indoor unit 101*k* of the air conditioner of the fifteenth embodiment, like the indoor unit 101*e* of the sixth embodiment, is essentially of the same type as those used in the first to fifth embodiments, although illustrated with a different touch in the figure. In the indoor unit 101*k*, the ion generating device 10 described under the section [A first embodiment of the ion generating device of the invention] is arranged between the indoor fan 126 and the air outlet 104.

The indoor unit 101k has a filter portion 280. The filter portion 280 is composed of, in order from the upstream side of the air flow passage 290 passing through the indoor heat exchanger 125, a deodorizing filter 282 containing activated carbon impregnated with an ozone decomposition catalyst and a prefilter formed out of a net of polypropylene.

How this indoor unit 101k eliminates airborne bacteria was evaluated, using as a reference of comparison an air conditioner that incorporated the ion generating device 10 but that had only a prefilter in its filter portion.

The evaluation tests were conducted in the following manner. In a target space 2.0 m long, 2.5 m wide, and 2.7 m high, the indoor unit 101k was installed, and common bacteria and fungi that had been cultured on a culture medium beforehand were sprayed in the target space. Then, the ion generating device 10 was activated, and the operation of the air conditioner was started. Then, at predetermined time intervals, the concentration of bacteria was measured using an air sampler. The air sampler sucked the air in the target space at a rate of 40 l/min, and sampled the air for 4 minutes.

After the sampling, the sample was applied evenly to a culture medium, and a predetermined period thereafter, the number of colonies formed on the culture medium was counted as the number of bacteria. The results are shown in a table in FIG. 50. In the table are also given the reduction rates of bacteria as calculated from the numbers of bacteria measured at the predetermined time intervals, assuming the number of bacteria immediately after the start of the test to be 100%.

In three hours after the start of operation, the air conditioner used as a reference of comparison removed 87% of the common bacteria and 90% of the fungi, and the air conditioner of this embodiment removed 89% of the common bacteria and 92% of the fungi. These results are considered to be ascribable to the fact that, in this embodiment, a deodorizing filter 44 formed out of activated carbon impregnated with ozone decomposition catalyst was used, and this deodorizing filter functioned as a dust-collecting filter. Moreover, ozone generated together with positive and negative ions was quickly decomposed and removed by the ozone decomposition catalyst, and thus no odor peculiar to ozone was recognized.

As will be clear from the descriptions above, the ion generating device used in the air conditioner of this embodiment offers a satisfactory sterilizing effect when the root-mean-square value of the high alternating-current voltage applied thereto is about 1.1 to 2.0 kV.

Moreover, by arranging the filter portion and the ion generating device respectively on the upstream and downstream sides of the air flow passage, it is possible to keep the ion generating element almost free from dirt, to generate ions stably, and to ensure an extended period of use.

In particular, in a case where a deodorizing filter is used as the filter portion, it is possible to safely use ozone that is generated as a byproduct by the ion generating device as it generates positive and negative ions, and the sterilizing effect of ozone makes it possible to synergistically augment the sterilizing effect of the radical generated through the chemical reaction between positive and negative ions.

Figure 51:
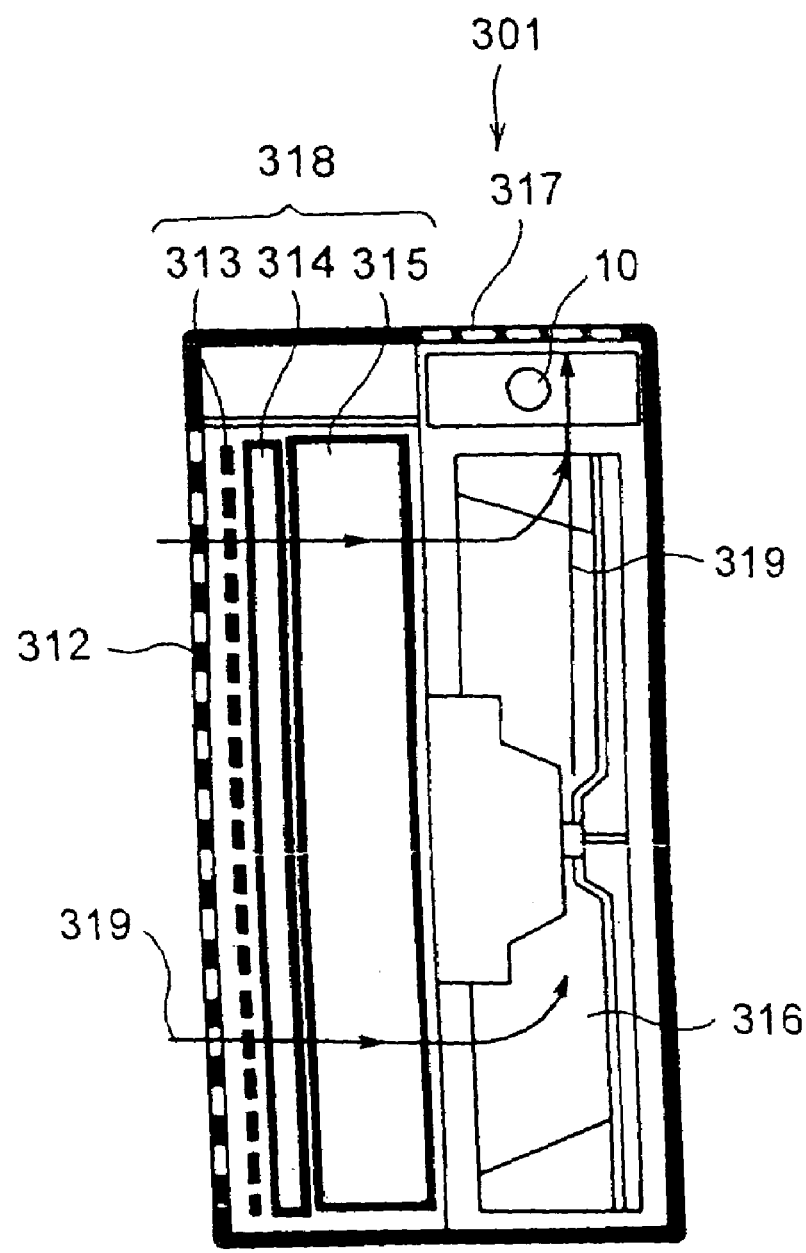
FIG. 51 is a sectional view of an air purifier as a sixteenth embodiment of the air conditioning apparatus of the invention.

FIG. 51 shows a sixteenth embodiment of the air conditioning apparatus of the invention. The air conditioning apparatus of the sixteenth embodiment is realized as an air purifier. This air purifier is provided with an ion generating device that generates positive and negative ions when an alternating-current voltage is applied between the electrodes thereof and a filter portion that performs deodorization and/or dust collection, with the filter portion arranged on the upstream side of an air flow passage leading from an air inlet to an air outlet and the ion generating device arranged on the downstream side of the air flow passage.

In this construction, as in the fifteenth embodiment, the filter portion arranged on the upstream side of the ion generating device removes organic compounds, dust, and the like, and thereby makes it possible to keep the ion generating device almost free from dirt, to use the ion generating device for an extended period, and to generate ions stably. Moreover, ozone is generated as a byproduct as ions are generated, and the sterilizing effect of ozone can be used to synergistically augment the sterilizing effect of positive and negative ions.

This sixteenth embodiment is characterized in that its filter portion is composed of, in order from the upstream side of the air flow passage, a prefilter, a deodorizing filter, and a HEPA filter. As the deodorizing filter is used a filter that can remove foul-smelling, hazardous gasses, such as ozone, and volatile organic compounds (VOCs), such as formaldehyde and toluene. More specifically, it is possible to use a filter of a type having an absorption function by containing an absorber such as activated carbon, or of a type having a decomposition function by being impregnated with a photocatalyst that decomposes substances when irradiated with light such as ultraviolet light. A dust-collecting filter composed of a HEPA (high-efficiency particulate air) filter can collect 99.97% or more of dust particles 0.3 μm across and remove bacteria killed by the action of ions and ozone. A HEPA filter is prone to clogging precisely because of its high performance. Therefore, on the upstream side of the HEPA filter is arranged the prefilter that removes larger particles of dust, and the deodorizing filter is arranged to follow it. Thus, clogging associated with dust collection occurs largely in the prefilter, and gases, such as VOCs, and ozone, which degrades the HEPA filter, are removed by the deodorizing filter. This alleviates the clogging and degradation of the HEPA filter, and thus helps make its replacement necessary less frequently than the prefilter and the deodorizing filter.

As in the fifteenth embodiment, the deodorizing filter may be of any type as long as it can remove ozone. However, when the filter is of an absorption type that uses activated carbon, the activated carbon itself is likely to be degraded by the absorbed ozone, leading to poor filtering performance. To avoid this, as the deodorizing filter, an activated carbon filter impregnated with an ozone decomposition catalyst may be adopted. This helps prevent degradation of active carbon by ozone, and thus makes it possible to use the deodorizing filter for an extended period. Examples of the ozone decomposition catalyst include manganese dioxide and activated alumina, a particularly preferred example being manganese dioxide. Using a granular absorbent such as granular activated carbon as the gas absorbent in the deodorizing filter offers the advantage that the gaps formed among granules of the absorbent function as a kind of dust-collecting filter, making it possible to remove dust.

Moreover, arranging the ion generating device in the vicinity of the inside of the air outlet of the air flow passage formed inside the air purifier makes it possible to spread opposite ions efficiently all around the room. This air purifier can be used in any location as long as it is used for the purpose of purifying the air; for example, it can be used in a room in a building, in a vehicle, or in a toilet.

In the air purifier 301 shown in FIG. 51, an air flow passage 319 is formed that has an air inlet 312 through which air is taken in from the outside and an air outlet 317 through which the air thus taken in is discharged back to the outside after being purified. In the vicinity of the air outlet 317 of the air flow passage 319, the ion generating device 10 described under the section [A first embodiment of the ion generating device of the invention] is arranged. Between this ion generating device 10 and a filter portion 318, a blower fan 316 is arranged.

The filter portion 318 is composed of, in order from the upstream side of the air flow passage 319, a prefilter 313 formed out of a net of polypropylene, a deodorizing filter 314 containing activated carbon impregnated with an ozone decomposition catalyst, and a HEPA filter 315. In this arrangement, ordinary dust is largely removed by the prefilter 313, gasses, such as VOCs, and ozone are removed by the deodorizing filter 314, and fine particles, such as pollen and killed bacteria, are removed by the HEPA filter 315. This helps make the replacement of the HEPA filter 315 necessary less frequently.

As described under the section [A first embodiment of the ion generating device of the invention], when a voltage of 1.1 to 2.0 kV (in an root-mean-square value) having a frequency of 15 kHz was applied to the ion generating device 10, detecting small ions with mobility of 1 $cm^2/V \cdot sec$ or higher at a distance of 20 cm from the side surface of the glass tube 11 resulted in counting 200,000 to 400,000 ions/cc of positive and negative ions simultaneously.

As shown FIG. 51, the ion generating device 10 having the characteristics described above was placed in the vicinity of the air outlet 317 of the air flow passage 319, and how it removes airborne bacteria was evaluated. As a reference of comparison, an air purifier that incorporated the ion generating device 10 but that had only an ordinary filter in its filter portion was used so that its performance was compared with that of the air purifier 301 of this embodiment.

The evaluation tests were conducted in the following manner. In a target space 2.0 m long, 2.5 m wide, and 2.7 m high, the air purifier was installed, and common bacteria and fungi that had been cultured on a culture medium beforehand were sprayed in the target space. Then, the ion generating device 10 was activated and the operation of the air purifier was started. Then, at predetermined time intervals, the concentration of bacteria was measured using an air sampler. The air sampler sucked the air in the target space at a rate of 40 l/min, and sampled the air for 4 minutes.

After the sampling, the sample was applied evenly to a culture medium, and a predetermined period thereafter, the number of colonies formed on the culture medium was counted as the number of bacteria. The results are shown in a table in FIG. 52. In the table are also given the reduction rates of bacteria as calculated from the numbers of bacteria measured at the predetermined time intervals, assuming the number of bacteria immediately after the start of the test to be 100%.

In three hours after the start of operation, the air purifier used as a reference of comparison removed 83% of the common bacteria and 88% of the fungi, and the air purifier of this embodiment removed 90% of the common bacteria and 91% of the fungi.

Thus, the air purifier 301 incorporating the ion generating device of this embodiment was found to be able to remove most airborne bacteria (microorganisms) very effectively. Moreover, ozone generated together with positive and negative ions was decomposed and removed by the ozone decomposition catalyst, and thus, even when the air purifier was operated continuously, no odor peculiar to ozone was recognized.

As will be clear from the descriptions above, the ion generating device used in the air purifier of this embodiment offers a satisfactory sterilizing effect when the root-mean-square value of the high alternating-current voltage applied thereto is about 1.1 to 2.0 kV.

Moreover, by arranging the filter portion and the ion generating device respectively on the upstream and downstream sides of the air flow passage, it is possible to keep the ion generating device almost free from dirt, to generate ions stably, and to ensure an extended period of use.

In particular, in a case where a deodorizing filter is used as the filter portion, it is possible to safely use ozone that is generated as a byproduct by the ion generating device as it generates positive and negative ions, and the sterilizing effect of ozone makes it possible to synergistically augment the sterilizing effect of the radical generated through the chemical reaction between positive and negative ions.

Alternatively, in a case where, as the filter portion, a dust-collecting filter consisting of a prefilter and a HEPA filter is used in combination with a deodorizing filter, with the prefilter and the HEPA filter arranged respectively on the upstream and downstream sides of the deodorizing filter, it is possible to alleviate the clogging and degradation of the HEPA filter and thereby make its replacement necessary less frequently than the prefilter and the deodorizing filter.

FIGS. 53 to 61 show a seventeenth embodiment of the air conditioning apparatus of the invention. The air conditioning apparatus of the seventeenth embodiment is also realized as an air purifier. This air purifier 401 has a body 410 having the shape of a flat box placed upright, a base 411 that supports the body 410, and a front panel 412 that is fitted on one side face (in the example under discussion, the front face) of the body 410 with a gap left in between. The front panel 412 is gently curved along the curvature of the front face of the body 410, and has an air inlet 413, in the form of a plurality of vertical slits arranged horizontally, formed in a central portion thereof. Although not illustrated in the figures, horizontal bars for reinforcing the vertical bars separating the slits are provided in some positions on the rear surface of the front panel 412. Air is sucked in not only through this air inlet 413, but also through a side air inlets 414 formed in the gap between the front panel 412 and the body 410 at four sides of the front panel 412. The inlet area (the area of the opening through which air passes) of the side air inlets 414 is larger than the inlet area of the air inlet 413.

Figure 54:
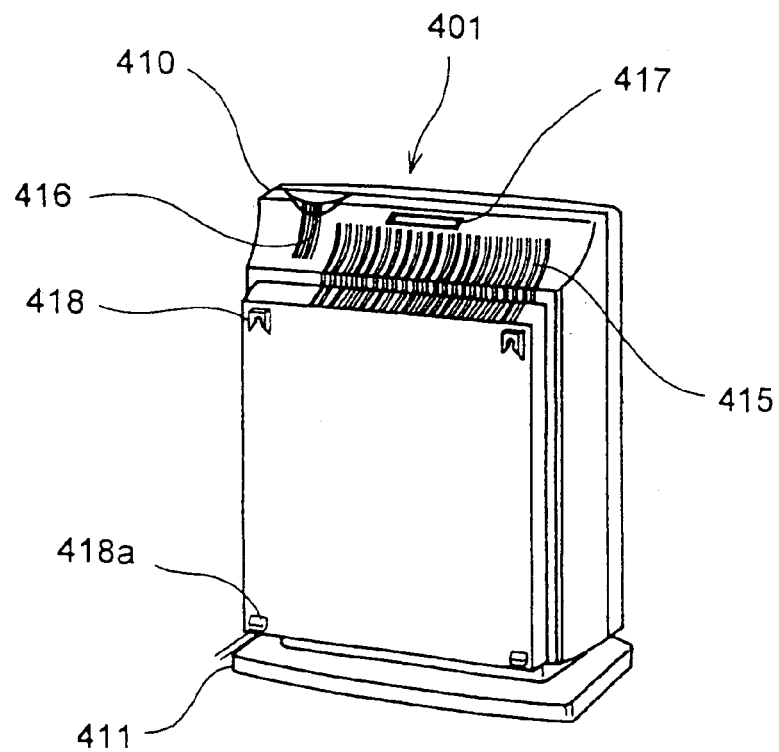
FIG. 54 is a rear perspective view of the air purifier of the seventeenth embodiment.

As FIG. 54 shows, in an upper portion of the rear face of the body 410, a main air outlet 415 and a sub air outlet 416 are formed. The main air outlet 415 and the sub air outlet 416 are both in the form of a plurality of vertical slits arranged horizontally. Reference numeral 417 represents a grip, and reference numeral 418 represents wall hanging holes used when the body 410 is hung on a wall by the use of separately provided metal fittings (not shown) or the like for wall hanging. In a lower portion of the rear face of the body 410, wall rests 418a are provided that are used to keep the body 410 upright when it is hung on a wall by the use of the wall hanging holes 418. These are formed on a rear shell 475 (described later) of the body 410.

Figure 56:
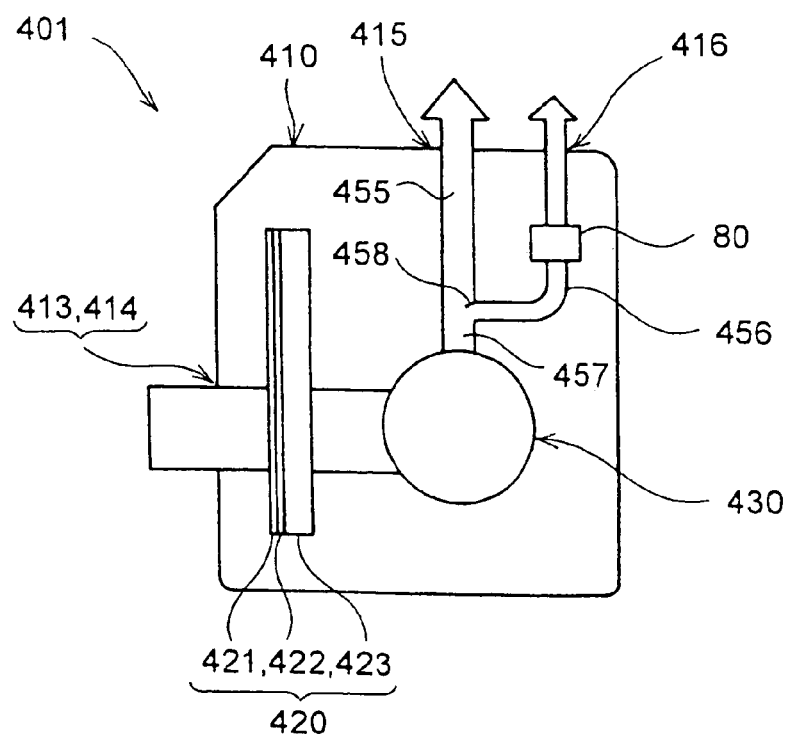
FIG. 56 is a diagram schematically illustrating the flow of air inside the air purifier of the seventeenth embodiment.
Figure 57:
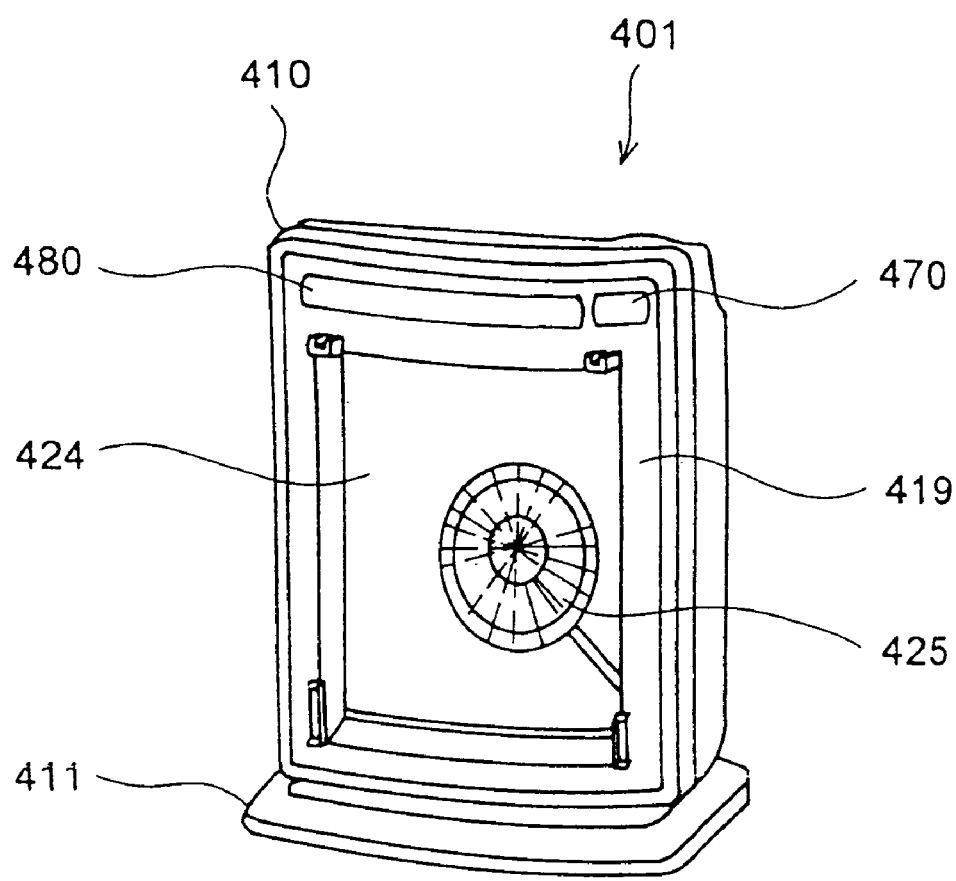
FIG. 57 is a perspective view of the air purifier of the seventeenth embodiment, with its front panel and filter portion removed.

FIG. 56 schematically shows the arrangement of principal components and the flow of air inside the body 410. Reference numeral 420 represents a filter portion, reference numeral 430 represents a blower, and reference numeral 80 represents an ion generating device. The ion generating device 80 is the one described under the section of [A fourth embodiment of the ion generating device of the invention]. When the blower 430 is driven, air is sucked in through the air inlet 413 and the side air inlets 414, and is directed through the filter portion 420 to the blower 430. On the downstream side of the blower 430, the air flow passage bifurcates into two branch passages. One of the two branch passages forms a main passage 455 that leads to the main air outlet 415, and the other forms a bypass passage 456 that leads to the sub air outlet 416.

Most of the air that has left the blower 430 is blown out through the main air outlet 415, and the rest of the air is blown out through the sub air outlet 416. In the middle of the bypass passage 456 leading to the sub air outlet 416, the ion generating element 80 is arranged so that the positive and negative ions generated by the ion generating element 80 are blown out into the air.

Figure 59:
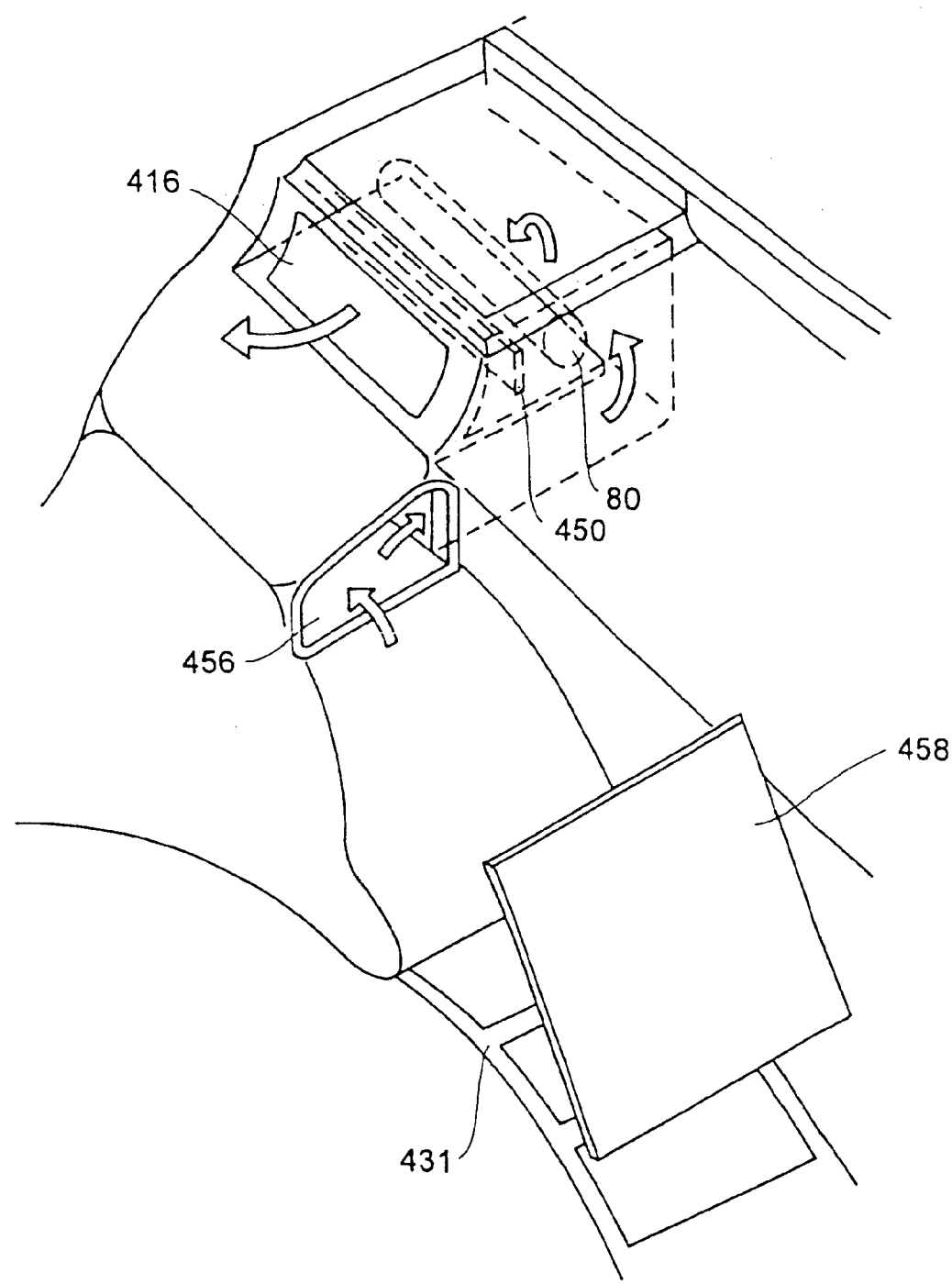
FIG. 59 is a perspective view of a portion of the inside of the air purifier of the seventeenth embodiment.

At the branch portion 457 between the main passage 455 and the bypass passage 456, a means for adjusting the flow rate of air is provided. The air flow-rate adjusting means is realized, for example, by the use of a damper 458 as shown in FIG. 59. The damper 458 is so configured that how open it is can be adjusted manually or electrically. A single damper 458 may be shared between the main passage 455 and the bypass passage 456 so that, as it becomes wider open to one passage, it becomes accordingly narrower to the other passage. Alternatively, two dampers may be provided separately in the main passage 455 and the bypass passage 456. The provision of such an air flow-rate adjusting means permits adjustment of the overall flow rate of air, or adjustment of the distribution of the flow rates of air through the main passage 455 and the bypass passage 456. This makes it possible to keep the concentration of ions generated by the ion generating element 80 substantially constant irrespective of the volume of air.

Figure 55:
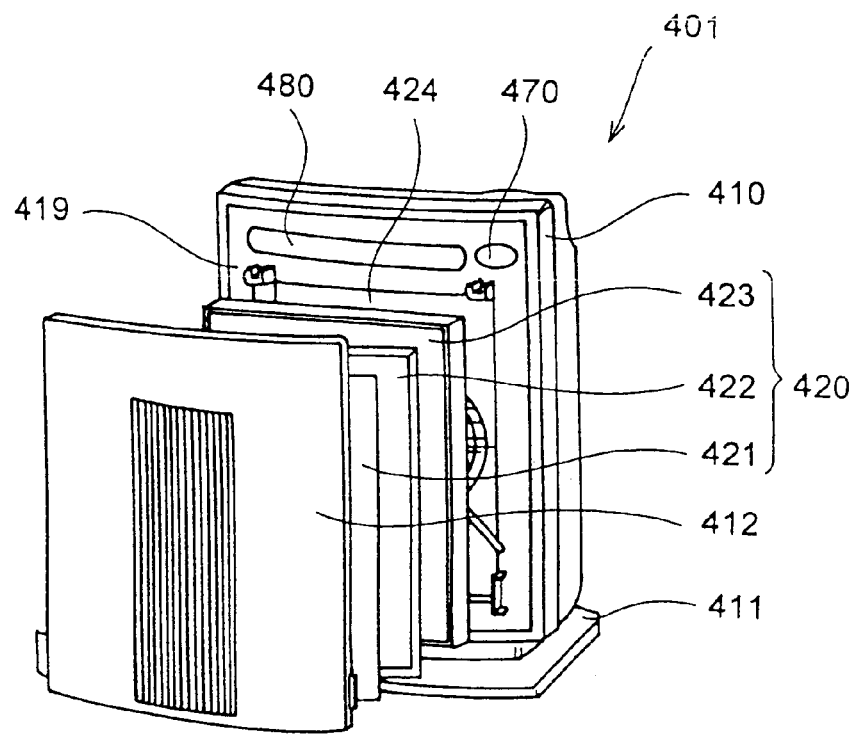
FIG. 55 is an exploded perspective view of the air purifier of the seventeenth embodiment, showing how its front panel and filters are arranged.

Next, the configuration of the filter portion 420 will be described. The filter portion 420 is composed of three types of filter, namely, as FIG. 55 shows, from the front side, a prefilter 421, a deodorizing filer 422, and a dust-collecting filter 423. The prefilter 421 is formed out of polypropylene, and collects larger particles of dust from the air sucked in. The deodorizing filer 422 has a three-layer structure; specifically, it is produced by stretching a piece of nonwoven fabric of polyester on a rectangular frame, then dispersing activated carbon evenly over it, and then stretching another piece of nonwoven fabric of polyester over it. The deodorizing filer 422 absorbs odor-causing molecules, such as acetaldehyde, ammonia, and acetic acid, present in the air. The dust-collecting filter 423 is a HEPA filter produced by forming a filtering material by laying an electric-type melt-blown nonwoven fabric over a structural material formed out of polyester/vinylon-based unwoven cloth, then folding up the filtering material, then laying and thermocompression-bonding antibacterial sheets formed out of unwoven cloth treated with hydroxyapatite over the top and bottom surfaces thereof, and then fusion-bonding a frame formed out of unwoven cloth with hot-melt adhesive thereto. The dust-collecting filter 423 collects fine particles of dust.

In the front face of the body 410, a rectangular recess 424 is formed, and the three types of filter described above are housed in this recess 424. In the innermost wall of the recess 424, a ventilation opening 425 is formed that leads to the blower 430 (see FIG. 57).

Next, the structure of the blower 430 will be described with reference to FIG. 58. Reference numeral 431 represents a fan, and the reference numeral 432 represents a motor by which the fan 413 is rotated. In the figure, a turbo fan is used as the fan 431, but the fan 413 may be of any other type; for example, a propeller fan or cross-flow fan may be used. The turbo fan shown in the figure is made relatively thick as compared with its fan diameter with a view to reducing the rotation speed and thereby reducing the noise level. As the motor 432, a DC motor is used for its good controllability.

The air that has left the fan 431 flows upward. Then, most of the air is discharged through the main air outlet 415, and the rest thereof enters the bypass passage 456. The bypass passage 456 leads to the sub air outlet 416, and the ion generating element 80 is arranged on the way.

On the downstream side of the ion generating element 80 is provided an ozone reducing device 450, which is for reducing ozone that is generated inevitably when ions are generated by applying an alternating-current voltage between electrodes. Although ozone naturally decomposes to oxygen, the presence of an ozone decomposition catalyst prompts the decomposition. Therefore, a metal mesh having an ozone decomposition catalyst deposited on its surface is prepared as the ozone reducing device 450. As the ozone decomposition catalyst, any substance known as such can be used, examples including manganese dioxide, platinum, lead dioxide, copper (II) oxide, and nickel.

To impregnate the metal mesh with the ozone decomposition catalyst, first the ozone decomposition catalyst is dispersed in the binder material, and then the surface of the metal mesh is coated with the mixture by a coating process such as dipping, spinning, or spraying. The amount of the ozone decomposition catalyst used is determined according to the amount of ozone to be generated.

Instead of preparing an ozone reducing device separately, it is also possible to provide the ion generating element 80 itself with an ozone reducing function. In that case, at least one of the dielectric 27, the inner electrode 28, and the outer electrode 29 is impregnated with an ozone decomposition catalyst.

Figure 58:
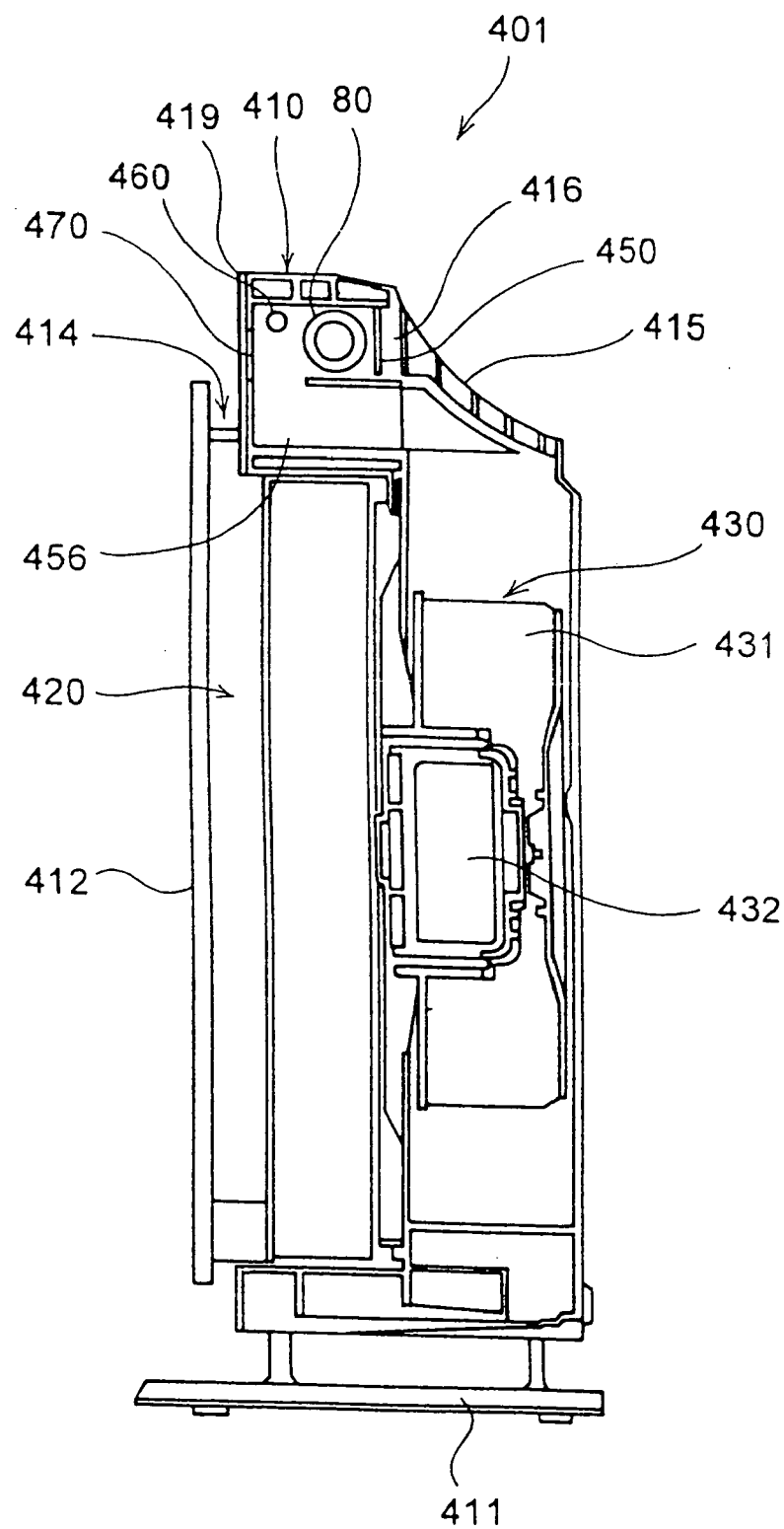
FIG. 58 is a vertical sectional view of the air purifier of the seventeenth embodiment.
Figure 60:
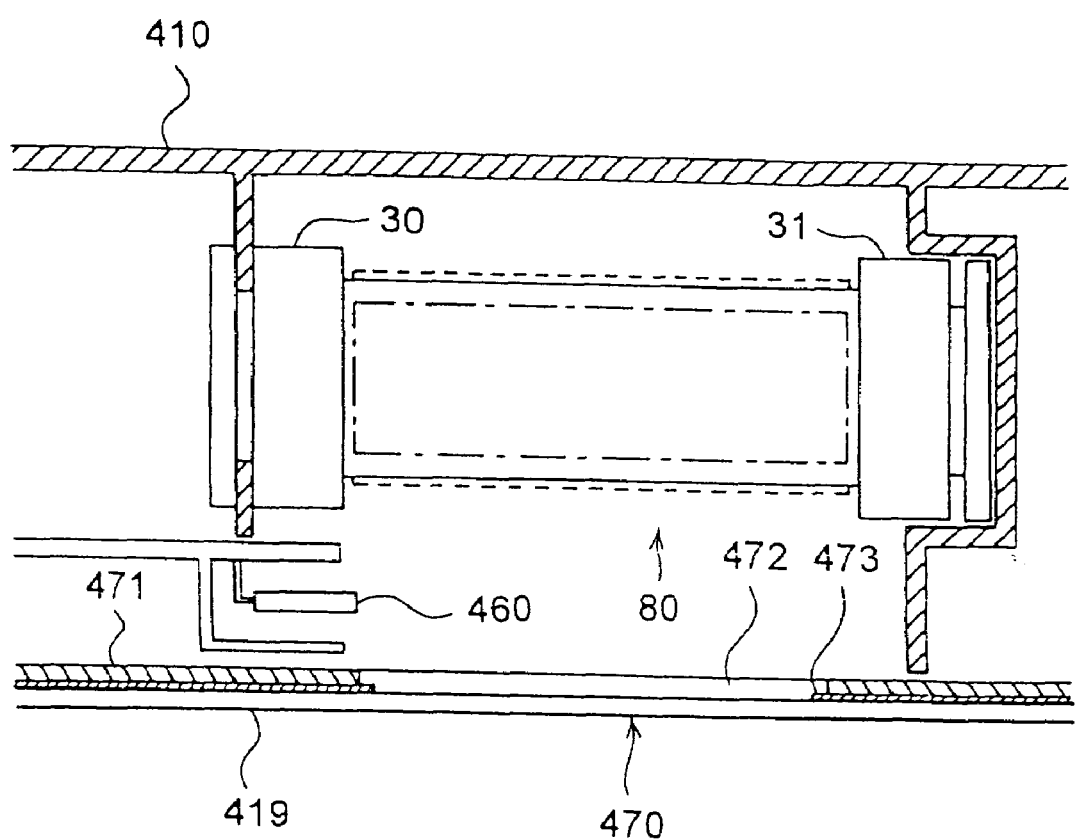
FIG. 60 is a horizontal sectional view of a portion, where the ion generating device is arranged, of the air purifier of the seventeenth embodiment.

As FIGS. 58 and 60 show, in the vicinity of the ion generating element 80 is provided a light-emitting portion 460. The light-emitting portion 460 has a light-emitting element so that, when the ion generating element 80 is being driven, it is illuminated with blue, green, or other light emitted by the light-emitting element. This contributes to clear indication of the operation status of the ion generating element 80 when it is being operated, and thus helps increase usability.

Figure 53:
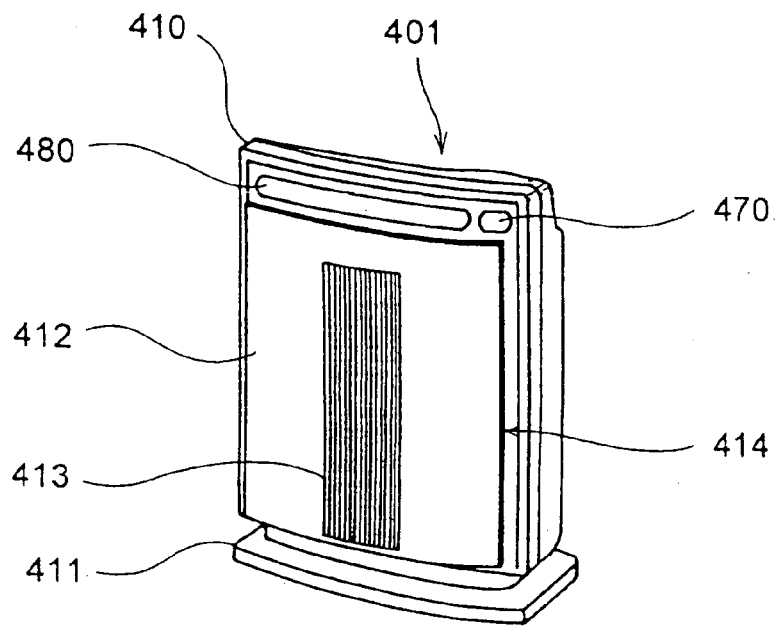
FIG. 53 is a front perspective view of an air purifier as a seventeenth embodiment of the air conditioning apparatus of the invention.

As FIG. 53 shows, the front panel 412 is put on the front face of the body 410, is somewhat larger than the recess 424 in which the filter portion 420 is housed, has a shape slightly curved so as to be convex, and is arranged so as to cover and hide the filter portion 420 as viewed from ahead.

On the front face of the body 410, a front cover 419 is laid. The front cover 419 is molded out of transparent plastic, and its rear surface is coated with a thin film of paint so as to offer a tone of color associated with cleanliness as a whole. This helps emphasize the image of the air purifier 401 as a health-related product. Specifically, paint of a metallic silver color is used to emphasize cleanliness. Instead of painting, silk-screen printing may be used.

In an upper right portion of the front face of the body 410, a sight window 470 is provided so as to permit the ion generating element 80 to be checked from outside the body. As FIG. 60 shows, the portion of the front face of the body 410 in which the sight window 470 is provided has a two-layer structure, with an outer shell 471 laid beneath the front cover 419.

The outer shell 471 of the body 410 is formed out of opaque synthetic resin, and has an elliptic hole 472 formed therein. As described above, on the outer surface of the outer shell 471, the front cover 419 formed out of transparent synthetic resin is laid. As described above, on the rear surface of the front cover 419, a film 473 of paint or silk-screen printing is formed, but this film 473 dos not cover the portion of the front cover 419 that faces the hole 472 so as to leave this portion transparent as the sight window 470. Through this transparent sight window 470, the ion generating element 80 can be checked. The hole 472 is covered with the front cover 419, and therefore it never occurs that the user's finger slips into the hole 472 and touches the ion generating element 80. This helps ensure safety. Through the sight window 470, it is possible to make various checks relating to the ion generating element 80, such as checking for dust that has settled thereon.

By the side of the sight window 470 is provided an operation panel portion 480, in which switches for turning the operation on/off and switching the operation mode are provided.

Next, the operation and functions of the air purifier 401 will be described. When the air purifier 401 starts being operated, the motor 432 starts rotating the fan 431, and thus the air inside the room is sucked in through the air inlet 413 of the front panel 412 and through the side air inlets 414. The air sucked in is passed through the prefilter 421, which collects larger particles of dust, and is then passed through the deodorizing filer 422, which absorbs odor-causing molecules such as acetaldehyde, ammonia, and acetic acid. The air that has passed through the deodorizing filer 422 is then passed through the dust-collecting filter 423, which collects finer particles of dust, and is then, as clean air free from odors or dust, blown out through the main air outlet 415 into the room.

Not all of the air that has left the fan 431 is blown out through the main air outlet 415, but part of it enters the bypass passage 456 and flows to the ion generating element 80. In the ion generating element 80, an alternating-current voltage of about 1.75 kV is applied between the inner and outer electrodes 28 and 29, and positive and negative ions are generated outside the dielectric 27. While the ion generating element 80 is generating ions, the light-emitting portion 460 illuminates the ion generating element 80 and thereby permits it to be checked from the outside through the sight window 470. The light-emitting portion 460 may be placed inside the glass tube constituting the dielectric 27 so that the ion generating element 80 appears to be emitting light from within. It is also possible to apply to the glass tube constituting the dielectric 27 special paint sensitive to an electric field so that the color of the paint changes according to whether the high alternating-current voltage is being applied between the inner and outer electrodes 28 and 29 or not and thus the glass tube constituting the dielectric 27 appears to change its color accordingly.

Figure 61:
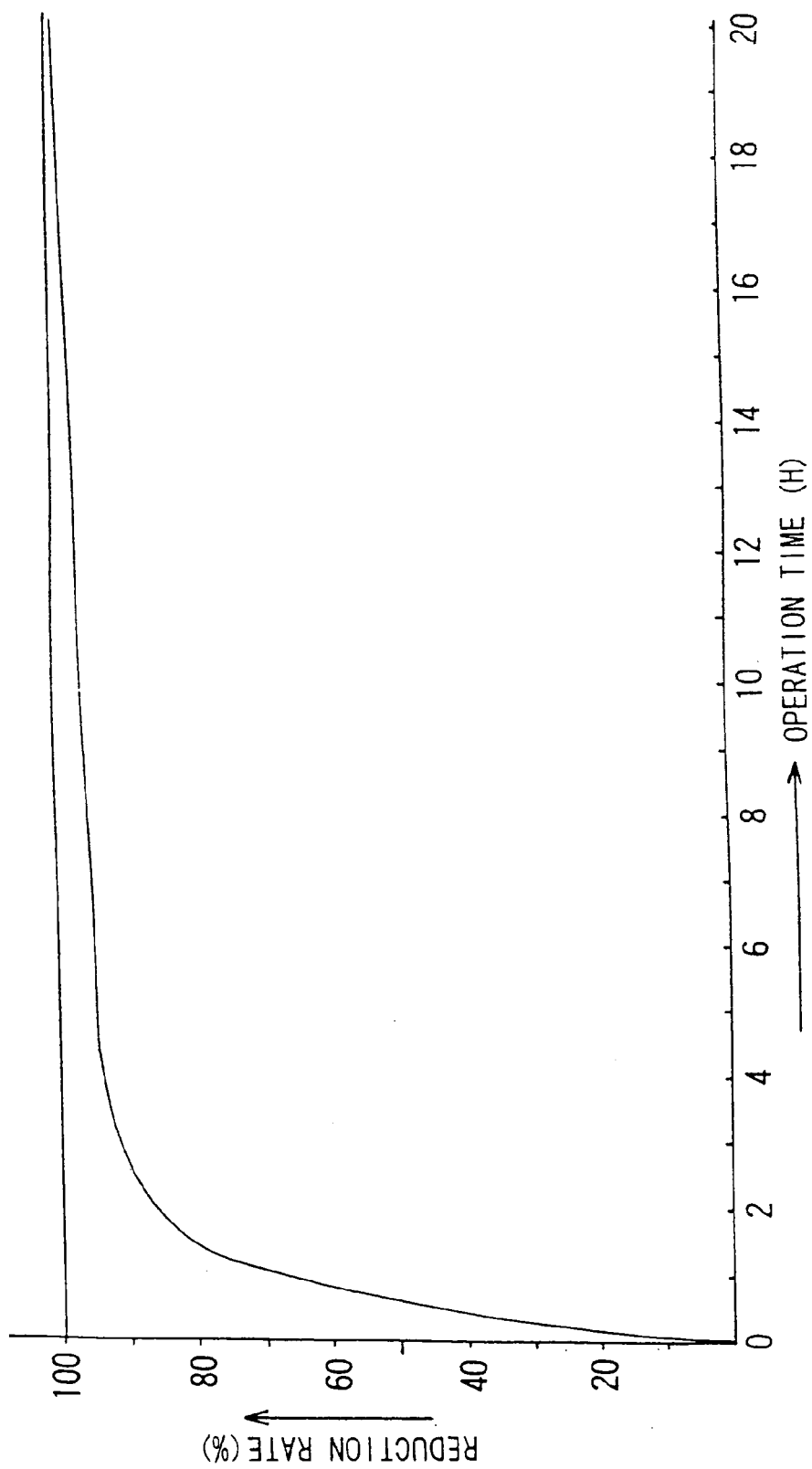
FIG. 61 is a diagram showing how the air purifier of the seventeenth embodiment removes airborne bacteria.

The positive and negative ions discharged through the sub air outlet 416 chemically react with each other and generate hydrogen peroxide $H_2O_2$ or radical hydroxyl (.OH) as a radical. By the strong activity of hydrogen peroxide $H_2O_2$ or radical hydroxyl (.OH), airborne bacteria present in the air are killed. As the results of performance tests listed in FIG. 61 show, in two hours, four hours, and twenty hours after the start of operation, it was possible to remove 86%, 93%, and 99%, respectively, of fungi.

The ion generating element 80 generates positive and negative ions, and simultaneously generates also ozone. Since ozone is hazardous to the human body, an increase in the amount of ozone present in the air is undesirable, and therefore it is necessary to keep its concentration to a permissible level. This is the reason that the ozone reducing device 450 having a metal mesh impregnated with an ozone decomposition catalyst is arranged on the downstream side of the ion generating element 80. As air containing ozone passes through the ozone reducing device 450, the ozone is decomposed. Thus, the concentration of ozone in the air discharged through the sub air outlet 416 can be held down to one-tenth or less of the level 0.1 ppm stipulated as a safety standard by Japan Society for Occupational Health. In this way, it is possible to discharge positive and negative ions together with air that has been subjected to dust collection and deodorization into the room and thereby remove airborne bacteria present in the air inside the room.

As will be clear from the descriptions above, the air purifier of this embodiment, provided with a blower that circulates the air inside the room, is further provided with an ion generating device including as its principal component an ion generating element that generates positive and negative ions when an alternating-current voltage is applied between the electrodes thereof. Thus, it is possible to spread positive and negative ions all around the room to achieve sterilization by the action of the radical generated through the chemical reaction between positive and negative ions. Moreover, an ion reducing device that reduces ozone generated as a byproduct as ions are generated is provided on the downstream side of the ion generating device. Thus, it is possible to limit the amount of ozone to a level safe for the human body.

In addition, a filter that removes dust from the air is provided on the upstream side of the ion generating device. This makes it possible to remove dust from the air circulated and thereby keep the ion generating device free from dust. Furthermore, by providing a filter that deodorizes the air on the upstream side of the ion generating device, it is possible to enhance the freshness of the air inside the room.

Moreover, by providing a branch portion of the air flow passage on the downstream side of the blower and arranging the ion generating device in one of the branch passages, and in addition providing a means for adjusting the flow rate of air at the branch portion, it is possible to adjust the total volume of air or the distribution of volumes of air through different passages. As a result, it is possible to eliminate the effect of the volume of air on the amount of ions generated by the ion generating device and thereby obtain a substantially fixed concentration of ions.

Moreover, by providing a light-emitting portion in the vicinity of the ion generating device and controlling the emission of light therefrom in a manner interlocked with the driving of the ion generating device, it is possible to permit the user to confirm the operation status of the ion generating device and thereby enhance usability. Moreover, a sight window through which the ion generating device can be viewed is provided in front of the ion generating device, and this permits the user to check and monitor the ion generating device from outside the body.

Moreover, by laying on the outer shell of the body a cover formed out of a transparent material having its rear surface coated with a thin film of paint so as to give a clean appearance, it is possible to emphasize the image of the air purifier as a health-related product.

FIGS. 62 to 83 show an eighteenth embodiment of the air conditioning apparatus of the invention. The air purifier 401a of this eighteenth embodiment is the same as the air purifier 401 of the seventeenth embodiment in many respects, and therefore such components as are common to both embodiments are identified with the previously used reference numerals, and their explanations will not be repeated; that is, only new components will be described.

Figure 62:
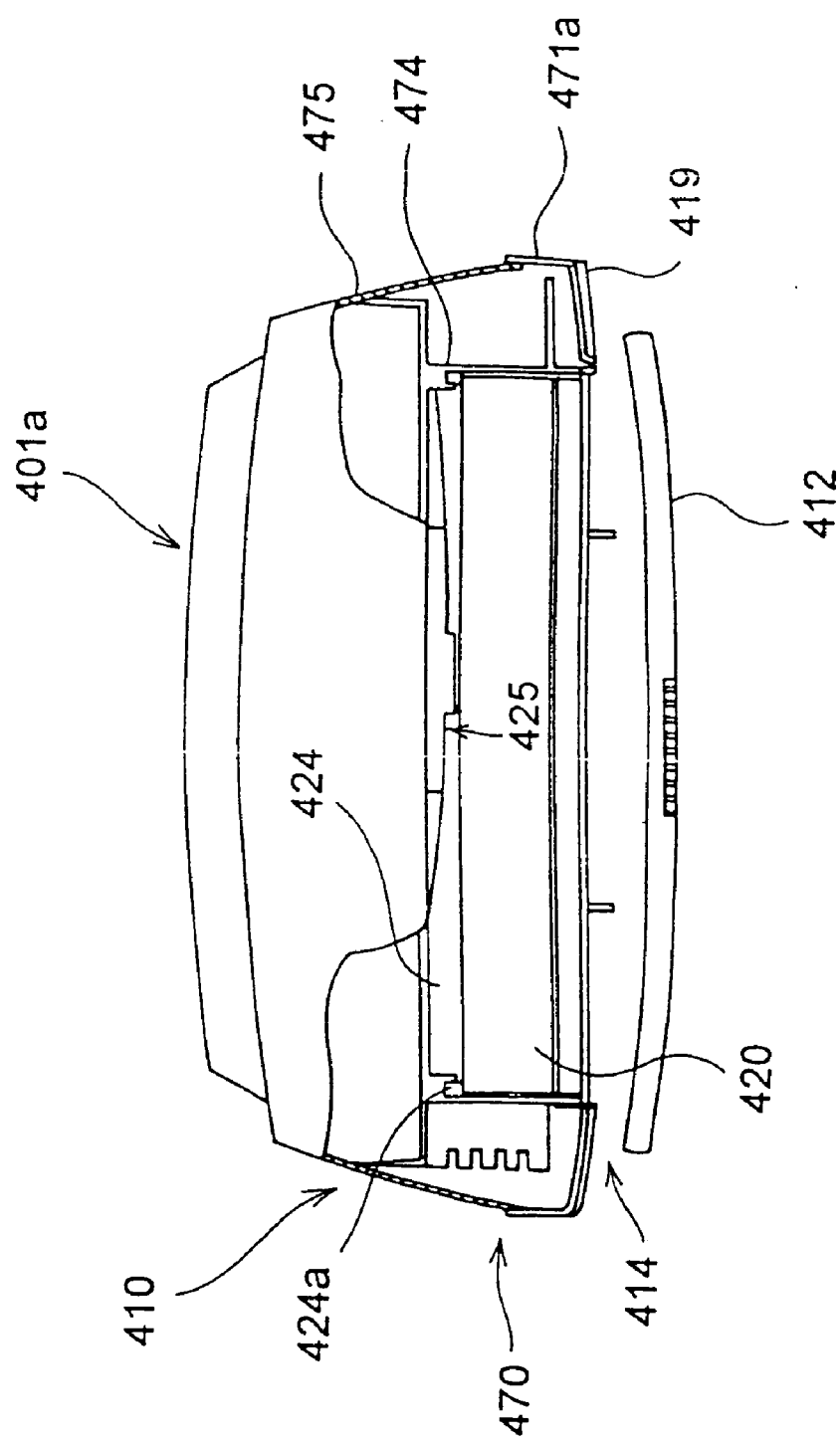
FIG. 62 is a sectional view, as seen from the top, of a portion of an air purifier as an eighteenth embodiment of the air conditioning apparatus of the invention.

The outer shell 471 of the body 410 of this air purifier 401a is composed of four parts made of synthetic resin as shown in FIG. 62. Specifically, a central shell 474 serves as a core, and a front shell 471a and a rear shell 475 sandwich it from ahead and from behind. The front shell 471a and the rear shell 475 are fixed to the central shell 471 with screws (not shown). A front cover 419, the fourth part, is laid closely over the front surface of the front shell 471a, and is fixed, at four corners, to the front shell 471a with special screws that cannot be unscrewed with a common screw driver. These special screws are used for the purpose of securing safety, because they prevent the user from removing the front cover 419 and touching the control circuit board or other components provided behind it.

Figure 63:
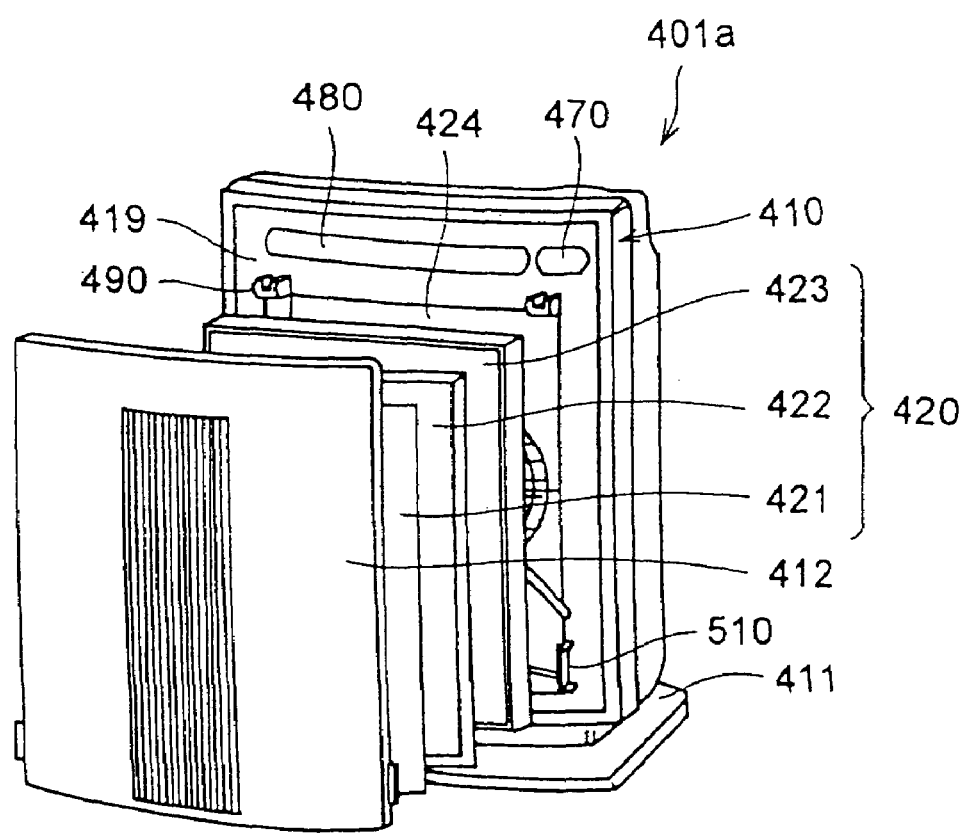
FIG. 63 is an exploded perspective view of the air purifier of the eighteenth embodiment, showing how its front panel and filters are arranged.

In a central portion of the front face of the central shell 474, i.e. the face thereof that faces the front shell 471a, a filter housing 424 is formed (see FIG. 63). The filter housing 424 is formed as a recess of which the entrance is rectangular, and the front shell 471a and the front cover 419 have portions thereof corresponding to the filter housing 424 cut out. Thus, the filter housing 424 is exposed at the front face of the body 410.

As FIG. 62 shows, in the innermost wall of the filter housing 424, a sealing member 424a is fitted around the edges. The sealing member 424a makes close contact with the dust-collecting filter 423 so as to prevent entry of air through the gap between the outer periphery of the filter unit 420 and the inner periphery of the filter housing 424. That is, the sealing member 424a ensures that only air that has passed through the filter unit 420 is sucked by the blower 430. The filter housing 424 serves also to keep the rear surface of the dust-collecting filter 423 lifted off the innermost wall of the filter housing 424 so as to secure a gap through which air is permitted to flow.

Figure 64:
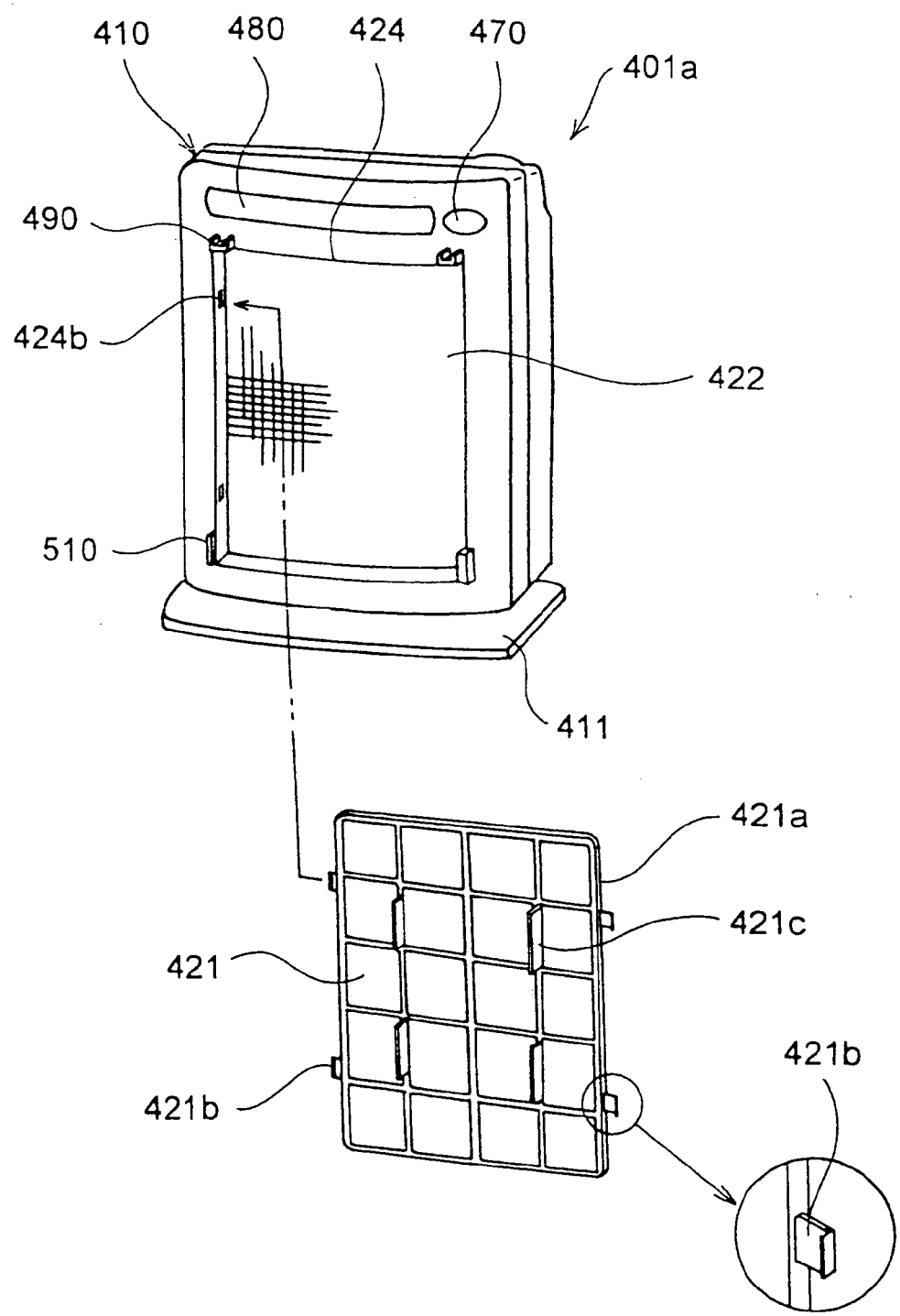
FIG. 64 is an exploded perspective view of the air purifier of the eighteenth embodiment, showing the structure of its prefilter and how it is fitted.

The prefilter 421 is fitted on a grid 421a made of synthetic resin as shown in FIG. 64. On the left and right sides of the grid 421a, four engagement pieces 421b (two on each side) are formed so as to protrude outward therefrom. Correspondingly, in the vertical walls inside the filter housing 424, four holes 424b are formed so as to receive the engagement pieces 421b. After the dust-collecting filter 423 and the deodorizing filer 422 are put in the filter housing 424, the prefilter 421 is put on the front surface of the deodorizing filer 422, and then, with the grid 421a held bent, the engagement pieces 421b are fitted into the holes 424b. Thus, the filter unit 420 is held in the filter housing 424 without the risk of dropping out.

In appropriate portions of the grid 421a, handles 421c are formed so as to be held between fingers when the prefilter 421 is pulled out of the filter housing 424. To prevent the filter portion 420 from dropping out easily, the engagement pieces 421b have their tips formed into hooks bent forward as shown in the detail view portion of the FIG. 64 so as to require a moderate force when pulled out of the holes 424b.

Figure 65:
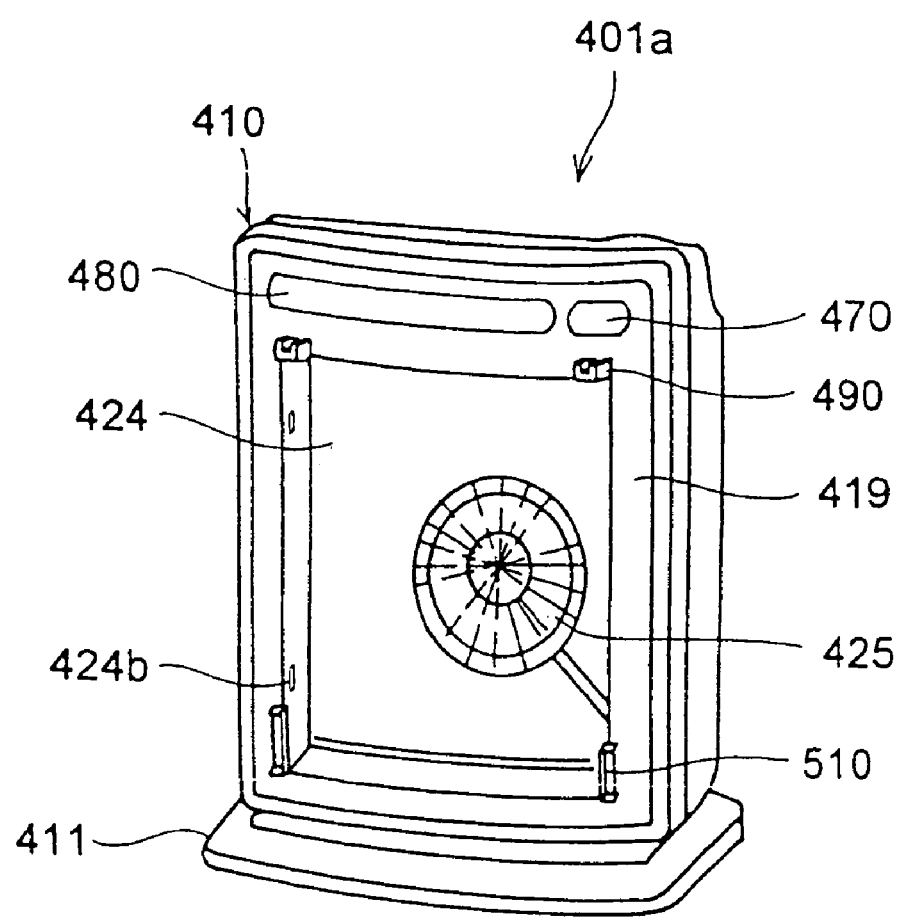
FIG. 65 is a perspective view of the air purifier of the eighteenth embodiment, with its front panel and filter portion removed.

As FIG. 65 shows, in the innermost vertical wall inside the filter housing 424, a ventilation opening 425 is formed that leads to the blower 430. The ventilation opening 425 consists of a number of holes formed radially in the central shell 474. As FIG. 62 shows, the portion of the central shell 474 corresponding to the ventilation opening 425 is so formed that its central portion protrudes a little toward the front face of the body 410 and supports the central portion of the dust-collecting filter 423. This, together with the presence of the sealing member 424a, helps secure an air passage behind the dust-collecting filter 423.

Figure 66:
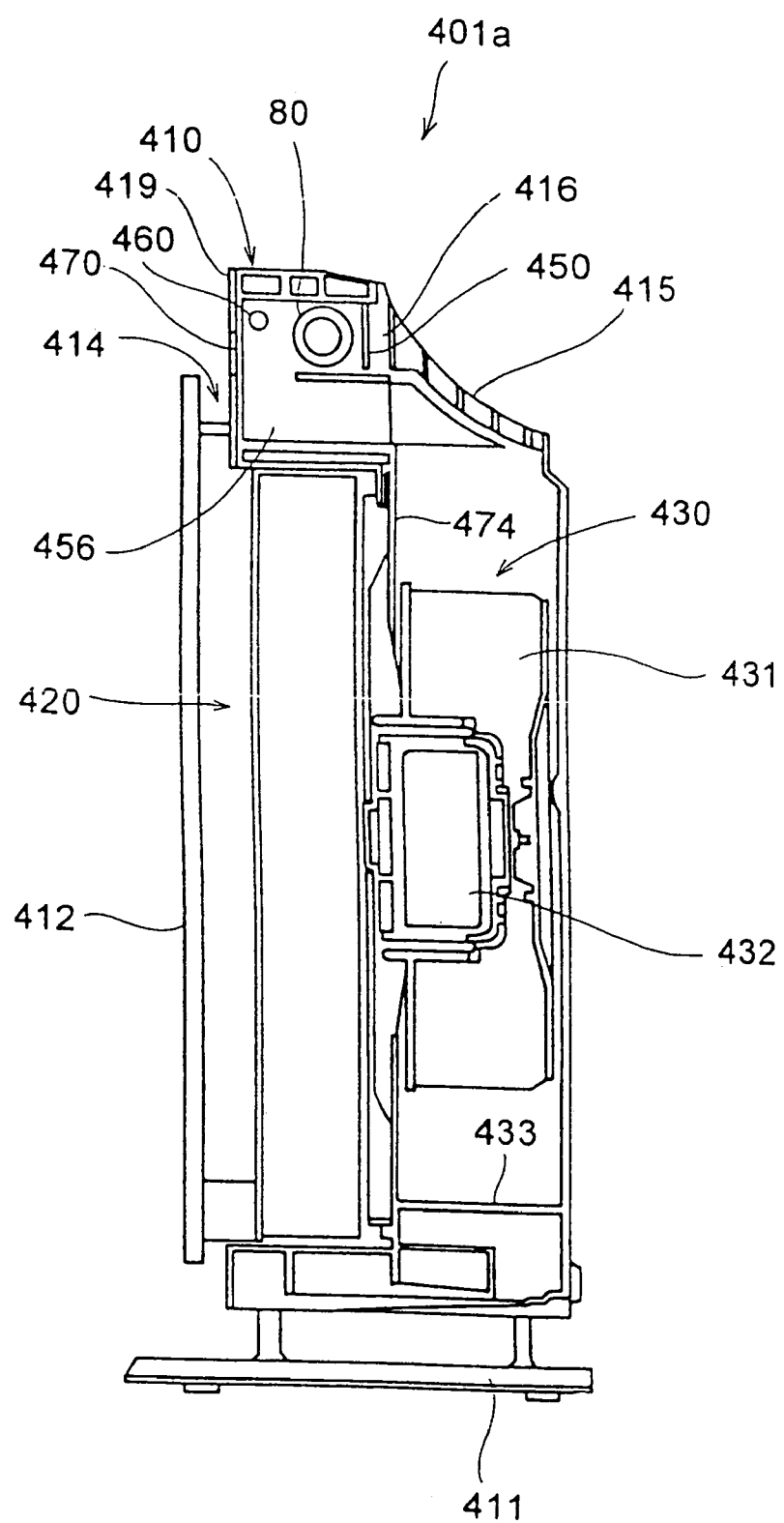
FIG. 66 is a vertical sectional view of the air purifier of the eighteenth embodiment.

FIG. 66 shows how the blower 30 is fitted. The motor 432 is fixed on the rear surface of the central shell 474, in a position corresponding to the center of the ventilation opening 425, with screws or the like. The fan 431 is surrounded by a guide wall 433 formed on the central shell 474. The guide wall 433 is so formed as to describe an involute curve, and serves to direct the flow of air produced by the fan 431 to where the air is discharged, i.e., in the example under discussion, the branch portion 457 (see FIG. 56) of the air passage.

The air that has left the fan 431 flows to the air passage above. Then, most of the air is passed through the main passage 455 (see FIG. 56) so as to be discharged through the main air outlet 415, and the rest of the air is passed through the bypass passage 456. The bypass passage 456 is formed in the central shell 474, and is connected to the sub air outlet 416 at its downstream end. As in the seventeenth embodiment, the ion generating element 80 is arranged in the bypass passage 456.

Figure 67:
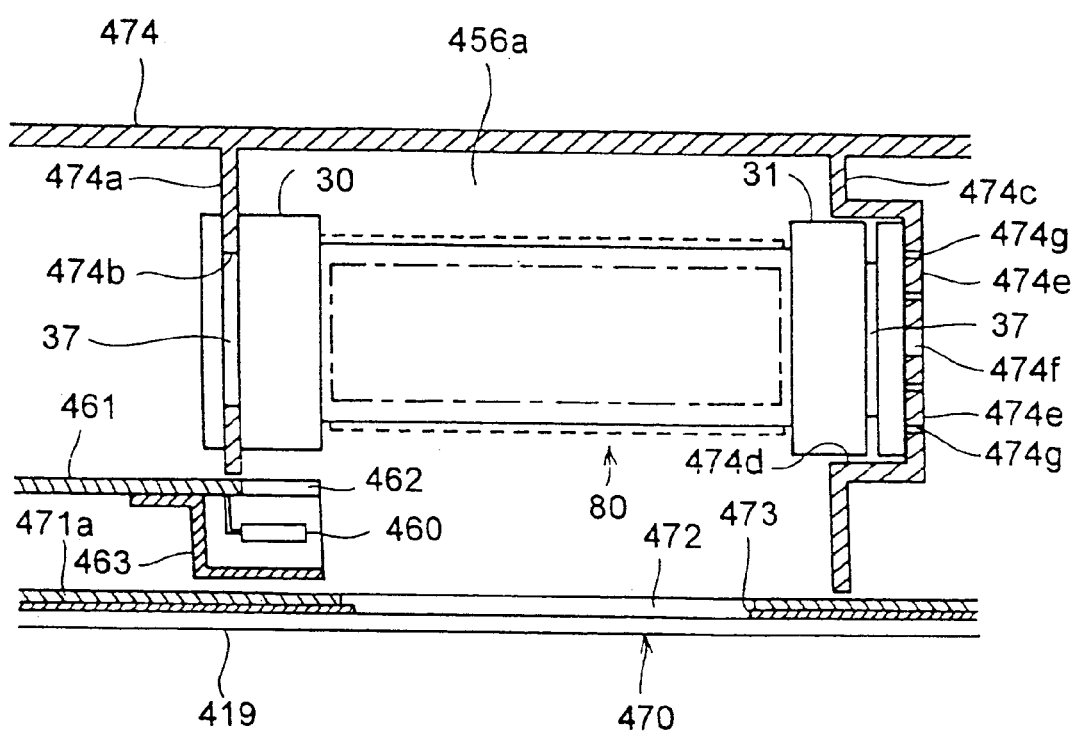
FIG. 67 is a horizontal sectional view of a portion, where the ion generating element is arranged, of the air purifier of the eighteenth embodiment.

The ion generating element 80 is fitted to the body 410 as shown in FIG. 67 by the use of the caps 30 and 31, which have ring-shaped grooves 37 formed in their peripheral surfaces. One cap 30 is fitted, along its ring-shaped groove 37 in a cut 474b formed in a rib 474a of the central shell 474, which is one of the components that form the bypass passage 456 (see FIGS. 67 and 69). This fitting is achieved by pushing the cap 30 along its ring-shaped groove 37 into the cut 474b from a direction perpendicular to the axis of the dielectric 27. The other cap 31 engages with a rib 474c that is formed on the central shell 474 so as to face the rib 474a and which is another of the components that form the bypass passage 456. In the rib 474c is formed a groove 474d having a width roughly equal to the diameter of the cap 30. The distance from the bottom of this groove 474d to the rib 474a is made somewhat smaller than the distance from the outer end surface of the cap 31 to the ring-shaped groove 37 of the cap 30 so that, as the cap 31 is pushed into the groove 474d, the outer end surface of the cap 31 is pressed by the bottom of the groove 474d (illustrated as a vertical plane in the figure), and thus the dielectric 27 receives a force that presses it from the direction of its axis. As a result, the caps 30 and 31 are kept in close contact with the ribs 474a and 474b by their own resilience, and thus the ion generating element 80 is fixed firmly on the central shell 474.

Figure 68:
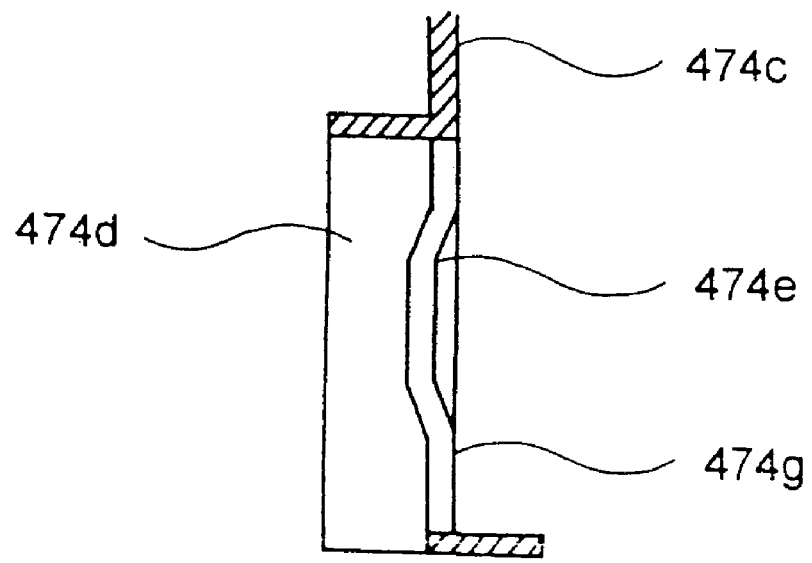
FIG. 68 is a sectional view of a portion, where the ion generating element is fitted, of the air purifier of the eighteenth embodiment.
Figure 69:
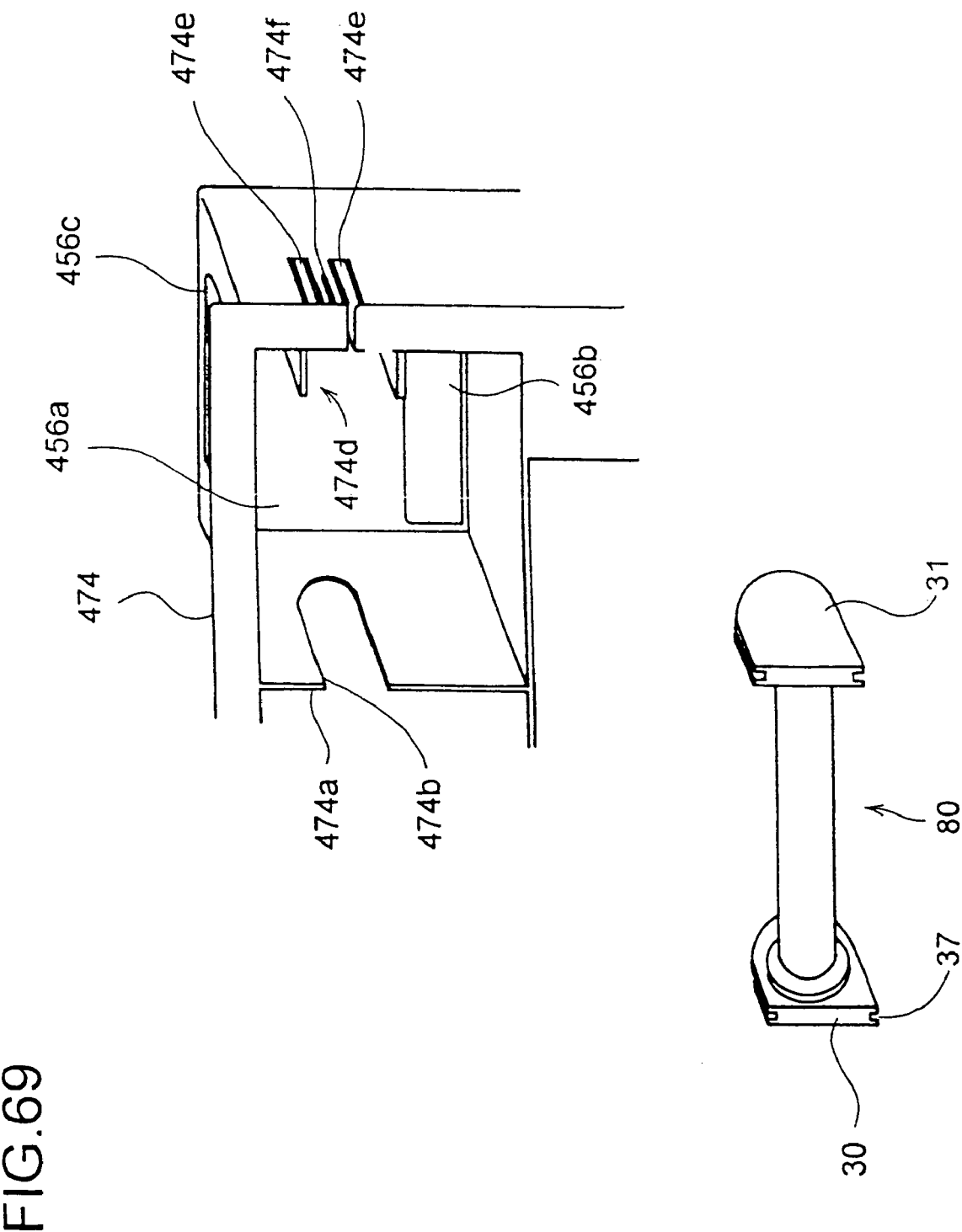
FIG. 69 is an exploded perspective view showing how the ion generating element is fitted in the air purifier of the eighteenth embodiment.

FIG. 69 shows how the ribs 474a and 474c form an ion generating device housing chamber 456a as part of the bypass passage 456. Reference numeral 456b represents an air inlet to the ion generating device housing chamber 456a, and reference numeral 456c represents an air outlet from the ion generating device housing chamber 456a. Reference numeral 474e represents a pair of upper and lower resilient pieces formed on the bottom of the groove 474d so as to extend in the same direction in which the groove 474d itself extends. These resilient pieces 474e serve to increase the resilience of the bottom of the groove 474d. The resilient pieces 474e are formed by forming two parallel slits 474g in the bottom of the groove 474d, and, to increase the resilience obtained, those portions of the resilient pieces 474e that make contact with the central portion of the cap 31 are so bent or curved as to protrude into the groove 474d as shown in FIG. 68. Reference numeral 474f represents a cut formed between the elongate holes 474e and 474e, and is used to lay the lead 32 (see FIG. 9) through.

On the downstream side of the ion generating element 80, the ozone reducing device 450 is arranged. The air that has passed through the ozone reducing device 450 is blown out through the sub air outlet 416. Here, this flow of air is blown out not parallel to the flow of air that is blown out through the main air outlet 415, but is deflected toward the flow of air blown out through the main air outlet 415 by a wind direction setting means. By this wind direction setting means, the air containing ions that is blown out through the sub air outlet 416 is made to join, outside the body 410, the other flow of air that has not been passed through the ion generating element 80 and is blown out through the main air outlet 415.

Figure 70:
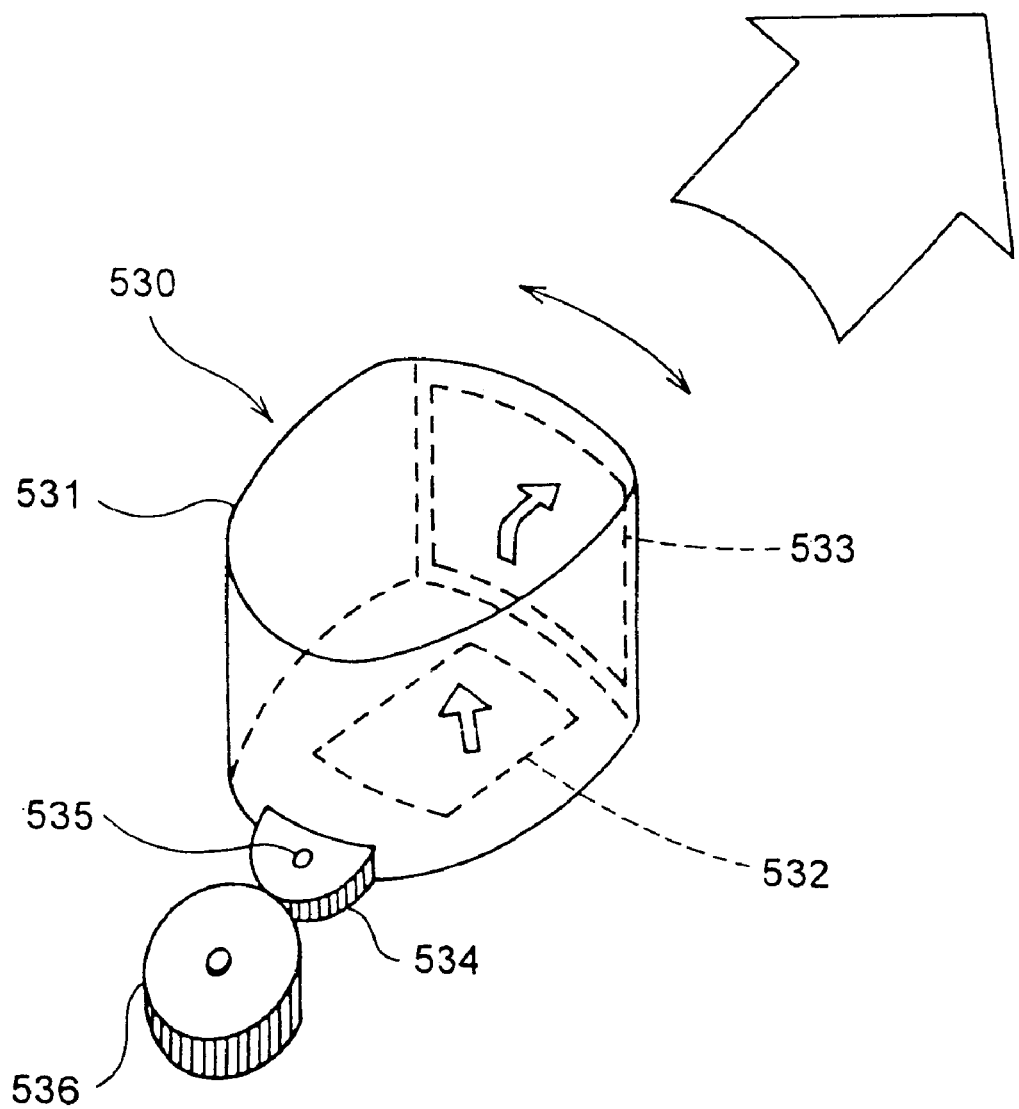
FIG. 70 is a perspective view showing one example of the wind direction setting means of the air purifier of the eighteenth embodiment.

The wind direction setting means may be realized in many ways, of which one example is shown in FIG. 70. The wind direction setting means 530 shown here has a hollow casing 531. This casing 513 has an air inlet 532, which communicates with the sub air outlet 416, formed in its bottom surface, and has an air outlet 533 formed in one of its side surfaces. On the side surface opposite to the air outlet 533, a gear portion 534 is formed so as to protrude therefrom. The casing 531 can swing in a horizontal plane about the shaft 535 of the gear portion 534. The gear portion 534 meshes with a swing gear 536 coupled to reduction gearing and a motor (not shown).

The swing gear 536 rotates reciprocatively within a predetermined range of angles. The movement of the swing gear 536 is slow, and its speed can be varied as required. As the swing gear 536 rotates reciprocatively, the casing swings from side to side and back repeatedly. Thus, the air containing ions that is blown out through the sub air outlet 416 has its flow direction continuously changed by the casing 531, and is then blown out through the air outlet 533 in a horizontal direction. The air containing ions that has exited from the air outlet 533 joins the air that is blown out through the main air outlet 415 as if the former were sprayed into the latter, and thus the air containing ions is spread all around the room.

In FIG. 70, the flow angle of the air blown out of the air outlet 533 as measured on a vertical plane is not considered. However, it is possible to adopt an arrangement that permits the flow angle to be adjusted also vertically by providing, at the air outlet 533, a louver for changing the direction of the flow of air vertically as is used in the indoor unit of an air conditioner.

As another way to realize the wind direction setting means, it is also possible to provide a louver as described above at the sub air outlet 416 so that the air blown out through the sub air outlet 416 is deflected toward the air blown out through the main air outlet 415. In this case, it is advisable to provide two types of louver, namely one for changing the direction of the flow of air in a horizontal plane and the other for changing it in a vertical direction.

Alternatively, it is also possible to provide a nozzle at the sub air outlet 416, with the outlet of the nozzle pointing toward the flow of air blown out through the main air outlet 415.

As a modified version of this arrangement employing a nozzle, it is possible to extend the tip of the nozzle so as to reach into the flow of air blown out through the main air outlet 415 so that air containing ions is sucked out of the nozzle through the outlet at its tip.

In FIG. 67 is shown a light-emitting portion 460 that illuminates the ion generating element 80. This light-emitting portion 460 is fitted to a circuit board 461 of the air purifier 401*a*. On the circuit board 461 are mounted a CPU, i.e. the control center, a memory, and other electronic devices. The circuit board 461 is arranged in a space next to the ion generating device housing chamber 456*a*, and is fixed to the central shell 474 with screws (not shown), with only the light-emitting portion 460 reaching into the ion generating device housing chamber 456*a*. The circuit board 461 has a cut 462 formed therein to permit the light emitted by the light-emitting portion 460 to reach the ion generating element 80. Reference numeral 463 represents a reflective cover fixed to the circuit board 461. The reflective cover 463 covers the light-emitting portion 460 entirely except from the directions in which the head portion of the light-emitting portion 460 points and in which the cut 462 is formed. The reflective cover 463 reflects the light emitted by the light-emitting portion 460 toward the ion generating element 80, and is formed out of a material that exhibits a high reflectivity toward light, such as synthetic resin having a light color, or a metal. To increase the reflectivity, it is advisable to coat the inner surface of the reflective cover 463 with plating. The light-emitting portion 460 is supported inside the reflective cover 463, with the head portion of the former retracted a little from the end of the latter.

The sight window 470 provided in an upper right portion of the front face of the body 410 is formed by forming an elliptic hole 472 in the front shell 471*a*, i.e. in the same manner as in the seventeenth embodiment.

Now, how the front panel 412 is fitted will be described. The front panel 412 has a rectangular front face that is geometrically identical with the filter housing 424 but that is larger than the filter housing 424 in size so as to cover and hide the filter unit 420 completely. When viewed from above, the front panel 412 is so curved as to protrude outward at the center (see FIG. 62).

Figure 71:
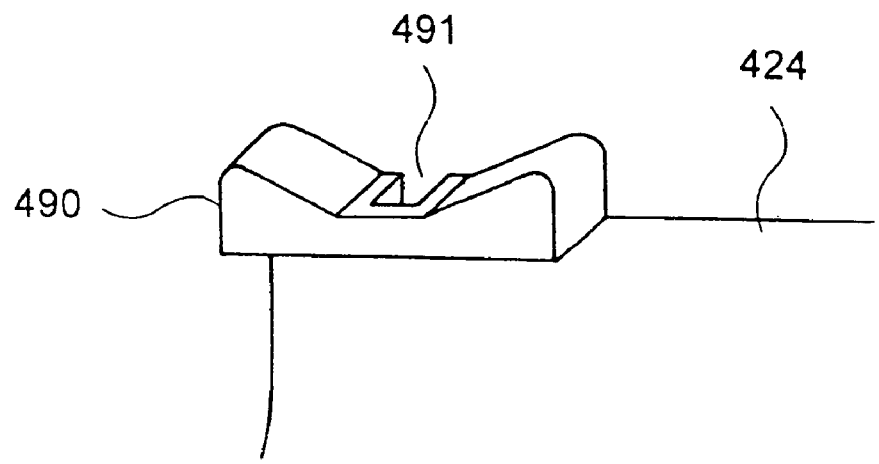
FIG. 71 is a perspective view of the panel support for supporting the front panel of the air purifier of the eighteenth embodiment.
Figure 78:
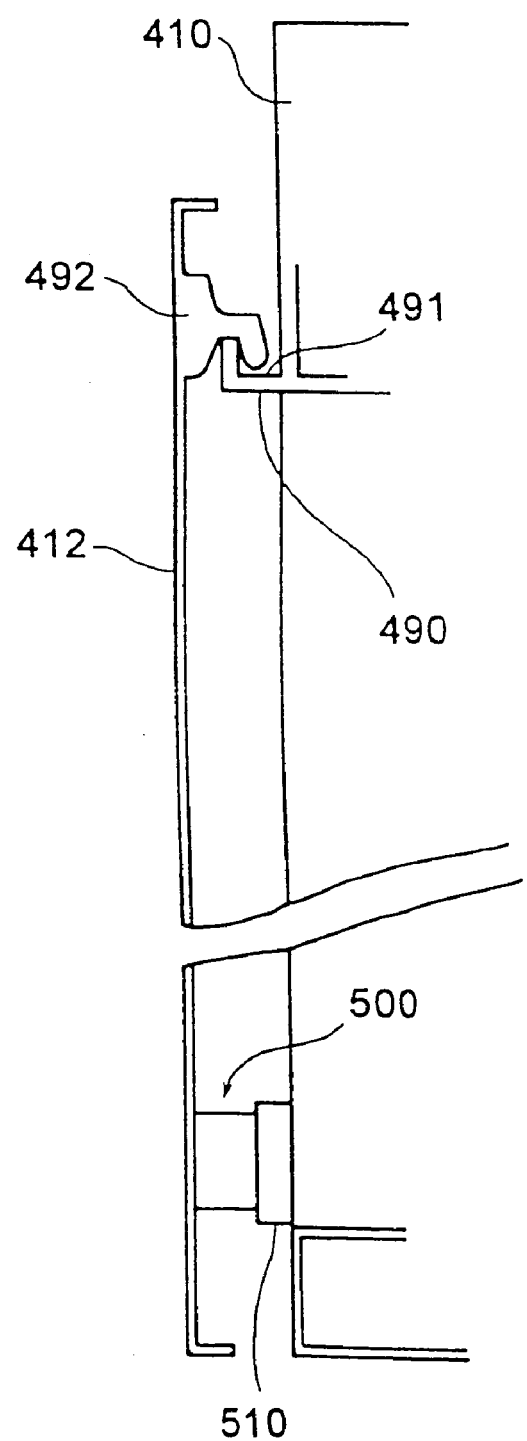
FIG. 78 is a vertical sectional view of a portion of the air purifier of the eighteenth embodiment, showing how its front panel is fitted.

The front panel 412 is fitted to the body 410 in the following manner. First, on the front shell 471*a*, immediately above the filter housing 424, a pair of left and right panel rests 490 are formed so as to protrude frontward. As FIG. 71 shows, the top surface of the panel rests 490 is depressed in the form of an inverted trapezoid, with a recess 491 formed in the bottom of the depression. On the rear surface of the front panel 412, engagement projections 492 are formed so as to correspond to the panel rests 490 (see FIG. 74). The engagement projections 492 are shaped like a hook pointing downward. As FIG. 78 shows, when the tips of the engagement projections 492 are fitted into the recesses 491 of the panel rests 490, the front panel 412, with its weight borne by the engagement projections 492, is supported on the front surface of the body 410.

In a lower portion of the front panel 412, movable engagement pieces 500 that removably engage with the body 410 are provided (see FIGS. 75, 76, 77, and 79). The movable engagement pieces 500 are each molded as a single component out of elastic synthetic resin, and have the following structure. A plate-shaped main part 501, forming the core of the movable engagement piece 500, has one end thereof formed into a push button portion 502 having a rather small width, and has a spring portion 503 having a U-shaped section formed at the other end. At about the center of the main part 501, a hook portion 504 is formed so as to protrude therefrom. On both sides of the main part 501, leg portions 505 are formed, two on each side, that have their tip bent outward like a hook and that have an L-shaped section. On both sides of the main part 501 are also formed projecting pieces 506, three on each side, so as not to overlap with the leg portions 505.

To permit the movable engagement pieces 500 to be fitted thereto, the lower portion of the front panel 412 is structured in the following manner. First, on each side of the front panel 412, in a bent edge portion 412*a* thereof, a hole 412*b*. is formed through which to put the corresponding push button portion 502. On the rear surface of the panel, a spring rest 412*c* is formed so as to protrude therefrom and face the hole 412*b*. The hole 412*b* and the spring rest 412*c* are arranged along a horizontal line, and between them are formed a pair of slide guides 507. The slide guides 507 have horizontally extending guide grooves 508 formed in those surfaces thereof that face each other.

Figure 76:
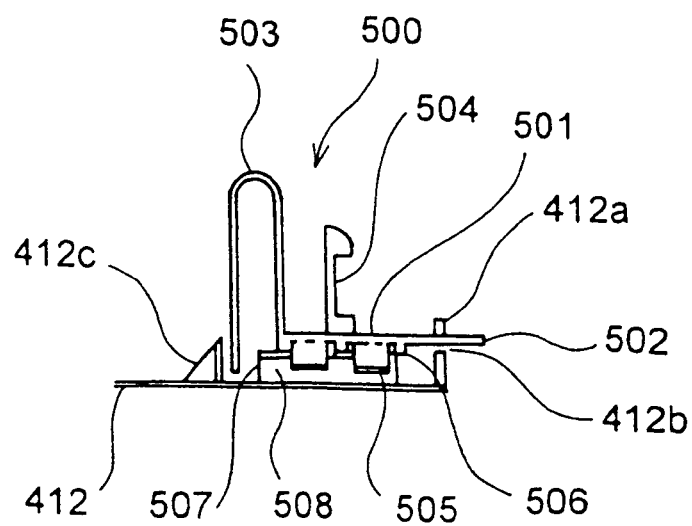
FIG. 76 is a sectional view taken along line B-B shown in FIG. 75.
Figure 77:
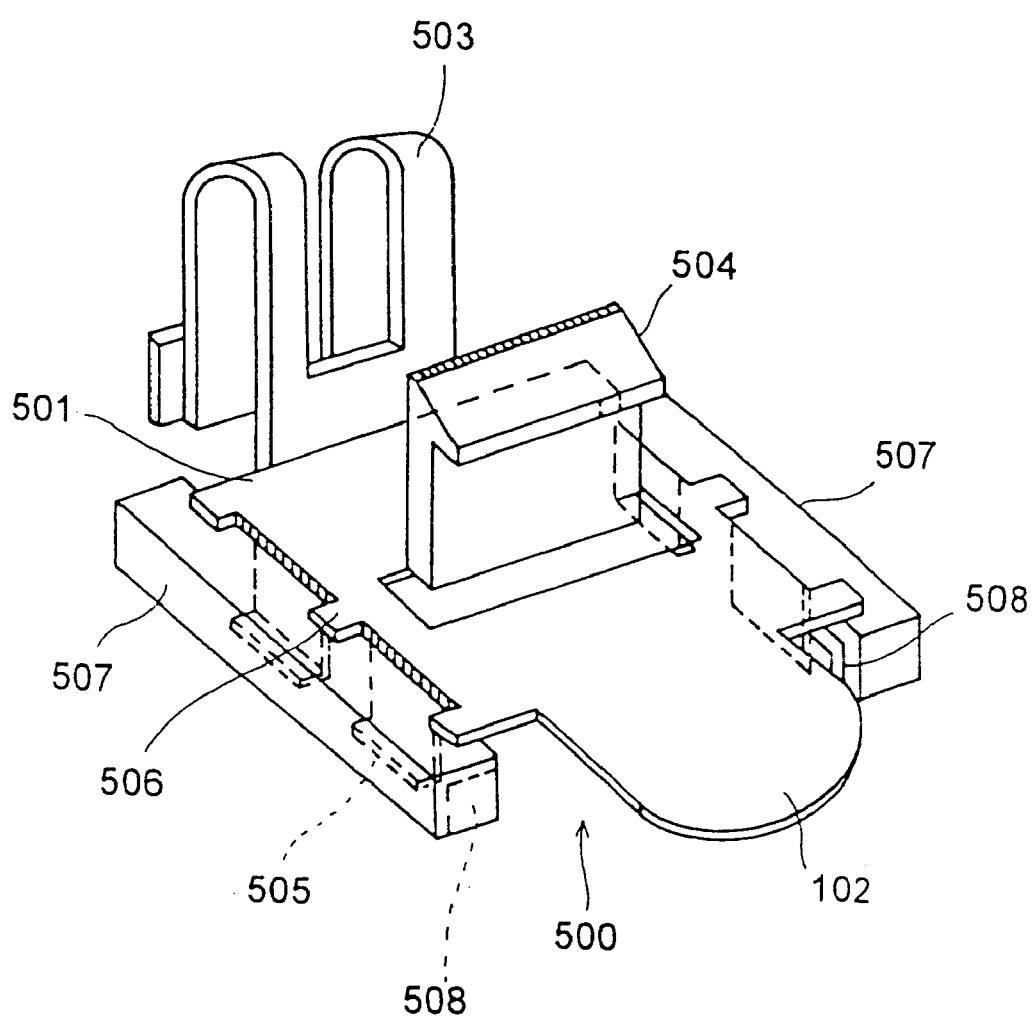
FIG. 77 is a perspective view of the movable engagement piece and the slide guide of the air purifier of the eighteenth embodiment.

To fit the movable engagement piece 500, first, the push button portion 502 is put through the hole 412b from the inside, then the end of the spring portion 503 is engaged with the side surface of the spring rest 412c, then the leg portions 505 are put to the edges of the slide guides 507, and the main part 501 is pressed onto the slide guides 507. This causes the leg portions 505 to bend because of their elasticity and fit into the guide grooves 508. As a result, the portions of the slide guides 507 that overhang the guide grooves 508 as viewed in FIG. 76 are sandwiched between the tip portions, bent like hooks, of the leg portions 505 and the projecting pieces 506. In this way, the movable engagement piece 500 is fitted so as to be slidable along the slide guides 507, with the push button portion 502 loaded by the spring portion 503 with a force that presses the push button portion 502 in the direction in which it pops out of the hole 412b.

Figure 72:
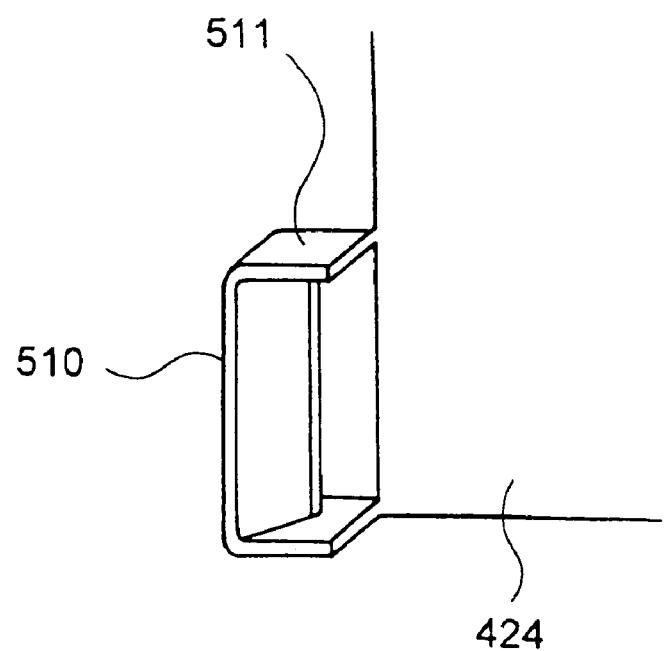
FIG. 72 is a perspective view of the hook portion used to fit the front panel of the air purifier of the eighteenth embodiment.
Figure 73:
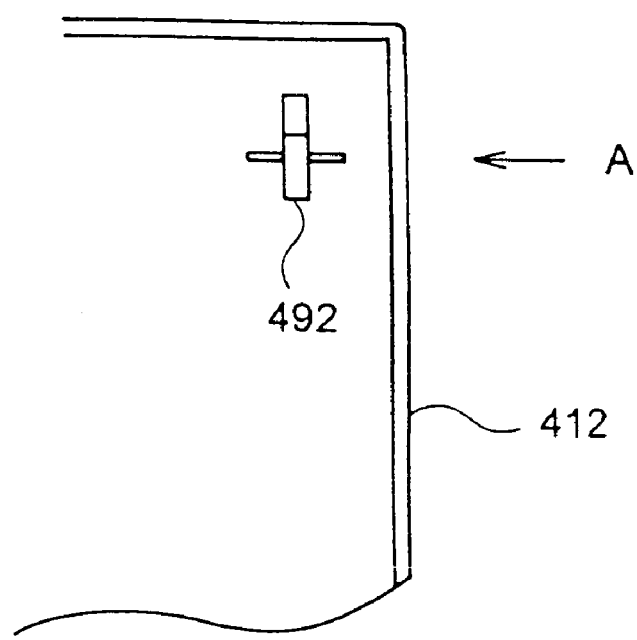
FIG. 73 is a rear view of a portion of the front panel of the air purifier of the eighteenth embodiment, showing how an engagement projection is formed thereon.
Figure 74:
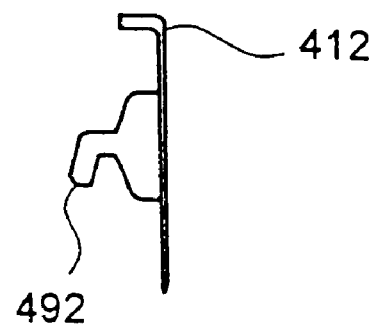
FIG. 74 is a view taken from the direction indicated by arrow A shown in FIG. 73.
Figure 75:
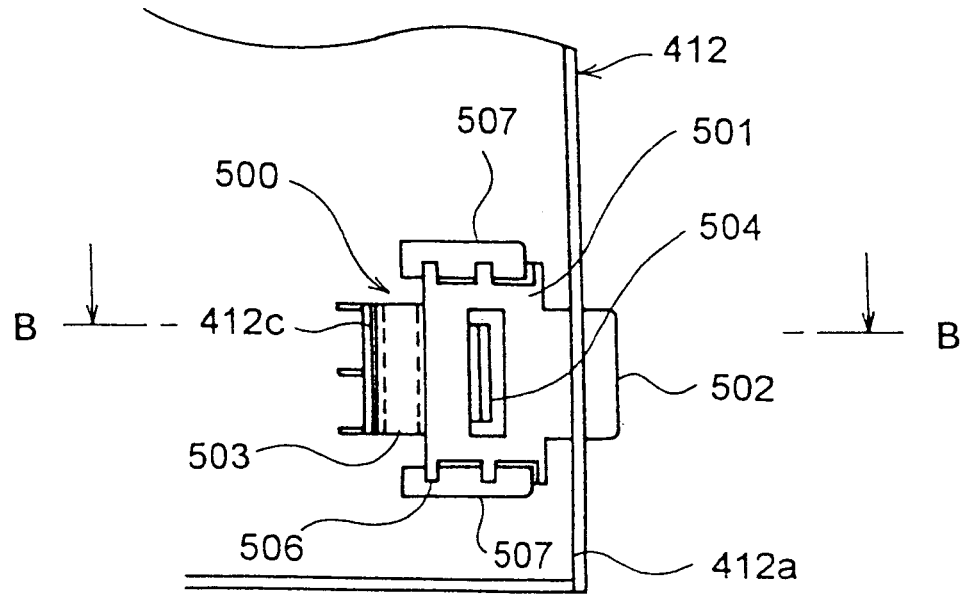
FIG. 75 is a rear view of a portion of the front panel of the air purifier of the eighteenth embodiment, showing how a movable engagement piece is fitted thereon.
Figure 79:
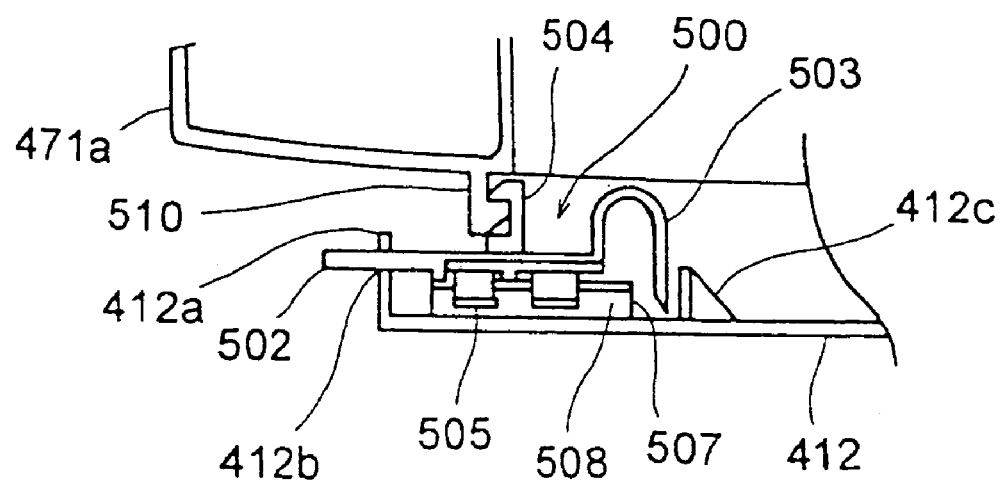
FIG. 79 is a horizontal sectional view of a portion of the air purifier of the eighteenth embodiment, showing how its front panel is fitted.
Figure 80:
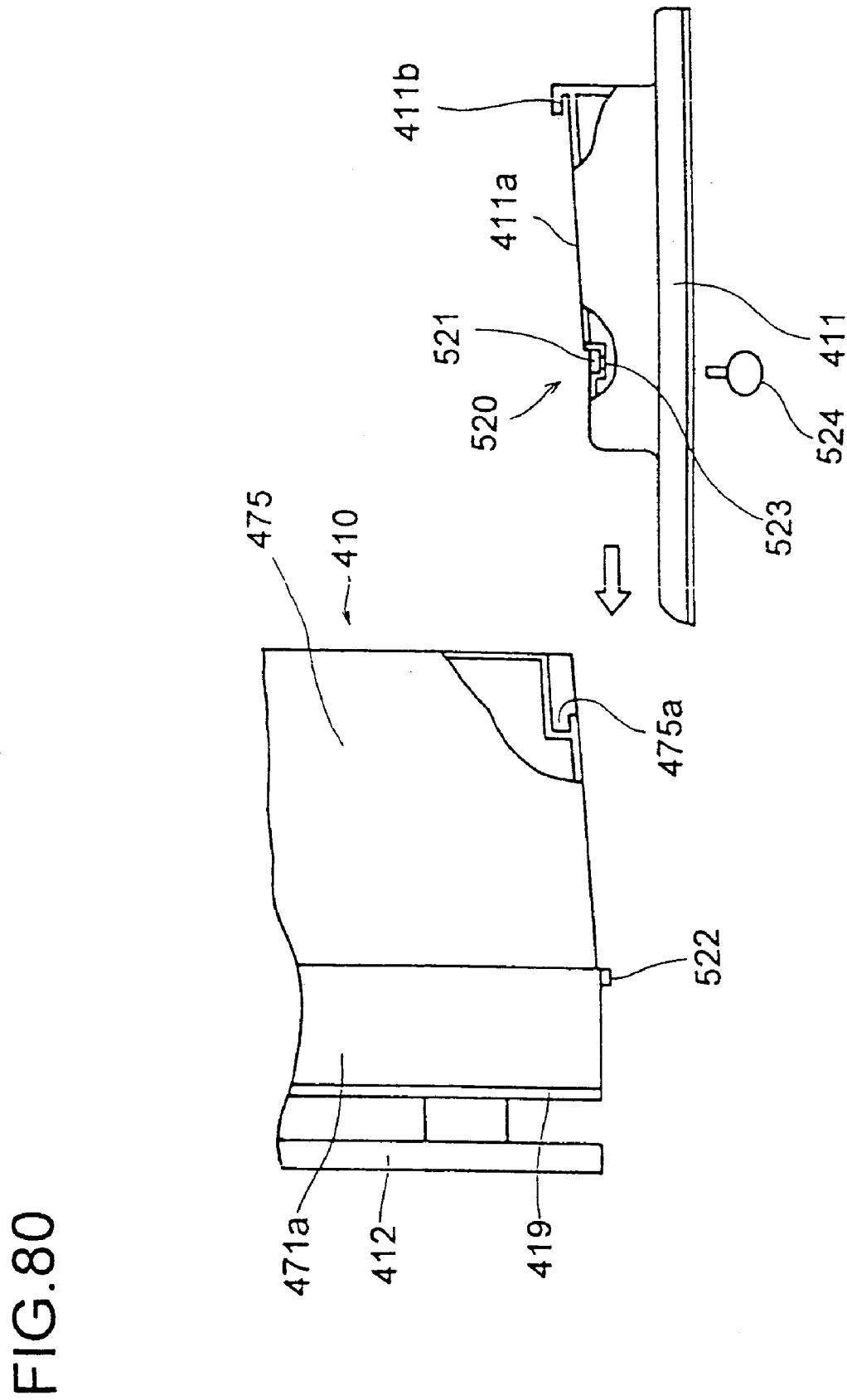
FIG. 80 is a partially cutaway side view of a portion of the air purifier of the eighteenth embodiment, showing its body about to be mounted on its base.

As FIGS. 72 and 79 show, on the front shell 471a, in positions facing each hook portion 504, a hook portion 510 is formed so as to protrude therefrom. When the engagement projections 492 are hung on the panel rests 490, the tip of the hook portion 504 makes contact with the tip of the hook portion 510. Where they make contact with each other, the hook portions 504 and 510 have slant surfaces. Therefore, in this state, when the lower portion of the front panel 412 is pressed onto the body 410, the slant surfaces of the hook portions 504 and 510 enable the movable engagement piece 500 to slide against the force with which it is loaded by the spring 503. Eventually, the hook portions 504 and 510 engage with each other as FIG. 79 shows, with the result that, even if the lower portion of the front panel 412 is pulled frontward, the front panel 412 does not come off. Moverover, as FIG. 72 shows, the hook portion 510 has a barrier 511 at the top, and therefore, even if the front panel 412 receives a force that tends to slide it upward, the hook portion 504 does not come out of the hook portion 510. To bring the hook portion 504 out of the hook portion 501, the push button portion 502 is pressed.

The movable engagement pieces 500 are arranged symmetrically on both sides of the front panel 412. Instead of arranging the movable engagement pieces 500 on the part of the front panel 412 in this way, it is also possible to arrange them on the part of the body 410 and provide the hook portions 510 on the part of the front panel 412.

Now, how the base 411 is fitted will be described. The base 411 also is molded out of synthetic resin, and its top surface, i.e. the body mount surface 411a, is formed with a gentle upward inclination from front to back (see FIG. 80). The body 410 has its bottom surface formed with a corresponding inclination. At the rear end of the body mount surface 411a, a hook-like engagement portion 411b, bent forward, is formed. In the bottom surface of the rear shell 475 of the body 410, a recess-like engagement portion 475a that receives the engagement portion 411b is formed. In a front portion of the body mount surface 411a, a locking means 520 is provided. The locking means 520 consists of a locking recess 521 formed in the body mount surface 411a, a locking projection 522 formed on the bottom surface of the front shell 471a of the body 410 so as to protrude therefrom and fit into the locking recess 521, and a thumbscrew 524 that is screw-engaged with the locking projection 522 through a hole 523 formed in the bottom of the locking recess 521.

Figure 81:
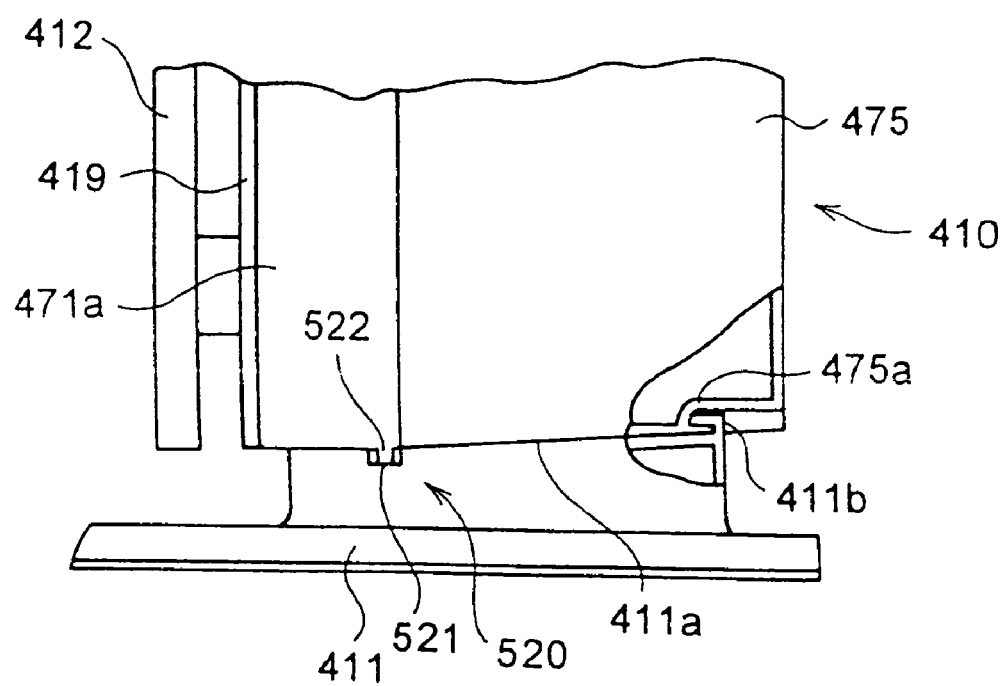
FIG. 81 is a partially cutaway side view of a portion of the air purifier of the eighteenth embodiment, showing its body mounted on its base.

When the bottom surface of the body 410 is put on the body mount surface 411a of the base 411 and the body 410 is slid backward relative to the base 411, the engagement portion 411b engages with the engagement portion 475a at the end of the sliding stroke, and the locking projection 522 fits into the locking recess 521 (see FIG. 81). With the locking projection 522 fitted into the locking recess 521, the body 410 can no longer slide in the opposite direction relative to the base 411. This means that the engagement portion 411b is kept engaged with the engagement portion 475a. In this state, the thumbscrew 524 is screw-engaged with the locking projection 522 so that the front portion of the body mount surface 411a is fixed to the front shell 471a. Now, the base 411 is firmly fixed to the body 410.

The locking means 520 may be structured in any other manner than is specifically described above. For example, it is also possible to arrange the locking recess 521 in the front shell 471a and arrange the locking projection 522 on the base. It is also possible to omit the locking recess and the locking projection and use only the thumbscrew 524 to keep the body 412 from sliding relative to the base 411. Many other modifications are possible.

Figure 82:
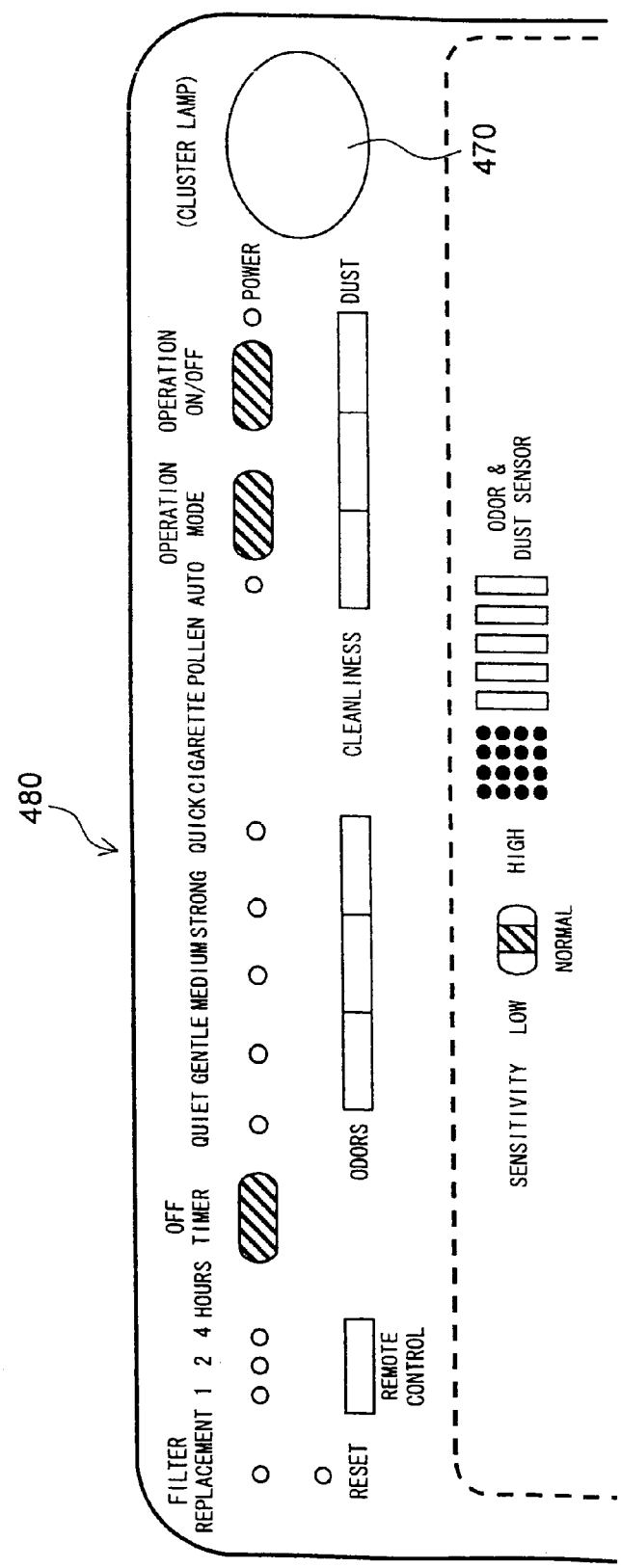
FIG. 82 is a front view of the operation panel portion of the air purifier of the eighteen embodiment.
Figure 83:
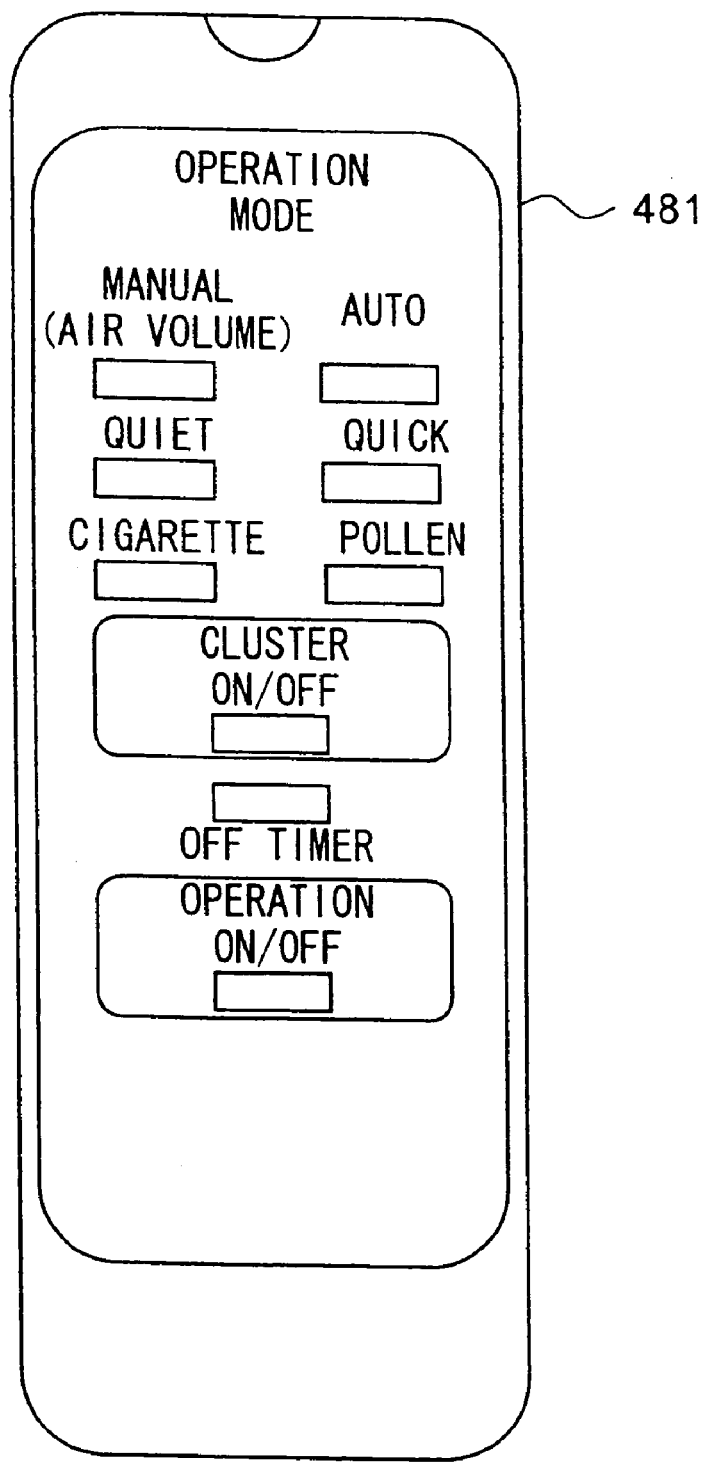
FIG. 83 is a front view of the remote control unit that comes along with the air purifier of the eighteenth embodiment.

As FIG. 82 shows, by the side of the sight window 470 is provided an operation panel 480, on which are provided switches for turning the operation on/off and for switching the operation mode. As part of the operation panel 480 is also provided a remote control unit light-sensing portion 482 for receiving control signals from a remote control unit 481 shown in FIG. 83.

Next, the operation and functions of the air purifier 401a will be described. When the air purifier 401a starts being operated, the motor 432 starts rotating the fan 431, and thus the air inside the room is sucked in through the air inlet 413 of the front panel 412 and through the side air inlets 414. The air sucked in is passed through the prefilter 421, which collects larger particles of dust, and is then passed through the deodorizing filer 422, which absorbs odor-causing molecules such as acetaldehyde, ammonia, and acetic acid. The air that has passed through the deodorizing filer 422 is then passed through the dust-collecting filter 423, which collects finer particles of dust, and is then, as clean air free from odors or dust, blown out through the main air outlet 415 into the room.

Not all of the air that has left the fan 431 is blown out through the main air outlet 415, but part of it enters the bypass passage 456 and flows to the ion generating element 80. In the ion generating element 80, an alternating-current voltage of about 1.75 kV is applied between the inner and outer electrodes 28 and 29, and positive and negative ions are generated outside the dielectric 27. While the ion generating element 80 is generating ions, the light-emitting portion 460 emits light, for example blue light, to illuminate the ion generating element 80. By visually checking this illumination through the sight window 470 from the outside, the user can confirm that the ion generating element 80 is being driven and thus can use the air purifier with a feeling of safety. The light-emitting portion 460 is covered with the reflective cover 463, and thus does not directly illuminate the sight window 470. Therefore, even when the air purifier 401a is used in a dark place, the user can visually check the ion generating element 80 without being dazzled by the illumination light coming directly from the light-emitting portion 460.

As in the seventeenth embodiment, the ozone generated together with the positive and negative ions by the ion generating element 80 is decomposed by the ozone reducing device 450. Thus, the concentration of ozone in the air discharged through the sub air outlet 416 can be held down to one-tenth or less of the level 0.1 ppm stipulated as a safety standard by Japan Society for Occupational Health.

The air that has passed by the ion generating element 80 and now contains the positive and negative ions generated by the ion generating element 80 is blown out through the sub air outlet 416, and is then deflected by the wind direction setting means 530 toward the flow of air blown out through the main air outlet 415 so as to join, above the main air outlet 415, the other flow of air that has not passed through the ion generating element 80. The positive and negative ions are carried by the strong flow of air blown out of the main air outlet 415 and are thereby spread all around the room. In this way, it is possible to discharge positive and negative ions together with air that has been subjected to dust collection and deodorization into the room and thereby kill airborne bacteria present in the air inside the room.

When the air purifier 401 is operated for an extended period, dust is caught in the air inlet 413 and obstructs the flow of air. Even in such a situation, an ample amount of air flows in through the side air inlets 414, making a drop in air purification efficiency unlikely.

As will be clear from the descriptions above, the air purifier of this embodiment, provided with a blower that circulates the air inside the room, is further provided with an ion generating device including as its principal component an ion generating element that generates positive and negative ions when an alternating-current voltage is applied between the electrodes thereof. Thus, it is possible to spread positive and negative ions all around the room to achieve sterilization by the action of the radical generated through the chemical reaction between positive and negative ions. Moreover, a filter that removes dust from the air is provided on the upstream side of the ion generating device. This makes it possible to remove dust from the air circulated and thereby keep the ion generating device free from dust. Moreover, part of the air that has passed through the filter is fed to the ion generating device, and the resulting air containing the ions generated by the ion generating device is mixed with the remaining air that has passed through the filter. This makes it possible to carry the ions on a strong flow of air and thereby spread them all around the room.

Moreover, the air containing the ions generated by the ion generating device and the air that has passed through the filter are made to join outside the body of the air purifier. Thus, as opposed to a case where those two flows of air are made to join inside the body of the air purifier, it does not occur that the air containing ions is forced back by the pressure of wind, and thus it is possible to make the flow of air containing ions join the main flow of air effectively.

Moreover, by providing a wind direction setting means at the air outlet through which the air that has passed through the ion generating device is blown out, it is possible to deflect the flow of air containing ions in a direction in which it easily joins the main flow of air.

Moreover, the ion generating element, which is a principal component of the ion generating device, is fixed inside the body of the air purifier by forming the dielectric of the ion generating element into a cylinder, fitting caps made of an elastic material on both ends of the dielectric, fitting one cap into the body of the air purifier from a direction perpendicular to the axis of the dielectric, and putting the other cap in contact with the body of the air purifier in such a way that the dielectric receives a force that presses it from the direction of its axis. This makes it possible to fit the ion generating element securely by exploiting the structures of the components involved.

Moreover, a filter housing is formed in a central portion of the front face of the body of the air purifier, and, in front of the filter housing, a front panel that is larger than the filter housing in size is fitted with a predetermined gap left between the body of the air purifier and the front panel. Thus, when the front panel is removed, the filter housing is exposed, permitting easy fitting, cleaning, and replacement of the filters. Moreover, the filters are covered and hidden by the front cover so as not to spoil the appearance of the air purifier.

Moreover, the gap between the front panel and the body of the air purifier is used as an air inlet through which to suck in the air inside the room, and another air inlet is formed in the front panel itself, with the former having a larger inlet area than the latter. This helps always secure a more than sufficient capacity of the air inlets for the air passing therethrough so that the filters receive an ample supply of air. This arrangement is especially effective when the air inlet of the front panel is clogged.

Moreover, engagement projection formed in an upper portion of the front panel are engaged with panel rests formed on the body of the air purifier so as to protrude therefrom so that the weight of the front panel is borne by the panel rests. In addition, movable engagement pieces that engage with the body of the air purifier is arranged in a lower portion of the front panel, or movable engagement pieces that engage with a lower portion of the front panel is arranged on the body of the air purifier. Thus, the front panel can be fitted without the use of screws. This makes the fitting and removing of the front panel easy, and thus makes the cleaning and replacement of the filters easy.

Moreover, a base that supports the body of the air purifier is provided separately, and, on this base and the body of the air purifier are provided an engagement portion that engages them together by sliding them relative to each other and a locking means that keeps them engaged by preventing them from sliding in the opposite direction relative to each other. This ensures easy and secure mounting of the body of the air purifier on the base that supports it stably on the floor surface.

Moreover, a sight window that permits visual inspection of the ion generating element is provided in the body of the air purifier, and a light-emitting element that illuminates the ion generating device in a manner interlocked with the driving of the ion generating element is mounted on a circuit board arranged inside the body of the air purifier. This permits the driving status of the ion generating element to be checked visually and easily, and also makes the deployment of a light-emitting element for this purpose easy.

Moreover, a reflective cover is provided that reflects the light emitted by the light-emitting element toward the ion generating element. This makes it possible to concentrate the light emitted by the light-emitting element on the ion generating element and thereby illuminate the ion generating element efficiently even when the brightness of the light-emitting element is low. The light from the light-emitting element does not directly illuminate the sight window. This prevents the user from being dazzled and thus helps enhance viewability.

Figure 84:
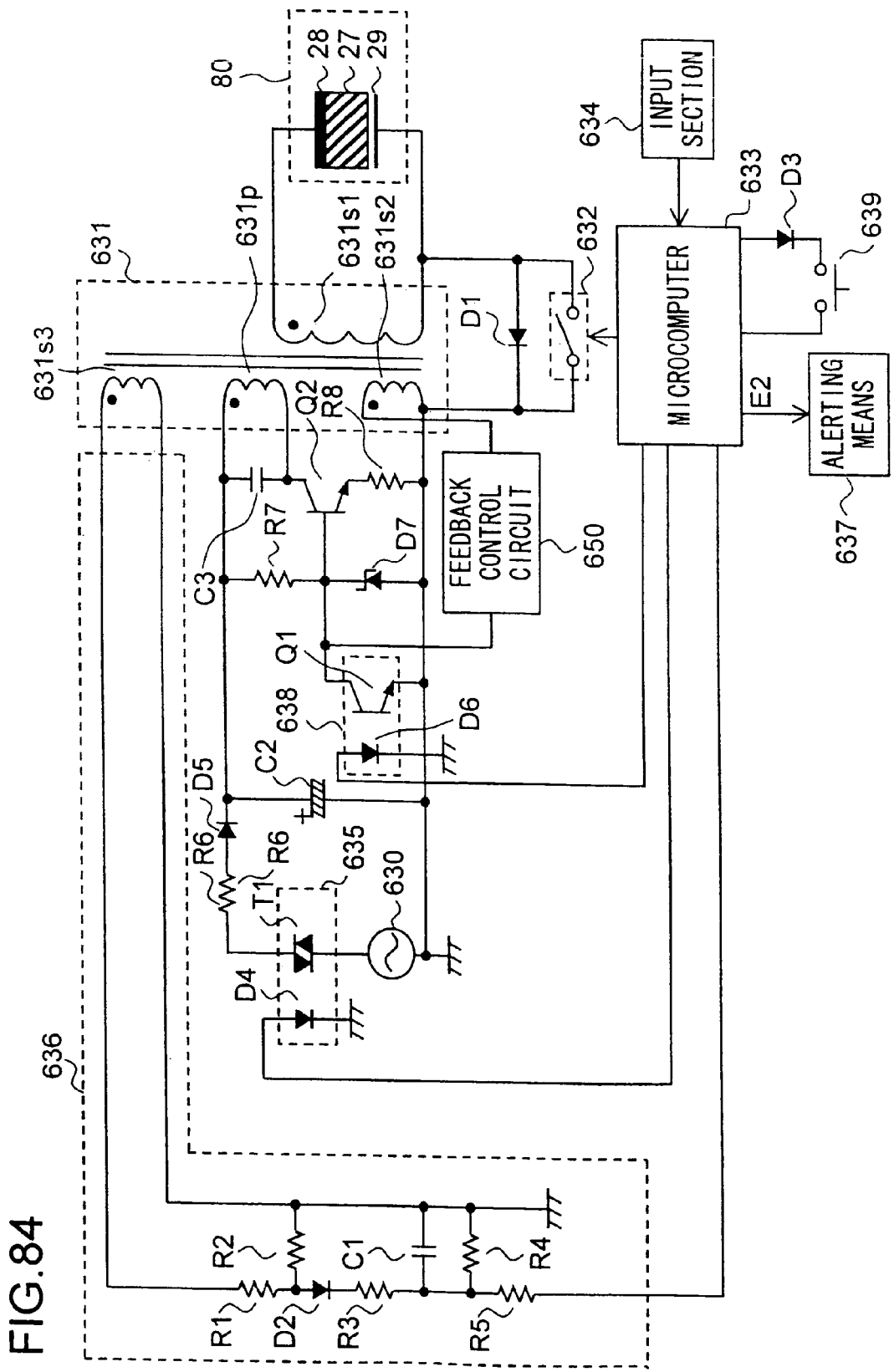
FIG. 84 is a circuit diagram of an ion generating device as a nineteenth embodiment of the air conditioning apparatus of the invention.
Figure 85:
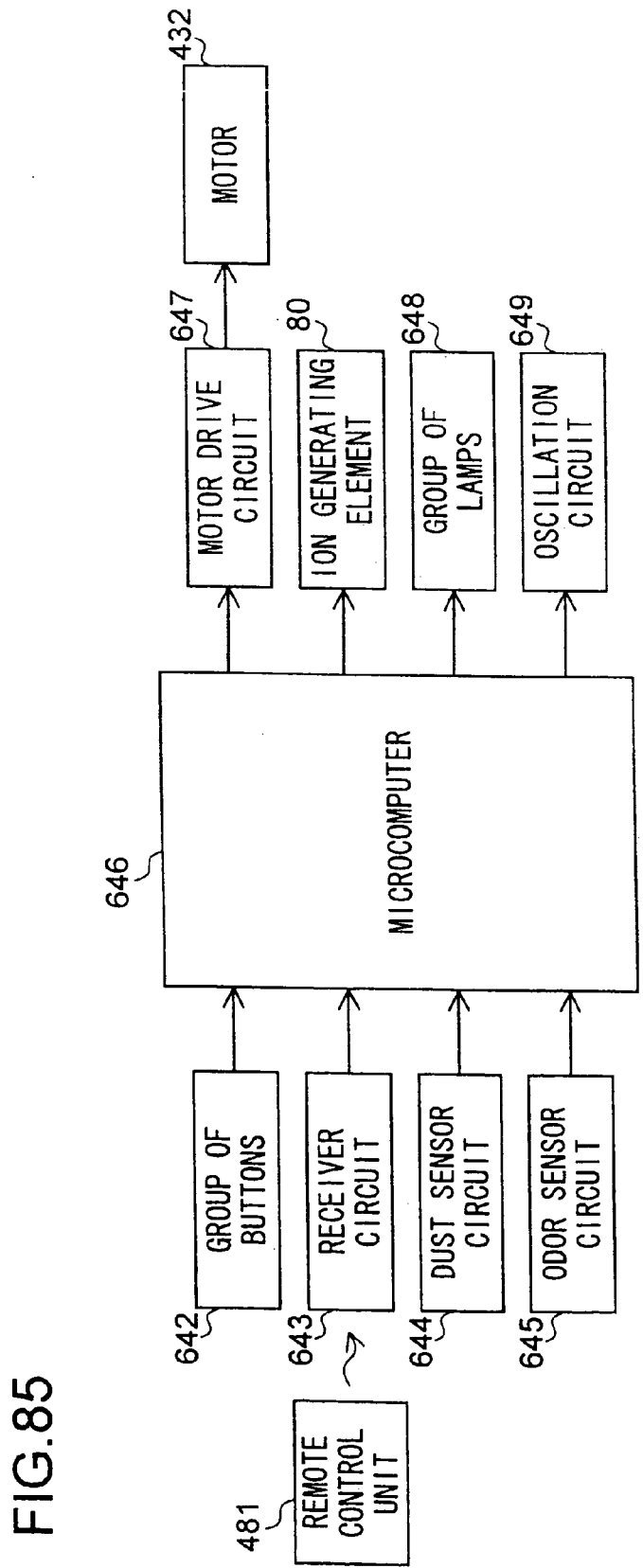
FIG. 85 is a circuit block diagram of the air conditioning apparatus of the nineteenth embodiment.

FIGS. 84 and 85 show a nineteenth embodiment of the air conditioning apparatus of the invention. This nineteenth embodiment relates to a control circuit for an ion generating device, and the example taken up here is configured as a control circuit for use in the air purifier 401a of the eighteenth embodiment.

A phototriac T1 is connected to a commercial power source 630. A light-emitting diode D4 is optically coupled with the phototriac T1, and the light-emitting diode D4 is connected to a microcomputer 633. The phototriac and the light-emitting diode D4 together constitute an SSR 635.

The terminal of the SSR 635, which is not connected to the commercial power source 630, is connected through a resistor R6 to the anode of the diode D5. The cathode of the diode D5 is connected to the positive terminal of the capacitor C2. The node between the negative terminal of the capacitor C2 and the commercial power source 630 is grounded.

The positive terminal of the capacitor C2 is connected through a resistor R7 to the cathode of a zener diode D7, and the anode of the zener diode D7 is connected to the negative terminal of the capacitor C2. Moreover, the positive terminal of the capacitor 2 is connected to one end of the primary winding 631$p$ of a switching transformer 631. The other end of the primary winding 631$p$ of the switching transformer 631 is connected to the collector of an npn-type switching transistor Q2, and the emitter of the switching transistor Q2 is connected through a resistor R8 to the negative terminal of the capacitor C2. Moreover, a capacitor C3 is connected between the two terminals of the primary winding 631$p$ of the switching transformer 631.

The node between the resistor R7 and the zener diode D7 is connected to the base of the switching transistor Q2 and to the collector of an npn-type phototransistor Q1. The emitter of the phototransistor Q1 is connected to the negative terminal of the capacitor C2. A light-emitting diode D6 is optically coupled with the phototransistor Q1, and the light-emitting diode D6 is connected to the microcomputer 633. The phototransistor Q1 and the light-emitting diode D6 together constitute a photocoupler 638.

The switching transformer 631 has, on its secondary side, three secondary windings 631$s$1, 631$s$2, and 631$s$3. The secondary winding 631$s$1 of the switching transformer 631 is connected to an ion generating element 80. The ion generating element 80 has a dielectric 27, and has an inner electrode 28 and an outer electrode 29 that face each other with the dielectric 27 sandwiched in between. One end of the secondary winding 631$s$2 of the switching transformer 631 is connected to the input side of a feedback control circuit 650. The output side of the feedback control circuit 650 is connected to the node between the resistor R7 and the zener diode D7. The other end of the secondary winding 631$s$2 of the switching transformer 631 is connected to the negative terminal of the capacitor C2. The secondary winding 631$s$3 of the switching transformer 631 is connected to a fault detection circuit 636, which will be described later.

In this circuit configuration, the AC (alternating-current) voltage obtained from the commercial power source 630 is rectified and smoothed by the diode D5 and the capacitor C2, and is thereby converted into a DC (direct-current) voltage. When the switching transistor Q2 is in an on state, this DC voltage is fed to the primary winding 631$p$ of the switching transformer 631. On the basis of the voltage induced in the secondary winding 631$s$2 of the switching transformer 631, the feedback control circuit 650 controls the on/off state of the switching transistor Q2, and thereby stabilizes the voltage induced in the secondary winding 631$s$1 of the switching transformer 631, i.e. the high voltage supplied to the ion generating element 80.

The anode of a diode D1 is connected to the node between the secondary winding 631$s$1 of the switching transformer 631 and the outer electrode 29, and the cathode of the diode D1 is connected to the negative terminal of the capacitor C2. A relay 632 is connected in parallel with the diode D1.

On the basis of signals fed from an input section 634, the microcomputer 633 controls the on/off state of the relay 632. The input section 634 includes an operation console from which the user can select the operation mode, a control circuit that determines the operation mode automatically according to the ambient conditions, and the like.

When the relay 632 is in an on state, the outer electrode 29 is grounded, and a sine-wave voltage is applied to the inner electrode 28. In this state, the ion generating element 80 generates positive and negative ions simultaneously from air. Thus, airborne bacteria present in the air are killed.

On the other hand, when the relay 632 is in an off state, if the inner electrode 28 is at a negative potential, electrons flow from ground to the diode D1 to the secondary winding 631$s$1 to the inner electrode 28, and are discharged into the air between the electrodes. Thus, negative ions are generated. By contrast, if the inner electrode 28 is at a positive potential, electrons do not flow from the inner electrode 28 to the secondary winding 631$s$1 to the diode D1 to ground, and therefore the inner electrode 28 cannot receive electrons from the air between the electrodes. Thus, no positive ions are generated. In this way, when the relay 632 is in an off state, the ion generating element 80 generates only negative ions from air, offering a relaxing effect.

Moreover, on the basis of the signals fed from the input section 634, the microcomputer 633 controls the on/off state of the SSR 635. Bringing the SSR 635 into an on state causes the ion generating device to start operating, and bringing the SSR 635 into an off state causes the ion generating device to stop operating.

Next, the fault detection circuit 636 described above which is connected to the secondary winding 631$s$3 of the switching transformer 631 will be described. One end of the secondary winding 631$s$3 of the switching transformer 631 is connected to one end of a resistor R1, and the other end of the secondary winding 631$s$3 of the switching transformer 631 is connected to one end of a resistor R2. The other end of the resistor R1 and the other end of the resistor R2 are both connected to the anode of a diode D2. The cathode of the diode D2 is connected through a resistor R3 to one end of a capacitor C1. The other end of the capacitor C1 is connected to the one end of the resistor R2. A resistor R4 is connected in parallel with the capacitor C1. One end of the resistor R4 is connected through a resistor R5 to the microcomputer 633, and the other end of the resistor R4 is grounded.

In this circuit configuration, a voltage commensurate with the voltage across the secondary winding 631$s$1 of the switching transformer 631 is induced in the secondary winding 31$s$3 of the switching transformer 631. The voltage induced in the secondary winding 631$s$3 of the switching transformer 631 is rectified and smoothed, and is then fed to the microcomputer 633. When a short circuit occurs in the ion generating element 80, the current induced in the secondary winding 631$s$3 of the switching transformer 631 becomes smaller than its normal level. Thus, the voltage signal fed to the microcomputer 633 becomes lower than its normal level. On the other hand, if the inner or outer electrode 28 or 29 is disconnected, the voltage induced in the secondary winding 631$s$3 of the switching transformer 631 becomes higher than its normal level. Thus, the voltage signal fed to the microcomputer 633 becomes higher than its normal level. When the voltage signal fed to the microcomputer 633 is out of a predetermined range, the microcomputer 633 recognizes a fault and activates an alerting means 637. The alerting means 637 is realized, for example, with a means that notifies the user of a fault by emitting light or giving a sound.

To the microcomputer 633, a light-emitting diode D3 and a push switch 639 are connected. The push switch 639 is normally in an on state, so that, when the ion generating device is operating, the light-emitting diode D3 emits light and, when the ion generating device stops operating, the light-emitting diode D3 stops emitting light. If the light emitted by the light-emitting diode D3 is not desired, as in the night time the push switch 639 is brought into an off state. This makes it possible to stop the light emission of the light-emitting diode D3 even when the ion generating device is operating.

Moreover, by controlling the on/off state of the photocoupler 638, the microcomputer 633 can turn on and off at regular intervals the output of the high voltage supplied from the switching transformer 631 to the ion generating element 80. This makes it possible to reduce the amount of ozone generated. For example, by driving the ion generating device with a period of 10 seconds consisting of a 5-second on period and a 5-second off period, it is possible to reduce the amount of ozone generated to about a half or less of the amount generated when no such control is exercised. The on/off periods of the photocoupler 638 may be varied according to the operation mode (the volume of air) so as to be optimized in each operation mode.

Now, how the operation of the air purifier provided with the control circuit described above is controlled will be described with reference to a circuit block diagram shown in FIG. 85. A microcomputer 646 receives command signals individually from a group of buttons 642, a receiver circuit 643, a dust sensor circuit 644, and an odor sensor circuit 645, and, on the basis of these command signals, outputs control signals individually to a motor drive circuit 647, the ion generating element 80, a group of lamps 648, and an oscillation circuit 649.

The group of buttons 642 is provided on the operation panel 480 (see FIG. 82). The group of buttons 642 includes an "operation on/off" button, an "operation mode switch" button, and a "turn-off timer" button. The remote control unit 481 is provided with, in addition to an "operation on/off" button and a "turn-off timer" button, a "cluster on/off" button, a "cluster mode switch" button, an "automatic operation" button, a "quick operation" button, a "pollen operation" button, "manual (air volume) operation" button, a "quiet operation" button, and a "cigarette smoke operation" button, and is also provided with a transmitter circuit that transmits infrared light.

The receiver circuit 643 receives the infrared light emitted from the transmitter circuit of the remote control unit 481. The light-sensing portion of the receiver circuit 643 is provided on the operation panel 480. The dust sensor circuit 644 is provided with a photointerruptor consisting of a light-emitting element and a light-sensing element that is optically coupled with the light-emitting element. As the amount of dust in the air increases, more light is reflected by dust and is received by the light-sensing element. This makes the output voltage higher. The dust sensor circuit is operated only when the motor 432 is being operated. The odor sensor circuit 645 is provided with an odor sensor employing a metal oxide semiconductor, and senses odors produced in everyday life, such as cigarette smoke, by exploiting the property of the metal oxide semiconductor of which the resistance varies when its surface absorbs molecules of particular gases. The odor sensor circuit 645 is operated continuously when the motor 432 is operating, and is operated for a predetermined short period every predetermined period when the motor 432 is at rest.

The motor drive circuit 647 receives a control signal from the microcomputer 646, and controls the motor 432 by PWM so that the motor 432 rotates at a predetermined rotation speed according to the control signal. The operation of the ion generating element 80 can be switched, as described earlier, between a mode in which it generates both negative and positive ions and a mode in which it generates only negative ions. The "cluster" lamp described later corresponds to the light-emitting diode D3 (see FIG. 84), and the microcomputer 646 corresponds to the input section 634 (see FIG. 84). Moreover, the light-emitting diode D3 serves also as the alerting means 637 (see FIG. 84).

The group of lamps 648 includes a "power" lamp, an "automatic operation" lamp, a "quiet operation" lamp, a "pollen operation" lamp, a "cigarette smoke operation" lamp, a "gentle wind operation" lamp, a "moderate wind operation" lamp, a "strong wind operation" lamp, a "quick operation" lamp, a "one hour" lamp, a "two hours" lamp, a "four hours" lamp, a "cluster mode switch" lamp, and a "cluster" lamp. The group of lamps 648 is provided on the operation panel 480. The oscillation circuit 649 generates an electronic sound according to the control signal from the microcomputer 646.

The microcomputer 646 exercises control in the following manner. When the "operation on/off" button in the group of buttons 642 is pressed, the air purifier starts operating in an 'automatic operation mode'. The 'automatic operation mode' is a mode in which the rotation speed of the motor 432 is varied according to the amounts of dust and odor-causing molecules detected by the dust sensor circuit 644 and the odor sensor circuit 645 (this is achieved by selecting one among the 'quiet operation, gentle wind operation, moderate wind operation, strong wind operation, and quick operation modes' described later). Now, the "automatic operation" lamp in the group of lamps 648 is lit, and the ion generating element 80 starts operating. When the "operation on/off" button in the group of buttons 642 is pressed in the middle of operation, the motor 432 is stopped, the operation of the ion generating element 80 is stopped, and the "automatic operation" lamp in the group of lamps 648 is extinguished.

Every time the "operation mode switch" button in the group of buttons 642 is pressed, the operation mode switches from the 'automatic operation mode' to a 'quiet operation mode' to a 'gentle wind operation mode' to a 'moderate wind operation mode' to a 'strong wind operation mode' to a 'quick operation mode' to a 'cigarette smoke operation mode' to a 'pollen operation mode' to the 'automatic operation mode,' and so forth. Correspondingly, the lamp that is lit in the group of lamps 648 switches from the "automatic operation" lamp to a "quiet operation" lamp to a "gentle wind operation" lamp to a "moderate wind operation" lamp to a "strong wind operation" lamp to a "quick operation" lamp to a "cigarette smoke operation" lamp to a "pollen operation" lamp to the "automatic operation" lamp, and so forth. On the remote control unit 481 are provided buttons corresponding to the 'automatic operation, quiet operation, cigarette smoke operation, and pollen operation modes,' and here the switching among the 'gentle wind operation, moderate wind operation, strong wind operation, and quick operation modes' is achieved by pressing the "manual (air volume) operation" button.

In the 'quiet operation mode,' the motor 423 is controlled so as to rotate at a rotation speed of 300 rpm. This mode, in which the air purifier produces little noise, is suitable, for example, for operation at night.

The motor 432 is controlled so as to rotate at rotation speeds of 550 rpm in the 'gentle wind operation mode,' 750 rpm in the 'moderate wind operation mode,' and 900 rpm in the 'strong wind operation mode.'

In the 'quick operation mode,' the motor 432 is controlled so as to rotate at a rotation speed of 1,100 rpm. This mode, in which air flows through the filter 420 (see FIG. 63) at a high flow rate, is suitable when the air needs to be purified quickly.

In the 'cigarette smoke operation mode,' the air purifier is first operated in the 'strong wind operation mode' for a predetermined period, and is then switched to the 'automatic operation mode.' This mode is suitable to remove the smoke and odor of cigarettes.

In the 'pollen operation mode,' the air purifier is first operated in the 'strong wind operation mode' for a predetermined period, and is then switched alternately between the 'gentle wind operation mode' and the 'strong wind operation mode' at predetermined time intervals. This mode is suitable to remove pollen.

By pressing the "turn-off timer" button provided in the group of buttons 642 or on the remote control unit 481 in the middle of operation, it is possible to stop the operation of the air purifier automatically a specified period of time thereafter. Every time the "turn-off timer" button is pressed, the specified period switches from "one hour" to "two hours" to "four hours" to "timer cancelled" to "one hour," and so forth. Correspondingly, among the "one hour," "two hours," and "four hours" lamps provided in the group of lamps 648, the one that is lit is switched from the "one hour" lamp to the "two hours" lamp to the "four hours" lamp to none to the "one hour" lamp, and so forth. Moreover, when the "turn-off timer" button provided on the remote control unit 481 is pressed, the oscillation circuit 649 generates a number of electronic sounds that corresponds to the specified period. If the "turn-off timer" button is pressed when the ion generating element 80 is operating, the operation of the ion generating element 80, too, is stopped the specified period of time thereafter in an interlocked fashion.

Pressing the "cluster on/off" button when the ion generating element 80 is not operating brings the SSR 635 into an on state. Thus, the ion generating element 80 starts operating, and the "cluster" lamp is lit. Pressing the "cluster on/off" button when the ion generating element 80 is operating brings the SSR 635 into an off state. Thus, the ion generating element 80 stops operating. The control signal for the SSR 635 and the PWM control signal from the motor drive circuit 647 are independent of each other, and therefore the on/off state of the ion generating element 80 can be controlled irrespective of the on/off state of the motor 432.

By pressing the push switch 639 (see FIG. 84) provided on the outer peripheral surface of the body 410 of the air purifier 401a, it is possible to turn the "cluster" lamp off even when the ion generating element 80 is on. This permits the user to turn off the "cluster" lamp if its light is not desired as when the air purifier is used in the night time, and thus enhances usability.

As described earlier, the "cluster" lamp serves also as the alerting means. When the dielectric 27 of the ion generating element 80 is broken, and a short circuit occurs on the secondary side of the switching transformer 631, the microcomputer 633, on the basis of a fault signal output from the fault detection circuit 636, feeds a pulsating driving signal to the light-emitting diode D3 (see FIG. 84). Thus, the "cluster" lamp blinks and thereby notifies the user of the fault. Here, if the push switch 639 (see FIG. 84) is in an off state, it is not possible to make the "cluster" lamp blink and thereby notify the user of the fault. This can be overcome by connecting a relay (not shown) in parallel with the push switch 639 and controlling the relay in such a way that it is brought into an on state only when the microcomputer 633 has recognized a fault on the basis of the fault signal output from the fault detection circuit 636. Instead of connecting a relay in parallel with the push switch 639, it is also possible to adopt a circuit configuration in which the microcomputer 633 controls the on/off state of the push switch 639.

Every time the "cluster mode switch" button is pressed, the on/off state of the relay 632 is toggled. When the relay 632 is in an on state, i.e. when the ion generating element 80 generates positive and negative ions, the "cluster mode switch" lamp is lit; when the relay 632 is in an off state, i.e. when the ion generating element 80 generates only negative ions, the "cluster mode switch" lamp is extinguished.

Next, an example of how the air purifier 401 a operates will be described. First, when the "operation on/off" button on the operation panel 480 is pressed, the air purifier starts operating in the 'automatic operation mode.' The motor 432 rotates the fan 431, so that air is sucked into the air purifier through the air inlet 413 of the front panel 412 and the side air inlets 414. From the air, the prefilter 421 collects larger particles of dust, the deodorizing filer 422 absorbs and thereby removes odor-causing molecules, and the dust-collecting filter 423 collects fine particles of dust. The air, having the dust and odor-causing molecules contained therein removed by the filter 420, is then discharged out of the air purifier through the main air outlet 415 by the fan 431, with part of the air passed through the bypass passage 456 so as to be fed to the ion generating element 80.

As soon as the air purifier starts operating, an alternating-current voltage of about 1.75 V starts being applied to the ion generating element 80. On the other hand, in the 'automatic operation mode,' the relay 632 and the SSR 635 are in an on state. Thus, the ion generating element 80 produces positive and negative ions from air. Simultaneously, ozone is produced as a byproduct. In this case, the concentrations of negative and positive ions are both 20,000 ions/cc, and the concentration of ozone is 0.01 ppm or lower. By the action of the negative and positive ions generated by the ion generating element 80, airborne bacteria present in the air are removed. According to the tests conducted by the inventors, the elimination rate of bacteria was 86% in two hours, 93% in four hours, and 99% in twenty hours after the start of operation. When the "cluster mode switch" button is pressed to bring the relay 632 into an off state, the ion generating element 80 generates negative ions from air, and ozone is generated simultaneously as a byproduct. In this case, the concentration of the negative ions is 20,000 ions/cc, and the concentration of ozone is 0.01 ppm or lower.

Although the nineteenth embodiment deals with an air purifier as an example, the control circuit described above is applicable also to air conditioners, dehumidifiers, humidifiers, and the like.

Figure 86:
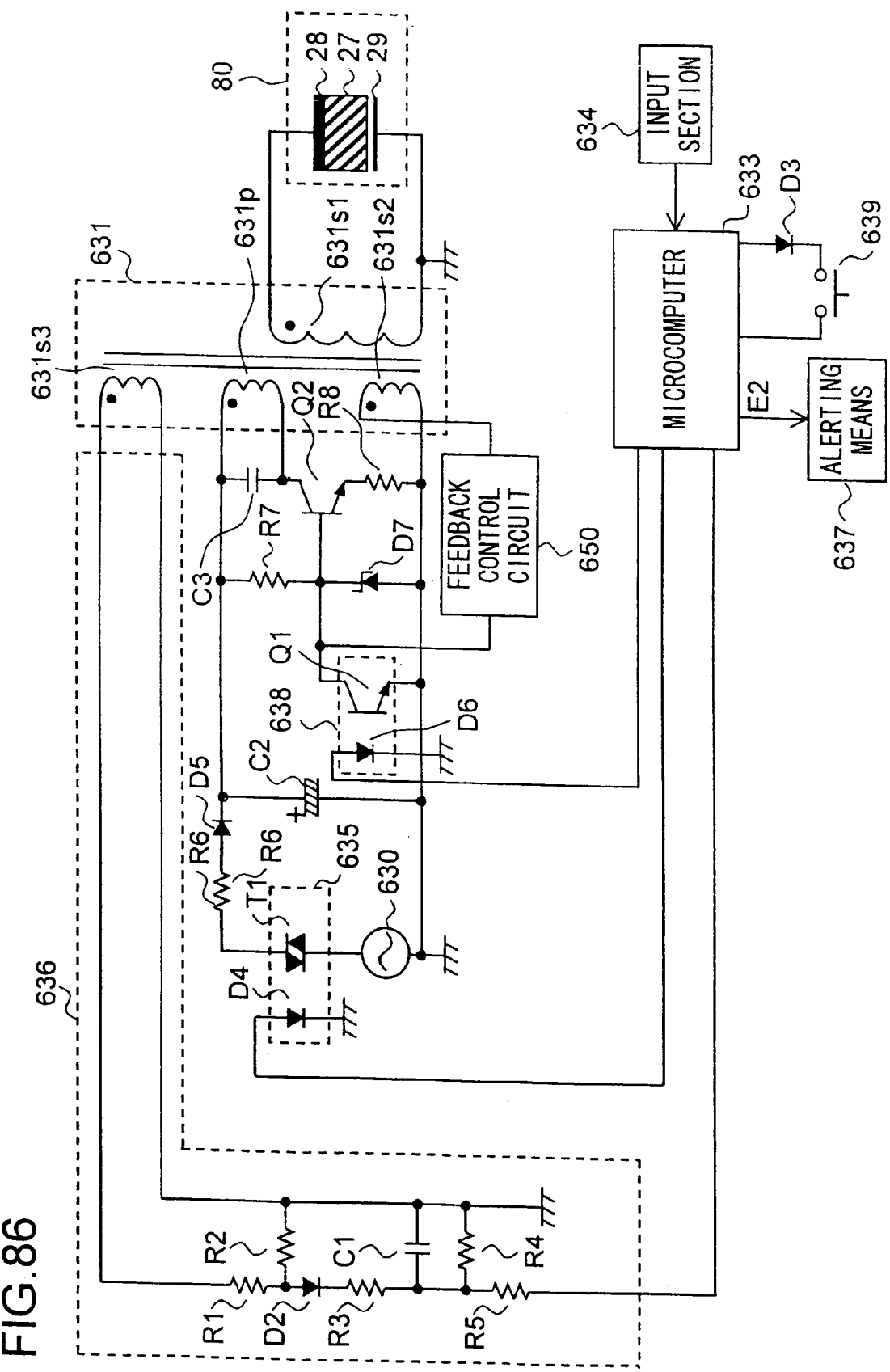
FIG. 86 is a circuit diagram of a modified example of the circuit shown in FIG. 84.

In a case where switching between operation yielding only negative ions and operation yielding both negative and positive ions is not necessary, i.e. where only the function of generating negative and positive ions is required, the ion generating device may be configured as shown in FIG. 86. In this ion generating device, such circuit components and blocks as are found also in the ion generating device shown in FIG. 84 are identified with the same reference numerals, and their explanations will not be repeated.

As will be clear from the descriptions above, the ion generating device used in the air conditioning apparatus of this embodiment is provided with a first generating means for generating positive and negative ions and a second generating means for generating only negative ions, and is equipped with a switching means for switching between the first and second generating means. This makes it possible to switch between operation that yields only negative ions to achieve a relaxing effect and operation that yields both negative and positive ions to achieve a sterilizing effect.

Moreover the switching means for switching between the first and second generating means is provided with a diode having its anode connected to that one of the electrodes to which the voltage is not applied and having its cathode grounded, and a switching device connected between the two ends of the diode. Thus, by switching the on/off state of the switching device, it is possible to achieve the aforementioned effects. Moreover, the switching means for switching between the first and second generating means is realized with a simple configuration. This helps reduce costs.

Moreover, by using a relay as the switching device, it is possible to insulate the alternating-current voltage generating means from the control circuit that controls the relay. This helps simplify the circuit configuration.

Moreover, by providing a light-emitting means that emits light when the ion generating device is being driven and a stopping means that can stop the driving of the light-emitting means, it is possible to stop the emission of light by the display means in the night time even in the middle of operation if the light is not desirable. This enhances usability.

Moreover, the air conditioning apparatus is provided with an ion generating device that can be switched between operation yielding only negative ions and operation yielding both negative and positive ions. This makes it possible to achieve, in addition to the functions of adjusting the temperature and humidity of the air, a relaxing effect and a sterilizing effect.

Moreover, the air conditioning apparatus is provided with a first driving control means for controlling the driving of the ion generating device and a second driving control means for controlling the driving of the air-conditioning means. Thus, the ion generating device and the air-conditioning means can be controlled independently irrespective of the driving status of each other. That is, it is possible to turn on the ion generating device alone, or turn on the air-conditioning means alone. This makes it possible to realize an operation mode in which only air conditioning is performed, an operation mode in which only a relaxing effect is achieved, and an operation mode in which only a sterilizing effect is achieved.

FIGS. 87 to 99 show a twentieth embodiment of the air conditioning apparatus of the invention. The air conditioning apparatus of the twentieth embodiment is realized as a dehumidifier.

Figure 87:
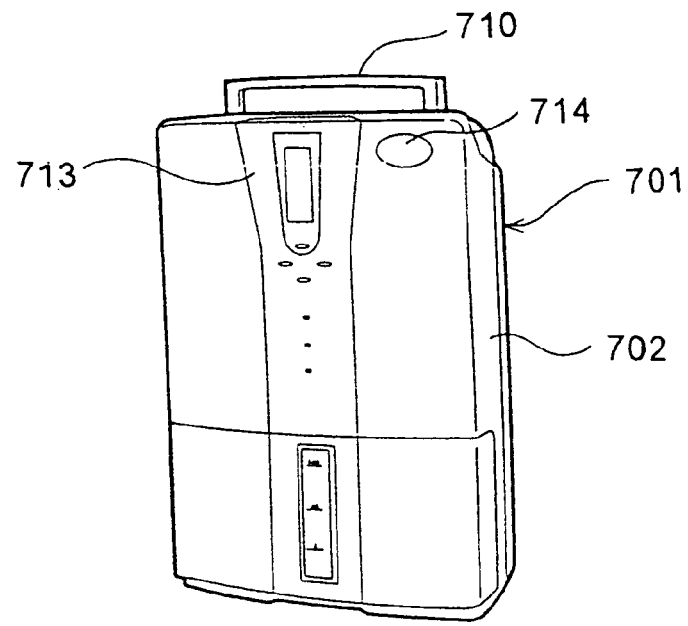
FIG. 87 is a front perspective view showing the front face of a dehumidifier as a twentieth embodiment of the air conditioning apparatus of the invention.
Figure 88:
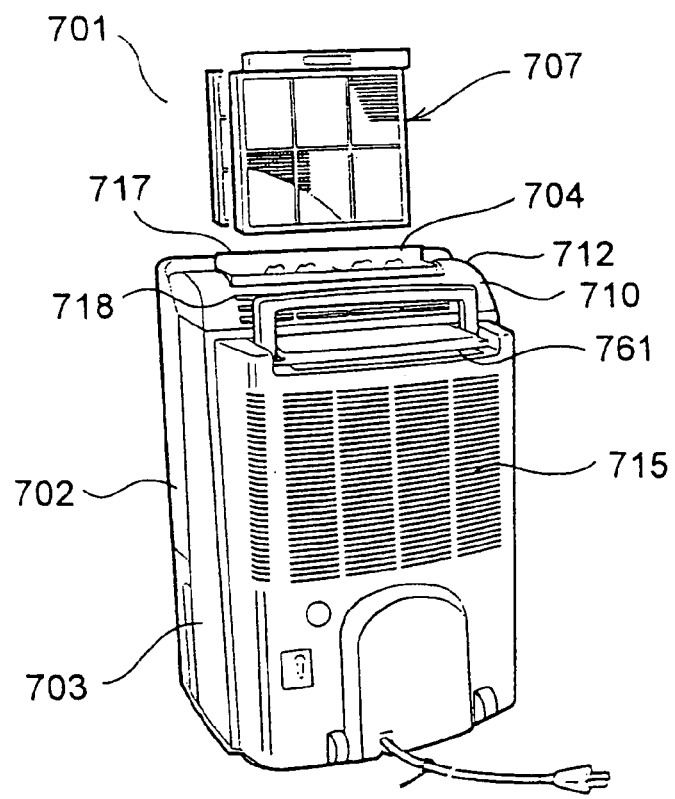
FIG. 88 is a rear perspective view showing the rear face of the dehumidifier of the twentieth embodiment.

FIG. 87 is a front perspective view of the dehumidifier 701, and FIG. 88 is a rear perspective view of the dehumidifier 701. In the following descriptions, the direction from the rear face to the front face as viewed in FIGS. 87 and 88 is referred to as the frontward direction, and the direction from the front face to the rear face is referred to as the rearward direction. In actual use, the dehumidifier 701 is installed in an orientation as shown in FIGS. 87 and 88 on a floor surface or the like, and the vertical direction in these figures coincides with the vertical direction at the site of installation.

First, the construction of the dehumidifier 701 will be described. The dehumidifier 701 has front portions of the side and bottom faces thereof and the entire front face thereof covered with a front frame 702, and has rear portions of the side and bottom faces thereof and the entire rear face thereof covered with a rear frame 703.

The front and rear frames 702 and 703 are engaged with each other by the use of engagement claws (not shown) formed at the peripheral edges of the side and bottom surfaces thereof, and are thereby coupled together with an opening left in the top surface. In the opening, an exhaust portion 712 is fitted through which air is discharged. In the exhaust portion 712, in top and rear portions thereof, air outlets 704 and 718 are formed through which dry air is blown out upward and rearward, respectively. In the air outlet 704 of the exhaust portion 712, a wind direction adjustment device 717, of which a detailed description will be given later, is fitted so as to obstruct the air outlet 704 and change the direction of wind by driving a wind deflector plate (not shown).

Moreover, in the rear surface of the rear frame 703, an air inlet 715 is formed through which the air inside the room is taken into the humidifier. On the inside of the rear surface of the rear frame 703, in a position facing the air inlet 715, a filter 707 is fitted that removes dust and the like from the air sucked in through the air inlet 715.

The filter 707 is made antibacterial by the use of apatite or the like, and collects dust, pollen, viruses, nitrogen oxides and the like contained in the air flowing into the dehumidifier 701 through the air inlet 715. The filter 707 is removably fitted by being inserted through an opening 761 formed in the top surface of the rear frame 703.

Behind the exhaust portion 712, a handle 710 is pivoted that permits the dehumidifier 701 to be carried around. In an upper side portion of the front surface of the front frame 702, a sight window 714 is provided that permits inspection of the inside of the dehumidifier 701, and, in an upper central portion of the front surface of the front frame 702, an operation panel 713 is provided from which the dehumidifier 701 is operated and on which indications related to its operation are displayed.

Figure 89:
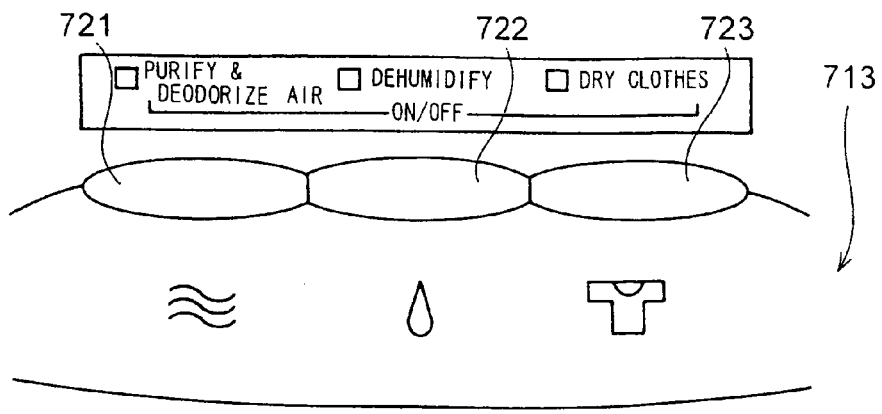
FIG. 89 is a top view of the operation panel of the dehumidifier of the twentieth embodiment.
Figure 90:
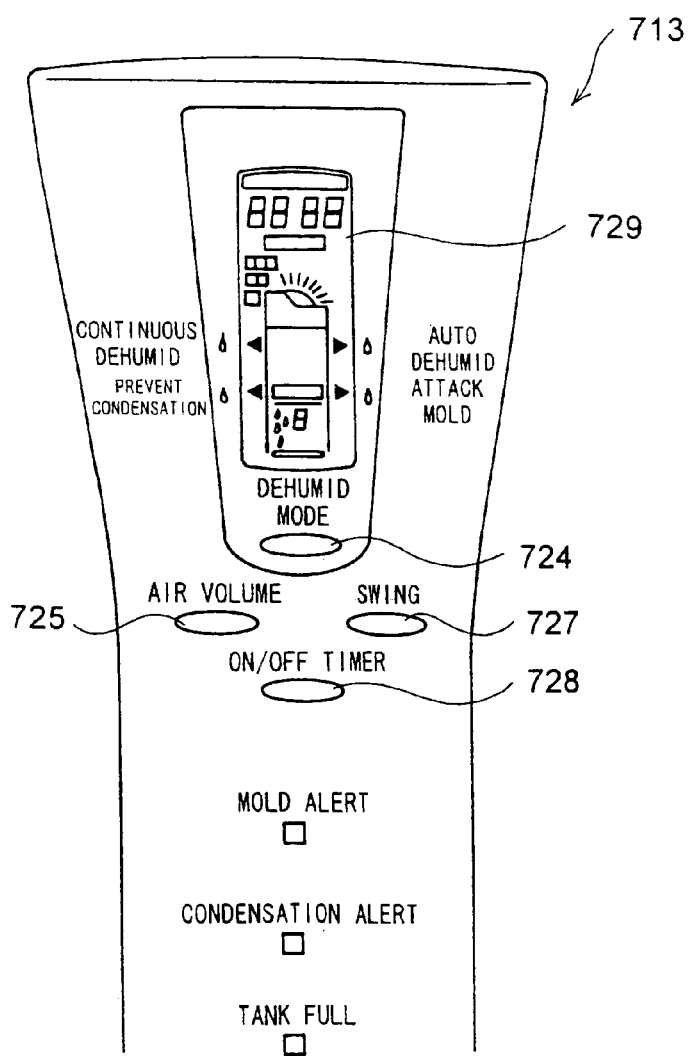
FIG. 90 is a front view of the operation panel of the dehumidifier of the twentieth embodiment.

Now, an example of the operation panel 713 will be described. FIGS. 89 and 90 are a top view and a front view, respectively, showing the details of the operation panel 713. In a top-face portion of the operation panel 713 are provided an air purification button 721, a dehumidification button 722, and a clothes drying button 723.

When the dehumidification button 722 is pressed, a compressor, described later, is driven with a normal output power so that the air inside the room is dehumidified. When the clothes drying button 723 is pressed, the compressor is driven with an output power higher than the normal output power so that the air inside the room is dehumidified and moreover wet clothes hung inside the room are dried. An ion generating device as described earlier is driven simultaneously in air-purifying, dehumidifying, and clothes-drying operation.

In a front-face portion of the operation panel 713, a display panel 729 is provided that displays the indoor temperature and the operation status. Below the display panel 729 are arranged a dehumidification switch button 724, an air volume switch button 725, a swing button 727, and a timer switch button 728. Every time the dehumidification switch button 724 is pressed, the operation mode is switched from "automatic dehumidification" to "continuous dehumidification" to "condensation prevention," and so forth.

Every time the air volume switch button 725 is pressed, the volume of air that is blown out into the room is switched from "medium" to "quiet" to "strong," and so forth. Every time the swing button 727 is pressed, the position of the wind deflector plate is switched from "off" to "upward" to "rearward" to "wide-angle," and so forth, and thus the direction of the flow of air that is blown out into the room can be changed. Pressing the timer switch button 728 permits the timer to be turned on and off and set for a length of time in the range of 1 to 9 hours.

Figure 91:
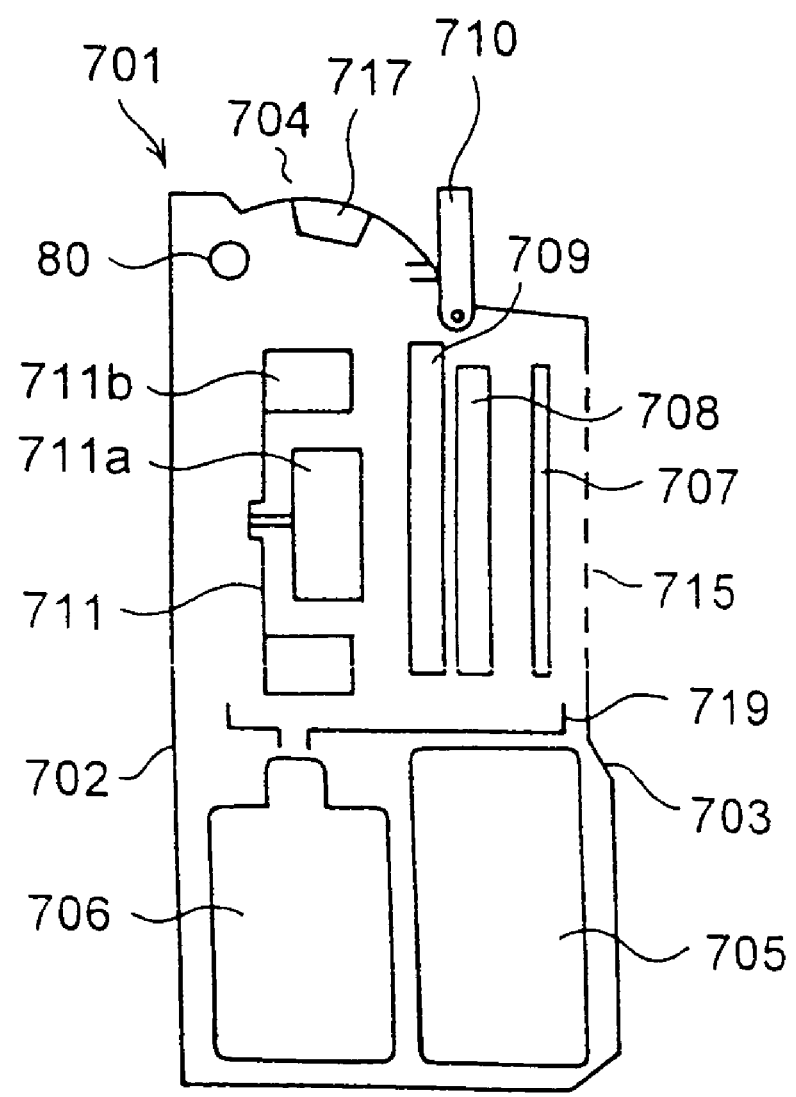
FIG. 91 is a side view showing the internal construction of the dehumidifier of the twentieth embodiment.

FIG. 91 is a sectional view showing an outline of the inside of the dehumidifier 701 shown in FIGS. 87 and 88, taken along a plane parallel to its side faces. In FIG. 91, directions are referred to in the same manner as in FIG. 87. In a lower rear portion inside the dehumidifier 701, a compressor 705 is provided; in a lower front portion inside the dehumidifier 701, a tank 706 is provided in which condensed water is collected through a drain pan 719. Part of the front frame 702 is made openable so that the tank 706 can be taken out of the dehumidifier 701 for the disposal of the condensed water collected therein. Above the compressor 705 are arranged, in order from the filter 707 arranged so as to face the air inlet 715, an evaporator 708, a condenser 709, and a blower 711. In the passage leading from the discharge outlet of the blower 711 to the air outlet, the ion generating element 80 described earlier is arranged.

The blower 711 is built as a sirocco fan in which, as a motor 711a is driven, an impeller 711b provided around the motor 711a is rotated so that air is sucked in through the air inlet 715 formed in the rear surface of the dehumidifier 701 and is blown out radially through the impeller 711b. This directs the air in the direction in which the ion generating element 80 and the air outlets 704 and 718 are arranged.

One end of the evaporator 708 and one end of the condenser 709 are connected together by a first connection pipe (not shown) by way of the compressor 705, and the other end of the evaporator 708 and the other end of the condenser 709 are connected together by a second connection pipe (not shown) by way of an expansion valve (not shown). When the compressor 705 is driven, the cooling medium inside the first and second connection pipes flows, and thereby operates a refrigerating cycle. Specifically, the hot cooling medium compressed by the compressor 705 releases heat and condenses in the condenser 709. The cooling medium thus condensed and thereby liquefied is then decompressed by the expansion valve, and, as it evaporates as a result, it takes away heat of vaporization in the evaporator 708, and then returns to the compressor 705.

When the compressor 705 and the blower 711 are operated simultaneously, the air inside the room sucked in through the air inlet 715 is first passed through the filter 707, which removes dust, pollen, viruses, nitrogen oxides, and the like from the air. Then, the air sucked in is cooled by being subjected to heat exchange with the evaporator 708, which is kept at a lower temperature. Here, when the temperature of the air becomes below the dew point on or near the surface of the evaporator 708, the moisture contained in the air condenses on the surface of the evaporator 708. The moisture condensed on the heat exchanger flows down along the evaporator 708, and is collected as condensed water in the tank 706.

Then, the air sucked in is directed to the condenser 709, which is kept at a higher temperature, so as to be subjected to heat exchange with the condenser and thereby heated to about the same temperature as it had before being dehumidified. In this way, air having about the same temperature as the air before being sucked into the dehumidifier 701 and containing a smaller amount of moisture than this air is produced (hereinafter referred to as the dry air).

Thereafter, the dry air passes through the blower 711 so that part of the dry air is directed to the ion generating element 80 and the rest is directed to the air outlets 704 and 718 (see FIG. 88). The dry air that has passed by the ion generating element 80 and now containing positive and negative ions then joins the rest of the dry air, and is then blown out into the room. In this way, dehumidification and sterilization of the air inside the room is achieved.

Figure 92:
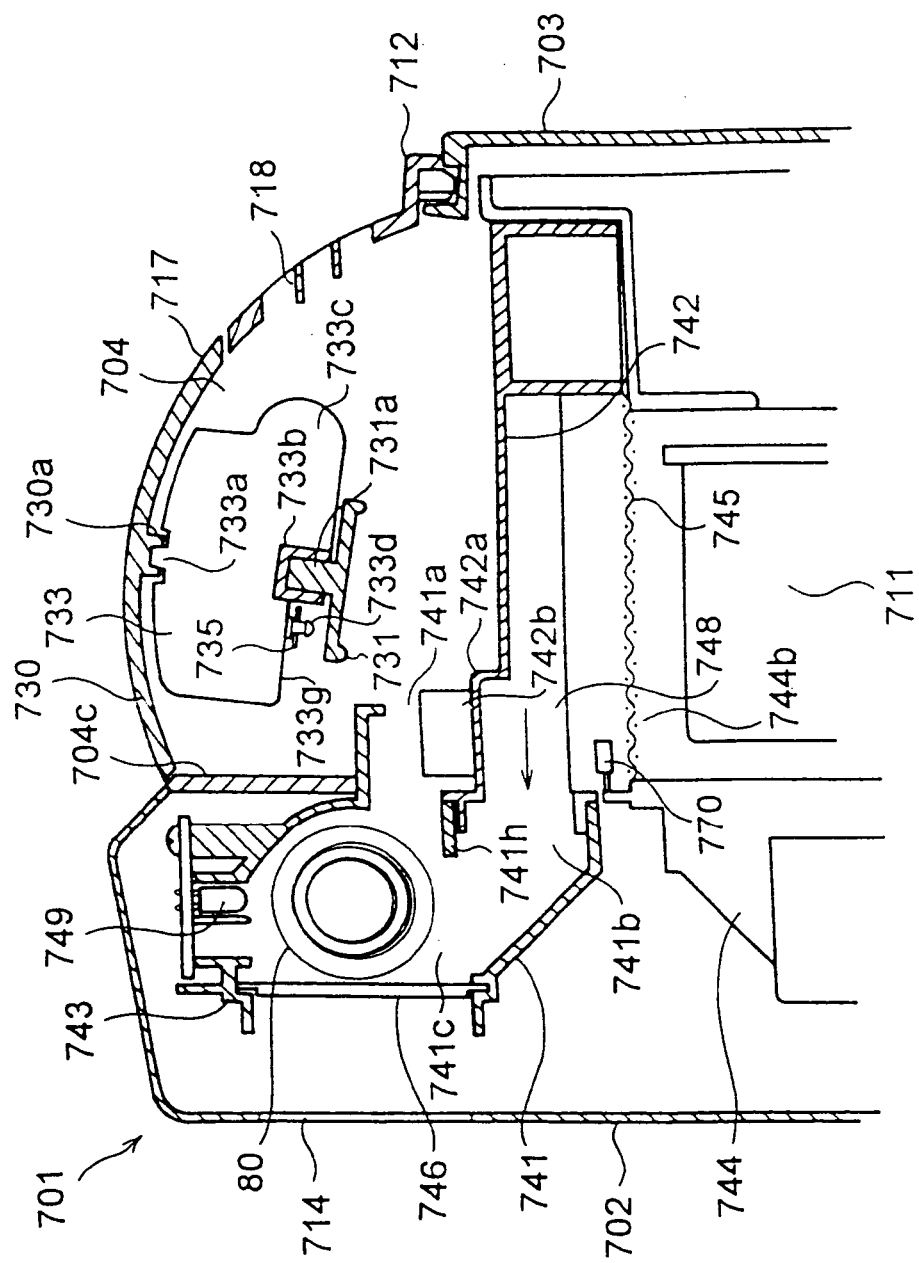
FIG. 92 is a sectional view, as seen from the side, showing an outline of the construction of an upper portion of the dehumidifier of the twentieth embodiment.
Figure 93:
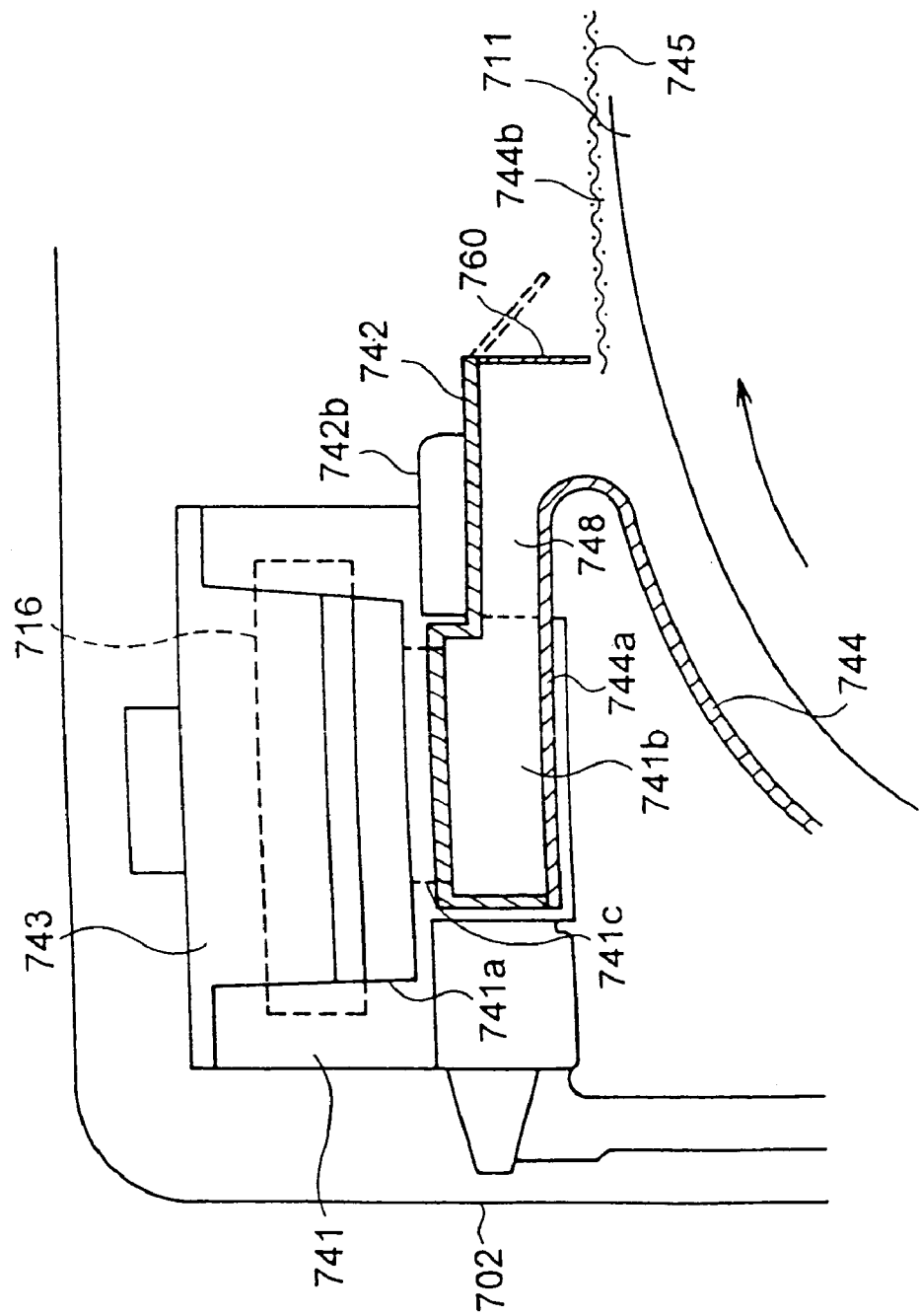
FIG. 93 is a sectional view, as seen from the back, showing an outline of the construction of an upper portion of the dehumidifier of the twentieth embodiment.
Figure 94:
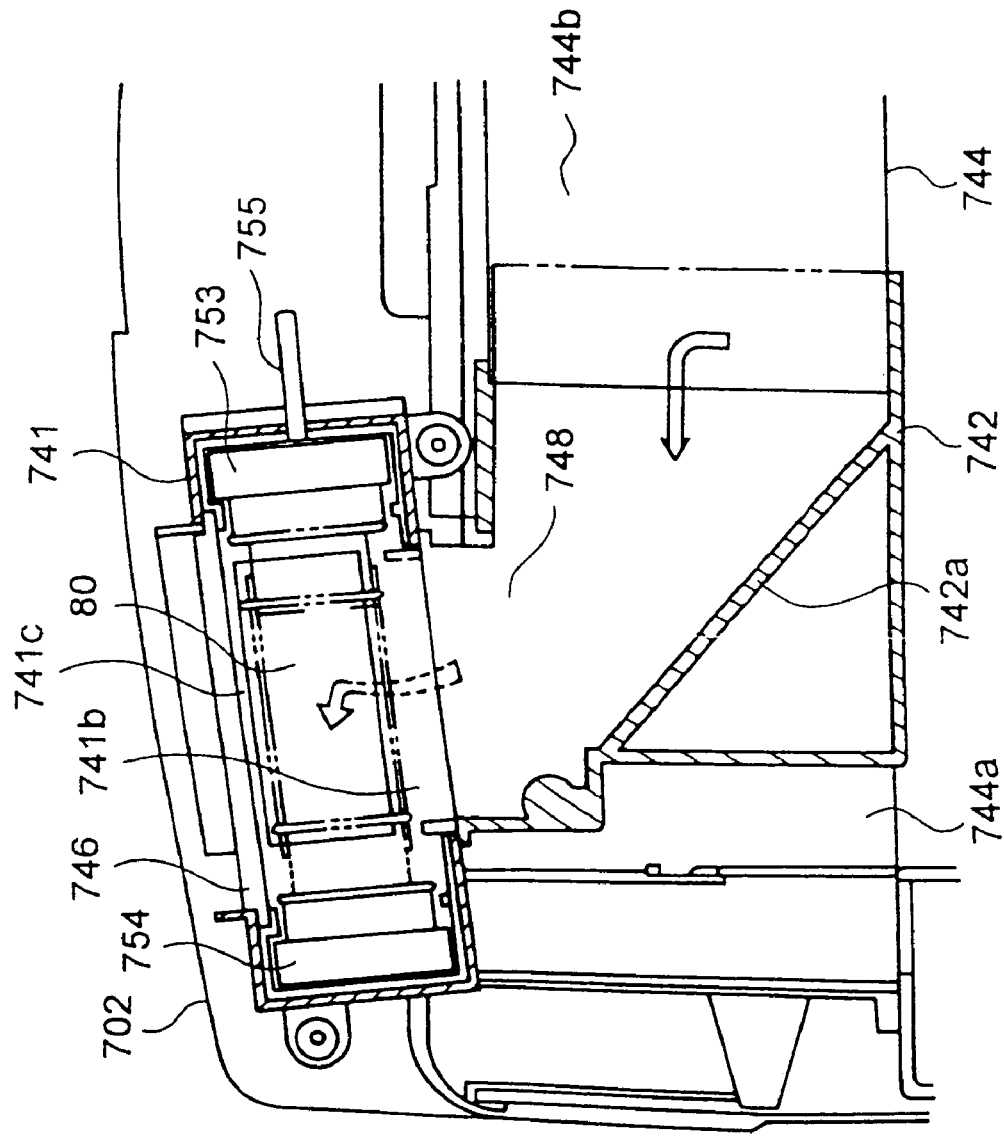
FIG. 94 is a sectional view, as seen from the top, showing an outline of the construction of an upper portion of the dehumidifier of the twentieth embodiment.
Figure 95:
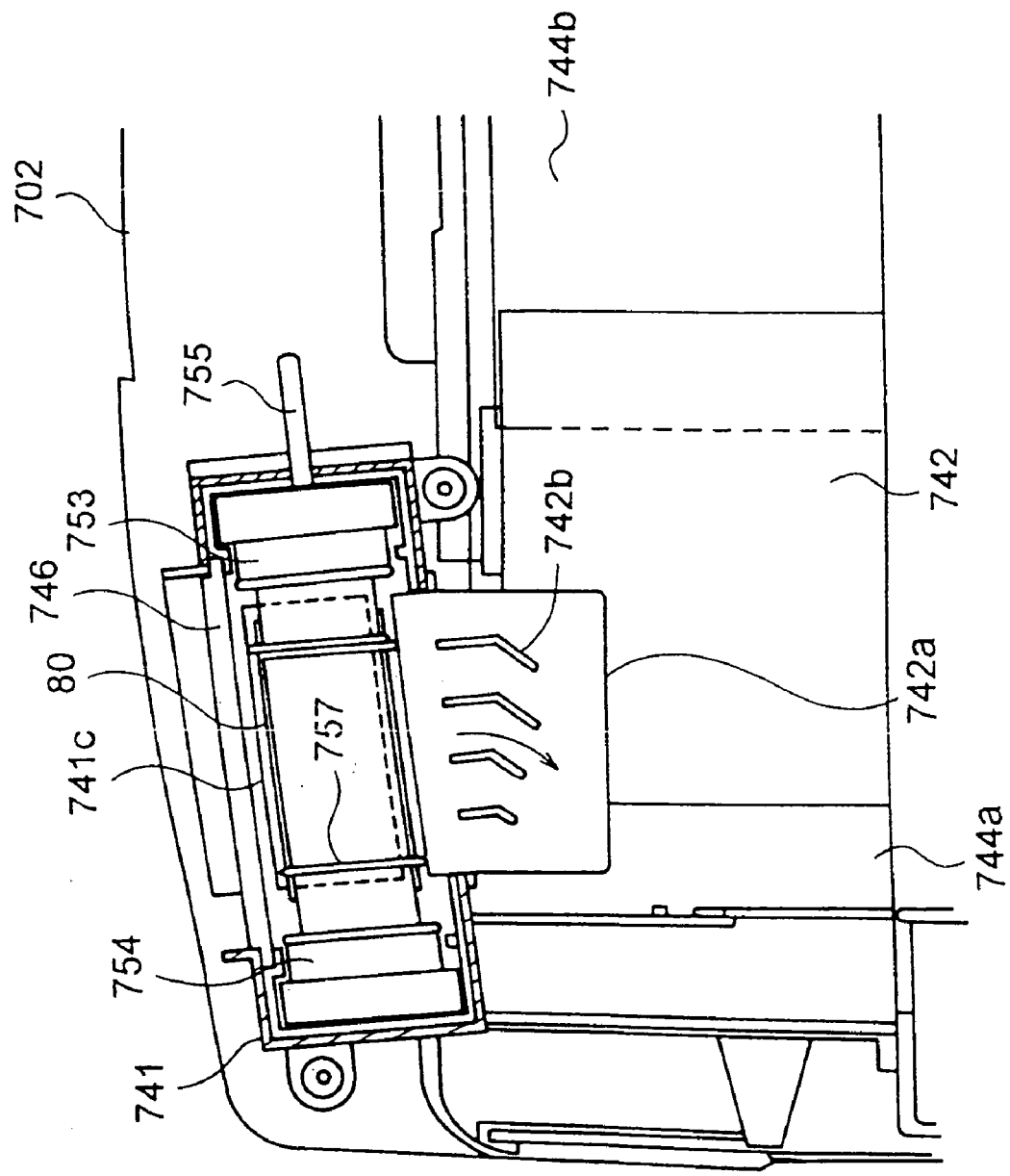
FIG. 95 is a sectional view, as seen from the top but from a different angle, showing an outline of the construction of an upper portion of the dehumidifier of the twentieth embodiment.

Now, the structure of the passage through which air is blown from the blower 711 out into the room will be described in detail. FIGS. 92, 93, and 94 are sectional views, as seen from the side, from behind, and from above, respectively, showing an outline of the construction of an upper portion of the dehumidifier 701. In an upper front portion of the dehumidifier 701, the ion generating element 80 is arranged so as to face the sight window 714. The bottom and side faces of the ion generating element 80 are covered with a casing 741. The casing 741 is fitted and fixed to a fan case 744 for covering the blower 711 by a tightening means such as screws or a locking means such as engagement claws. The top and rear faces of the casing 741 are covered with an upper cover 743, with an opening left in the rear face of the casing 741.

The opening formed in the rear face of the casing 741 is divided into upper and lower portions by a separator plate 741h that is fitted to a separator portion 742. The portion of the opening located below the separator plate 741h serves as an inflow port 741b through which the air from the blower 711 is directed to the ion generating element 80, and the portion of the opening located above the separator plate 741h serves as an outflow port 741a through which the positive and negative ions generated by the ion generating element 80 are discharged out of the casing 741.

Moreover, to the upper cover 743, a lamp 749 (for example, blue) composed of a light-emitting diode or the like for illuminating the ion generating element 80 is fitted. In the front face of the casing 741, in a position facing the sight window 714, a transparent plate 746 is fitted. This arrangement permits the lamp 749 to emit light in a manner interlocked with the operation of the ion generating element 80, and thus permits the user to visually check the operation status of the ion generating element 80 through the sight window 714.

Furthermore, the impeller 711b of the blower 711 is enclosed in the fan case 744. In an upper portion of the fan case 744, an opening 744b is formed through which dry air is blown out into the room. The opening 744b is fitted with a protection plate 745 formed out of a metal mesh or the like for preventing entry of foreign objects.

Moreover, in the fan case 744, a bypass passage lower portion 744a is formed so as to extend substantially horizontally from the opening 744b side end of the fan case 744. Above the bypass passage lower portion 744a is provided a separator portion 742 for separating the outflow port 741a of the ion generating element 80 from a bypass passage 748 to the ion generating element 80. The separator portion 742 is provided for the purpose of preventing the dry air blown out through the opening 744b from disturbing the flow of air flowing out of the outflow port 741a. Here, providing a movable air volume adjustment plate (not shown) at the end of the separator portion 742 makes it possible to adjust the amount of dry air that flows into the bypass passage 748.

The air that has flown into the casing 741 through the inflow port 741b passes through an opening 741c formed between the transparent plate 746 and the separator plate 741h to the ion generating element 80. Here, if a voltage is being applied to the ion generating element 80, negative and positive ions are generated alternately at the frequency of the voltage, and thus opposite ions are mixed with the air passing by. The air that has passed by the ion generating element 80 flows out through the outflow port 741a.

Part of the separator portion 742 is formed into an elevated portion 742a, on which are formed separator ribs 742b for smoothing the flow of air flowing out through the outflow port 741a. These separator ribs 42b do not necessarily have to be formed on the upper surface of the elevated portion 742a, but may be designed suitably according to the flow of dry air that is directed to the air outlet.

The air that has flown out through the outflow port 741a is directed to the exhaust portion 712. In the exhaust portion 712, this air joins the air that has not passed by the ion generating element 80, and is then blown out into the room, in a direction determined by the wind direction adjustment device 717.

Figure 96:
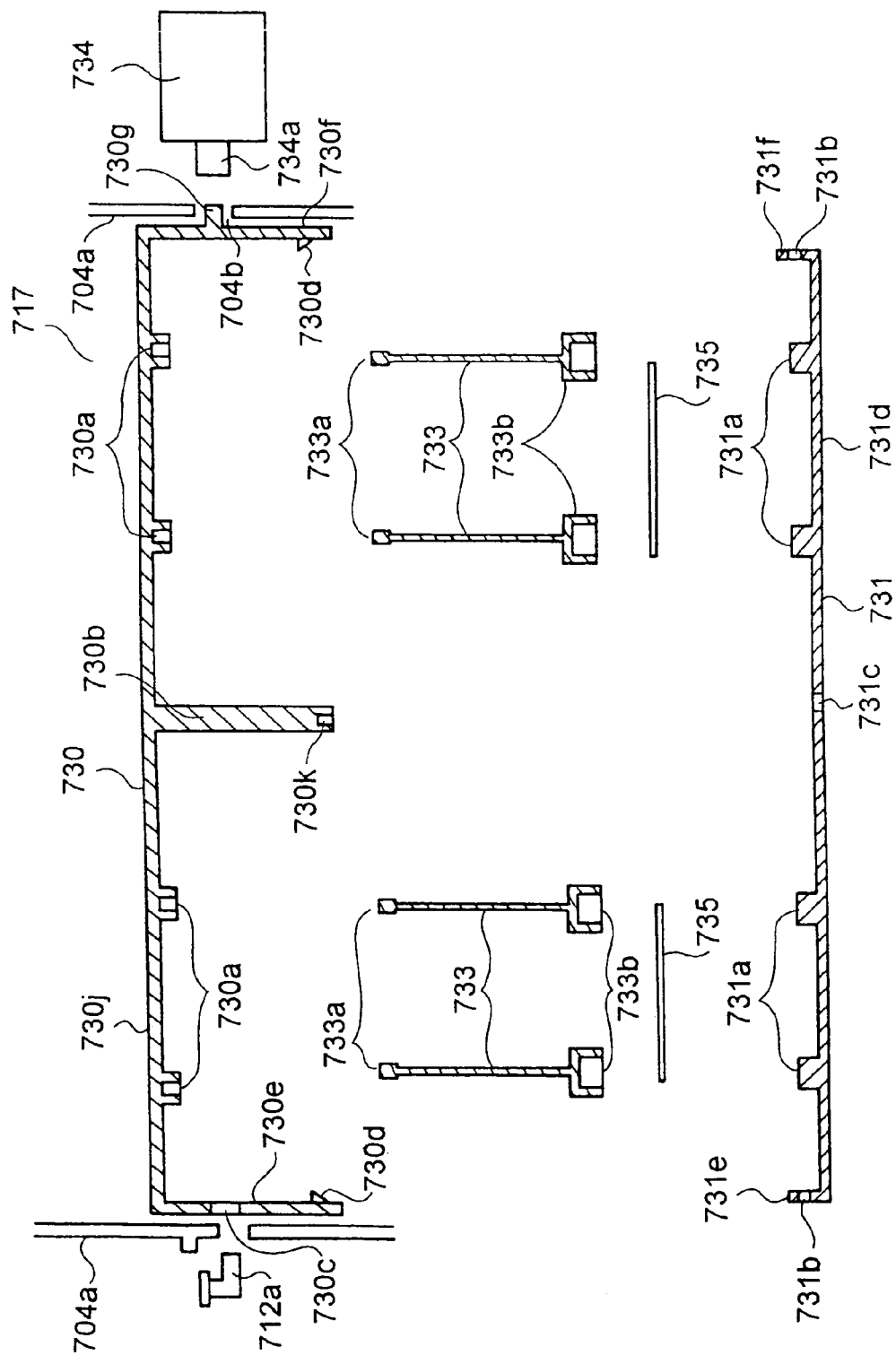
FIG. 96 is an exploded view of the wind deflecting device of the dehumidifier of the twentieth embodiment.

FIG. 96 is an exploded view of the wind direction adjustment device 717. In FIGS. 92 and 96, the wind direction adjustment device 717 has first and second longitudinal wind deflector plates 730 and 731 and four lateral wind deflector plates 733, and how these components are turned determines the direction of the flow of air. The first longitudinal wind deflector plate 730 is curved along the external shape of the exhaust portion 712. The first longitudinal wind deflector plate 730 pivots on a horizontal axis, and rotates together with the second longitudinal wind deflector plate 731, which is arranged substantially parallel to the first longitudinal wind deflector plate 730, to change the direction of the flow of air in the front-rear direction. The lateral wind deflector plates 733 pivot on the first and second longitudinal wind deflector plates 730 and 731, and rotate to change the direction of the flow of air in the right-left direction as seen from in front of the dehumidifier 701.

On one side wall 704a of the air outlet 704 formed in the exhaust portion 712, a shaft portion 712a is provided. On the outside of the other side wall 704a, a stepping motor 734 is arranged. The first longitudinal wind deflector plate 730 has an E-shaped section, and has a top plate 730j, side walls 730e and 730f, and a middle wall 730b.

In one side wall 730e of the first longitudinal wind deflector plate 730, a shaft hole 730c is formed, and, on the other side wall 730f, a shaft portion 730g is formed. The shaft portion 712a fits into the shaft hole 730c, and the shaft portion 730g and the shaft portion 734a of the stepping motor 734 are coupled together through a hole 704b formed in the side wall 704a. In this way, the first longitudinal wind deflector plate 730 is pivoted.

Figure 98:
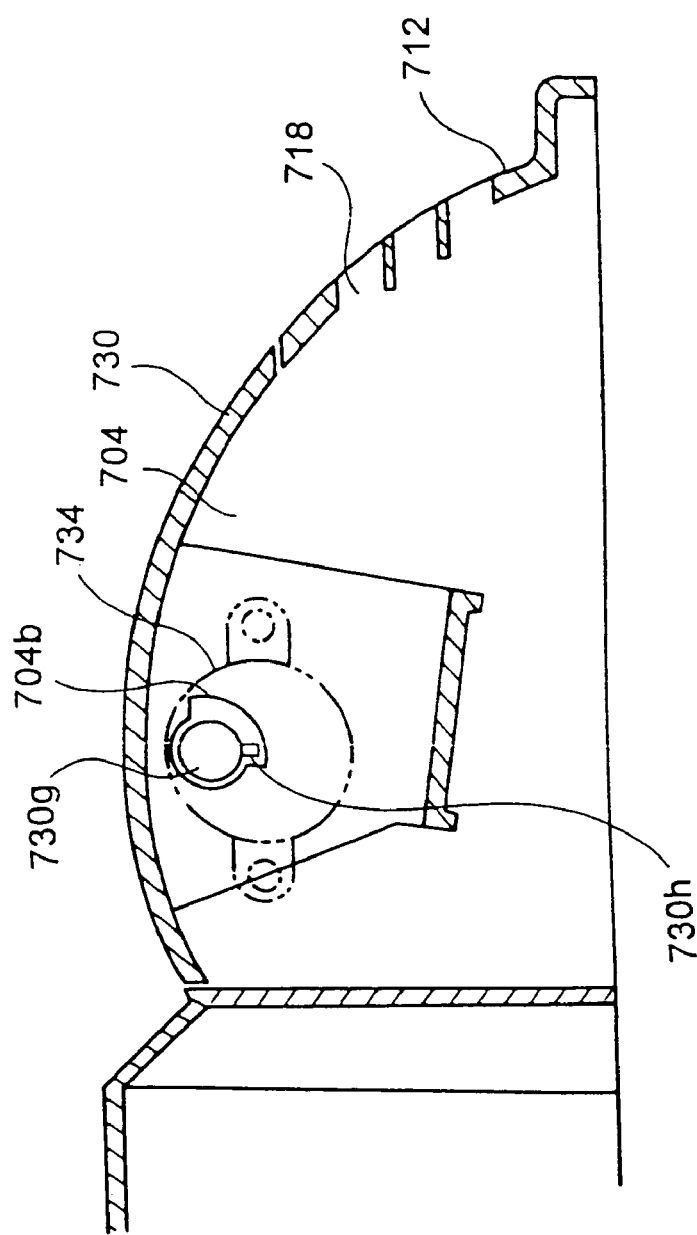
FIG. 98 is a sectional view, as seen from the side, showing the structure of a portion of an upper portion of the dehumidifier of the twentieth embodiment.

As FIG. 98 shows, the hole 704b has part of its rim cut out in the shape of a fan, so that the rotation angle of the first longitudinal wind deflector plate 730 is limited by a stopper piece 730h, formed on the peripheral surface of the shaft portion 730g of the first longitudinal wind deflector plate 730 so as to protrude therefrom, hitting the end surfaces of this cut.

The second longitudinal wind deflector plate 731 has a C-shaped section, and has a bottom plate 731d and side walls 731e and 731f. At the center of the bottom plate 731d, a hole 731c is formed, and, in the side walls 731e and 731f, holes 731b are formed. With the holes 731b, claws 730d formed on the side walls 730e and 730f of the first longitudinal wind deflector plate 730 engage. Through the hole 731c, a screw (not shown) is put, and is screwed into a hole 730k formed in the middle wall 31b of the first longitudinal wind deflector plate 730. In this way, the first and second longitudinal wind deflector plates 730 and 731 are integrally combined together so as to be parallel to each other.

In the top plate 730j of the first longitudinal wind deflector plate 730, four boss holes 730a each having a circular section are formed. On the bottom plate 731d of the second longitudinal wind deflector plate 731, four bosses 731a, each having a circular section, are formed. At the top and bottom of each of the lateral wind deflector plates 733 are respectively formed a boss 733a and a boss hole 733b, each having a circular section. The bosses 733a fit into the boss holes 730a, and the bosses 731a fit into the boss holes 733b. In this way, the lateral wind deflector plates 733 are pivoted.

Each of the lateral wind deflector plates 733 has a cut-out portion 733g formed in the surface thereof facing the second longitudinal wind deflector plate 731, and in this cut-out portion 733g, a boss 733d having a circular section is formed so as to protrude toward the second longitudinal wind deflector plate 731. The bosses 733d of every two lateral wind deflector plates 733 are loosely fit into holes (not shown) formed in a coupling plate 735. In this way, every two lateral wind deflector plates 733 are coupled together by the coupling plate 735 so as to rotate in an interlocked fashion.

When the swing button 727 (see FIG. 90) is operated, the stepping motor 734 is driven, and the first and second longitudinal wind deflector plates 730 and 731 rotate about the shaft portions 712a and 730g. When the dehumidifier 701 is not in use, as FIG. 92 shows, the first longitudinal wind deflector plate 730 closes the air outlet 704. This prevents entry of dust and the like through the air outlet 704.

Figure 97:
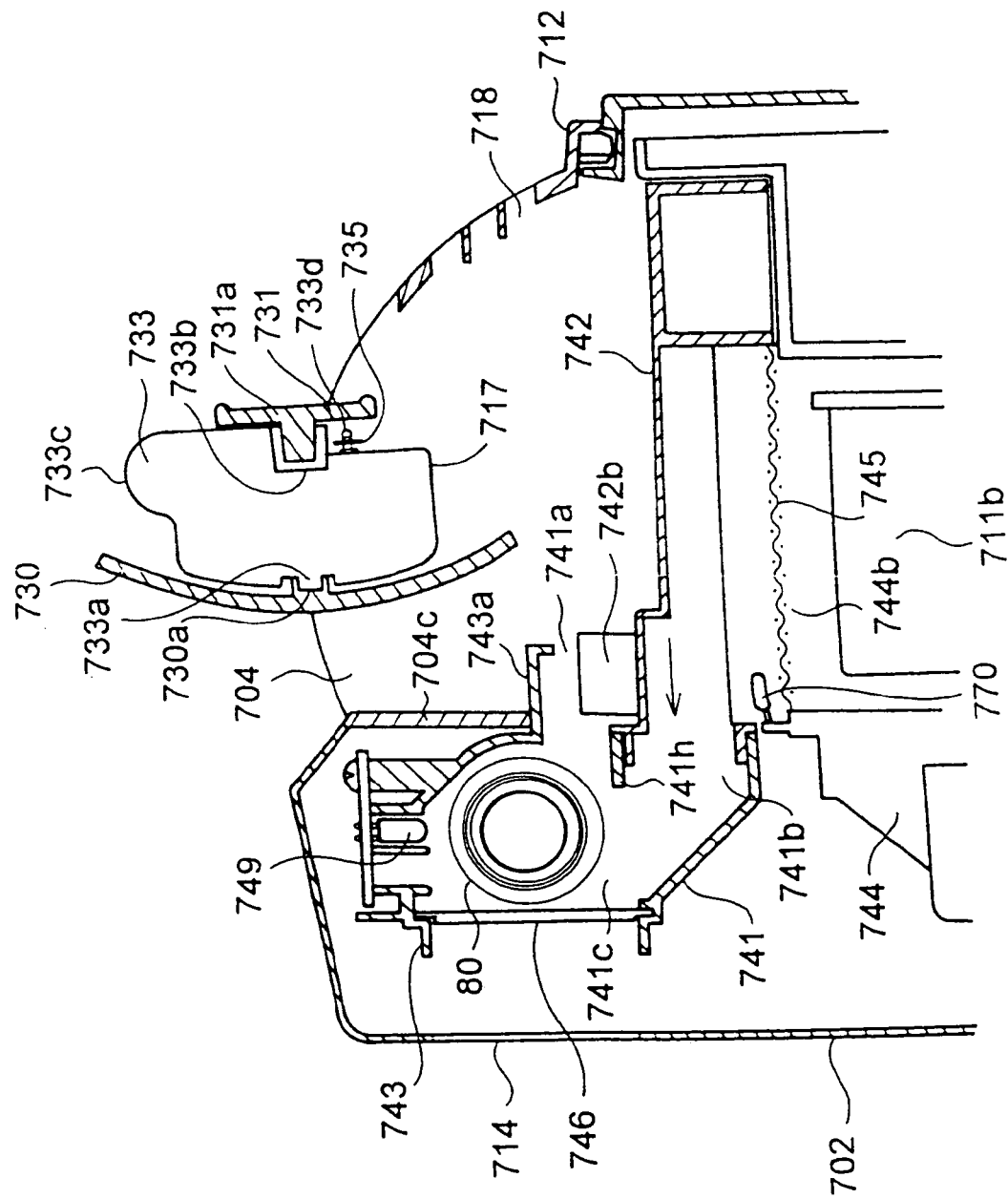
FIG. 97 is a sectional view, as seen from the side, showing an outline of the construction of an upper portion of the dehumidifier of the twentieth embodiment, as seen when it is in a different state from that shown in FIG. 92.

FIG. 97 shows the state of the first and second longitudinal wind deflector plates 730 and 731 when they are rotated through about 100°. In this state, the air outlet 704 is open, and, by rotating the lateral wind deflector plates 733 with one of their projecting portions 733c held between fingers, it is possible to turn their direction. Moreover, as will be described later, by operating the swing button 727, it is also possible to make the first and second longitudinal wind deflector plates 730 and 731 swing within a predetermined range of angles.

The front wall 704c of the air outlet 704 and the upper wall 743a of the outflow port 741a together constitute a shielding means for preventing the user's fingers, which may be put into the air outlet 704 when it is open, from making contact with the ion generating element 80. This helps prevent accidents such as an electric shock that the user receives when his or her finger touches the ion generating element 80, and also helps arrange the ion generating element 80 closer to the air outlet 704 and thereby reduce the loss of ions resulting from collision of the generated ions with the wall surface or the like inside the distribution passage.

Next, the operation of the dehumidifier 701 constructed as described above will be described. When the dehumidifier 701 is turned on, it waits until one of the air purification button 721, the dehumidification button 722, and the clothes drying button 723 is pressed. When the dehumidification button 722 is pressed, the compressor 705 is driven with the normal output power, and the blower 711 is driven so as to blow out a "medium" volume of air. Moreover, the stepping motor 734 of the wind direction adjustment device 717 is driven to set the wind direction to "upward."

By pressing the air volume switch button 725, the volume of air can be switched to "quiet" so that a smaller volume of air is blown out and thus the blower 711 operates with less noise than when the volume of air is "medium," and to "strong" so that a larger volume of air is blown out than when the volume of air is "medium."

Moreover, as described earlier, every time the swing button 727 (see FIG. 90) is pressed, the state of the wind direction adjustment device 717 is switched from "off" to "wide-angle" to "upward" to "rearward," and so forth. When "wide-angle" is selected, the first and second longitudinal wind deflector plates 730 and 731 are swung within a range of angles of about 100° from the substantially horizontal state shown in FIG. 92 to the substantially vertical state shown in FIG. 97.

When "upward" is selected, the first and second longitudinal wind deflector plates 730 and 731 are swung within a range of angles of about 50° from the substantially vertical state shown in FIG. 97 in the direction in which the air outlet 704 is closed, so that air is blown out mainly through the air outlet 704 at the top. When the "rearward" is selected, the first and second longitudinal wind deflector plates 730 and 731 are swung within a range of angles of about 50° from the substantially horizontal state shown in FIG. 92 in the direction in which the air outlet 704 is open, so that air is blow out through the air outlet 704 at the top and the air outlet 718 at the back. By selecting "off", it is possible to stop the swinging first and second longitudinal wind deflector plates 730 and 731 in the desired position. When the dehumidifying, clothes-drying, or air-purifying operation of the dehumidifier 701 is stopped, the air outlet 704 is closed as shown in FIG. 92.

In dehumidifying operation, the operation mode is initially set to "automatic." Specifically, if the room temperature is lower than 28° C., the compressor 705 stops when the humidity becomes equal to or lower than 60%; if the room temperature is equal to or higher than 28° C., the compressor 705 stops when the humidity becomes equal to or lower than 55%.

By pressing the dehumidification button 722, the operation mode can be switched to "attack mold," in which case the compressor 705 stops when the humidity becomes equal to or lower than 49%.

The operation mode can be switched to "continuous dehumidification," in which case the compressor 705 is operated continuously. However, the compressor 705 is stopped when the humidity becomes, for example, equal to or lower than 30%, because then the efficiency of dehumidification is too low. The operation mode can be switched to "condensation prevention," in which case the volume of air is automatically switched to "strong" when the room temperature falls below 15° C. to prevent condensation on the condenser 709.

When the compressor 705 is driven to operated the refrigerating cycle, and the blower 711 is driven, the air inside the room is taken into the dehumidifier 701 through the air inlet 715. The air inside the room containing moisture is cooled by the evaporator 708 placed on the low-temperature side. As a result, the moisture is condensed, and thereby the air is dried. The air is then heated by the condenser 709 placed on the high-temperature side back to its original temperature, and is then discharged out of the fan case 744 through the opening 744b.

Part of the dry air from the fan case 744 is passed through the bypass passage 748 so as to be directed through the inflow port 741b to the ion generating element 80. The dry air that passes by the ion generating element 80 carries the ions generated by the ion generating element 80, and is then blown out through the air outlet 704 into the room.

Figure 99:
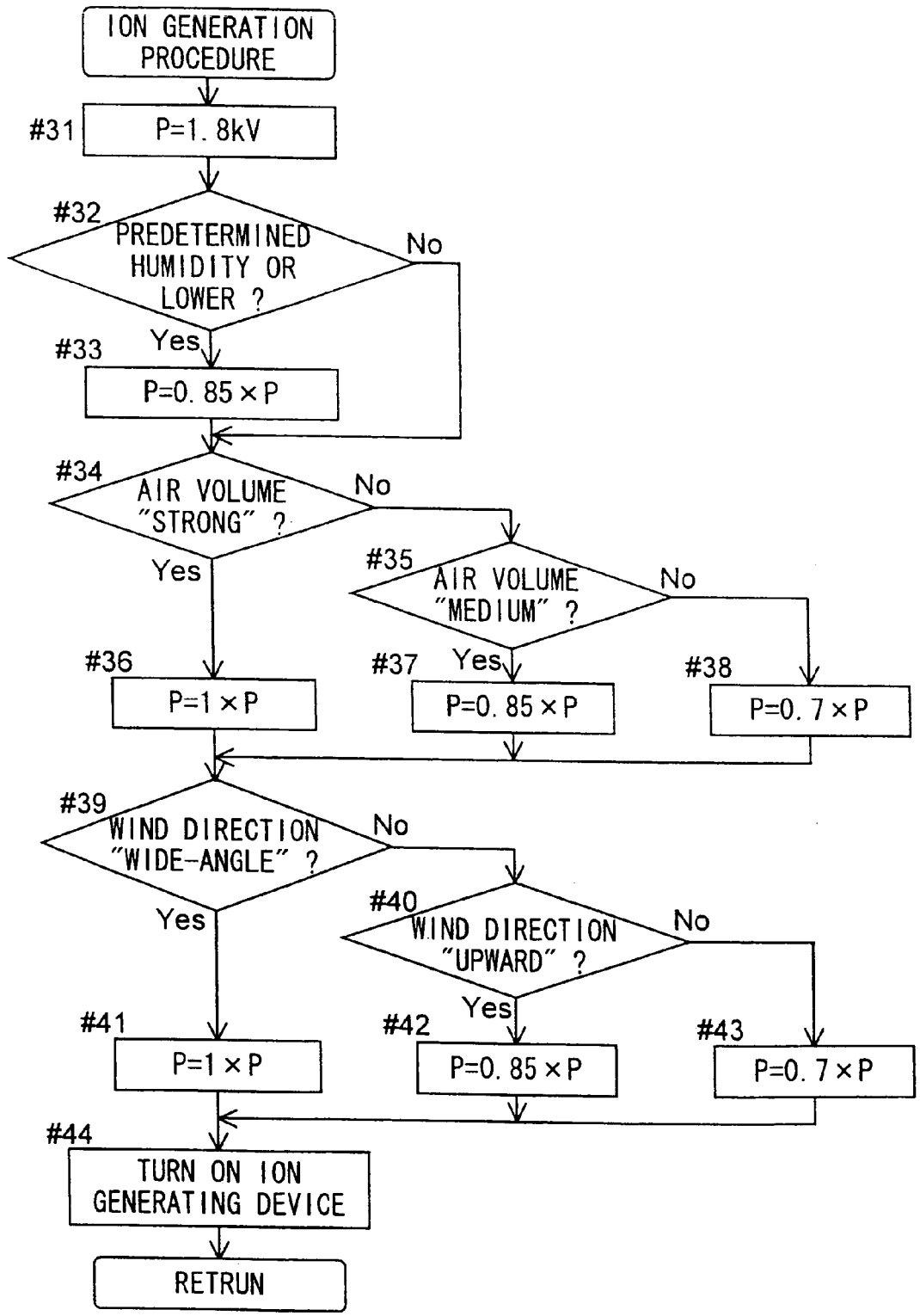
FIG. 99 is a flow chart of the procedure that the dehumidifier of the twentieth embodiment undergoes while generating ions.

The ion generating element 80 is so configured as to generate ions with the voltage applied thereto determined according to the flow chart of the procedure for generating ions shown in FIG. 99. In step #31, the maximum voltage P applied to the ion generating element 80 is set. In this embodiment, P=1.8 kV. In step #32, whether the humidity of the dry air detected by a humidity sensor 770 is equal to or lower than a predetermined humidity or not is checked. If the humidity is found higher than the predetermined humidity, the applied voltage P is left unchanged and the flow proceeds to step #34.

If the humidity of the dry air is found equal to or lower than the predetermined humidity, then, in step #33, the applied voltage P is renewed with a new applied voltage P that is calculated by multiplying the original applied voltage P by a predetermined coefficient. Here, the coefficient is 0.85. The amount of ions generated by the ion generating element 80 decreases as the humidity becomes higher, and therefore, in such a case, the applied voltage P is made higher so as to maintain an adequate concentration of ions.

In step #34, whether the volume of air blow out by the blower 711 is "strong" or not is checked. If the volume of air is found "strong," then, in step #36, the applied voltage P is renewed with a new applied voltage P that is calculated by multiplying the original applied voltage P by a predetermined coefficient. Here, the coefficient is 1, and therefore step #36 may be omitted.

If, in step #34, the volume of air is found not "strong," then, in step #35, whether the volume of air is "medium" or not is checked. If the volume of air is found "medium," then, in step #37, the applied voltage P is renewed with a new applied voltage P that is calculated by multiplying the original applied voltage P by a predetermined coefficient smaller than 1. Here, the coefficient is 0.85. If, in step #35, the volume of air is found not "medium," the volume of air blown out by the blower 711 is "quiet", and therefore, in step #38, the applied voltage P is renewed with a new applied voltage P that is calculated by multiplying the original applied voltage P by a predetermined coefficient smaller than 0.85. Here, the coefficient is 0.7.

As the volume of air blown out by the blower 711 increases, the concentration of ions decreases, making it impossible to achieve a satisfactory sterilizing effect on airborne bacteria. To avoid this, according to whether the blower 711 is blowing out a large or small volume of air, the applied voltage P is made higher or lower, respectively, to maintain an adequate concentration of ions.

Next, in step #39, whether the wind direction of the wind direction adjustment device 717 is "wide-angle" or not is checked. If, in step #39, the wind direction is found "wide-angle," then, in step #41, the applied voltage P is renewed with a new applied voltage P that is calculated by multiplying the original applied voltage P by a predetermined coefficient. Here, the coefficient is 1, and therefore step #41 may be omitted. If the wind direction is found not "wide-angle," then, in step #40, whether the wind direction is "upward" or not is checked.

If the wind direction is found "upward," then, in step #42, the applied voltage P is renewed with a new applied voltage P that is calculated by multiplying the original applied voltage P by a predetermined coefficient smaller than 1. Here, the coefficient is 0.85. If, in step #40, the wind direction is found not "upward," the wind direction of the wind direction adjustment device 17 is "rearward" or it is in a no-swing state ("off"), and therefore, in step #43, the applied voltage P is renewed with a new applied voltage P that is calculated by multiplying the original applied voltage P by a predetermined coefficient smaller than 0.85. Here, the coefficient is 0.7.

When the swing angle of the wind direction adjustment device 717 is large, ions are discharged into a wide area inside the room and are thus diffused, lowering the sterilizing effect on airborne bacteria. To avoid this, according to whether the swing angle of the wind direction adjustment device 717 is large or small, the applied voltage is made higher or lower, respectively. Thus, when the swinging is stopped, the applied voltage P is at its lowest. This makes it possible to maintain an adequate satirizing effect.

Moreover, although the swing angle is the same when the wind direction of the wind direction adjustment device 717 is set to "upward" as when it is set to "rearward," the dehumidifier 701 is usually installed along a wall surface inside the room, and thus ions are discharged into a wider area when the wind direction is set to "upward" than when it is set to "rearward." Therefore, the applied voltage P is made higher when the wind direction is set to "upward" than when it is set to "rearward."

Then, in step #44, the applied voltage P set in this way is applied to the ion generating element 80, which thus generates positive and negative ions. Simultaneously, the lamp 749 (see FIG. 92) is lit so that the operation status of the ion generating element 80 can be visually checked through the sight window 714.

As a result, part of the dry air that has been directed to the ion generating element 80 carries the ions and flows out of the casing 741 through the outflow port 741a. This air joins the rest of the dry air that flows out of the fan case 744 through the opening 744b, and thus the positive and negative ions are discharged through the air outlet 704 or the air outlet 718 into the room. In one hour after the ion generating element 80 starts being driven, about 80% of the airborne bacteria floating inside the room can be removed. In this way, the air inside the room is dehumidified, and simultaneously the airborne bacteria, hazardous to the human body, present inside the room are removed by the action of hydrogen peroxide and radical hydroxyl. This makes it possible to realize a comfortable living environment.

When the volume of air blown out by the blower 711 is set to "quiet," an air volume adjustment plate 760 shown in FIG. 93 described earlier is in the position indicated with solid lines. This makes the proportion of the dry air that flows into the bypass passage 748 higher. When the volume of air blown out by the blower 711 is set to "strong," the air volume adjustment plate 760 is in the position indicated with broken lines. This makes the proportion of the dry air that flows into the bypass passage 748 lower. When the volume of air blown out by the blower 711 is set to "medium," the air volume adjustment plate 760 is in a position intermediate between that indicated with solid lines and that indicated with broken lines.

Thus, the amount of dry air directed to the ion generating element 80 is kept constant irrespective of the volume of air blown out by the blower 711. This makes it possible to prevent loss of ions resulting from collision with a wall surface or the like when a large volume of air is blown out, and thus makes it possible to supply a stable amount of ions.

Next, when the clothes drying button 721 is pressed, the compressor 705 is driven with the maximum output power, and the blower 711 is driven so as to blow out a "medium" volume of air. Moreover, the stepping motor 734 of the wind direction adjustment device 717 is driven to set the wind direction to "upward." In this way, clothes-drying operation is performed, in which, with the evaporator 708 kept cooler than in dehumidifying operation, the air taken into the dehumidifier 701 is dehumidified quickly.

As a result, drier air is blown out through the air outlets 704 and 718 into the room, making it possible to dry clothes hung inside the room. Here, as in dehumidifying operation, the ion generating element 80 generates positive and negative ions, which are carried by the dry air and are discharged into the room. Thus, the airborne bacteria present inside the room are killed.

When the air purification button 723 is pressed, the compressor 705 is not driven, and the blower 711 is driven so as to blow out a "medium" volume of air. Moreover, the stepping motor 734 of the wind direction adjustment device 717 is driven to set the wind direction to "upward." In addition, the ion generating element 80 generates ions, which are discharged into the room. In this way, air-purifying operation is performed, in which the air inside the room is circulated and meanwhile airborne bacteria are removed.

The lamp 749 can be extinguished by pressing the dehumidification switch button 724 and the swing button 727 simultaneously for three seconds even when the ion generating element 80 is operating. This makes it possible to extinguish the lamp 749 and thereby reduce electric power consumption when the lamp 749 need not be lit as when the user is sleeping. Moreover, there is no need to provide a separate switch for extinguishing the lamp 749, and this helps reduce costs.

Moreover, the operation of the ion generating element 80 can be stopped by pressing the air volume switch button 725 and the timer switch button 728 simultaneously for five seconds. Pressing these buttons again restarts the operation of the ion generating element 80. This eliminates the need to provide a separate switch for turning on/off the ion generating element 80, and thus helps reduce costs and save space on the operation panel 713 (see FIG. 87).

In this embodiment, air that has been dried by being passed through the evaporator 708 is directed to the ion generating element 80. This makes it possible to generate the desired amount of ions stably. Thus, it is possible to achieve a stable sterilizing effect on the airborne bacteria present inside the room.

Moreover, part of the dry air that has passed through the evaporator 708 is directed to the ion generating element 80. This makes it possible to reduce the pressure of the dry air that is directed to the ion generating element 80. Thus, it is possible to reduce loss of ions resulting from collision with the wall surface or the like inside the passages from the ion generating element 80 to the air outlets 704 and 718. This air joins the rest of the air that has not passed by the ion generating element 80, so that ions in the desired concentration are discharged by being carried by a strong flow of air so as to be spread all around the room.

In the dehumidifier 701 of this embodiment, the compressor 705 is driven to operate a refrigerating cycle so that the dry air that has passed through the evaporator 708 is directed to the ion generating element 80. However, the dehumidifier may be configured in any other manner than is specifically described in connection with this embodiment; for example, the dehumidifier may be of the type that does not operate a refrigerating cycle. Even in that case, by directing dehumidified, dry air to the ion generating element 80, it is possible to achieve the same effects as in this embodiment.

As will be clear from the descriptions above, in the dehumidifier of the invention, dry air is directed to an ion generating device (more specifically, an ion generating element, which is the principal component of the ion generating device) so that positive and negative ions are carried by the dry air so as to be discharged into a room. Thus, even if the humidity inside the room is high, it is possible to generate the desired amount of ions stably. As a result, it is possible to achieve a stable sterilizing effect on the airborne bacteria present inside the room. In particular, when the humidity inside the room is high from wet clothes hung in the room, it is possible to effectively remove airborne bacteria that have settled on the clothes.

Moreover, only part of the dry air is directed to the ion generating device. This helps reduce the pressure of the dry air that is directed to the ion generating device. Thus, it is possible to reduce loss of ions resulting from collision with a wall surface or the like after the ions have flown out of the ion generating device. This air then joins the rest of the air that has not passed through the ion generating device, so that ions in the desired concentration are discharged by being carried by a strong flow of air so as to be spread all around the room.

Moreover, the proportion of the air directed to the ion generating device is varied according to the volume of air that is blown out into the room. Thus, the amount of air directed to the ion generating device is kept substantially constant irrespective of the volume of air blown out of the dehumidifier. This makes it possible to prevent loss of ions resulting from collision with the wall surface or the like inside the distribution passages within the dehumidifier even when the volume of air is increased, and thus makes it possible to supply a stable amount of ions.

Moreover, by varying the voltage applied to the ion generating device according to the humidity of the dry air directed to the ion generating device, it is possible to reduce the lowering of the amount of ions generated under high-humidity conditions and thereby maintain an adequate concentration of ions.

Moreover, by varying the amount of ions generated by the ion generating device according to the volume of air blown out into the room, it is possible to maintain an adequate concentration of ions in the air blown out into the room and thereby achieve a satisfactory sterilizing effect.

Moreover, by varying the amount of ions generated by the ion generating device according to the swing angle of a wind direction adjustment device, it is possible to prevent the lowering of the sterilizing effect on airborne bacteria when the swing angle is large and the degree of ion diffusion is higher.

The air outlet through which air is blown out into the room can be closed by the wind direction adjustment device. This helps prevent entry of dust or the like through the air outlet, and thus makes it possible to blow out clean air.

By providing the ion generating device in the vicinity of the air outlet, it is possible to reduce the loss of ions after the generation thereof. Moreover, by providing a shielding means for preventing the user's finger, which may be put into the air outlet when the wind direction adjustment device is open, from making contact with the ion generating device, it is possible to prevent accidents such as an electric shock that the user receives when his or her finger touches the ion generating device.

Moreover, a lamp is provided that illuminates the ion generating device when it is operating so that it can be visually checked, and this lamp can be extinguished by the operation of the user even when the ion generating device is operating. This makes it possible to extinguish the lamp and thereby reduce electric power consumption when the lamp need not be lit as when the user is sleeping.

The twenty-first embodiment deals mainly with the material of some structural members of the air conditioning apparatus of the invention. In the following descriptions, it is assumed that the twenty-first embodiment is built on the basis of the dehumidifier 701 of the twentieth embodiment. That is, the construction itself that is dealt with here is quite the same as that of the dehumidifier 701 of the twentieth embodiment.

When the dehumidifier 701 is operated, part of the dry air that is directed to the ion generating element 80 carries ions and flows out of the casing 741 through the outflow port 741a. This air then joins the rest of the dry air that flows out of the fan case 744 through the opening 744b, and thus positive and negative ions are discharged into the room through the air outlet 704 or 718. In this way, the same effects as those confirmed in the tests described above are achieved. Specifically, the air inside the room is dehumidified, and simultaneously the airborne bacteria, hazardous to the human body, present inside the room are killed by the action of hydrogen peroxide and radical hydroxyl. Thus, it is possible to realize a comfortable living environment.

However, if the members that constitute the passage through which the positive and negative ions generated by the ion generating element 80 are blown out, namely the exhaust portion 712, the separator portion 742, and the upper cover 743, and/or the wind direction adjustment device 717 provided in this passage for changing the direction in which the ions are blown out are made of ABS resin, PS resin, or AS resin having no antistatic agent added thereto, the following problem arises.

Molding materials such as ABS resin, PS resin, AS resin, and the like excel in moldability and in physical and mechanical properties, and in addition are relatively cheap. For these reasons, these materials are widely used in electric and other equipment. However, they have surface resistivity as high as $10^{15}$ Ω or higher, and are thus electrically charged too easily. This causes ions of the opposite polarity to the charge with which the material is charged to be attracted to it; that is, such a material is liable to upset the balance of the ions blown out into the room.

If this happens, it is possible to obtain only a sterilizing effect corresponding to one type of ions, i.e. either positive or negative, which is blown out in a smaller amount. This leads to a decline in the sterilizing effect.

Apparently, this can be overcome by designing with consideration given to the amount of ions that is likely to be inactivated by attraction. However, the polarity (positive or negative) and amount of charge with which the material is charged are not fixed but differ according to the use conditions and configuration of the apparatus. Thus, it is difficult to strike a proper balance between opposite ions generated, for example, by adjusting the voltage applied to the ion generating device with consideration given to the amount of ions that is likely to be inactivated at the time of designing.

To overcome this, in the present invention, the members that constitute the passage through which the ions generated by the ion generating device are passed and/or the members that are arranged in the passage through which the ions generated by the ion generating device are passed are made antistatic to prevent the ions from being attracted to those members.

A member that is made antistatic is less prone to be electrically charged, and is thus far less likely to attract and thereby inactivate one type of ions and thereby upset the balance between opposite ions. This makes it possible to maintain a proper balance between opposite ions and thereby prevent a decline in the sterilizing effect on airborne bacteria.

It is to be noted that the best balance between opposite ions is achieved when the amounts of positive and negative ions are equal.

FIG. 100 shows a table listing the results of tests conducted to measure the proportion of (balance between) the amounts of positive and negative ions generated under different conditions in an arrangement in which a member such as a wind direction adjustment device is provided in the passage through which the ions are passed. Specifically, in the table are listed measurement results obtained under conditions 1, where neither the members constituting the passage through which the ions were passed nor the members arranged in the passage through which the ions were passed were made antistatic, under conditions 2, where only the members constituting the passage through which the ions were passed were made antistatic, under conditions 3, where only the members arranged in the passage through which the ions were passed were made antistatic, and under conditions 4, where both the members constituting the passage through which the ions were passed and the members arranged in the passage through which the ions were passed were made antistatic.

In these tests, the dehumidifier 701 described earlier was used as the test appliance, with its exhaust portion 712 used as the member constituting the passage through which the ions were passed, and with its first and second longitudinal wind deflector plates 730 and 731 used as the members arranged in the passage through which the ions were passed.

These members were made antistatic by being formed out of ABS resin having 1.4% by weight of an antistatic agent (for example, "Elecon" manufactured by Dainichiseika Colour & Chemicals Mfg. Co., Ltd., Japan) added thereto. Moreover, measurements were taken with an ion counter (for example, model 83-1001B manufactured by Dan Kagaku Co., Ltd., Japan) placed at a distance of about 10 cm from the air outlet of the appliance in the direction in which it blows out air containing ions.

The table in FIG. 100 shows that, as compared with conditions 1, conditions 2, 3, and 4 yielded increasingly appropriate balances between the amounts of positive and negative ions, with the optimum balance achieved under conditions 4.

Even under conditions 2 and 3, the balance between opposite ions was improved. That is, by making antistatic either the members constituting the passage through which the ions generated by the ion generating device are passed or the members arranged in the passage through which the ions generated by the ion generating device are passed, it is possible to achieve the desired effect. Under conditions 4, the optimum balance between opposite ions was obtained. That is, by making antistatic both the members constituting the passage through which the ions generated by the ion generating device are passed and the members arranged in the passage through which the ions generated by the ion generating device are passed, it is possible to achieve the desired effect of striking a proper balance between opposite ions most effectively.

The aforementioned amount of antistatic agent added was determined by measuring the proportion of the amounts of positive and negative ions obtained with different amounts of antistatic agent. FIG. 101 shows a table listing the results of tests conducted to measure the proportion of opposite ions obtained with different amounts of antistatic agent. These tests were conducted under conditions 4 above.

The table in FIG. 101 shows that a proper balance between the amounts of positive and negative ions was obtained when 1.4% or more by weight of the antistatic agent (Elecon) was added.

Figure 102:
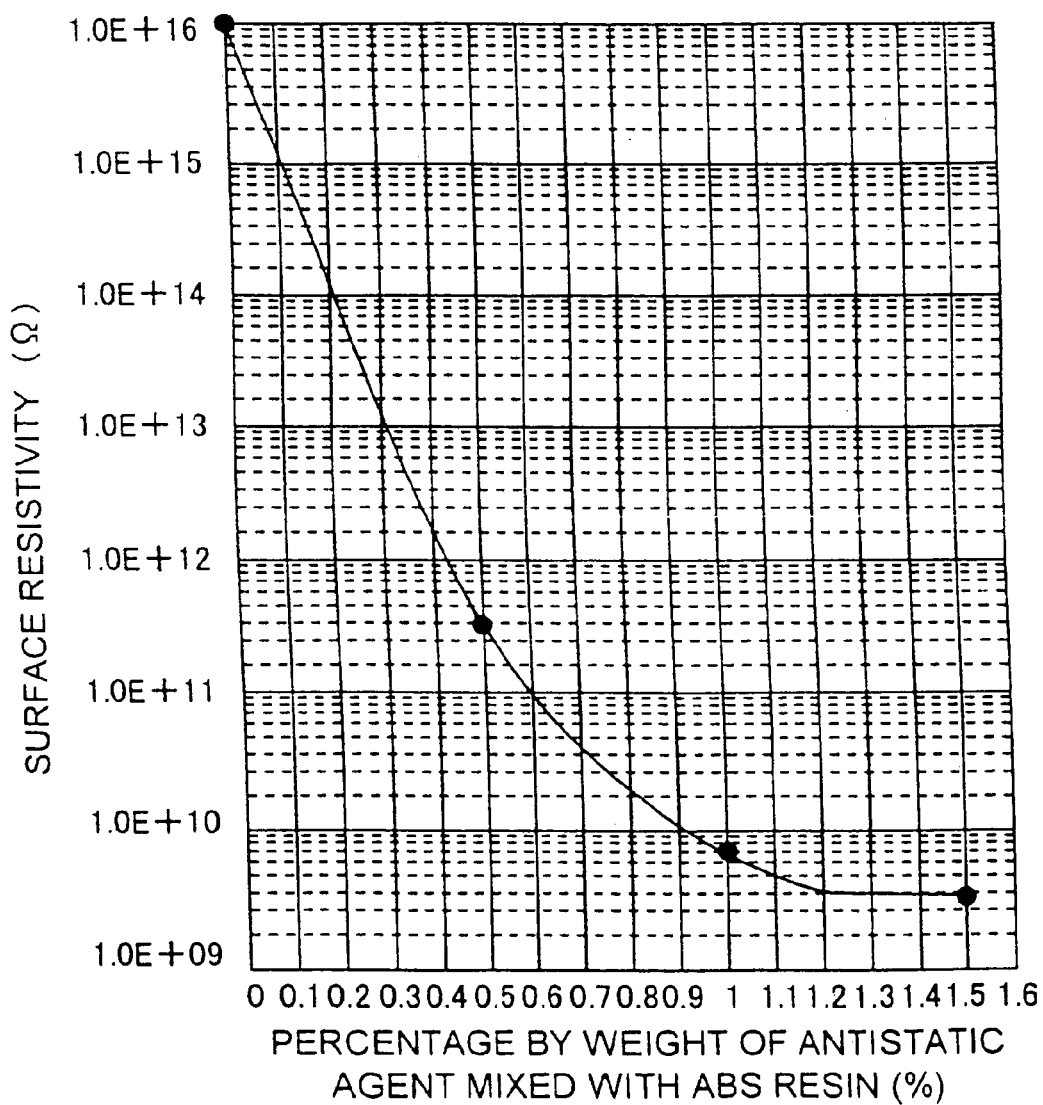
FIG. 102 is a diagram showing the relationship between the surface resistivity of ABS resin with respect to the ratio by weight of the antistatic agent mixed therewith in the air conditioning apparatus of the twenty-first embodiment.

The antistatic agent used here need not be of the specific type mentioned above. Therefore, now, a description will be given in terms of surface resistivity, which can be measured universally. The surface resistivity of the material when 1.4% by weight of the aforementioned antistatic agent (Elecon) is added thereto can be determined from FIG. 102. FIG. 102 shows a graph representing, for a case where Elecon is added to ABS resin, the relationship between the percentage by weight of Elecon added and the resulting surface resistivity. FIG. 102 shows that, when the percentage by weight of the antistatic agent (Elecon) added is 1.4%, the material has surface resistivity of about $4 \times 10^9$ Ω.

The results of the tests described above show that, by making antistatic the members constituting the passage through which ions are passed and/or the members arranged in the passage through which ions are passed, it is possible to keep a proper balance between the positive and negative ions blown out of an appliance incorporating an ion generating device, and that, by forming the members constituting the passage through which ions are passed and/or the members arranged in the passage through which ions are passed out of a material having surface resistivity of $4 \times 10^9$ Ω or lower, it is possible to maintain an appropriate balance between the positive and negative ions blown out.

Thus, the members constituting the passage through which ions are passed and/or the members arranged in the passage through which ions are passed may be formed out of a metal having high electric conductivity, for example aluminum or stainless, or a resin material, such as ABS resin, having its surface plated with a metal, such as nickel or chromium. This also prevents the material from being electrically charged, and thus makes it possible to achieve the same desired effects.

As compared with a metal or a resin material having its surface plated with a metal, a thermoplastic resin, such as ABS resin, PS resin, or AS resin, having an antistatic agent added thereto as described above is easier to mold. Thus, using such a material makes it possible to produce colorful, complex-shaped members inexpensively.

In the tests described above, the members constituting the passage through which ions were passed and/or the members arranged in the passage through which ions were passed were made antistatic by wholly changing their material. However, these members may be made antistatic in any other manner. For example, even by only partially making antistatic the members constituting the passage through which ions are passed and/or the members arranged in the passage through which ions are passed, it is possible to strike a proper balance between positive and negative ions. Specifically, it is possible, instead of wholly changing the material of those members, to use an antistatic material only in those portions thereof which are considered to constitute the passage through which ions are passed, or lay members made of a metal or the like only in portions of the passage through which ions are passed.

In the tests described above, the dehumidifier 701 was used. However, it is needless to say that it is possible to achieve the same effects by adopting a construction according to the present invention also in air conditioners, dehumidifiers, humidifiers, air purifiers, refrigerators, fan heaters, microwave ovens, laundry driers, vacuum cleaners, sterilizers, and any other type of appliance (air conditioning apparatus) incorporating an ion generating device as described above and designed for use inside a finite space, such as a room in a house or a building, a sickroom or operating room in a hospital, the inside of a car, aircraft, or vessel, or the inside of a warehouse or refrigerator.

Positive and negative ions have a finite life; that is, they vanish in about 3 to 5 seconds. Therefore, to achieve sterilization inside a given space, it is desirable to determine the speed and volume of air with which ions are blown out according to the size and shape of the space.

In the case of an air conditioning apparatus provided with a dehumidifying function, it is preferable to configure it in such a way that dehumidified air is fed to the ion generating device. The results of other tests show that the amount of ions generated by the ion generating device is influenced by humidity, and therefore it is preferable to feed dry air to the ion generating device. However, dry air is prone to cause static electricity, and is thus one of the factors that upset the balance between positive and negative ions blown out.

To overcome this, in the present invention, dehumidified air is fed to the ion generating device, and in addition the members constituting the passage through which ions are passed and/or the members arranged in the passage through which ions are passed are made antistatic. This makes it possible to prevent the lowering of the amount of ions generated by the ion generating device and in addition keep a proper balance between positive and negative ions. In this way, it is possible to realize the optimum environment for the discharge of opposite ions.

As will be clear from the descriptions above, in the air conditioning apparatus of this embodiment, which incorporates an ion generating device that generates positive and negative ions when an alternating-current voltage is applied between the electrodes thereof, the members constituting the passage through which the ions generated by the ion generating device are passed and/or the members arranged in the passage through which the ions generated by the ion generating device are passed are made antistatic. This helps prevent ions of one type from being attracted by those members and upsetting the balance between the amounts of positive and negative ions. Thus, it is possible to maintain an adequate sterilizing effect on airborne bacteria.

In particular, by providing the air conditioning apparatus with a dehumidifying function, configuring the air conditioning apparatus in such a way that dehumidified air is fed to the ion generating device, and making antistatic the members constituting the passage through which ions are passed and/or the members arranged in the passage through which ions are passed, it is possible to prevent the lowering of the amount of ions generated by the ion generating device and in addition keep a proper balance between positive and negative ions. Thus, it is possible to realize the optimum environment for the discharge of opposite ions.

The invention claimed is:

1. An ion generating device, comprising:
    a dielectric;
    a pair of electrodes arranged so as to face each other with the dielectric sandwiched in between;
    high alternating-current voltage generating means for applying an alternating-current voltage between the pair of electrode;
    first generating means generating positive and negative ions;
    second generating means for generating only negative ions; and
    switching means for switching between the first and second generating means.

2. An ion generating device as claimed in claim 1, wherein the switching means for switching between the first and second generating means comprises:
    a diode having an anode thereof connected to one of the electrodes to which the voltage is not applied and having a cathode thereof grounded; and
    a switching device connected between both ends of the diode.

3. An ion generating device as claimed in claim 2, wherein positive and negative ions are generated when the switching device is turned on and only negative ions are generated when the switching device is turned off.

4. An ion generating device as claimed in claim 2, wherein the switching device is a relay.

5. An ion generating device as claimed in claim 3, wherein the switching device is a relay.

6. An air conditioning apparatus provided with the ion generating device as claimed in claim 1 and capable of selecting between operation that yields positive and negative ions to achieve a sterilizing effect and operation that yields only negative ions to achieve a relaxation effect.

* * * * *